US007932436B2

(12) United States Patent
Frohberg et al.

(10) Patent No.: US 7,932,436 B2
(45) Date of Patent: Apr. 26, 2011

(54) PLANTS WITH INCREASED ACTIVITY OF MULTIPLE STARCH PHOSPHORYLATING ENZYMES

(75) Inventors: Claus Frohberg, Kleinmachnow (DE); Oliver Koetting, Zürich (CH); Gerhard Ritte, Potsdam (DE); Martin Steup, Berlin (DE)

(73) Assignee: Bayer CropCcience AG, Monheim am Rhein (DE)

( * ) Notice: Subject to any disclaimer, the term of this patent is extended or adjusted under 35 U.S.C. 154(b) by 961 days.

(21) Appl. No.: 10/591,432

(22) PCT Filed: Mar. 4, 2005

(86) PCT No.: PCT/EP2005/002457
§ 371 (c)(1),
(2), (4) Date: Sep. 1, 2006

(87) PCT Pub. No.: WO2005/095619
PCT Pub. Date: Oct. 13, 2005

(65) Prior Publication Data
US 2007/0163003 A1    Jul. 12, 2007

Related U.S. Application Data

(60) Provisional application No. 60/550,021, filed on Mar. 5, 2004.

(30) Foreign Application Priority Data

Mar. 5, 2004 (EP) .................... 04090089
Mar. 29, 2004 (EP) .................... 04090121
Jul. 21, 2004 (EP) .................... 04090284

(51) Int. Cl.
*C12N 15/82* (2006.01)
*C12N 15/00* (2006.01)
*C12N 15/29* (2006.01)
*C12N 15/63* (2006.01)
*A01H 5/00* (2006.01)

(52) U.S. Cl. ........ 800/284; 800/278; 800/296; 435/468; 435/183; 435/410; 435/320.1; 536/23.1; 536/23.2; 536/23.6

(58) Field of Classification Search .................. None
See application file for complete search history.

(56) References Cited

U.S. PATENT DOCUMENTS

| 6,307,123 B1 * | 10/2001 | Kriz et al. ................ 800/282 |
| 6,521,816 B1 * | 2/2003 | Frohberg ................ 800/284 |
| 6,734,340 B2 * | 5/2004 | Schewe et al. ........... 800/284 |
| 2006/0123505 A1 * | 6/2006 | Kikuchi et al. .......... 800/278 |

FOREIGN PATENT DOCUMENTS

| WO | WO 96/27674 | 9/1996 |
| WO | WO 97/11188 | 3/1997 |
| WO | WO 00/77229 | 12/2000 |
| WO | WO 02/10210 A2 | 2/2002 |
| WO | WO 02/22675 A2 | 3/2002 |
| WO | WO 02/34923 | 5/2002 |
| WO | WO 2005/095632 | 10/2005 |

OTHER PUBLICATIONS

Baunsgaard et al.; *A novel Isoform of Glucan, Water Dikinase Phosphorylates Pre-Phosphorylated α-glucans and is Involved in Starch Degradation in Arabidopsis*; The Plant Journal, 2005, vol. 41, pp. 595-605; XP-002339143.

Kötting et al., *Identification of a Novel Enzyme Required for Starch Metabolism in Arabidopsis Leaves. The Phosphoglucan, Water Dikinase*; Plant Physiology, Jan. 2005, vol. 137, pp. 242-252; XP-002339144.

Mikkelsen et al; *Functional Characterization of α-glucan, Water Dikinase, the Starch Phosphorylating Enzyme*; Biochem Journal, 2004, vol. 377, pp. 525-532; XP002339213.

Ritte et al.; *The starch-related R1 protein is an α-glucan, water dikinase*; PNAS; May 14, 2002; vol. 99; No. 10; pp. 7166-7171.

Blennow et al.; *Starch phosphorylation: a new front line in starch research*; Trends in Plant Science; Oct. 2002; vol. 7, No. 10; pp. 445-450.

Tabata et al.; *Studies on Starch Phosphate*; Die Stärke/Starch; 1971; vol. 23, pp. 267-272.

Blennow et al.; *The distribution of covalently bound phosphate in the starch granule in relation to starch crystallinity*; International Journal of Biological Macromolecules; 2000; vol. 27, pp. 211-218.

Blennow et al.; *Starch molecular structure and phosphorylation investigated by a combined chromatographic and chemometric approach*; Carbohydrate Polymers; 2000, vol. 41, pp. 163-174.

Jane et al., *Phosphorus in Rice and Other Starches*; Cereal Foods World, Nov.-Dec. 1996; vol. 41; No. 11; pp. 827-832.

(Continued)

*Primary Examiner* — Medina A Ibrahim
*Assistant Examiner* — Brent Page
(74) *Attorney, Agent, or Firm* — Hunton and Williams LLP

(57) ABSTRACT

The present invention relates to plant cells and plants, which are genetically modified, wherein the genetic modification leads to the increase of the activity of a starch phosphorylating OK1 protein and a starch phosphorylating R1 protein in comparison with corresponding wild type plant cells or wild type plants that have not been genetically modified. Furthermore, the present invention relates to means and methods for the manufacture of such plant cells and plants. Plant cells and plants of this type synthesize a modified starch. The present invention therefore also relates to the starch synthesized by the plant cells and plants according to the invention, methods for the manufacture of this starch, and the manufacture of starch derivatives of this modified starch, as well as flours containing starches according to the invention.

Furthermore, the present invention relates to nucleic acid molecules and vectors containing sequences which code for an OK1 protein and an R1 protein, as well as host cells which contain these nucleic acid molecules.

89 Claims, 5 Drawing Sheets

OTHER PUBLICATIONS

Lorberth et al.; *Inhibition of a starch-granule-bound protein leads to modified starch and repression of cold sweetening*; Nature Biotechnology; May 1998; vol. 16, pp. 473-477; XP002111459.

Yu et. al.; *The Arabidopsis sex1 Mutant is Defective in the R1 Protein, a General Regulator of Starch Degradation in Plants, and Not in the Chloroplast Hexose Transporter*; The Plant Cell; Aug. 2001; vol. 13, pp. 1907-1918; XP002252059.

Ritte et al.; *Compartmentation of the Starch-Related R1 Protein in Higher Plants*; Starch/Stärke; 2000; vol. 52; pp. 179-185.

NCBI Sequence Viewer; *Direct Submission*; Jul. 22, 2003; Y09533.

NCBI Sequence Viewer; *Expression and functional characterization of R1 in Escherichia coli*; Feb. 26, 2001; AY027522.

NCBI Sequence Viewer; *Nucleic acid molecules from wheat, transgenic plant cells and plants and the thereof for the production of modified starch*; Dec. 20, 2002; AAN93923 and AR236165.

NCBI Sequence Viewer; *Nucleic acid encoding a starch R1 phosphorylation protein homolog from maize*; Dec. 18, 2003; AR400813 and AAR61444.

NCBI Sequence Viewer; *Compositions and methods for the therapy and diagnosis of prostate cancer*; Dec. 18, 2003; AR400184.

NCBI Sequence Viewer; *Nucleic acid encoding a starch R1 phosphorylation protein homolog from maize*; Dec. 18, 2003; AAR61445.

NCBI Sequence Viewer; *Nucleic acid encoding a starch R1 phosphorylation protein homolog from maize*; Dec. 18, 2003; AR400815.

NCBI Sequence Viewer; *Nucleic acid encoding a starch R1 phosphorylation protein homolog from maize*; Dec. 18, 2003; AAR61446.

NCBI Sequence Viewer; *Effects of carbohydrate starvation on gene expression in citrus root*; Jul. 23, 2003; AY094062.

NCBI Sequence Viewer; *The Arabidopsis sex1 mutant is defective in the R1 protein . . .* ; Aug. 24, 2001; AF312027.

Alonso et al.(Aug. 1, 2003) "Genome-Wide Insertional Mutagenesis of Arabidopsis thaliana" *Science* 301: 653-657.

GenPept Accession No. B29959 (Jun. 18, 1999).

GenPept Accession No. S01446 (Jul. 21, 2000).

GenBank Accession No. AY747068 (Mar. 1, 2005).

Ritte et al. (2003) "Determination of the starch-phosphorylating enzyme activity in plant extracts." *Planta* 216(5): 798-801.

Sitohy et al. (2000) "Optimizing the Conditions for Starch Dry Phosphorylation with Sodium Mono-and Dihydrogen Orthophosphate under Heat and Vacuum." *Starch/Stärke* 52(4): 95-100.

UniProtKB/Swiss-Prot entry Q6ZY51 (Jun. 13, 2006).

UniProtKB/TrEMBL entry Q84T18 (Jun. 1, 2003).

\* cited by examiner

Fig.: 3

SEQUENCE LISTING

```
<160> NUMBER OF SEQ ID NOS: 39

<210> SEQ ID NO 1
<211> LENGTH: 3591
<212> TYPE: DNA
<213> ORGANISM: Arabidopsis thaliana
<220> FEATURE:
<221> NAME/KEY: CDS
<222> LOCATION: (1)..(3591)
<223> OTHER INFORMATION:

<400> SEQUENCE: 1 atg gag agc att ggc agc cat tgt tgc agc tct cct ttc acc ttc atc       48
Met Glu Ser Ile Gly Ser His Cys Cys Ser Ser Pro Phe Thr Phe Ile
1               5                   10                  15 act aga aac tca tca tca tca ctt cct aga ctc gtt aac atc act cac       96
Thr Arg Asn Ser Ser Ser Ser Leu Pro Arg Leu Val Asn Ile Thr His
            20                  25                  30 aga gtt aat ctc agc cac caa tct cac cga ctc aga aac tcc aat tct      144
Arg Val Asn Leu Ser His Gln Ser His Arg Leu Arg Asn Ser Asn Ser
        35                  40                  45 cgt ctc act tgc act gct act tct tct tcc acc att gag gaa caa cgg      192
Arg Leu Thr Cys Thr Ala Thr Ser Ser Ser Thr Ile Glu Glu Gln Arg
    50                  55                  60 aag aag aaa gat gga tca gga acg aaa gtg agg ttg aat gtg agg tta      240
Lys Lys Lys Asp Gly Ser Gly Thr Lys Val Arg Leu Asn Val Arg Leu
65                  70                  75                  80 gat cat caa gtt aat ttt ggt gac cat gtg gct atg ttt gga tca gct      288
Asp His Gln Val Asn Phe Gly Asp His Val Ala Met Phe Gly Ser Ala
                85                  90                  95 aaa gag att ggt tca tgg aaa aag aaa tcg cct ttg aat tgg agt gag      336
Lys Glu Ile Gly Ser Trp Lys Lys Lys Ser Pro Leu Asn Trp Ser Glu
            100                 105                 110 aat gga tgg gtt tgt gag ttg gaa ctt gac ggt ggt cag gtt ttg gag      384
Asn Gly Trp Val Cys Glu Leu Glu Leu Asp Gly Gly Gln Val Leu Glu
        115                 120                 125 tat aag ttt gtc att gtt aag aat gat ggt tca ctt tca tgg gaa tct      432
Tyr Lys Phe Val Ile Val Lys Asn Asp Gly Ser Leu Ser Trp Glu Ser
    130                 135                 140
```

```
                                                            -continued
ggt gat aat cgt gtc ctt aag gtt cca aat tct ggg aat ttt tct gtt      480
Gly Asp Asn Arg Val Leu Lys Val Pro Asn Ser Gly Asn Phe Ser Val
145                 150                 155                 160 gtt tgt cat tgg gat gct act aga gaa acc ctt gat ttg cct cag gag      528
Val Cys His Trp Asp Ala Thr Arg Glu Thr Leu Asp Leu Pro Gln Glu
                165                 170                 175 gtt ggt aat gat gat gat gtt ggt gat ggt ggg cat gag agg gat aat      576
Val Gly Asn Asp Asp Asp Val Gly Asp Gly Gly His Glu Arg Asp Asn
            180                 185                 190 cat gat gtt ggt gat gat aga gta gtg gga agt gaa aat ggt gcg cag      624
His Asp Val Gly Asp Asp Arg Val Val Gly Ser Glu Asn Gly Ala Gln
        195                 200                 205 ctt cag aag agt aca ttg ggt ggg caa tgg caa ggt aaa gat gcg tcc      672
Leu Gln Lys Ser Thr Leu Gly Gly Gln Trp Gln Gly Lys Asp Ala Ser
    210                 215                 220 ttt atg cgt tct aat gat cat ggt aac aga gaa gtt ggt aga aat tgg      720
Phe Met Arg Ser Asn Asp His Gly Asn Arg Glu Val Gly Arg Asn Trp
225                 230                 235                 240 gat act agt ggt ctt gaa ggc aca gct ctt aag atg gtt gag ggt gat      768
Asp Thr Ser Gly Leu Glu Gly Thr Ala Leu Lys Met Val Glu Gly Asp
                245                 250                 255 cgc aac tct aag aac tgg tgg aga aag ctt gaa atg gta cgc gag gtt      816
Arg Asn Ser Lys Asn Trp Trp Arg Lys Leu Glu Met Val Arg Glu Val
            260                 265                 270 ata gtt ggg agt gtt gag agg gag gaa cga ttg aag gcg ctc ata tac      864
Ile Val Gly Ser Val Glu Arg Glu Glu Arg Leu Lys Ala Leu Ile Tyr
        275                 280                 285 tct gca att tat ttg aag tgg ata aac aca ggt cag att cct tgt ttt      912
Ser Ala Ile Tyr Leu Lys Trp Ile Asn Thr Gly Gln Ile Pro Cys Phe
    290                 295                 300 gaa gat gga ggg cat cac cgt cca aac agg cat gcc gag att tcc aga      960
Glu Asp Gly Gly His His Arg Pro Asn Arg His Ala Glu Ile Ser Arg
305                 310                 315                 320 ctt ata ttc cgt gag ttg gag cac att tgc agt aag aaa gat gct act     1008
Leu Ile Phe Arg Glu Leu Glu His Ile Cys Ser Lys Lys Asp Ala Thr
                325                 330                 335 cca gag gaa gtg ctt gtt gct cgg aaa atc cat ccg tgt tta cct tct     1056
Pro Glu Glu Val Leu Val Ala Arg Lys Ile His Pro Cys Leu Pro Ser
            340                 345                 350 ttc aaa gca gag ttt act gca gct gtc cct cta act cgg att agg gac     1104
Phe Lys Ala Glu Phe Thr Ala Ala Val Pro Leu Thr Arg Ile Arg Asp
        355                 360                 365 ata gcc cat cgg aat gat att cct cat gat ctc aag caa gaa atc aag     1152
Ile Ala His Arg Asn Asp Ile Pro His Asp Leu Lys Gln Glu Ile Lys
    370                 375                 380 cat acg ata caa aat aag ctt cac cgg aat gct ggt cca gaa gat cta     1200
His Thr Ile Gln Asn Lys Leu His Arg Asn Ala Gly Pro Glu Asp Leu
385                 390                 395                 400 att gca aca gaa gca atg ctt caa cga att acc gag acc cca gga aaa     1248
Ile Ala Thr Glu Ala Met Leu Gln Arg Ile Thr Glu Thr Pro Gly Lys
                405                 410                 415 tat agt gga gac ttt gtg gag cag ttt aaa ata ttc cat aat gag ctt     1296
Tyr Ser Gly Asp Phe Val Glu Gln Phe Lys Ile Phe His Asn Glu Leu
            420                 425                 430 aaa gat ttc ttt aat gct gga agt ctc act gaa cag ctt gat tct atg     1344
Lys Asp Phe Phe Asn Ala Gly Ser Leu Thr Glu Gln Leu Asp Ser Met
        435                 440                 445 aaa att tct atg gat gat aga ggt ctt tct gcg ctc aat ttg ttt ttt     1392
Lys Ile Ser Met Asp Asp Arg Gly Leu Ser Ala Leu Asn Leu Phe Phe
    450                 455                 460
```

```
gaa tgt aaa aag cgc ctt gac aca tca gga gaa tca agc aat gtt ttg       1440
Glu Cys Lys Lys Arg Leu Asp Thr Ser Gly Glu Ser Ser Asn Val Leu
465                 470                 475                 480 gag ttg att aaa acc atg cat tct cta gct tct tta aga gaa aca att       1488
Glu Leu Ile Lys Thr Met His Ser Leu Ala Ser Leu Arg Glu Thr Ile
                485                 490                 495 ata aag gaa ctt aat agc ggc ttg cga aat gat gct cct gat act gcc       1536
Ile Lys Glu Leu Asn Ser Gly Leu Arg Asn Asp Ala Pro Asp Thr Ala
            500                 505                 510 att gca atg cgc cag aag tgg cgc ctt tgt gag atc ggc ctc gag gac       1584
Ile Ala Met Arg Gln Lys Trp Arg Leu Cys Glu Ile Gly Leu Glu Asp
        515                 520                 525 tac ttt ttt gtt cta cta agc aga ttc ctc aat gct ctt gaa act atg       1632
Tyr Phe Phe Val Leu Leu Ser Arg Phe Leu Asn Ala Leu Glu Thr Met
    530                 535                 540 gga gga gct gat caa ctg gca aaa gat gtg gga tca aga aac gtt gcc       1680
Gly Gly Ala Asp Gln Leu Ala Lys Asp Val Gly Ser Arg Asn Val Ala
545                 550                 555                 560 tca tgg aat gat cca cta gat gct ttg gtg ttg ggt gtt cac caa gta       1728
Ser Trp Asn Asp Pro Leu Asp Ala Leu Val Leu Gly Val His Gln Val
                565                 570                 575 ggt cta tct ggt tgg aag caa gaa gaa tgt tta gcc att gga aat gaa       1776
Gly Leu Ser Gly Trp Lys Gln Glu Glu Cys Leu Ala Ile Gly Asn Glu
            580                 585                 590 ctc ctt gct tgg cga gaa agg gac cta ctt gaa aaa gaa ggg gaa gag       1824
Leu Leu Ala Trp Arg Glu Arg Asp Leu Leu Glu Lys Glu Gly Glu Glu
        595                 600                 605 gat gga aaa aca att tgg gcc atg agg ctg aaa gca act ctt gat cga       1872
Asp Gly Lys Thr Ile Trp Ala Met Arg Leu Lys Ala Thr Leu Asp Arg
    610                 615                 620 gca cgc aga tta aca gca gaa tat tct gat ttg ctt ctt caa ata ttt       1920
Ala Arg Arg Leu Thr Ala Glu Tyr Ser Asp Leu Leu Leu Gln Ile Phe
625                 630                 635                 640 cct cct aat gtg gag att tta gga aaa gct cta gga att cca gag aat       1968
Pro Pro Asn Val Glu Ile Leu Gly Lys Ala Leu Gly Ile Pro Glu Asn
                645                 650                 655 agt gtc aag acc tat aca gaa gca gag att cgt gct gga att att ttc       2016
Ser Val Lys Thr Tyr Thr Glu Ala Glu Ile Arg Ala Gly Ile Ile Phe
            660                 665                 670 cag atc tca aag ctc tgc act gtt ctt cta aaa gct gta aga aat tca       2064
Gln Ile Ser Lys Leu Cys Thr Val Leu Leu Lys Ala Val Arg Asn Ser
        675                 680                 685 ctt ggt tct gag ggc tgg gat gtc gtt gta cct gga tcg acg tct ggg       2112
Leu Gly Ser Glu Gly Trp Asp Val Val Val Pro Gly Ser Thr Ser Gly
    690                 695                 700 aca tta gtt cag gtt gag agc att gtt ccg gga tca ttg cca gca act       2160
Thr Leu Val Gln Val Glu Ser Ile Val Pro Gly Ser Leu Pro Ala Thr
705                 710                 715                 720 tct ggt ggt cct att att ctc ttg gtc aat aaa gct gat ggc gat gaa       2208
Ser Gly Gly Pro Ile Ile Leu Leu Val Asn Lys Ala Asp Gly Asp Glu
                725                 730                 735 gag gta agt gct gct aat ggg aac ata gct gga gtc atg ctt ctg cag       2256
Glu Val Ser Ala Ala Asn Gly Asn Ile Ala Gly Val Met Leu Leu Gln
            740                 745                 750 gag ctg cct cac ttg tct cac ctt ggc gtt aga gcg cgg cag gag aaa       2304
Glu Leu Pro His Leu Ser His Leu Gly Val Arg Ala Arg Gln Glu Lys
        755                 760                 765 att gtc ttt gtg aca tgt gat gat gat gac aag gtt gct gat ata cga       2352
Ile Val Phe Val Thr Cys Asp Asp Asp Asp Lys Val Ala Asp Ile Arg
    770                 775                 780
```

```
cga ctt gtg gga aaa ttt gtg agg ttg gaa gca tct cca agt cat gtg        2400
Arg Leu Val Gly Lys Phe Val Arg Leu Glu Ala Ser Pro Ser His Val
785                 790                 795                 800 aat ctg ata ctt tca act gag ggt agg agt cgc act tcc aaa tcc agt        2448
Asn Leu Ile Leu Ser Thr Glu Gly Arg Ser Arg Thr Ser Lys Ser Ser
            805                 810                 815 gcg acc aaa aaa acg gat aag aac agc tta tct aag aaa aca gat            2496
Ala Thr Lys Lys Thr Asp Lys Asn Ser Leu Ser Lys Lys Thr Asp
        820                 825                 830 aag aag agc tta tct atc gat gat gaa gaa tca aag cct ggt tcc tca        2544
Lys Lys Ser Leu Ser Ile Asp Asp Glu Glu Ser Lys Pro Gly Ser Ser
            835                 840                 845 tct tcc aat agc ctc ctt tac tct tcc aag gat atc cct agt gga gga        2592
Ser Ser Asn Ser Leu Leu Tyr Ser Ser Lys Asp Ile Pro Ser Gly Gly
        850                 855                 860 atc ata gca ctt gct gat gca gat gta cca act tct ggt tca aaa tct        2640
Ile Ile Ala Leu Ala Asp Ala Asp Val Pro Thr Ser Gly Ser Lys Ser
865                 870                 875                 880 gct gca tgt ggt ctt ctt gca tct tta gca gaa gcc tct agt aaa gtg        2688
Ala Ala Cys Gly Leu Leu Ala Ser Leu Ala Glu Ala Ser Ser Lys Val
            885                 890                 895 cac agc gaa cac gga gtt ccg gca tca ttt aag gtt cca act gga gtt        2736
His Ser Glu His Gly Val Pro Ala Ser Phe Lys Val Pro Thr Gly Val
        900                 905                 910 gtc ata cct ttt gga tcg atg gaa tta gct tta aag caa aat aat tcg        2784
Val Ile Pro Phe Gly Ser Met Glu Leu Ala Leu Lys Gln Asn Asn Ser
            915                 920                 925 gaa gaa aag ttt gcg tct ttg cta gaa aaa cta gaa acc gcc aga cct        2832
Glu Glu Lys Phe Ala Ser Leu Leu Glu Lys Leu Glu Thr Ala Arg Pro
930                 935                 940 gag ggt ggt gag cta gac gac ata tgt gac cag atc cat gaa gtg atg        2880
Glu Gly Gly Glu Leu Asp Asp Ile Cys Asp Gln Ile His Glu Val Met
945                 950                 955                 960 aaa acg ttg caa gtg cct aaa gaa aca atc aac agc ata agc aaa gcg        2928
Lys Thr Leu Gln Val Pro Lys Glu Thr Ile Asn Ser Ile Ser Lys Ala
            965                 970                 975 ttt ctc aaa gat gct cgt ctc att gtt cgt tca agt gct aac gtc gag        2976
Phe Leu Lys Asp Ala Arg Leu Ile Val Arg Ser Ser Ala Asn Val Glu
        980                 985                 990 gac tta gcc gga atg tca gct gca gga ctc tat gaa tca atc cct aac        3024
Asp Leu Ala Gly Met Ser Ala Ala Gly Leu Tyr Glu Ser Ile Pro Asn
            995                 1000                1005 gtg agt ccc tcg gat cct ttg gtg ttt tca gat tcg gtt tgc caa            3069
Val Ser Pro Ser Asp Pro Leu Val Phe Ser Asp Ser Val Cys Gln
        1010                1015                1020 gtt tgg gct tct ctc tac aca aga aga gct gtt cta agc cgt aga            3114
Val Trp Ala Ser Leu Tyr Thr Arg Arg Ala Val Leu Ser Arg Arg
    1025                1030                1035 gct gct ggt gtc tct caa aga gaa gct tca atg gct gtt ctc gtt            3159
Ala Ala Gly Val Ser Gln Arg Glu Ala Ser Met Ala Val Leu Val
    1040                1045                1050 caa gaa atg ctt tcg ccg gac tta tca ttc gtt ctg cac aca gtg            3204
Gln Glu Met Leu Ser Pro Asp Leu Ser Phe Val Leu His Thr Val
    1055                1060                1065 agt cca gct gat ccg gac agt aac ctt gtg gaa gcc gag atc gct            3249
Ser Pro Ala Asp Pro Asp Ser Asn Leu Val Glu Ala Glu Ile Ala
    1070                1075                1080 cct ggt tta ggt gag act ttg gct tca gga aca aga gga aca cca            3294
Pro Gly Leu Gly Glu Thr Leu Ala Ser Gly Thr Arg Gly Thr Pro
    1085                1090                1095
```

```
tgg aga ctc gct tcg ggt aag ctc gac ggg att gta caa acc tta      3339
Trp Arg Leu Ala Ser Gly Lys Leu Asp Gly Ile Val Gln Thr Leu
    1100                1105                1110 gct ttc gca aac ttc agc gaa gag ctt ctt gtg tca gga aca ggt      3384
Ala Phe Ala Asn Phe Ser Glu Glu Leu Leu Val Ser Gly Thr Gly
1115                1120                1125 cct gct gat gga aaa tac gtt cgg ttg acc gtg gac tat agc aaa      3429
Pro Ala Asp Gly Lys Tyr Val Arg Leu Thr Val Asp Tyr Ser Lys
        1130                1135                1140 aaa cgt tta act gtt gac tcg gtg ttt aga cag cag ctc ggt cag      3474
Lys Arg Leu Thr Val Asp Ser Val Phe Arg Gln Gln Leu Gly Gln
    1145                1150                1155 aga ctc ggt tcg gtt ggt ttc ttc ttg gaa aga aac ttt ggc tgt      3519
Arg Leu Gly Ser Val Gly Phe Phe Leu Glu Arg Asn Phe Gly Cys
        1160                1165                1170 gct caa gac gtt gaa ggt tgt ttg gtt ggt gaa gat gtt tac att      3564
Ala Gln Asp Val Glu Gly Cys Leu Val Gly Glu Asp Val Tyr Ile
    1175                1180                1185 gtt cag tca agg cca caa cct ctg tag                              3591
Val Gln Ser Arg Pro Gln Pro Leu
        1190                1195

<210> SEQ ID NO 2
<211> LENGTH: 1196
<212> TYPE: PRT
<213> ORGANISM: Arabidopsis thaliana

<400> SEQUENCE: 2

Met Glu Ser Ile Gly Ser His Cys Cys Ser Ser Pro Phe Thr Phe Ile
1               5                   10                  15

Thr Arg Asn Ser Ser Ser Ser Leu Pro Arg Leu Val Asn Ile Thr His
            20                  25                  30

Arg Val Asn Leu Ser His Gln Ser His Arg Leu Arg Asn Ser Asn Ser
        35                  40                  45

Arg Leu Thr Cys Thr Ala Thr Ser Ser Ser Thr Ile Glu Glu Gln Arg
    50                  55                  60

Lys Lys Lys Asp Gly Ser Gly Thr Lys Val Arg Leu Asn Val Arg Leu
65                  70                  75                  80

Asp His Gln Val Asn Phe Gly Asp His Val Ala Met Phe Gly Ser Ala
                85                  90                  95

Lys Glu Ile Gly Ser Trp Lys Lys Ser Pro Leu Asn Trp Ser Glu
            100                 105                 110

Asn Gly Trp Val Cys Glu Leu Glu Leu Asp Gly Gly Gln Val Leu Glu
        115                 120                 125

Tyr Lys Phe Val Ile Val Lys Asn Asp Gly Ser Leu Ser Trp Glu Ser
    130                 135                 140

Gly Asp Asn Arg Val Leu Lys Val Pro Asn Ser Gly Asn Phe Ser Val
145                 150                 155                 160

Val Cys His Trp Asp Ala Thr Arg Glu Thr Leu Asp Leu Pro Gln Glu
                165                 170                 175

Val Gly Asn Asp Asp Val Gly Asp Gly Gly His Glu Arg Asp Asn
            180                 185                 190

His Asp Val Gly Asp Asp Arg Val Val Gly Ser Glu Asn Gly Ala Gln
        195                 200                 205

Leu Gln Lys Ser Thr Leu Gly Gly Gln Trp Gln Gly Lys Asp Ala Ser
    210                 215                 220

Phe Met Arg Ser Asn Asp His Gly Asn Arg Glu Val Gly Arg Asn Trp
225                 230                 235                 240
```

```
Asp Thr Ser Gly Leu Glu Gly Thr Ala Leu Lys Met Val Glu Gly Asp
                245                 250                 255

Arg Asn Ser Lys Asn Trp Trp Arg Lys Leu Glu Met Val Arg Glu Val
                260                 265                 270

Ile Val Gly Ser Val Glu Arg Glu Arg Leu Lys Ala Leu Ile Tyr
                275                 280                 285

Ser Ala Ile Tyr Leu Lys Trp Ile Asn Thr Gly Gln Ile Pro Cys Phe
                290                 295                 300

Glu Asp Gly Gly His His Arg Pro Asn Arg His Ala Glu Ile Ser Arg
305                 310                 315                 320

Leu Ile Phe Arg Glu Leu His Ile Cys Ser Lys Lys Asp Ala Thr
                325                 330                 335

Pro Glu Glu Val Leu Val Ala Arg Lys Ile His Pro Cys Leu Pro Ser
                340                 345                 350

Phe Lys Ala Glu Phe Thr Ala Ala Val Pro Leu Thr Arg Ile Arg Asp
                355                 360                 365

Ile Ala His Arg Asn Asp Ile Pro His Asp Leu Lys Gln Glu Ile Lys
                370                 375                 380

His Thr Ile Gln Asn Lys Leu His Arg Asn Ala Gly Pro Glu Asp Leu
385                 390                 395                 400

Ile Ala Thr Glu Ala Met Leu Gln Arg Ile Thr Glu Thr Pro Gly Lys
                405                 410                 415

Tyr Ser Gly Asp Phe Val Glu Gln Phe Lys Ile Phe His Asn Glu Leu
                420                 425                 430

Lys Asp Phe Phe Asn Ala Gly Ser Leu Thr Glu Gln Leu Asp Ser Met
                435                 440                 445

Lys Ile Ser Met Asp Asp Arg Gly Leu Ser Ala Leu Asn Leu Phe Phe
                450                 455                 460

Glu Cys Lys Lys Arg Leu Asp Thr Ser Gly Glu Ser Ser Asn Val Leu
465                 470                 475                 480

Glu Leu Ile Lys Thr Met His Ser Leu Ala Ser Leu Arg Glu Thr Ile
                485                 490                 495

Ile Lys Glu Leu Asn Ser Gly Leu Arg Asn Asp Ala Pro Asp Thr Ala
                500                 505                 510

Ile Ala Met Arg Gln Lys Trp Arg Leu Cys Glu Ile Gly Leu Glu Asp
                515                 520                 525

Tyr Phe Phe Val Leu Leu Ser Arg Phe Leu Asn Ala Leu Glu Thr Met
                530                 535                 540

Gly Gly Ala Asp Gln Leu Ala Lys Asp Val Gly Ser Arg Asn Val Ala
545                 550                 555                 560

Ser Trp Asn Asp Pro Leu Asp Ala Leu Val Leu Gly Val His Gln Val
                565                 570                 575

Gly Leu Ser Gly Trp Lys Gln Glu Glu Cys Leu Ala Ile Gly Asn Glu
                580                 585                 590

Leu Leu Ala Trp Arg Glu Arg Asp Leu Leu Glu Lys Glu Gly Glu Glu
                595                 600                 605

Asp Gly Lys Thr Ile Trp Ala Met Arg Leu Lys Ala Thr Leu Asp Arg
                610                 615                 620

Ala Arg Arg Leu Thr Ala Glu Tyr Ser Asp Leu Leu Gln Ile Phe
625                 630                 635                 640

Pro Pro Asn Val Glu Ile Leu Gly Lys Ala Leu Gly Ile Pro Glu Asn
                645                 650                 655

Ser Val Lys Thr Tyr Thr Glu Ala Glu Ile Arg Ala Gly Ile Ile Phe
```

-continued

```
                660                 665                 670
Gln Ile Ser Lys Leu Cys Thr Val Leu Leu Lys Ala Val Arg Asn Ser
            675                 680                 685

Leu Gly Ser Glu Gly Trp Asp Val Val Val Pro Gly Ser Thr Ser Gly
            690                 695                 700

Thr Leu Val Gln Val Glu Ser Ile Val Pro Gly Ser Leu Pro Ala Thr
705                 710                 715                 720

Ser Gly Gly Pro Ile Ile Leu Leu Val Asn Lys Ala Asp Gly Asp Glu
                725                 730                 735

Glu Val Ser Ala Ala Asn Gly Asn Ile Ala Gly Val Met Leu Leu Gln
            740                 745                 750

Glu Leu Pro His Leu Ser His Leu Gly Val Arg Ala Arg Gln Glu Lys
            755                 760                 765

Ile Val Phe Val Thr Cys Asp Asp Asp Lys Val Ala Asp Ile Arg
            770                 775                 780

Arg Leu Val Gly Lys Phe Val Arg Leu Glu Ala Ser Pro Ser His Val
785                 790                 795                 800

Asn Leu Ile Leu Ser Thr Glu Gly Arg Ser Arg Thr Ser Lys Ser Ser
                805                 810                 815

Ala Thr Lys Lys Thr Asp Lys Asn Ser Leu Ser Lys Lys Lys Thr Asp
                820                 825                 830

Lys Lys Ser Leu Ser Ile Asp Asp Glu Ser Lys Pro Gly Ser Ser
            835                 840                 845

Ser Ser Asn Ser Leu Leu Tyr Ser Ser Lys Asp Ile Pro Ser Gly Gly
            850                 855                 860

Ile Ile Ala Leu Ala Asp Ala Asp Val Pro Thr Ser Gly Ser Lys Ser
865                 870                 875                 880

Ala Ala Cys Gly Leu Leu Ala Ser Leu Ala Glu Ala Ser Ser Lys Val
                885                 890                 895

His Ser Glu His Gly Val Pro Ala Ser Phe Lys Val Pro Thr Gly Val
            900                 905                 910

Val Ile Pro Phe Gly Ser Met Glu Leu Ala Leu Lys Gln Asn Asn Ser
            915                 920                 925

Glu Glu Lys Phe Ala Ser Leu Leu Glu Lys Leu Glu Thr Ala Arg Pro
            930                 935                 940

Glu Gly Gly Glu Leu Asp Asp Ile Cys Asp Gln Ile His Glu Val Met
945                 950                 955                 960

Lys Thr Leu Gln Val Pro Lys Glu Thr Ile Asn Ser Ile Ser Lys Ala
                965                 970                 975

Phe Leu Lys Asp Ala Arg Leu Ile Val Arg Ser Ser Ala Asn Val Glu
            980                 985                 990

Asp Leu Ala Gly Met Ser Ala Ala Gly Leu Tyr Glu Ser Ile Pro Asn
            995                 1000                1005

Val Ser Pro Ser Asp Pro Leu Val Phe Asp Ser Val Cys Gln
            1010                1015                1020

Val Trp Ala Ser Leu Tyr Thr Arg Arg Ala Val Leu Ser Arg Arg
            1025                1030                1035

Ala Ala Gly Val Ser Gln Arg Glu Ala Ser Met Ala Val Leu Val
            1040                1045                1050

Gln Glu Met Leu Ser Pro Asp Leu Ser Phe Val Leu His Thr Val
            1055                1060                1065

Ser Pro Ala Asp Pro Asp Ser Asn Leu Val Glu Ala Glu Ile Ala
            1070                1075                1080
```

-continued

```
Pro Gly Leu Gly Glu Thr Leu Ala Ser Gly Thr Arg Gly Thr Pro
    1085            1090                1095

Trp Arg Leu Ala Ser Gly Lys Leu Asp Gly Ile Val Gln Thr Leu
    1100            1105                1110

Ala Phe Ala Asn Phe Ser Glu Glu Leu Leu Val Ser Gly Thr Gly
    1115            1120                1125

Pro Ala Asp Gly Lys Tyr Val Arg Leu Thr Val Asp Tyr Ser Lys
    1130            1135                1140

Lys Arg Leu Thr Val Asp Ser Val Phe Arg Gln Gln Leu Gly Gln
    1145            1150                1155

Arg Leu Gly Ser Val Gly Phe Phe Leu Glu Arg Asn Phe Gly Cys
    1160            1165                1170

Ala Gln Asp Val Glu Gly Cys Leu Val Gly Glu Asp Val Tyr Ile
    1175            1180                1185

Val Gln Ser Arg Pro Gln Pro Leu
    1190            1195

<210> SEQ ID NO 3
<211> LENGTH: 3644
<212> TYPE: DNA
<213> ORGANISM: Oryza sativa
<220> FEATURE:
<221> NAME/KEY: CDS
<222> LOCATION: (13)..(3633)
<223> OTHER INFORMATION:

<400> SEQUENCE: 3
cgaggaggat ca atg acg tcg ctg cgg ccc ctc gaa acc tcg ctc tcc ata      51
              Met Thr Ser Leu Arg Pro Leu Glu Thr Ser Leu Ser Ile
              1               5                   10 ggc ggc agg ccg cgc cgt ggt ctc gtc ctc ccg ccg ccc gga gtc ggt        99
Gly Gly Arg Pro Arg Arg Gly Leu Val Leu Pro Pro Pro Gly Val Gly
    15                  20                  25 gcg ggt gtg ctg ctc cgc cgg gga gcg atg gcg ctc cct ggg cgg cgc       147
Ala Gly Val Leu Leu Arg Arg Gly Ala Met Ala Leu Pro Gly Arg Arg
30                  35                  40                  45 ggc ttc gcg tgc cgc ggg aga tcc gcg gcc tcg gcg gca gag aga aca       195
Gly Phe Ala Cys Arg Gly Arg Ser Ala Ala Ser Ala Ala Glu Arg Thr
                50                  55                  60 aag gag aaa aag aga aga gat tct tca aag cag cca ttg gtg cat ctc       243
Lys Glu Lys Lys Arg Arg Asp Ser Ser Lys Gln Pro Leu Val His Leu
            65                  70                  75 cag gtt tgt cta gag cac cag gtt aag ttt ggt gag cat gta ggc att       291
Gln Val Cys Leu Glu His Gln Val Lys Phe Gly Glu His Val Gly Ile
        80                  85                  90 atc ggt tcc aca aag gag ctt ggt tca tgg gag gag cag gtt gaa ctg       339
Ile Gly Ser Thr Lys Glu Leu Gly Ser Trp Glu Glu Gln Val Glu Leu
    95                  100                 105 gaa tgg act aca aat ggt tgg gtc tgc cag ctt aag ctc cct gga gaa       387
Glu Trp Thr Thr Asn Gly Trp Val Cys Gln Leu Lys Leu Pro Gly Glu
110                 115                 120                 125 aca ctt gtg gag ttt aaa ttt gtt ata ttt ttg gtg gga gga aaa gat       435
Thr Leu Val Glu Phe Lys Phe Val Ile Phe Leu Val Gly Gly Lys Asp
                130                 135                 140 aaa ata tgg gaa gat ggt aat aac cgt gtt gtt gag ctg ccg aag gat       483
Lys Ile Trp Glu Asp Gly Asn Asn Arg Val Val Glu Leu Pro Lys Asp
            145                 150                 155 ggt aag ttt gat ata gta tgc cac tgg aat aga aca gaa gag cca tta       531
Gly Lys Phe Asp Ile Val Cys His Trp Asn Arg Thr Glu Glu Pro Leu
        160                 165                 170
```

```
gaa ctt tta gga aca cca aag ttt gag ttg gtc gga gaa gct gaa aag    579
Glu Leu Leu Gly Thr Pro Lys Phe Glu Leu Val Gly Glu Ala Glu Lys
        175                 180                 185 aat act ggc gag gat gct tca gca tct gta act ttt gca cct gaa aaa    627
Asn Thr Gly Glu Asp Ala Ser Ala Ser Val Thr Phe Ala Pro Glu Lys
190                 195                 200                 205 gtt caa gat att tca gtt gtt gag aat ggt gat cca gca cca gag gcc    675
Val Gln Asp Ile Ser Val Val Glu Asn Gly Asp Pro Ala Pro Glu Ala
                    210                 215                 220 gag tca agc aaa ttt ggt ggg caa tgg caa gga agt aaa act gtt ttc    723
Glu Ser Ser Lys Phe Gly Gly Gln Trp Gln Gly Ser Lys Thr Val Phe
                225                 230                 235 atg aga tca aat gag cat ctg aat aag gag gct gat agg atg tgg gat    771
Met Arg Ser Asn Glu His Leu Asn Lys Glu Ala Asp Arg Met Trp Asp
            240                 245                 250 aca act ggg ctt gat gga ata gca ctg aaa ctg gtg gag ggc gat aaa    819
Thr Thr Gly Leu Asp Gly Ile Ala Leu Lys Leu Val Glu Gly Asp Lys
        255                 260                 265 gca tcc agg aac tgg tgg cgg aag tta gag gtt gtt cgc ggg ata ttg    867
Ala Ser Arg Asn Trp Trp Arg Lys Leu Glu Val Val Arg Gly Ile Leu
270                 275                 280                 285 tca gaa tct ttt gat gac cag agt cgt ctg ggg gcc ctt gta tac tca    915
Ser Glu Ser Phe Asp Asp Gln Ser Arg Leu Gly Ala Leu Val Tyr Ser
                    290                 295                 300 gct att tat ctg aag tgg att tat aca ggt cag ata tcg tgc ttt gaa    963
Ala Ile Tyr Leu Lys Trp Ile Tyr Thr Gly Gln Ile Ser Cys Phe Glu
                305                 310                 315 gat ggt ggc cac cat cgg cct aac aaa cat gct gag ata tcg agg caa   1011
Asp Gly Gly His His Arg Pro Asn Lys His Ala Glu Ile Ser Arg Gln
            320                 325                 330 ata ttc cgt gaa ctt gaa atg atg tat tat ggg aaa acc aca tca gcc   1059
Ile Phe Arg Glu Leu Glu Met Met Tyr Tyr Gly Lys Thr Thr Ser Ala
        335                 340                 345 aag gat gtt ctc gtg att cgc aaa att cat ccc ttt tta cct tca ttt   1107
Lys Asp Val Leu Val Ile Arg Lys Ile His Pro Phe Leu Pro Ser Phe
350                 355                 360                 365 aag tca gag ttt aca gcc tct gtc cct cta aca cga att cgt gat att   1155
Lys Ser Glu Phe Thr Ala Ser Val Pro Leu Thr Arg Ile Arg Asp Ile
                    370                 375                 380 gct cac cgg aat gac atc cca cat gat ctc aag caa gaa atc aag cat   1203
Ala His Arg Asn Asp Ile Pro His Asp Leu Lys Gln Glu Ile Lys His
                385                 390                 395 act ata caa aac aaa ctt cat cgt aat gct gga cct gag gat ctt att   1251
Thr Ile Gln Asn Lys Leu His Arg Asn Ala Gly Pro Glu Asp Leu Ile
            400                 405                 410 gct aca gaa gtc atg ctt gct agg att act aag acc cct gga gaa tac   1299
Ala Thr Glu Val Met Leu Ala Arg Ile Thr Lys Thr Pro Gly Glu Tyr
        415                 420                 425 agt gaa aca ttt gtt gaa caa ttc acg ata ttt tat agc gaa cta aaa   1347
Ser Glu Thr Phe Val Glu Gln Phe Thr Ile Phe Tyr Ser Glu Leu Lys
430                 435                 440                 445 gat ttc ttc aat gct ggc agc cta ttt gag caa ctg gag tcc atc aag   1395
Asp Phe Phe Asn Ala Gly Ser Leu Phe Glu Gln Leu Glu Ser Ile Lys
                    450                 455                 460 gaa tct ctg aac gag tca ggc tta gaa gtt ctc tca tcc ttt gtg gaa   1443
Glu Ser Leu Asn Glu Ser Gly Leu Glu Val Leu Ser Ser Phe Val Glu
                465                 470                 475 acc aaa agg agt ttg gac caa gtg gat cat gca gaa gat ttg gat aaa   1491
Thr Lys Arg Ser Leu Asp Gln Val Asp His Ala Glu Asp Leu Asp Lys
            480                 485                 490
```

```
aat gat acc att caa att ttg atg act acc ttg caa tca tta tct tct    1539
Asn Asp Thr Ile Gln Ile Leu Met Thr Thr Leu Gln Ser Leu Ser Ser
    495                 500                 505 cta aga tcg gtt cta atg aag ggc ctt gaa agt ggc ctt aga aat gat    1587
Leu Arg Ser Val Leu Met Lys Gly Leu Glu Ser Gly Leu Arg Asn Asp
510                 515                 520                 525 gcg cct gat aat gct ata gca atg cga caa aag tgg cgc ctt tgt gaa    1635
Ala Pro Asp Asn Ala Ile Ala Met Arg Gln Lys Trp Arg Leu Cys Glu
                    530                 535                 540 att agt ctt gag gat tat tca ttt gtt ctg tta agc aga ttc atc aat    1683
Ile Ser Leu Glu Asp Tyr Ser Phe Val Leu Leu Ser Arg Phe Ile Asn
                545                 550                 555 act ctt gaa gcc tta ggt gga tca gct tca ctt gca aag gat gta gct    1731
Thr Leu Glu Ala Leu Gly Gly Ser Ala Ser Leu Ala Lys Asp Val Ala
            560                 565                 570 aga aat act act cta tgg gat act act ctt gat gcc ctt gtc att ggc    1779
Arg Asn Thr Thr Leu Trp Asp Thr Thr Leu Asp Ala Leu Val Ile Gly
        575                 580                 585 atc aat caa gtt agc ttt tca ggt tgg aaa aca gat gaa tgt att gcc    1827
Ile Asn Gln Val Ser Phe Ser Gly Trp Lys Thr Asp Glu Cys Ile Ala
590                 595                 600                 605 ata ggg aat gag att ctt tcc tgg aag caa aaa ggt cta tct gaa agt    1875
Ile Gly Asn Glu Ile Leu Ser Trp Lys Gln Lys Gly Leu Ser Glu Ser
                    610                 615                 620 gaa ggt tgt gaa gat ggg aaa tat att tgg tca cta aga ctt aaa gct    1923
Glu Gly Cys Glu Asp Gly Lys Tyr Ile Trp Ser Leu Arg Leu Lys Ala
                625                 630                 635 aca ctg gac aga gca cgg aga tta acg gaa gag tac tct gaa gca ctt    1971
Thr Leu Asp Arg Ala Arg Arg Leu Thr Glu Glu Tyr Ser Glu Ala Leu
            640                 645                 650 ctt tct ata ttc cct gaa aaa gta atg gtt att ggg aaa gcc ctt gga    2019
Leu Ser Ile Phe Pro Glu Lys Val Met Val Ile Gly Lys Ala Leu Gly
        655                 660                 665 ata cca gat aac agt gtg aga act tac aca gag gca gaa att cgt gct    2067
Ile Pro Asp Asn Ser Val Arg Thr Tyr Thr Glu Ala Glu Ile Arg Ala
670                 675                 680                 685 ggc att gtt ttt cag gta tct aaa cta tgc aca gta ctt cag aaa gca    2115
Gly Ile Val Phe Gln Val Ser Lys Leu Cys Thr Val Leu Gln Lys Ala
                    690                 695                 700 att cga gaa gta ctt gga tca act ggc tgg gat gtt ctt gtt cct gga    2163
Ile Arg Glu Val Leu Gly Ser Thr Gly Trp Asp Val Leu Val Pro Gly
                705                 710                 715 gtg gcc cat gga act ctg atg cgg gtg gaa aga att ctt cct gga tca    2211
Val Ala His Gly Thr Leu Met Arg Val Glu Arg Ile Leu Pro Gly Ser
            720                 725                 730 tta cct tca tct gtc aaa gaa cct gtg gtt cta att gta gat aag gct    2259
Leu Pro Ser Ser Val Lys Glu Pro Val Val Leu Ile Val Asp Lys Ala
        735                 740                 745 gat gga gat gaa gag gtc aaa gct gct ggg gat aat ata gtt ggt gtt    2307
Asp Gly Asp Glu Glu Val Lys Ala Ala Gly Asp Asn Ile Val Gly Val
750                 755                 760                 765 att ctt ctt cag gaa cta cct cac ctt tca cat ctt ggt gtt aga gct    2355
Ile Leu Leu Gln Glu Leu Pro His Leu Ser His Leu Gly Val Arg Ala
                    770                 775                 780 cgt caa gag aat gtt gta ttt gta act tgt gaa tat gat gac aca gtt    2403
Arg Gln Glu Asn Val Val Phe Val Thr Cys Glu Tyr Asp Asp Thr Val
                785                 790                 795 aca gat gtg tat ttg ctt gag gga aaa tat atc aga tta gaa gca tca    2451
Thr Asp Val Tyr Leu Leu Glu Gly Lys Tyr Ile Arg Leu Glu Ala Ser
            800                 805                 810
```

```
tcc atc aat gtc aat ctc tca ata gtt tca gaa aaa aat gac aat gct    2499
Ser Ile Asn Val Asn Leu Ser Ile Val Ser Glu Lys Asn Asp Asn Ala
815                 820                 825 gtc tct aca gaa cca aat agt aca ggg aat cca ttt caa cag aaa ctc    2547
Val Ser Thr Glu Pro Asn Ser Thr Gly Asn Pro Phe Gln Gln Lys Leu
830                 835                 840                 845 caa aat gaa ttc tct cta cca tcg gat atc gag atg cca ctg caa atg    2595
Gln Asn Glu Phe Ser Leu Pro Ser Asp Ile Glu Met Pro Leu Gln Met
                850                 855                 860 tct aag caa aaa agc aaa tca gga gtg aat ggt agt ttt gct gct ctt    2643
Ser Lys Gln Lys Ser Lys Ser Gly Val Asn Gly Ser Phe Ala Ala Leu
                865                 870                 875 gag ctt tca gaa gct tca gtg gaa tca gct ggt gca aaa gct gct gca    2691
Glu Leu Ser Glu Ala Ser Val Glu Ser Ala Gly Ala Lys Ala Ala Ala
        880                 885                 890 tgc aga act ctt tct gtt ctt gct tca ttg tct aat aaa gtc tat agt    2739
Cys Arg Thr Leu Ser Val Leu Ala Ser Leu Ser Asn Lys Val Tyr Ser
895                 900                 905 gat caa gga gtt cca gca gcc ttt aga gtc cct tct ggt gct gtg ata    2787
Asp Gln Gly Val Pro Ala Ala Phe Arg Val Pro Ser Gly Ala Val Ile
910                 915                 920                 925 cca ttt gga tca atg gag gat gcg ctc aag aaa agt gga tca ctg gaa    2835
Pro Phe Gly Ser Met Glu Asp Ala Leu Lys Lys Ser Gly Ser Leu Glu
                930                 935                 940 tcc ttt aca agc ctt cta gaa aag att gaa aca gcc aaa gtc gaa aat    2883
Ser Phe Thr Ser Leu Leu Glu Lys Ile Glu Thr Ala Lys Val Glu Asn
                945                 950                 955 ggt gaa gtt gat agc ctg gcg ttg gag cta caa gca ata att tca cat    2931
Gly Glu Val Asp Ser Leu Ala Leu Glu Leu Gln Ala Ile Ile Ser His
        960                 965                 970 ctt tcc cca ccg gag gag act att ata ttt ctc aaa aga atc ttc cca    2979
Leu Ser Pro Pro Glu Glu Thr Ile Ile Phe Leu Lys Arg Ile Phe Pro
975                 980                 985 cag gat gtc cgg ttg att gtt aga tct agt gct    aat gtg gag gat ttg    3027
Gln Asp Val Arg Leu Ile Val Arg Ser Ser Ala    Asn Val Glu Asp Leu
990                 995                 1000               1005 gct ggt atg tca gct gct ggt ctc tat gat    tca att ccc aat gtc        3072
Ala Gly Met Ser Ala Ala Gly Leu Tyr Asp    Ser Ile Pro Asn Val
                1010                1015                1020 agt ctc atg gac cca tgt gcc ttt gga gct gcg gtt ggg aag gtt          3117
Ser Leu Met Asp Pro Cys Ala Phe Gly Ala Ala Val Gly Lys Val
                1025                1030                1035 tgg gct tct tta tac aca agg aga gcc atc cta agc cgt cga gcc          3162
Trp Ala Ser Leu Tyr Thr Arg Arg Ala Ile Leu Ser Arg Arg Ala
                1040                1045                1050 gct ggt gtt tat cag aga gac gcg aca atg gct gtt ctt gtc caa          3207
Ala Gly Val Tyr Gln Arg Asp Ala Thr Met Ala Val Leu Val Gln
                1055                1060                1065 gaa ata ctg cag cca gat ctc tcc ttc gtg ctt cat act gtt tgc          3252
Glu Ile Leu Gln Pro Asp Leu Ser Phe Val Leu His Thr Val Cys
                1070                1075                1080 ccc gct gac cat gac ccc aag gtt gtc cag gct gag gtc gcc cct          3297
Pro Ala Asp His Asp Pro Lys Val Val Gln Ala Glu Val Ala Pro
                1085                1090                1095 ggg ctg ggt gaa acg ctt gct tca gga acc cgt ggc acc ccg tgg          3342
Gly Leu Gly Glu Thr Leu Ala Ser Gly Thr Arg Gly Thr Pro Trp
                1100                1105                1110 agg ctg tca tgt aac aaa ttc gat gga aaa gtt gcc act ctt gcc          3387
Arg Leu Ser Cys Asn Lys Phe Asp Gly Lys Val Ala Thr Leu Ala
                1115                1120                1125
```

```
ttt tca aat ttc agt gag gag atg gtg gtg cac aac tct ggt cct    3432
Phe Ser Asn Phe Ser Glu Glu Met Val Val His Asn Ser Gly Pro
            1130                1135                1140 gcc aat gga gaa gta att cgt ctt act gtt gat tac agc aag aag    3477
Ala Asn Gly Glu Val Ile Arg Leu Thr Val Asp Tyr Ser Lys Lys
            1145                1150                1155 cca ttg tcg gtt gat aca acc ttt agg aag cag ttt ggt cag cga    3522
Pro Leu Ser Val Asp Thr Thr Phe Arg Lys Gln Phe Gly Gln Arg
            1160                1165                1170 ctg gct gcg att ggc cag tat ctg gag cag aag ttc ggg agt gca    3567
Leu Ala Ala Ile Gly Gln Tyr Leu Glu Gln Lys Phe Gly Ser Ala
            1175                1180                1185 cag gat gtg gaa ggt tgc ctg gtt ggg aaa gat att ttt ata gtg    3612
Gln Asp Val Glu Gly Cys Leu Val Gly Lys Asp Ile Phe Ile Val
            1190                1195                1200 caa agc agg cca cag cca tag aagccgaatt c                       3644
Gln Ser Arg Pro Gln Pro
            1205

<210> SEQ ID NO 4
<211> LENGTH: 1206
<212> TYPE: PRT
<213> ORGANISM: Oryza sativa

<400> SEQUENCE: 4

Met Thr Ser Leu Arg Pro Leu Glu Thr Ser Leu Ser Ile Gly Gly Arg
1               5                   10                  15

Pro Arg Arg Gly Leu Val Leu Pro Pro Gly Val Gly Ala Gly Val
            20                  25                  30

Leu Leu Arg Arg Gly Ala Met Ala Leu Pro Gly Arg Gly Phe Ala
            35                  40                  45

Cys Arg Gly Arg Ser Ala Ala Ser Ala Ala Glu Arg Thr Lys Glu Lys
    50                  55                  60

Lys Arg Arg Asp Ser Ser Lys Gln Pro Leu Val His Leu Gln Val Cys
65                  70                  75                  80

Leu Glu His Gln Val Lys Phe Gly Glu His Val Gly Ile Ile Gly Ser
                85                  90                  95

Thr Lys Glu Leu Gly Ser Trp Glu Glu Gln Val Glu Leu Glu Trp Thr
            100                 105                 110

Thr Asn Gly Trp Val Cys Gln Leu Lys Leu Pro Gly Glu Thr Leu Val
            115                 120                 125

Glu Phe Lys Phe Val Ile Phe Leu Val Gly Gly Lys Asp Lys Ile Trp
        130                 135                 140

Glu Asp Gly Asn Asn Arg Val Val Glu Leu Pro Lys Asp Gly Lys Phe
145                 150                 155                 160

Asp Ile Val Cys His Trp Asn Arg Thr Glu Glu Pro Leu Glu Leu Leu
                165                 170                 175

Gly Thr Pro Lys Phe Glu Leu Val Gly Glu Ala Glu Lys Asn Thr Gly
            180                 185                 190

Glu Asp Ala Ser Ala Ser Val Thr Phe Ala Pro Glu Lys Val Gln Asp
        195                 200                 205

Ile Ser Val Val Glu Asn Gly Asp Pro Ala Pro Glu Ala Glu Ser Ser
    210                 215                 220

Lys Phe Gly Gly Gln Trp Gln Gly Ser Lys Thr Val Phe Met Arg Ser
225                 230                 235                 240

Asn Glu His Leu Asn Lys Glu Ala Asp Arg Met Trp Asp Thr Thr Gly
                245                 250                 255
```

```
Leu Asp Gly Ile Ala Leu Lys Leu Val Glu Gly Asp Lys Ala Ser Arg
            260                 265                 270

Asn Trp Trp Arg Lys Leu Glu Val Arg Gly Ile Leu Ser Glu Ser
        275                 280                 285

Phe Asp Asp Gln Ser Arg Leu Gly Ala Leu Val Tyr Ser Ala Ile Tyr
        290                 295                 300

Leu Lys Trp Ile Tyr Thr Gly Gln Ile Ser Cys Phe Glu Asp Gly Gly
305                 310                 315                 320

His His Arg Pro Asn Lys His Ala Glu Ile Ser Arg Gln Ile Phe Arg
                325                 330                 335

Glu Leu Glu Met Met Tyr Tyr Gly Lys Thr Thr Ser Ala Lys Asp Val
            340                 345                 350

Leu Val Ile Arg Lys Ile His Pro Phe Leu Pro Ser Phe Lys Ser Glu
            355                 360                 365

Phe Thr Ala Ser Val Pro Leu Thr Arg Ile Arg Asp Ile Ala His Arg
        370                 375                 380

Asn Asp Ile Pro His Asp Leu Lys Gln Glu Ile Lys His Thr Ile Gln
385                 390                 395                 400

Asn Lys Leu His Arg Asn Ala Gly Pro Glu Asp Leu Ile Ala Thr Glu
                405                 410                 415

Val Met Leu Ala Arg Ile Thr Lys Thr Pro Gly Glu Tyr Ser Glu Thr
            420                 425                 430

Phe Val Glu Gln Phe Thr Ile Phe Tyr Ser Glu Leu Lys Asp Phe Phe
        435                 440                 445

Asn Ala Gly Ser Leu Phe Glu Gln Leu Glu Ser Ile Lys Glu Ser Leu
        450                 455                 460

Asn Glu Ser Gly Leu Glu Val Leu Ser Ser Phe Val Glu Thr Lys Arg
465                 470                 475                 480

Ser Leu Asp Gln Val Asp His Ala Glu Asp Leu Asp Lys Asn Asp Thr
                485                 490                 495

Ile Gln Ile Leu Met Thr Thr Leu Gln Ser Leu Ser Ser Leu Arg Ser
            500                 505                 510

Val Leu Met Lys Gly Leu Glu Ser Gly Leu Arg Asn Asp Ala Pro Asp
            515                 520                 525

Asn Ala Ile Ala Met Arg Gln Lys Trp Arg Leu Cys Glu Ile Ser Leu
530                 535                 540

Glu Asp Tyr Ser Phe Val Leu Leu Ser Arg Phe Ile Asn Thr Leu Glu
545                 550                 555                 560

Ala Leu Gly Gly Ser Ala Ser Leu Ala Lys Asp Val Ala Arg Asn Thr
                565                 570                 575

Thr Leu Trp Asp Thr Thr Leu Asp Ala Leu Val Ile Gly Ile Asn Gln
            580                 585                 590

Val Ser Phe Ser Gly Trp Lys Thr Asp Glu Cys Ile Ala Ile Gly Asn
            595                 600                 605

Glu Ile Leu Ser Trp Lys Gln Lys Gly Leu Ser Glu Ser Glu Gly Cys
610                 615                 620

Glu Asp Gly Lys Tyr Ile Trp Ser Leu Arg Leu Lys Ala Thr Leu Asp
625                 630                 635                 640

Arg Ala Arg Arg Leu Thr Glu Glu Tyr Ser Glu Ala Leu Leu Ser Ile
                645                 650                 655

Phe Pro Glu Lys Val Met Val Ile Gly Lys Ala Leu Gly Ile Pro Asp
            660                 665                 670

Asn Ser Val Arg Thr Tyr Thr Glu Ala Glu Ile Arg Ala Gly Ile Val
            675                 680                 685
```

```
Phe Gln Val Ser Lys Leu Cys Thr Val Leu Gln Lys Ala Ile Arg Glu
    690             695             700

Val Leu Gly Ser Thr Gly Trp Asp Val Leu Val Pro Gly Val Ala His
705             710             715             720

Gly Thr Leu Met Arg Val Glu Arg Ile Leu Pro Gly Ser Leu Pro Ser
                725             730             735

Ser Val Lys Glu Pro Val Leu Ile Val Asp Lys Ala Asp Gly Asp
            740             745             750

Glu Glu Val Lys Ala Ala Gly Asp Asn Ile Val Gly Val Ile Leu Leu
            755             760             765

Gln Glu Leu Pro His Leu Ser His Leu Gly Val Arg Ala Arg Gln Glu
    770             775             780

Asn Val Val Phe Val Thr Cys Glu Tyr Asp Asp Thr Val Thr Asp Val
785             790             795             800

Tyr Leu Leu Glu Gly Lys Tyr Ile Arg Leu Glu Ala Ser Ser Ile Asn
                805             810             815

Val Asn Leu Ser Ile Val Ser Glu Lys Asn Asp Asn Ala Val Ser Thr
            820             825             830

Glu Pro Asn Ser Thr Gly Asn Pro Phe Gln Gln Lys Leu Gln Asn Glu
            835             840             845

Phe Ser Leu Pro Ser Asp Ile Glu Met Pro Leu Gln Met Ser Lys Gln
850             855             860

Lys Ser Lys Ser Gly Val Asn Gly Ser Phe Ala Ala Leu Glu Leu Ser
865             870             875             880

Glu Ala Ser Val Glu Ser Ala Gly Ala Lys Ala Ala Cys Arg Thr
            885             890             895

Leu Ser Val Leu Ala Ser Leu Ser Asn Lys Val Tyr Ser Asp Gln Gly
            900             905             910

Val Pro Ala Ala Phe Arg Val Pro Ser Gly Ala Val Ile Pro Phe Gly
            915             920             925

Ser Met Glu Asp Ala Leu Lys Lys Ser Gly Ser Leu Glu Ser Phe Thr
930             935             940

Ser Leu Leu Glu Lys Ile Glu Thr Ala Lys Val Glu Asn Gly Glu Val
945             950             955             960

Asp Ser Leu Ala Leu Glu Leu Gln Ala Ile Ile Ser His Leu Ser Pro
            965             970             975

Pro Glu Glu Thr Ile Ile Phe Leu Lys Arg Ile Phe Pro Gln Asp Val
            980             985             990

Arg Leu Ile Val Arg Ser Ser Ala Asn Val Glu Asp Leu Ala Gly Met
    995             1000            1005

Ser Ala Ala Gly Leu Tyr Asp Ser Ile Pro Asn Val Ser Leu Met
    1010            1015            1020

Asp Pro Cys Ala Phe Gly Ala Val Gly Lys Val Trp Ala Ser
    1025            1030            1035

Leu Tyr Thr Arg Arg Ala Ile Leu Ser Arg Arg Ala Ala Gly Val
    1040            1045            1050

Tyr Gln Arg Asp Ala Thr Met Ala Val Leu Val Gln Glu Ile Leu
    1055            1060            1065

Gln Pro Asp Leu Ser Phe Val Leu His Thr Val Cys Pro Ala Asp
    1070            1075            1080

His Asp Pro Lys Val Val Gln Ala Glu Val Ala Pro Gly Leu Gly
    1085            1090            1095

Glu Thr Leu Ala Ser Gly Thr Arg Gly Thr Pro Trp Arg Leu Ser
```

-continued

```
                1100                1105                1110

Cys  Asn  Lys  Phe  Asp  Gly  Lys  Val  Ala  Thr  Leu  Ala  Phe  Ser  Asn
        1115                1120                1125

Phe  Ser  Glu  Glu  Met  Val  Val  His  Asn  Ser  Gly  Pro  Ala  Asn  Gly
    1130                1135                1140

Glu  Val  Ile  Arg  Leu  Thr  Val  Asp  Tyr  Ser  Lys  Lys  Pro  Leu  Ser
        1145                1150                1155

Val  Asp  Thr  Thr  Phe  Arg  Lys  Gln  Phe  Gly  Gln  Arg  Leu  Ala  Ala
    1160                1165                1170

Ile  Gly  Gln  Tyr  Leu  Glu  Gln  Lys  Phe  Gly  Ser  Ala  Gln  Asp  Val
        1175                1180                1185

Glu  Gly  Cys  Leu  Val  Gly  Lys  Asp  Ile  Phe  Ile  Val  Gln  Ser  Arg
    1190                1195                1200

Pro  Gln  Pro
    1205

<210> SEQ ID NO 5
<211> LENGTH: 12
<212> TYPE: PRT
<213> ORGANISM: Arabidopsis thaliana, Oryza sativa

<400> SEQUENCE: 5

Leu  Pro  His  Leu  Ser  His  Leu  Gly  Val  Arg  Ala  Arg
1                  5                  10

<210> SEQ ID NO 6
<211> LENGTH: 5124
<212> TYPE: DNA
<213> ORGANISM: Citrus reticulata
<220> FEATURE:
<221> NAME/KEY: CDS
<222> LOCATION: (257)..(4684)
<223> OTHER INFORMATION:
<300> PUBLICATION INFORMATION:
<308> DATABASE ACCESSION NUMBER: EMBL / AY094062
<309> DATABASE ENTRY DATE: 2003-05-03

<400> SEQUENCE: 6
gcacgagctc ttattacaag gtgccacgcg tcgtccgcga ctgagataaa tcgcaagtgt      60
cgctccagat tttagtactt gtttcttacg gactccgtga aaaaaaccaa aatcaaataa     120
tagcgaatag ccatagtcac attctcagct tcatcaatat ctctaccaag cagtatctct     180
tcgtatattc accatccact tatcgtttca tgctccaatt actctgagct aagaagtgta     240
cttattgtag aggaat atg agc aat agc ata ggc cgt aat gta ctc cac cag    292
              Met Ser Asn Ser Ile Gly Arg Asn Val Leu His Gln
                1               5                  10 agc ttg ctt tgt tca acg gtt ttt gag cat caa agc aac cgt cat tct       340
Ser Leu Leu Cys Ser Thr Val Phe Glu His Gln Ser Asn Arg His Ser
            15                  20                  25 tct ggc att cct gca aac tct ttg ttt caa gct gtc tct ata aat caa       388
Ser Gly Ile Pro Ala Asn Ser Leu Phe Gln Ala Val Ser Ile Asn Gln
        30                  35                  40 ccg gcg ggg gcg tcg gca gca cgc aag tcg cct tta tct acc aaa ttt       436
Pro Ala Gly Ala Ser Ala Ala Arg Lys Ser Pro Leu Ser Thr Lys Phe
45                  50                  55                  60 tac ggg acg agt ttg aat gct aga cca aag atg gcc atg gga agg cat       484
Tyr Gly Thr Ser Leu Asn Ala Arg Pro Lys Met Ala Met Gly Arg His
                65                  70                  75 cgc cct gtt ttg atc act cca cgt gct gta tta gcc gtg gat tca gct       532
Arg Pro Val Leu Ile Thr Pro Arg Ala Val Leu Ala Val Asp Ser Ala
            80                  85                  90
```

```
tct gag ctt gca gga aaa ttc aac ctt gaa ggg aat gtt gaa ttg cag      580
Ser Glu Leu Ala Gly Lys Phe Asn Leu Glu Gly Asn Val Glu Leu Gln
         95                 100                 105 att aca gtt ggt gct cca act cca ggg tct ttg aca caa gta aat att      628
Ile Thr Val Gly Ala Pro Thr Pro Gly Ser Leu Thr Gln Val Asn Ile
110                 115                 120 gag atc tca tat agt agc aat tcc ttg ctt ctg cac tgg ggt gcg ata      676
Glu Ile Ser Tyr Ser Ser Asn Ser Leu Leu Leu His Trp Gly Ala Ile
125                 130                 135                 140 cgt gac aaa aag gaa aag tgg gta ctt cct tct cgt ccg cca gat ggg      724
Arg Asp Lys Lys Glu Lys Trp Val Leu Pro Ser Arg Pro Pro Asp Gly
             145                 150                 155 acc aaa ata tta aag aat aga gcc ctt aga act ccc ttt gtg agc tct      772
Thr Lys Ile Leu Lys Asn Arg Ala Leu Arg Thr Pro Phe Val Ser Ser
         160                 165                 170 ggt tcc aaa tct ctc gtt aaa tta gag ata gat gat cct gca ata gaa      820
Gly Ser Lys Ser Leu Val Lys Leu Glu Ile Asp Asp Pro Ala Ile Glu
     175                 180                 185 gca gta gag ttt ctt ata ctc gat gaa gcc cag aat aaa tgg ttc aaa      868
Ala Val Glu Phe Leu Ile Leu Asp Glu Ala Gln Asn Lys Trp Phe Lys
190                 195                 200 aac aat ggt gca aat ttt cat gta aag tta cca tca gag agg agt ttg      916
Asn Asn Gly Ala Asn Phe His Val Lys Leu Pro Ser Glu Arg Ser Leu
205                 210                 215                 220 att caa aat gtt tca gtt cct gaa gat ctt gta cag act caa gca tat      964
Ile Gln Asn Val Ser Val Pro Glu Asp Leu Val Gln Thr Gln Ala Tyr
             225                 230                 235 tta agg tgg gaa aga aag ggt aaa cag att tat act cct gaa caa gag     1012
Leu Arg Trp Glu Arg Lys Gly Lys Gln Ile Tyr Thr Pro Glu Gln Glu
         240                 245                 250 aag gag gag tat gaa gca gct cgc act gag ctg ctg gaa gaa att gtt     1060
Lys Glu Glu Tyr Glu Ala Ala Arg Thr Glu Leu Leu Glu Glu Ile Val
     255                 260                 265 aga ggt act tct gtg gag gac ctg cga gca aaa cta aca aac aaa aat     1108
Arg Gly Thr Ser Val Glu Asp Leu Arg Ala Lys Leu Thr Asn Lys Asn
270                 275                 280 gat aga caa gaa att aag gaa tct tct tcc cat gga aca aaa aat gcg     1156
Asp Arg Gln Glu Ile Lys Glu Ser Ser Ser His Gly Thr Lys Asn Ala
285                 290                 295                 300 ata ccg gat gat ctt gtg caa ata caa tct tat ata cgg tgg gag aga     1204
Ile Pro Asp Asp Leu Val Gln Ile Gln Ser Tyr Ile Arg Trp Glu Arg
             305                 310                 315 gct ggg aag ccc aat tac tct gca gac caa cag ctt aga gaa ttt gag     1252
Ala Gly Lys Pro Asn Tyr Ser Ala Asp Gln Gln Leu Arg Glu Phe Glu
         320                 325                 330 gaa gca aga aaa gaa ttg caa tct gaa cta gag aag ggt atc tct ctt     1300
Glu Ala Arg Lys Glu Leu Gln Ser Glu Leu Glu Lys Gly Ile Ser Leu
     335                 340                 345 gat gaa ata tgg aaa aag att aca aaa ggg gag atc cag act aag gtc     1348
Asp Glu Ile Trp Lys Lys Ile Thr Lys Gly Glu Ile Gln Thr Lys Val
350                 355                 360 tct gat caa ctt aaa act aaa aag tat ttt aga act gaa agg att cag     1396
Ser Asp Gln Leu Lys Thr Lys Lys Tyr Phe Arg Thr Glu Arg Ile Gln
365                 370                 375                 380 agg aag cag agg gac ttt atg cag att cta aac aaa cat gtg gct gaa     1444
Arg Lys Gln Arg Asp Phe Met Gln Ile Leu Asn Lys His Val Ala Glu
             385                 390                 395 ccc aca gag aag aag aat att tca gtt gaa cca aaa gcc ttg aca cca     1492
Pro Thr Glu Lys Lys Asn Ile Ser Val Glu Pro Lys Ala Leu Thr Pro
         400                 405                 410
```

```
gtt gaa ctt ttc gtc ggg gca act gaa gaa cag gag ggt gat tct att     1540
Val Glu Leu Phe Val Gly Ala Thr Glu Glu Gln Glu Gly Asp Ser Ile
    415                 420                 425 ctt aac aag aag atc tac aag ctt gct ggc aaa gaa ctt ctg gta ctt     1588
Leu Asn Lys Lys Ile Tyr Lys Leu Ala Gly Lys Glu Leu Leu Val Leu
430                 435                 440 gtg cac aag cct ggt ggc aag acc aaa att cac cta gct act gat ggc     1636
Val His Lys Pro Gly Gly Lys Thr Lys Ile His Leu Ala Thr Asp Gly
445                 450                 455                 460 aaa gag cca ctc att ctc cac tgg gct ttg tct aag aag gct gga gaa     1684
Lys Glu Pro Leu Ile Leu His Trp Ala Leu Ser Lys Lys Ala Gly Glu
                465                 470                 475 tgg ttg gct ccg cct cca agt gta ctg cct gca ggt tca gtt ttg ctg     1732
Trp Leu Ala Pro Pro Pro Ser Val Leu Pro Ala Gly Ser Val Leu Leu
            480                 485                 490 agt ggg tca gtt gaa aca aca ttc aca act agc tct ctt gcg gat ctg     1780
Ser Gly Ser Val Glu Thr Thr Phe Thr Thr Ser Ser Leu Ala Asp Leu
        495                 500                 505 cct tat cag gtc caa tca att gaa ata gag att gaa gaa gaa ggt tat     1828
Pro Tyr Gln Val Gln Ser Ile Glu Ile Glu Ile Glu Glu Glu Gly Tyr
510                 515                 520 gtt gga atg cca tct gtc ctt cag tct ggc gga aac tgg ata aag aat     1876
Val Gly Met Pro Ser Val Leu Gln Ser Gly Gly Asn Trp Ile Lys Asn
525                 530                 535                 540 aag ggc tct gac ttc tat gtt gac ttt agc tat gaa tct aag caa gtt     1924
Lys Gly Ser Asp Phe Tyr Val Asp Phe Ser Tyr Glu Ser Lys Gln Val
                545                 550                 555 caa cag gat ttt ggc gat ggc aaa ggt acg gcc aag gct ttg ttg gag     1972
Gln Gln Asp Phe Gly Asp Gly Lys Gly Thr Ala Lys Ala Leu Leu Glu
            560                 565                 570 aaa ata gca gga ttg gaa att gag gca cag aag tcc ttt atg cac cgg     2020
Lys Ile Ala Gly Leu Glu Ile Glu Ala Gln Lys Ser Phe Met His Arg
        575                 580                 585 ttt aac att gca gca gac ttg ata caa gaa gcc aaa gag gct ggt gaa     2068
Phe Asn Ile Ala Ala Asp Leu Ile Gln Glu Ala Lys Glu Ala Gly Glu
590                 595                 600 ctg ggc ttt gct ggg atc ttg gtg tgg atg agg ttt atg gct aca agg     2116
Leu Gly Phe Ala Gly Ile Leu Val Trp Met Arg Phe Met Ala Thr Arg
605                 610                 615                 620 cag cta ata tgg aat aaa aac tac aat gtt aaa cca cgt gaa atc agt     2164
Gln Leu Ile Trp Asn Lys Asn Tyr Asn Val Lys Pro Arg Glu Ile Ser
                625                 630                 635 aaa gcc cag gat agg ctt aca gac ctg ctc cag aat gtc tac att agt     2212
Lys Ala Gln Asp Arg Leu Thr Asp Leu Leu Gln Asn Val Tyr Ile Ser
            640                 645                 650 aat cca gag tat agg gaa att gtg cgc atg att ttg tct act gtt ggc     2260
Asn Pro Glu Tyr Arg Glu Ile Val Arg Met Ile Leu Ser Thr Val Gly
        655                 660                 665 cgt gga ggt gaa gga gat gtg gga cag cga att cgc gat gaa atc ctg     2308
Arg Gly Gly Glu Gly Asp Val Gly Gln Arg Ile Arg Asp Glu Ile Leu
670                 675                 680 gtt atc cag aga aac aat aat tgc aag ggt gga atg atg gaa gaa tgg     2356
Val Ile Gln Arg Asn Asn Asn Cys Lys Gly Gly Met Met Glu Glu Trp
685                 690                 695                 700 cat cag aag ttg cat aat aac act agt cct gat gat gtt ata att tgt     2404
His Gln Lys Leu His Asn Asn Thr Ser Pro Asp Asp Val Ile Ile Cys
                705                 710                 715 cag gca ttg att gat tat att aaa agt gac ttc gac atc agt gcc tac     2452
Gln Ala Leu Ile Asp Tyr Ile Lys Ser Asp Phe Asp Ile Ser Ala Tyr
            720                 725                 730
```

```
tgg aag act ttg aat gac aat ggc att acg aaa gaa cgt ctt cta agt      2500
Trp Lys Thr Leu Asn Asp Asn Gly Ile Thr Lys Glu Arg Leu Leu Ser
        735                 740                 745 tat gat cgt gcg atc cat tct gag cca aac ttc aga aga gat cag aag      2548
Tyr Asp Arg Ala Ile His Ser Glu Pro Asn Phe Arg Arg Asp Gln Lys
    750                 755                 760 gat ggt ctg ctg cgt gac cta gga aac tac atg aga acc tta aag gcg      2596
Asp Gly Leu Leu Arg Asp Leu Gly Asn Tyr Met Arg Thr Leu Lys Ala
765                 770                 775                 780 gtt cat tca ggt gca gat ctt gag tct gct atc acg aat tgc ttg ggc      2644
Val His Ser Gly Ala Asp Leu Glu Ser Ala Ile Thr Asn Cys Leu Gly
                785                 790                 795 tac aga tct gag ggt caa ggg ttc atg gtc ggg gtg cag ata aat cct      2692
Tyr Arg Ser Glu Gly Gln Gly Phe Met Val Gly Val Gln Ile Asn Pro
            800                 805                 810 ata ccg aac ttg cca tct gga ttt cca gaa ttg ctt caa ttt gtc tct      2740
Ile Pro Asn Leu Pro Ser Gly Phe Pro Glu Leu Leu Gln Phe Val Ser
        815                 820                 825 gag cat gtt gaa gat aga aat gta gaa gca ttg ctt gag ggt ttg ctg      2788
Glu His Val Glu Asp Arg Asn Val Glu Ala Leu Leu Glu Gly Leu Leu
    830                 835                 840 gag gct cgt caa gag att cgg cca ttg ctg tgc aag cac aat gat cgt      2836
Glu Ala Arg Gln Glu Ile Arg Pro Leu Leu Cys Lys His Asn Asp Arg
845                 850                 855                 860 ctg aag gat cta tta ttt ttg gac ata gcc ctt gag tct agt gtt agg      2884
Leu Lys Asp Leu Leu Phe Leu Asp Ile Ala Leu Glu Ser Ser Val Arg
                865                 870                 875 aca gct att gaa aaa gga tac gag gaa ttg aac gag gct gga ccg gag      2932
Thr Ala Ile Glu Lys Gly Tyr Glu Glu Leu Asn Glu Ala Gly Pro Glu
            880                 885                 890 aaa atc atg tac ttt gtc tct ctg att ctt gaa aat ctc gca ctt tca      2980
Lys Ile Met Tyr Phe Val Ser Leu Ile Leu Glu Asn Leu Ala Leu Ser
        895                 900                 905 tta gat gac aat gag gat ctc atc tac tgt tta aag ggt tgg agt aat      3028
Leu Asp Asp Asn Glu Asp Leu Ile Tyr Cys Leu Lys Gly Trp Ser Asn
    910                 915                 920 gct tta agc atg tcc aag agt aaa agt gat aac tgg gca tta ttt gca      3076
Ala Leu Ser Met Ser Lys Ser Lys Ser Asp Asn Trp Ala Leu Phe Ala
925                 930                 935                 940 aaa tca gtt ctt gac aga act cgc ctt gca ctc gcc ggc aag gca gac      3124
Lys Ser Val Leu Asp Arg Thr Arg Leu Ala Leu Ala Gly Lys Ala Asp
                945                 950                 955 tgg tac cag aaa gtt ttg caa cct tcg gca gag tat ctt gga acg ctg      3172
Trp Tyr Gln Lys Val Leu Gln Pro Ser Ala Glu Tyr Leu Gly Thr Leu
            960                 965                 970 ttg agt gtt gat aag tgg gct gtg gac ata ttt aca gaa gaa atg atc      3220
Leu Ser Val Asp Lys Trp Ala Val Asp Ile Phe Thr Glu Glu Met Ile
        975                 980                 985 cgt gct gga tca gct gca gct cta tcc tta ctc ctt  aat cga ctt gat    3268
Arg Ala Gly Ser Ala Ala Ala Leu Ser Leu Leu Leu  Asn Arg Leu Asp
    990                 995                 1000 cca gtt ctt cgg aag aca gct agt ctg gga agt tgg cag gtt atc         3313
Pro Val Leu Arg Lys Thr Ala Ser Leu Gly Ser Trp Gln Val Ile
1005                1010                1015 agc cct gtt gaa gtt ttt gga tat gtc gca gtt gtg gat gag tta          3358
Ser Pro Val Glu Val Phe Gly Tyr Val Ala Val Val Asp Glu Leu
1020                1025                1030 cta gct gtg cag gat aaa tct tat gat cag cct aca ata tta ctg          3403
Leu Ala Val Gln Asp Lys Ser Tyr Asp Gln Pro Thr Ile Leu Leu
1035                1040                1045
```

```
gca aga cgt gta aaa gga gag gaa gaa att cca cat ggc aca gtt      3448
Ala Arg Arg Val Lys Gly Glu Glu Glu Ile Pro His Gly Thr Val
1050                1055                1060 gct gta ctg aca gcg gat atg cca gat gtc cta tca cat gtt tca      3493
Ala Val Leu Thr Ala Asp Met Pro Asp Val Leu Ser His Val Ser
1065                1070                1075 gtt cga gct aga aat tgc aag gtt tgc ttc gct aca tgc ttt gat      3538
Val Arg Ala Arg Asn Cys Lys Val Cys Phe Ala Thr Cys Phe Asp
1080                1085                1090 ccc aat atc ttg gct gac cta caa tca aat gaa ggg aaa atg ctg      3583
Pro Asn Ile Leu Ala Asp Leu Gln Ser Asn Glu Gly Lys Met Leu
1095                1100                1105 cac cta aaa cca aca tct gct gat att gca tat agt gtg gtg gag      3628
His Leu Lys Pro Thr Ser Ala Asp Ile Ala Tyr Ser Val Val Glu
1110                1115                1120 ggc agt gag cta caa gat tca agt tca gct aac ttg aaa gaa gaa      3673
Gly Ser Glu Leu Gln Asp Ser Ser Ser Ala Asn Leu Lys Glu Glu
1125                1130                1135 gat ggt cct tca tct tct gtt gca tta gtc aaa aag cag ttt gct      3718
Asp Gly Pro Ser Ser Ser Val Ala Leu Val Lys Lys Gln Phe Ala
1140                1145                1150 ggc aga tat gct ata aca tct gat gag ttc act ggt gaa ctg gtg      3763
Gly Arg Tyr Ala Ile Thr Ser Asp Glu Phe Thr Gly Glu Leu Val
1155                1160                1165 ggt gct aaa tca cgt aat att gca tat ctg aaa gga aaa gta ccg      3808
Gly Ala Lys Ser Arg Asn Ile Ala Tyr Leu Lys Gly Lys Val Pro
1170                1175                1180 tct tgg att ggg att ccg aca tca gtt gcc cta cca ttt gga gtg      3853
Ser Trp Ile Gly Ile Pro Thr Ser Val Ala Leu Pro Phe Gly Val
1185                1190                1195 ttt gag aag gtt ctt tca gat gac ata aat cag gca gtg gca gag      3898
Phe Glu Lys Val Leu Ser Asp Asp Ile Asn Gln Ala Val Ala Glu
1200                1205                1210 aag ttg caa att ttg aaa caa aag tta gga gag gaa gac cat agt      3943
Lys Leu Gln Ile Leu Lys Gln Lys Leu Gly Glu Glu Asp His Ser
1215                1220                1225 gcc ctt agg gag att cgg gaa aca gtt tta cag atg aaa gca cca      3988
Ala Leu Arg Glu Ile Arg Glu Thr Val Leu Gln Met Lys Ala Pro
1230                1235                1240 aac cag ttg gtc caa gaa ctg aag aca gag atg aaa agt tct ggt      4033
Asn Gln Leu Val Gln Glu Leu Lys Thr Glu Met Lys Ser Ser Gly
1245                1250                1255 atg cct tgg cct ggt gat gaa ggt gag cag cgc tgg gag caa gca      4078
Met Pro Trp Pro Gly Asp Glu Gly Glu Gln Arg Trp Glu Gln Ala
1260                1265                1270 tgg atg gct atc aag aag gtc tgg gct tca aaa tgg aat gag aga      4123
Trp Met Ala Ile Lys Lys Val Trp Ala Ser Lys Trp Asn Glu Arg
1275                1280                1285 gca ttc ttc agc aca agg aga gta aaa tta gat cat gaa tat ctc      4168
Ala Phe Phe Ser Thr Arg Arg Val Lys Leu Asp His Glu Tyr Leu
1290                1295                1300 tgc atg gct gtc ctg gtt cag gaa ata atc aat gct gac tat gca      4213
Cys Met Ala Val Leu Val Gln Glu Ile Ile Asn Ala Asp Tyr Ala
1305                1310                1315 ttt gtt atc cat aca act aat ccc tct tca gga gat tca tca gaa      4258
Phe Val Ile His Thr Thr Asn Pro Ser Ser Gly Asp Ser Ser Glu
1320                1325                1330 ata tat gct gag gtg gtg aag gga ctt gga gaa act ctc gtt gga      4303
Ile Tyr Ala Glu Val Val Lys Gly Leu Gly Glu Thr Leu Val Gly
1335                1340                1345
```

```
gct tat cca ggc cgt gct ttg agt ttt gtc tgc aag aaa aat gat    4348
Ala Tyr Pro Gly Arg Ala Leu Ser Phe Val Cys Lys Lys Asn Asp
1350                1355                1360 ttg aag tct cct cgg gtt ttg ggt tat cca agc aag ccc att ggg    4393
Leu Lys Ser Pro Arg Val Leu Gly Tyr Pro Ser Lys Pro Ile Gly
1365                1370                1375 ctt ttt ata aga cga tca atc atc ttc cga tct gat tcc aat ggt    4438
Leu Phe Ile Arg Arg Ser Ile Ile Phe Arg Ser Asp Ser Asn Gly
1380                1385                1390 gaa gat ctg gaa ggt tat gct ggt gct ggc ctt tat gat agt gtg    4483
Glu Asp Leu Glu Gly Tyr Ala Gly Ala Gly Leu Tyr Asp Ser Val
1395                1400                1405 cca atg gat gaa gcc gag aaa gtt gtg ctt gat tac tct tca gac    4528
Pro Met Asp Glu Ala Glu Lys Val Val Leu Asp Tyr Ser Ser Asp
1410                1415                1420 cat ctg atc act gac gga cac ttc cag caa tca att ctc tct tcc    4573
His Leu Ile Thr Asp Gly His Phe Gln Gln Ser Ile Leu Ser Ser
1425                1430                1435 att gct cgt gca gga tgt gag att gag gag cta ttt gga tct gca    4618
Ile Ala Arg Ala Gly Cys Glu Ile Glu Glu Leu Phe Gly Ser Ala
1440                1445                1450 caa gac att gaa ggt gtg gtt agg gat ggg aaa ata tat gtt gtc    4663
Gln Asp Ile Glu Gly Val Val Arg Asp Gly Lys Ile Tyr Val Val
1455                1460                1465 cag aca aga ccc caa atg tga ggctgttctt tttcttttt attttttcct    4714
Gln Thr Arg Pro Gln Met
1470                1475 gattgggaag ctattgataa aagcattata tcaatgaaaa aaattaaaaa gaaattatag    4774
aggtcaagcc tagaaaggag gaaagggag tgagtattta tttggaagca agtgaaataa    4834
aggtacaaaa ggagagagga ataaagttgc aatttcccag aacatgtaaa ttcacttgga    4894
aattgtgtac tggatgcttt gctctgtatg aagactaccg ggtcgaaatg acaacatttt    4954
tgtccatagg catgtaatgt tacatttgat tctgggtaat accatacgct tcattatagg    5014
ggatcagcag atactatgtt gtagttgaaa tgtaatgtta taataaaatg ttaatacaaa    5074
tgttataaca tttgtattaa cctgtaacgt gaaaaaaaaa aaaaaaaaaa            5124

<210> SEQ ID NO 7
<211> LENGTH: 1475
<212> TYPE: PRT
<213> ORGANISM: Citrus reticulata

<400> SEQUENCE: 7

Met Ser Asn Ser Ile Gly Arg Asn Val Leu His Gln Ser Leu Leu Cys
1               5                   10                  15

Ser Thr Val Phe Glu His Gln Ser Asn Arg His Ser Ser Gly Ile Pro
            20                  25                  30

Ala Asn Ser Leu Phe Gln Ala Val Ser Ile Asn Gln Pro Ala Gly Ala
        35                  40                  45

Ser Ala Ala Arg Lys Ser Pro Leu Ser Thr Lys Phe Tyr Gly Thr Ser
    50                  55                  60

Leu Asn Ala Arg Pro Lys Met Ala Met Gly Arg His Arg Pro Val Leu
65                  70                  75                  80

Ile Thr Pro Arg Ala Val Leu Ala Val Asp Ser Ala Ser Glu Leu Ala
                85                  90                  95

Gly Lys Phe Asn Leu Glu Gly Asn Val Glu Leu Gln Ile Thr Val Gly
            100                 105                 110
```

-continued

```
Ala Pro Thr Pro Gly Ser Leu Thr Gln Val Asn Ile Glu Ile Ser Tyr
        115                 120                 125

Ser Ser Asn Ser Leu Leu His Trp Gly Ala Ile Arg Asp Lys Lys
    130                 135                 140

Glu Lys Trp Val Leu Pro Ser Arg Pro Asp Gly Thr Lys Ile Leu
145                 150                 155                 160

Lys Asn Arg Ala Leu Arg Thr Pro Phe Val Ser Ser Gly Ser Lys Ser
                165                 170                 175

Leu Val Lys Leu Glu Ile Asp Asp Pro Ala Ile Glu Ala Val Glu Phe
            180                 185                 190

Leu Ile Leu Asp Glu Ala Gln Asn Lys Trp Phe Lys Asn Asn Gly Ala
        195                 200                 205

Asn Phe His Val Lys Leu Pro Ser Glu Arg Ser Leu Ile Gln Asn Val
    210                 215                 220

Ser Val Pro Glu Asp Leu Val Gln Thr Gln Ala Tyr Leu Arg Trp Glu
225                 230                 235                 240

Arg Lys Gly Lys Gln Ile Tyr Thr Pro Glu Gln Lys Glu Glu Tyr
                245                 250                 255

Glu Ala Ala Arg Thr Glu Leu Leu Glu Glu Ile Val Arg Gly Thr Ser
                260                 265                 270

Val Glu Asp Leu Arg Ala Lys Leu Thr Asn Lys Asn Asp Arg Gln Glu
            275                 280                 285

Ile Lys Glu Ser Ser Ser His Gly Thr Lys Asn Ala Ile Pro Asp Asp
        290                 295                 300

Leu Val Gln Ile Gln Ser Tyr Ile Arg Trp Arg Ala Gly Lys Pro
305                 310                 315                 320

Asn Tyr Ser Ala Asp Gln Gln Leu Arg Glu Phe Glu Glu Ala Arg Lys
                325                 330                 335

Glu Leu Gln Ser Glu Leu Glu Lys Gly Ile Ser Leu Asp Glu Ile Trp
            340                 345                 350

Lys Lys Ile Thr Lys Gly Glu Ile Gln Thr Lys Val Ser Asp Gln Leu
        355                 360                 365

Lys Thr Lys Lys Tyr Phe Arg Thr Glu Arg Ile Gln Arg Lys Gln Arg
    370                 375                 380

Asp Phe Met Gln Ile Leu Asn Lys His Val Ala Glu Pro Thr Glu Lys
385                 390                 395                 400

Lys Asn Ile Ser Val Glu Pro Lys Ala Leu Thr Pro Val Glu Leu Phe
                405                 410                 415

Val Gly Ala Thr Glu Glu Gln Glu Gly Asp Ser Ile Leu Asn Lys Lys
            420                 425                 430

Ile Tyr Lys Leu Ala Gly Lys Glu Leu Leu Val Leu His Lys Pro
        435                 440                 445

Gly Gly Lys Thr Lys Ile His Leu Ala Thr Asp Gly Lys Glu Pro Leu
    450                 455                 460

Ile Leu His Trp Ala Leu Ser Lys Lys Ala Gly Glu Trp Leu Ala Pro
465                 470                 475                 480

Pro Pro Ser Val Leu Pro Ala Gly Ser Val Leu Leu Ser Gly Ser Val
                485                 490                 495

Glu Thr Thr Phe Thr Thr Ser Ser Leu Ala Asp Leu Pro Tyr Gln Val
            500                 505                 510

Gln Ser Ile Glu Ile Glu Ile Glu Glu Glu Gly Tyr Val Gly Met Pro
        515                 520                 525

Ser Val Leu Gln Ser Gly Gly Asn Trp Ile Lys Asn Lys Gly Ser Asp
    530                 535                 540
```

```
Phe Tyr Val Asp Phe Ser Tyr Glu Ser Lys Gln Val Gln Gln Asp Phe
545                 550                 555                 560

Gly Asp Gly Lys Gly Thr Ala Lys Ala Leu Leu Glu Lys Ile Ala Gly
                565                 570                 575

Leu Glu Ile Glu Ala Gln Lys Ser Phe Met His Arg Phe Asn Ile Ala
            580                 585                 590

Ala Asp Leu Ile Gln Glu Ala Lys Glu Ala Gly Glu Leu Gly Phe Ala
            595                 600                 605

Gly Ile Leu Val Trp Met Arg Phe Met Ala Thr Arg Gln Leu Ile Trp
610                 615                 620

Asn Lys Asn Tyr Asn Val Lys Pro Arg Glu Ile Ser Lys Ala Gln Asp
625                 630                 635                 640

Arg Leu Thr Asp Leu Leu Gln Asn Val Tyr Ile Ser Asn Pro Glu Tyr
                645                 650                 655

Arg Glu Ile Val Arg Met Ile Leu Ser Thr Val Gly Arg Gly Gly Glu
                660                 665                 670

Gly Asp Val Gly Gln Arg Ile Arg Asp Glu Ile Leu Val Ile Gln Arg
            675                 680                 685

Asn Asn Asn Cys Lys Gly Gly Met Met Glu Glu Trp His Gln Lys Leu
690                 695                 700

His Asn Asn Thr Ser Pro Asp Asp Val Ile Ile Cys Gln Ala Leu Ile
705                 710                 715                 720

Asp Tyr Ile Lys Ser Asp Phe Asp Ile Ser Ala Tyr Trp Lys Thr Leu
                725                 730                 735

Asn Asp Asn Gly Ile Thr Lys Glu Arg Leu Leu Ser Tyr Asp Arg Ala
                740                 745                 750

Ile His Ser Glu Pro Asn Phe Arg Arg Asp Gln Lys Asp Gly Leu Leu
            755                 760                 765

Arg Asp Leu Gly Asn Tyr Met Arg Thr Leu Lys Ala Val His Ser Gly
770                 775                 780

Ala Asp Leu Glu Ser Ala Ile Thr Asn Cys Leu Gly Tyr Arg Ser Glu
785                 790                 795                 800

Gly Gln Gly Phe Met Val Gly Val Gln Ile Asn Pro Ile Pro Asn Leu
                805                 810                 815

Pro Ser Gly Phe Pro Glu Leu Leu Gln Phe Val Ser Glu His Val Glu
                820                 825                 830

Asp Arg Asn Val Glu Ala Leu Leu Glu Gly Leu Leu Glu Ala Arg Gln
            835                 840                 845

Glu Ile Arg Pro Leu Leu Cys Lys His Asn Asp Arg Leu Lys Asp Leu
850                 855                 860

Leu Phe Leu Asp Ile Ala Leu Glu Ser Ser Val Arg Thr Ala Ile Glu
865                 870                 875                 880

Lys Gly Tyr Glu Glu Leu Asn Glu Ala Gly Pro Glu Lys Ile Met Tyr
                885                 890                 895

Phe Val Ser Leu Ile Leu Glu Asn Leu Ala Leu Ser Leu Asp Asp Asn
                900                 905                 910

Glu Asp Leu Ile Tyr Cys Leu Lys Gly Trp Ser Asn Ala Leu Ser Met
            915                 920                 925

Ser Lys Lys Ser Asp Asn Trp Ala Leu Phe Ala Lys Ser Val Leu
            930                 935                 940

Asp Arg Thr Arg Leu Ala Leu Ala Gly Lys Ala Asp Trp Tyr Gln Lys
945                 950                 955                 960

Val Leu Gln Pro Ser Ala Glu Tyr Leu Gly Thr Leu Leu Ser Val Asp
```

-continued

```
                        965                 970                 975
Lys Trp Ala Val Asp Ile Phe Thr Glu Glu Met Ile Arg Ala Gly Ser
                980                 985                 990
Ala Ala Ala Leu Ser Leu Leu Leu Asn Arg Leu Asp Pro Val Leu Arg
                995                1000                1005
Lys Thr Ala Ser Leu Gly Ser Trp Gln Val Ile Ser Pro Val Glu
        1010                1015                1020
Val Phe Gly Tyr Val Ala Val Val Asp Glu Leu Leu Ala Val Gln
        1025                1030                1035
Asp Lys Ser Tyr Asp Gln Pro Thr Ile Leu Leu Ala Arg Arg Val
        1040                1045                1050
Lys Gly Glu Glu Glu Ile Pro His Gly Thr Val Ala Val Leu Thr
        1055                1060                1065
Ala Asp Met Pro Asp Val Leu Ser His Val Ser Val Arg Ala Arg
        1070                1075                1080
Asn Cys Lys Val Cys Phe Ala Thr Cys Phe Asp Pro Asn Ile Leu
        1085                1090                1095
Ala Asp Leu Gln Ser Asn Glu Gly Lys Met Leu His Leu Lys Pro
        1100                1105                1110
Thr Ser Ala Asp Ile Ala Tyr Ser Val Val Glu Gly Ser Glu Leu
        1115                1120                1125
Gln Asp Ser Ser Ser Ala Asn Leu Lys Glu Glu Asp Gly Pro Ser
        1130                1135                1140
Ser Ser Val Ala Leu Val Lys Lys Gln Phe Ala Gly Arg Tyr Ala
        1145                1150                1155
Ile Thr Ser Asp Glu Phe Thr Gly Glu Leu Val Gly Ala Lys Ser
        1160                1165                1170
Arg Asn Ile Ala Tyr Leu Lys Gly Lys Val Pro Ser Trp Ile Gly
        1175                1180                1185
Ile Pro Thr Ser Val Ala Leu Pro Phe Gly Val Phe Glu Lys Val
        1190                1195                1200
Leu Ser Asp Asp Ile Asn Gln Ala Val Ala Glu Lys Leu Gln Ile
        1205                1210                1215
Leu Lys Gln Lys Leu Gly Glu Glu Asp His Ser Ala Leu Arg Glu
        1220                1225                1230
Ile Arg Glu Thr Val Leu Gln Met Lys Ala Pro Asn Gln Leu Val
        1235                1240                1245
Gln Glu Leu Lys Thr Glu Met Lys Ser Ser Gly Met Pro Trp Pro
        1250                1255                1260
Gly Asp Glu Gly Glu Gln Arg Trp Glu Gln Ala Trp Met Ala Ile
        1265                1270                1275
Lys Lys Val Trp Ala Ser Lys Trp Asn Glu Arg Ala Phe Phe Ser
        1280                1285                1290
Thr Arg Arg Val Lys Leu Asp His Glu Tyr Leu Cys Met Ala Val
        1295                1300                1305
Leu Val Gln Glu Ile Ile Asn Ala Asp Tyr Ala Phe Val Ile His
        1310                1315                1320
Thr Thr Asn Pro Ser Ser Gly Asp Ser Ser Glu Ile Tyr Ala Glu
        1325                1330                1335
Val Val Lys Gly Leu Gly Glu Thr Leu Val Gly Ala Tyr Pro Gly
        1340                1345                1350
Arg Ala Leu Ser Phe Val Cys Lys Lys Asn Asp Leu Lys Ser Pro
        1355                1360                1365
```

```
Arg Val  Leu Gly Tyr Pro Ser  Lys Pro Ile Gly Leu  Phe Ile Arg
    1370            1375              1380

Arg Ser  Ile Ile Phe Arg Ser  Asp Ser Asn Gly Glu  Asp Leu Glu
    1385            1390              1395

Gly Tyr  Ala Gly Ala Gly Leu  Tyr Asp Ser Val Pro  Met Asp Glu
    1400            1405              1410

Ala Glu  Lys Val Val Leu Asp  Tyr Ser Ser Asp His  Leu Ile Thr
    1415            1420              1425

Asp Gly  His Phe Gln Gln Ser  Ile Leu Ser Ser Ile  Ala Arg Ala
    1430            1435              1440

Gly Cys  Glu Ile Glu Glu Leu  Phe Gly Ser Ala Gln  Asp Ile Glu
    1445            1450              1455

Gly Val  Val Arg Asp Gly Lys  Ile Tyr Val Val Gln  Thr Arg Pro
    1460            1465              1470

Gln Met
    1475

<210> SEQ ID NO 8
<211> LENGTH: 4200
<212> TYPE: DNA
<213> ORGANISM: Arabidopsis thaliana
<220> FEATURE:
<221> NAME/KEY: CDS
<222> LOCATION: (1)..(4200)
<223> OTHER INFORMATION:
<300> PUBLICATION INFORMATION:
<308> DATABASE ACCESSION NUMBER: EMBL / AF312027
<309> DATABASE ENTRY DATE: 2001-01-08

<400> SEQUENCE: 8 atg agt aac tct gta gtg cat aac tta ctt aac cgg ggt ttg att cgt      48
Met Ser Asn Ser Val Val His Asn Leu Leu Asn Arg Gly Leu Ile Arg
1               5                   10                  15 cct ctt aac ttt gaa cat caa aac aag ctc aac tcc tct gtg tac caa      96
Pro Leu Asn Phe Glu His Gln Asn Lys Leu Asn Ser Ser Val Tyr Gln
            20                  25                  30 act tca aca gca aat ccg gct ctt ggc aag att ggc aga tca aaa ctt     144
Thr Ser Thr Ala Asn Pro Ala Leu Gly Lys Ile Gly Arg Ser Lys Leu
        35                  40                  45 tac ggg aaa ggt ctt aag cag gca gga cgc agt ctg gtc act gaa aca     192
Tyr Gly Lys Gly Leu Lys Gln Ala Gly Arg Ser Leu Val Thr Glu Thr
    50                  55                  60 gga gga aga cct ctc tca ttt gtt cca cga gct gtc ctt gcc atg gat     240
Gly Gly Arg Pro Leu Ser Phe Val Pro Arg Ala Val Leu Ala Met Asp
65                  70                  75                  80 cct cag gca gcc gag aaa ttt agt ctt gac gga aat atc gat tta ctg     288
Pro Gln Ala Ala Glu Lys Phe Ser Leu Asp Gly Asn Ile Asp Leu Leu
                85                  90                  95 gtt gaa gtc act tct aca act gta aga gaa gta aat atc cag ata gct     336
Val Glu Val Thr Ser Thr Thr Val Arg Glu Val Asn Ile Gln Ile Ala
            100                 105                 110 tat aca agt gac aca ttg ttc cta cac tgg ggt gca att ctt gac aac     384
Tyr Thr Ser Asp Thr Leu Phe Leu His Trp Gly Ala Ile Leu Asp Asn
        115                 120                 125 aaa gaa aat tgg gtt cta cct tct cgc tct ccg gat aga act caa aac     432
Lys Glu Asn Trp Val Leu Pro Ser Arg Ser Pro Asp Arg Thr Gln Asn
    130                 135                 140 ttc aag aac agt gcg ctt aga act cca ttt gtg aaa tcc ggt ggc aat     480
Phe Lys Asn Ser Ala Leu Arg Thr Pro Phe Val Lys Ser Gly Gly Asn
145                 150                 155                 160 tct cac ctt aaa cta gag ata gat gat cct gcc ata cac gct att gag     528
```

```
                    -continued

Ser His Leu Lys Leu Glu Ile Asp Asp Pro Ala Ile His Ala Ile Glu
            165                 170                 175 ttc ctt ata ttt gac gaa agt cgg aac aaa tgg tat aaa aat aat ggt      576
Phe Leu Ile Phe Asp Glu Ser Arg Asn Lys Trp Tyr Lys Asn Asn Gly
            180                 185                 190 cag aat ttt cat ata aac tta cca acg gaa agg aat gtg aaa caa aat      624
Gln Asn Phe His Ile Asn Leu Pro Thr Glu Arg Asn Val Lys Gln Asn
            195                 200                 205 gtt tct gtt cct gaa gat ctt gta cag atc caa gca tat ctt aga tgg      672
Val Ser Val Pro Glu Asp Leu Val Gln Ile Gln Ala Tyr Leu Arg Trp
210             215                 220 gaa cgt aag ggt aaa caa atg tac aac cct gag aaa gag aag gag gag      720
Glu Arg Lys Gly Lys Gln Met Tyr Asn Pro Glu Lys Glu Lys Glu Glu
225             230                 235                 240 tat gaa gcc gcc cgg acg gag cta cgg gag gaa atg atg cga ggt gct      768
Tyr Glu Ala Ala Arg Thr Glu Leu Arg Glu Glu Met Met Arg Gly Ala
                245                 250                 255 tca gtg gaa gat ctc aga gca aag ctg ttg aag aaa gat aac agt aat      816
Ser Val Glu Asp Leu Arg Ala Lys Leu Leu Lys Lys Asp Asn Ser Asn
            260                 265                 270 gaa tcc cca aaa tct aat ggg aca tca tcc agt gga cgg gag gaa aag      864
Glu Ser Pro Lys Ser Asn Gly Thr Ser Ser Ser Gly Arg Glu Glu Lys
        275                 280                 285 aaa aaa gtt tcc aag caa cca gag cgt aaa aaa aat tat aac act gac      912
Lys Lys Val Ser Lys Gln Pro Glu Arg Lys Lys Asn Tyr Asn Thr Asp
290                 295                 300 aag atc cag cgc aag gga agg gac ctg act aag ctt atc tat aag cat      960
Lys Ile Gln Arg Lys Gly Arg Asp Leu Thr Lys Leu Ile Tyr Lys His
305                 310                 315                 320 gtt gct gat ttt gtt gaa cca gaa tcc aaa tcc tca tct gaa cca cgg     1008
Val Ala Asp Phe Val Glu Pro Glu Ser Lys Ser Ser Ser Glu Pro Arg
                325                 330                 335 tcc tta aca act ctg gag ata tac gcc aaa gca aag gag gaa caa gaa     1056
Ser Leu Thr Thr Leu Glu Ile Tyr Ala Lys Ala Lys Glu Glu Gln Glu
            340                 345                 350 acc act cca gtc ttt agc aag aaa aca ttc aag ctt gaa ggc agt gcg     1104
Thr Thr Pro Val Phe Ser Lys Lys Thr Phe Lys Leu Glu Gly Ser Ala
        355                 360                 365 att ttg gtg ttt gtt act aaa ctt tcc gga aag acg aaa att cat gtg     1152
Ile Leu Val Phe Val Thr Lys Leu Ser Gly Lys Thr Lys Ile His Val
370                 375                 380 gca act gat ttt aaa gag ccg gtt acc ctt cac tgg gct ttg tct caa     1200
Ala Thr Asp Phe Lys Glu Pro Val Thr Leu His Trp Ala Leu Ser Gln
385                 390                 395                 400 aag ggt gga gaa tgg ttg gac cca cct tca gat ata ctg cca cca aac     1248
Lys Gly Gly Glu Trp Leu Asp Pro Pro Ser Asp Ile Leu Pro Pro Asn
                405                 410                 415 tct ttg cca gta cgt ggt gct gtt gat aca aaa ctg acc atc act tca     1296
Ser Leu Pro Val Arg Gly Ala Val Asp Thr Lys Leu Thr Ile Thr Ser
            420                 425                 430 aca gat ctt cct agt ccg gtt caa act ttt gag ctg gaa ata gaa ggt     1344
Thr Asp Leu Pro Ser Pro Val Gln Thr Phe Glu Leu Glu Ile Glu Gly
        435                 440                 445 gac agc tac aag ggc atg ccg ttt gta ctc aat gct ggt gaa agg tgg     1392
Asp Ser Tyr Lys Gly Met Pro Phe Val Leu Asn Ala Gly Glu Arg Trp
450                 455                 460 att aaa aat aat gac agt gac ttt tat gtg gac ttt gct aaa gaa gaa     1440
Ile Lys Asn Asn Asp Ser Asp Phe Tyr Val Asp Phe Ala Lys Glu Glu
465                 470                 475                 480 aaa cat gtt cag aag gat tat ggc gat gga aag ggt aca gcc aag cat     1488
```

```
                    -continued

Lys His Val Gln Lys Asp Tyr Gly Asp Gly Lys Gly Thr Ala Lys His
            485                 490                 495 tta ctg gac aaa atc gca gat ttg gag agt gag gcc cag aag tct ttc      1536
Leu Leu Asp Lys Ile Ala Asp Leu Glu Ser Glu Ala Gln Lys Ser Phe
                500                 505                 510 atg cat cga ttc aac att gca gca gat ctt gtg gac gag gca aaa agt      1584
Met His Arg Phe Asn Ile Ala Ala Asp Leu Val Asp Glu Ala Lys Ser
                515                 520                 525 gct ggt caa ctg ggc ttt gca ggg atc cta gtc tgg atg agg ttt atg      1632
Ala Gly Gln Leu Gly Phe Ala Gly Ile Leu Val Trp Met Arg Phe Met
            530                 535                 540 gct aca aga cag ctt gtg tgg aac aaa aac tat aat gtt aag cca agg      1680
Ala Thr Arg Gln Leu Val Trp Asn Lys Asn Tyr Asn Val Lys Pro Arg
545                 550                 555                 560 gag ata agc aaa gcg cag gat aga ctg act gac ctt ctc cag gac gtt      1728
Glu Ile Ser Lys Ala Gln Asp Arg Leu Thr Asp Leu Leu Gln Asp Val
                565                 570                 575 tat gca agt tat cca gag tac aga gaa ctt ttg cgg atg ata atg tct      1776
Tyr Ala Ser Tyr Pro Glu Tyr Arg Glu Leu Leu Arg Met Ile Met Ser
                580                 585                 590 act gta ggt cga gga ggt gaa gga gat gtc ggg caa cga atc cgt gac      1824
Thr Val Gly Arg Gly Gly Glu Gly Asp Val Gly Gln Arg Ile Arg Asp
            595                 600                 605 gaa att cta gtc atc cag cgg aaa aat gac tgc aag ggt gga att atg      1872
Glu Ile Leu Val Ile Gln Arg Lys Asn Asp Cys Lys Gly Gly Ile Met
            610                 615                 620 gag gaa tgg cat cag aag ttg cat aac aac act agt cca gat gat gtt      1920
Glu Glu Trp His Gln Lys Leu His Asn Asn Thr Ser Pro Asp Asp Val
625                 630                 635                 640 gtc atc tgt cag gca ttg atg gat tat atc aaa agt gac ttt gac tta      1968
Val Ile Cys Gln Ala Leu Met Asp Tyr Ile Lys Ser Asp Phe Asp Leu
                645                 650                 655 agt gtt tac tgg aag acc ttg aac gat aat ggc ata acc aaa gag cga      2016
Ser Val Tyr Trp Lys Thr Leu Asn Asp Asn Gly Ile Thr Lys Glu Arg
                660                 665                 670 ctc tta agt tat gat cgt gct ata cat tct gaa cca aat ttt aga gga      2064
Leu Leu Ser Tyr Asp Arg Ala Ile His Ser Glu Pro Asn Phe Arg Gly
            675                 680                 685 gaa caa aaa gac ggt ctt ttg cgt gat ctt gga cac tac atg agg act      2112
Glu Gln Lys Asp Gly Leu Leu Arg Asp Leu Gly His Tyr Met Arg Thr
            690                 695                 700 tta aag gct gtt cat tca ggg gca gac ctt gag tcg gct ata caa aat      2160
Leu Lys Ala Val His Ser Gly Ala Asp Leu Glu Ser Ala Ile Gln Asn
705                 710                 715                 720 tgc atg ggc tac caa gat gac ggt gaa ggt ttc atg gtt ggg gtg cag      2208
Cys Met Gly Tyr Gln Asp Asp Gly Glu Gly Phe Met Val Gly Val Gln
                725                 730                 735 ata aat cct gta tca gga ttg cct tct gga tat cca gac ttg ctt cgt      2256
Ile Asn Pro Val Ser Gly Leu Pro Ser Gly Tyr Pro Asp Leu Leu Arg
            740                 745                 750 ttc gtc cta gaa cat gtt gaa gaa aag aat gta gag cca ctt ctt gag      2304
Phe Val Leu Glu His Val Glu Glu Lys Asn Val Glu Pro Leu Leu Glu
            755                 760                 765 ggt ttg ctt gaa gct cgt caa gag cta agg cca ctt ctg ctg aag tcc      2352
Gly Leu Leu Glu Ala Arg Gln Glu Leu Arg Pro Leu Leu Leu Lys Ser
770                 775                 780 cat gac cgc ctc aag gat ctg tta ttc ttg gac ctc gct ctt gat tct      2400
His Asp Arg Leu Lys Asp Leu Leu Phe Leu Asp Leu Ala Leu Asp Ser
785                 790                 795                 800 act gtc aga aca gcg att gaa aga gga tat gag caa ttg aat gat gct      2448
```

```
                    Thr Val Arg Thr Ala Ile Glu Arg Gly Tyr Glu Gln Leu Asn Asp Ala
                                    805                 810                 815 gga cct gag aaa atc atg tac ttc atc agc cta gtt ctt gaa aat ctt           2496
Gly Pro Glu Lys Ile Met Tyr Phe Ile Ser Leu Val Leu Glu Asn Leu
            820                 825                 830 gcc ctc tct tca gat gac aat gaa gac ctt ata tac tgc ttg aag gga           2544
Ala Leu Ser Ser Asp Asp Asn Glu Asp Leu Ile Tyr Cys Leu Lys Gly
            835                 840                 845 tgg caa ttt gcc ctc gac atg tgc aag agc aaa aaa gat cac tgg gct           2592
Trp Gln Phe Ala Leu Asp Met Cys Lys Ser Lys Lys Asp His Trp Ala
    850                 855                 860 ctg tat gca aaa tct gtt ctt gac aga agc cga cta gca ctg gca agc           2640
Leu Tyr Ala Lys Ser Val Leu Asp Arg Ser Arg Leu Ala Leu Ala Ser
865                 870                 875                 880 aaa gct gag agg tac ctt gaa att ctg caa cca tcg gct gaa tat ctt           2688
Lys Ala Glu Arg Tyr Leu Glu Ile Leu Gln Pro Ser Ala Glu Tyr Leu
                885                 890                 895 gga tct tgt ctt gga gtc gat cag tcg gct gtt agt ata ttt act gaa           2736
Gly Ser Cys Leu Gly Val Asp Gln Ser Ala Val Ser Ile Phe Thr Glu
            900                 905                 910 gag atc att cga gct gga tct gca gca gca ttg tcg tca ctt gtt aac           2784
Glu Ile Ile Arg Ala Gly Ser Ala Ala Ala Leu Ser Ser Leu Val Asn
            915                 920                 925 cga ctt gac cca gtt ctt agg aag act gct aac ttg gga agt tgg cag           2832
Arg Leu Asp Pro Val Leu Arg Lys Thr Ala Asn Leu Gly Ser Trp Gln
    930                 935                 940 gtt att agt cct gta gag gtc gtc gga tat gtc att gtt gtg gac gaa           2880
Val Ile Ser Pro Val Glu Val Val Gly Tyr Val Ile Val Val Asp Glu
945                 950                 955                 960 ttg ctc act gta cag aat aaa acc tac gat aga cct aca att ata gtt           2928
Leu Leu Thr Val Gln Asn Lys Thr Tyr Asp Arg Pro Thr Ile Ile Val
                965                 970                 975 gca aac aga gtg aga gga gag gag gaa atc cct gat ggt gca gtt gcg           2976
Ala Asn Arg Val Arg Gly Glu Glu Glu Ile Pro Asp Gly Ala Val Ala
            980                 985                 990 gta ctg aca cct gac atg ccg gat gta cta tct cat gtt tct gtt cga          3024
Val Leu Thr Pro Asp Met Pro Asp Val Leu Ser His Val Ser Val Arg
        995                 1000                1005 gca aga aat gga aag atc tgc ttt gcc aca tgt ttt gat tct ggt              3069
Ala Arg Asn Gly Lys Ile Cys Phe Ala Thr Cys Phe Asp Ser Gly
    1010                1015                1020 atc tta tct gac ctc caa gga aaa gat gga aaa ctg ttg agc cta              3114
Ile Leu Ser Asp Leu Gln Gly Lys Asp Gly Lys Leu Leu Ser Leu
    1025                1030                1035 caa cca acc tct gca gat gta gtc tat aaa gag gta aac gat agt              3159
Gln Pro Thr Ser Ala Asp Val Val Tyr Lys Glu Val Asn Asp Ser
    1040                1045                1050 gag ctt tcg agt cca agt tca gac aac ctg gaa gat gcc cct cca              3204
Glu Leu Ser Ser Pro Ser Ser Asp Asn Leu Glu Asp Ala Pro Pro
    1055                1060                1065 agt att tct ttg gtc aag aaa cag ttt gcg ggt aga tat gct ata              3249
Ser Ile Ser Leu Val Lys Lys Gln Phe Ala Gly Arg Tyr Ala Ile
    1070                1075                1080 tca tct gag gag ttc aca agt gac ttg gtt ggt gct aaa tca aga              3294
Ser Ser Glu Glu Phe Thr Ser Asp Leu Val Gly Ala Lys Ser Arg
    1085                1090                1095 aat atc ggg tat ctg aaa gga aaa gtt cct tct tgg gtt ggt atc              3339
Asn Ile Gly Tyr Leu Lys Gly Lys Val Pro Ser Trp Val Gly Ile
    1100                1105                1110 cca act tca gtt gcg ttg cca ttt ggt gtt ttt gag aag gtt atc              3384
```

|     |     |     |     |     |     |     |     |     |     |     |     |     |     |     |      |
|---|---|---|---|---|---|---|---|---|---|---|---|---|---|---|---|
| Pro | Thr | Ser | Val | Ala | Leu | Pro | Phe | Gly | Val | Phe | Glu | Lys | Val | Ile |      |
|     | 1115 |     |     |     | 1120 |     |     |     |     | 1125 |     |     |     |     |      |
| tcc | gaa | aag | gcg | aat | cag | gcg | gtg | aac | gat | aaa | ttg | cta | gta | ttg | 3429 |
| Ser | Glu | Lys | Ala | Asn | Gln | Ala | Val | Asn | Asp | Lys | Leu | Leu | Val | Leu |      |
|     | 1130 |     |     |     | 1135 |     |     |     |     | 1140 |     |     |     |     |      |
| aag | aaa | act | ctt | gat | gag | gga | gac | caa | ggt | gct | ctg | aag | gaa | atc | 3474 |
| Lys | Lys | Thr | Leu | Asp | Glu | Gly | Asp | Gln | Gly | Ala | Leu | Lys | Glu | Ile |      |
|     | 1145 |     |     |     | 1150 |     |     |     |     | 1155 |     |     |     |     |      |
| cgg | cag | aca | ctg | ttg | ggg | cta | gtt | gca | ccc | cca | gaa | ctg | gtt | gaa | 3519 |
| Arg | Gln | Thr | Leu | Leu | Gly | Leu | Val | Ala | Pro | Pro | Glu | Leu | Val | Glu |      |
|     | 1160 |     |     |     | 1165 |     |     |     |     | 1170 |     |     |     |     |      |
| gaa | ctg | aaa | agt | act | atg | aaa | agt | tct | gac | atg | cca | tgg | ccg | ggt | 3564 |
| Glu | Leu | Lys | Ser | Thr | Met | Lys | Ser | Ser | Asp | Met | Pro | Trp | Pro | Gly |      |
|     | 1175 |     |     |     | 1180 |     |     |     |     | 1185 |     |     |     |     |      |
| gat | gaa | ggt | gaa | cag | aga | tgg | gag | caa | gct | tgg | gca | gcc | att | aaa | 3609 |
| Asp | Glu | Gly | Glu | Gln | Arg | Trp | Glu | Gln | Ala | Trp | Ala | Ala | Ile | Lys |      |
|     | 1190 |     |     |     | 1195 |     |     |     |     | 1200 |     |     |     |     |      |
| aag | gtc | tgg | gct | tcg | aaa | tgg | aac | gag | aga | gca | tac | ttc | agc | acg | 3654 |
| Lys | Val | Trp | Ala | Ser | Lys | Trp | Asn | Glu | Arg | Ala | Tyr | Phe | Ser | Thr |      |
|     | 1205 |     |     |     | 1210 |     |     |     |     | 1215 |     |     |     |     |      |
| agg | aaa | gta | aaa | ctg | gat | cat | gac | tat | ctc | tgc | atg | gct | gtt | ttg | 3699 |
| Arg | Lys | Val | Lys | Leu | Asp | His | Asp | Tyr | Leu | Cys | Met | Ala | Val | Leu |      |
|     | 1220 |     |     |     | 1225 |     |     |     |     | 1230 |     |     |     |     |      |
| gtc | caa | gaa | gtc | atc | aat | gcg | gat | tac | gca | ttc | gtc | att | cac | aca | 3744 |
| Val | Gln | Glu | Val | Ile | Asn | Ala | Asp | Tyr | Ala | Phe | Val | Ile | His | Thr |      |
|     | 1235 |     |     |     | 1240 |     |     |     |     | 1245 |     |     |     |     |      |
| act | aat | cca | tct | tct | gga | gat | tca | tca | gag | att | tat | gcc | gag | gtg | 3789 |
| Thr | Asn | Pro | Ser | Ser | Gly | Asp | Ser | Ser | Glu | Ile | Tyr | Ala | Glu | Val |      |
|     | 1250 |     |     |     | 1255 |     |     |     |     | 1260 |     |     |     |     |      |
| gtc | aaa | ggc | ctt | ggg | gaa | act | ctt | gta | gga | gca | tat | ccc | ggt | cgg | 3834 |
| Val | Lys | Gly | Leu | Gly | Glu | Thr | Leu | Val | Gly | Ala | Tyr | Pro | Gly | Arg |      |
|     | 1265 |     |     |     | 1270 |     |     |     |     | 1275 |     |     |     |     |      |
| tct | ctg | agt | ttc | atc | tgc | aag | aaa | aac | aac | ctt | gat | tcg | cct | ctg | 3879 |
| Ser | Leu | Ser | Phe | Ile | Cys | Lys | Lys | Asn | Asn | Leu | Asp | Ser | Pro | Leu |      |
|     | 1280 |     |     |     | 1285 |     |     |     |     | 1290 |     |     |     |     |      |
| gtg | ttg | ggc | tac | cca | agc | aaa | ccg | att | ggg | ctg | ttc | ata | aga | cgt | 3924 |
| Val | Leu | Gly | Tyr | Pro | Ser | Lys | Pro | Ile | Gly | Leu | Phe | Ile | Arg | Arg |      |
|     | 1295 |     |     |     | 1300 |     |     |     |     | 1305 |     |     |     |     |      |
| tca | atc | atc | ttc | aga | tct | gat | tcc | aat | gga | gaa | gat | ctt | gaa | ggt | 3969 |
| Ser | Ile | Ile | Phe | Arg | Ser | Asp | Ser | Asn | Gly | Glu | Asp | Leu | Glu | Gly |      |
|     | 1310 |     |     |     | 1315 |     |     |     |     | 1320 |     |     |     |     |      |
| tat | gca | ggt | gca | ggc | ctc | tac | gac | agt | gta | cca | atg | gac | gag | gaa | 4014 |
| Tyr | Ala | Gly | Ala | Gly | Leu | Tyr | Asp | Ser | Val | Pro | Met | Asp | Glu | Glu |      |
|     | 1325 |     |     |     | 1330 |     |     |     |     | 1335 |     |     |     |     |      |
| gac | caa | gtc | gtg | ctc | gat | tac | aca | aca | gat | cct | ctg | atc | act | gac | 4059 |
| Asp | Gln | Val | Val | Leu | Asp | Tyr | Thr | Thr | Asp | Pro | Leu | Ile | Thr | Asp |      |
|     | 1340 |     |     |     | 1345 |     |     |     |     | 1350 |     |     |     |     |      |
| ttg | agc | ttc | cag | aaa | aag | gtt | ctc | tca | gac | att | gca | cgc | gct | gga | 4104 |
| Leu | Ser | Phe | Gln | Lys | Lys | Val | Leu | Ser | Asp | Ile | Ala | Arg | Ala | Gly |      |
|     | 1355 |     |     |     | 1360 |     |     |     |     | 1365 |     |     |     |     |      |
| gat | gcc | att | gag | aaa | ctc | tat | gga | act | gca | cag | gac | att | gaa | ggt | 4149 |
| Asp | Ala | Ile | Glu | Lys | Leu | Tyr | Gly | Thr | Ala | Gln | Asp | Ile | Glu | Gly |      |
|     | 1370 |     |     |     | 1375 |     |     |     |     | 1380 |     |     |     |     |      |
| gtg | atc | aga | gac | ggg | aag | ctc | tat | gtc | gtc | cag | aca | cga | cca | caa | 4194 |
| Val | Ile | Arg | Asp | Gly | Lys | Leu | Tyr | Val | Val | Gln | Thr | Arg | Pro | Gln |      |
|     | 1385 |     |     |     | 1390 |     |     |     |     | 1395 |     |     |     |     |      |
| gtg | tga |     |     |     |     |     |     |     |     |     |     |     |     |     | 4200 |
| Val |     |     |     |     |     |     |     |     |     |     |     |     |     |     |      |

<210> SEQ ID NO 9

```
<211> LENGTH: 1399
<212> TYPE: PRT
<213> ORGANISM: Arabidopsis thaliana

<400> SEQUENCE: 9
```

| | | | | | | | | | | | | | | |
|---|---|---|---|---|---|---|---|---|---|---|---|---|---|---|
| Met | Ser | Asn | Ser | Val | Val | His | Asn | Leu | Leu | Asn | Arg | Gly | Leu | Ile | Arg |
| 1 | | | | 5 | | | | | 10 | | | | | 15 | |

| Pro | Leu | Asn | Phe | Glu | His | Gln | Asn | Lys | Leu | Asn | Ser | Ser | Val | Tyr | Gln |
|---|---|---|---|---|---|---|---|---|---|---|---|---|---|---|---|
| | | | 20 | | | | 25 | | | | | 30 | | | |

| Thr | Ser | Thr | Ala | Asn | Pro | Ala | Leu | Gly | Lys | Ile | Gly | Arg | Ser | Lys | Leu |
| | | 35 | | | | | 40 | | | | | 45 | | | |

| Tyr | Gly | Lys | Gly | Leu | Lys | Gln | Ala | Gly | Arg | Ser | Leu | Val | Thr | Glu | Thr |
| | 50 | | | | | 55 | | | | | 60 | | | | |

| Gly | Gly | Arg | Pro | Leu | Ser | Phe | Val | Pro | Arg | Ala | Val | Leu | Ala | Met | Asp |
| 65 | | | | | 70 | | | | | 75 | | | | | 80 |

| Pro | Gln | Ala | Ala | Glu | Lys | Phe | Ser | Leu | Asp | Gly | Asn | Ile | Asp | Leu | Leu |
| | | | | 85 | | | | | 90 | | | | | 95 | |

| Val | Glu | Val | Thr | Ser | Thr | Thr | Val | Arg | Glu | Val | Asn | Ile | Gln | Ile | Ala |
| | | | 100 | | | | | 105 | | | | | 110 | | |

| Tyr | Thr | Ser | Asp | Thr | Leu | Phe | Leu | His | Trp | Gly | Ala | Ile | Leu | Asp | Asn |
| | | 115 | | | | | 120 | | | | | 125 | | | |

| Lys | Glu | Asn | Trp | Val | Leu | Pro | Ser | Arg | Ser | Pro | Asp | Arg | Thr | Gln | Asn |
| | 130 | | | | | 135 | | | | | 140 | | | | |

| Phe | Lys | Asn | Ser | Ala | Leu | Arg | Thr | Pro | Phe | Val | Lys | Ser | Gly | Gly | Asn |
| 145 | | | | | 150 | | | | | 155 | | | | | 160 |

| Ser | His | Leu | Lys | Leu | Glu | Ile | Asp | Asp | Pro | Ala | Ile | His | Ala | Ile | Glu |
| | | | | 165 | | | | | 170 | | | | | 175 | |

| Phe | Leu | Ile | Phe | Asp | Glu | Ser | Arg | Asn | Lys | Trp | Tyr | Lys | Asn | Asn | Gly |
| | | | 180 | | | | | 185 | | | | | 190 | | |

| Gln | Asn | Phe | His | Ile | Asn | Leu | Pro | Thr | Glu | Arg | Asn | Val | Lys | Gln | Asn |
| | | 195 | | | | | 200 | | | | | 205 | | | |

| Val | Ser | Val | Pro | Glu | Asp | Leu | Val | Gln | Ile | Gln | Ala | Tyr | Leu | Arg | Trp |
| | 210 | | | | | 215 | | | | | 220 | | | | |

| Glu | Arg | Lys | Gly | Lys | Gln | Met | Tyr | Asn | Pro | Glu | Lys | Glu | Lys | Glu | Glu |
| 225 | | | | | 230 | | | | | 235 | | | | | 240 |

| Tyr | Glu | Ala | Ala | Arg | Thr | Glu | Leu | Arg | Glu | Glu | Met | Met | Arg | Gly | Ala |
| | | | | 245 | | | | | 250 | | | | | 255 | |

| Ser | Val | Glu | Asp | Leu | Arg | Ala | Lys | Leu | Leu | Lys | Lys | Asp | Asn | Ser | Asn |
| | | | 260 | | | | | 265 | | | | | 270 | | |

| Glu | Ser | Pro | Lys | Ser | Asn | Gly | Thr | Ser | Ser | Ser | Gly | Arg | Glu | Glu | Lys |
| | | 275 | | | | | 280 | | | | | 285 | | | |

| Lys | Lys | Val | Ser | Lys | Gln | Pro | Glu | Arg | Lys | Lys | Asn | Tyr | Asn | Thr | Asp |
| | 290 | | | | | 295 | | | | | 300 | | | | |

| Lys | Ile | Gln | Arg | Lys | Gly | Arg | Asp | Leu | Thr | Lys | Leu | Ile | Tyr | Lys | His |
| 305 | | | | | 310 | | | | | 315 | | | | | 320 |

| Val | Ala | Asp | Phe | Val | Glu | Pro | Glu | Ser | Lys | Ser | Ser | Glu | Pro | Arg |
| | | | | 325 | | | | | 330 | | | | | 335 | |

| Ser | Leu | Thr | Thr | Leu | Glu | Ile | Tyr | Ala | Lys | Ala | Lys | Glu | Glu | Gln | Glu |
| | | | 340 | | | | | 345 | | | | | 350 | | |

| Thr | Thr | Pro | Val | Phe | Ser | Lys | Lys | Thr | Phe | Lys | Leu | Glu | Gly | Ser | Ala |
| | | 355 | | | | | 360 | | | | | 365 | | | |

| Ile | Leu | Val | Phe | Val | Thr | Lys | Leu | Ser | Gly | Lys | Thr | Lys | Ile | His | Val |
| | 370 | | | | | 375 | | | | | 380 | | | | |

| Ala | Thr | Asp | Phe | Lys | Glu | Pro | Val | Thr | Leu | His | Trp | Ala | Leu | Ser | Gln |
| 385 | | | | | 390 | | | | | 395 | | | | | 400 |

```
Lys Gly Gly Glu Trp Leu Asp Pro Pro Ser Asp Ile Leu Pro Pro Asn
                405             410             415

Ser Leu Pro Val Arg Gly Ala Val Asp Thr Lys Leu Thr Ile Thr Ser
            420             425             430

Thr Asp Leu Pro Ser Pro Val Gln Thr Phe Glu Leu Glu Ile Glu Gly
            435             440             445

Asp Ser Tyr Lys Gly Met Pro Phe Val Leu Asn Ala Gly Glu Arg Trp
            450             455             460

Ile Lys Asn Asn Asp Ser Asp Phe Tyr Val Asp Phe Ala Lys Glu Glu
465             470             475             480

Lys His Val Gln Lys Asp Tyr Gly Asp Gly Lys Gly Thr Ala Lys His
                485             490             495

Leu Leu Asp Lys Ile Ala Asp Leu Glu Ser Glu Ala Gln Lys Ser Phe
                500             505             510

Met His Arg Phe Asn Ile Ala Ala Asp Leu Val Asp Glu Ala Lys Ser
                515             520             525

Ala Gly Gln Leu Gly Phe Ala Gly Ile Leu Val Trp Met Arg Phe Met
            530             535             540

Ala Thr Arg Gln Leu Val Trp Asn Lys Asn Tyr Asn Val Lys Pro Arg
545             550             555             560

Glu Ile Ser Lys Ala Gln Asp Arg Leu Thr Asp Leu Leu Gln Asp Val
                565             570             575

Tyr Ala Ser Tyr Pro Glu Tyr Arg Glu Leu Leu Arg Met Ile Met Ser
                580             585             590

Thr Val Gly Arg Gly Gly Glu Gly Asp Val Gly Gln Arg Ile Arg Asp
            595             600             605

Glu Ile Leu Val Ile Gln Arg Lys Asn Asp Cys Lys Gly Gly Ile Met
            610             615             620

Glu Glu Trp His Gln Lys Leu His Asn Asn Thr Ser Pro Asp Asp Val
625             630             635             640

Val Ile Cys Gln Ala Leu Met Asp Tyr Ile Lys Ser Asp Phe Asp Leu
                645             650             655

Ser Val Tyr Trp Lys Thr Leu Asn Asp Asn Gly Ile Thr Lys Glu Arg
            660             665             670

Leu Leu Ser Tyr Asp Arg Ala Ile His Ser Glu Pro Asn Phe Arg Gly
            675             680             685

Glu Gln Lys Asp Gly Leu Leu Arg Asp Leu Gly His Tyr Met Arg Thr
            690             695             700

Leu Lys Ala Val His Ser Gly Ala Asp Leu Glu Ser Ala Ile Gln Asn
705             710             715             720

Cys Met Gly Tyr Gln Asp Asp Gly Glu Gly Phe Met Val Gly Val Gln
                725             730             735

Ile Asn Pro Val Ser Gly Leu Pro Ser Gly Tyr Pro Asp Leu Leu Arg
            740             745             750

Phe Val Leu Glu His Val Glu Glu Lys Asn Val Glu Pro Leu Leu Glu
            755             760             765

Gly Leu Leu Glu Ala Arg Gln Glu Leu Arg Pro Leu Leu Leu Lys Ser
            770             775             780

His Asp Arg Leu Lys Asp Leu Phe Leu Asp Leu Ala Leu Asp Ser
785             790             795             800

Thr Val Arg Thr Ala Ile Glu Arg Gly Tyr Glu Gln Leu Asn Asp Ala
            805             810             815

Gly Pro Glu Lys Ile Met Tyr Phe Ile Ser Leu Val Leu Glu Asn Leu
```

-continued

```
                820                 825                 830
Ala Leu Ser Ser Asp Asp Asn Glu Asp Leu Ile Tyr Cys Leu Lys Gly
            835                 840                 845
Trp Gln Phe Ala Leu Asp Met Cys Lys Ser Lys Lys Asp His Trp Ala
            850                 855                 860
Leu Tyr Ala Lys Ser Val Leu Asp Arg Ser Arg Leu Ala Leu Ala Ser
865                 870                 875                 880
Lys Ala Glu Arg Tyr Leu Glu Ile Leu Gln Pro Ser Ala Glu Tyr Leu
            885                 890                 895
Gly Ser Cys Leu Gly Val Asp Gln Ser Ala Val Ser Ile Phe Thr Glu
            900                 905                 910
Glu Ile Ile Arg Ala Gly Ser Ala Ala Leu Ser Ser Leu Val Asn
            915                 920                 925
Arg Leu Asp Pro Val Leu Arg Lys Thr Ala Asn Leu Gly Ser Trp Gln
            930                 935                 940
Val Ile Ser Pro Val Glu Val Gly Tyr Val Ile Val Asp Glu
945                 950                 955                 960
Leu Leu Thr Val Gln Asn Lys Thr Tyr Asp Arg Pro Thr Ile Ile Val
            965                 970                 975
Ala Asn Arg Val Arg Gly Glu Glu Ile Pro Asp Gly Ala Val Ala
            980                 985                 990
Val Leu Thr Pro Asp Met Pro Asp Val Leu Ser His Val Ser Val Arg
            995                 1000                1005
Ala Arg Asn Gly Lys Ile Cys Phe Ala Thr Cys Phe Asp Ser Gly
            1010                1015                1020
Ile Leu Ser Asp Leu Gln Gly Lys Asp Gly Lys Leu Leu Ser Leu
            1025                1030                1035
Gln Pro Thr Ser Ala Asp Val Val Tyr Lys Glu Val Asn Asp Ser
            1040                1045                1050
Glu Leu Ser Ser Pro Ser Asp Asn Leu Glu Asp Ala Pro Pro
            1055                1060                1065
Ser Ile Ser Leu Val Lys Gln Phe Ala Gly Arg Tyr Ala Ile
            1070                1075                1080
Ser Ser Glu Glu Phe Thr Ser Asp Leu Val Gly Ala Lys Ser Arg
            1085                1090                1095
Asn Ile Gly Tyr Leu Lys Gly Lys Val Pro Ser Trp Val Gly Ile
            1100                1105                1110
Pro Thr Ser Val Ala Leu Pro Phe Gly Val Phe Glu Lys Val Ile
            1115                1120                1125
Ser Glu Lys Ala Asn Gln Ala Val Asn Asp Lys Leu Leu Val Leu
            1130                1135                1140
Lys Lys Thr Leu Asp Glu Gly Asp Gln Gly Ala Leu Lys Glu Ile
            1145                1150                1155
Arg Gln Thr Leu Leu Gly Leu Val Ala Pro Pro Glu Leu Val Glu
            1160                1165                1170
Glu Leu Lys Ser Thr Met Lys Ser Ser Asp Met Pro Trp Pro Gly
            1175                1180                1185
Asp Glu Gly Glu Gln Arg Trp Glu Gln Ala Trp Ala Ala Ile Lys
            1190                1195                1200
Lys Val Trp Ala Ser Lys Trp Asn Glu Arg Ala Tyr Phe Ser Thr
            1205                1210                1215
Arg Lys Val Lys Leu Asp His Asp Tyr Leu Cys Met Ala Val Leu
            1220                1225                1230
```

```
Val Gln Glu Val Ile Asn Ala Asp Tyr Ala Phe Val Ile His Thr
    1235                1240                1245

Thr Asn Pro Ser Ser Gly Asp Ser Ser Glu Ile Tyr Ala Glu Val
    1250                1255                1260

Val Lys Gly Leu Gly Glu Thr Leu Val Gly Ala Tyr Pro Gly Arg
    1265                1270                1275

Ser Leu Ser Phe Ile Cys Lys Lys Asn Asn Leu Asp Ser Pro Leu
    1280                1285                1290

Val Leu Gly Tyr Pro Ser Lys Pro Ile Gly Leu Phe Ile Arg Arg
    1295                1300                1305

Ser Ile Ile Phe Arg Ser Asp Ser Asn Gly Glu Asp Leu Glu Gly
    1310                1315                1320

Tyr Ala Gly Ala Gly Leu Tyr Asp Ser Val Pro Met Asp Glu Glu
    1325                1330                1335

Asp Gln Val Val Leu Asp Tyr Thr Thr Asp Pro Leu Ile Thr Asp
    1340                1345                1350

Leu Ser Phe Gln Lys Lys Val Leu Ser Asp Ile Ala Arg Ala Gly
    1355                1360                1365

Asp Ala Ile Glu Lys Leu Tyr Gly Thr Ala Gln Asp Ile Glu Gly
    1370                1375                1380

Val Ile Arg Asp Gly Lys Leu Tyr Val Val Gln Thr Arg Pro Gln
    1385                1390                1395

Val

<210> SEQ ID NO 10
<211> LENGTH: 4851
<212> TYPE: DNA
<213> ORGANISM: Solanum tuberosum
<220> FEATURE:
<221> NAME/KEY: CDS
<222> LOCATION: (105)..(4499)
<223> OTHER INFORMATION:
<300> PUBLICATION INFORMATION:
<308> DATABASE ACCESSION NUMBER: EMBL / Y09533
<309> DATABASE ENTRY DATE: 1998-07-30

<400> SEQUENCE: 10
catcttcatc gaatttctcg aagcttcttc gctaatttcc tggtttcttc actcaaaatc      60
gacgtttcta gctgaacttg agtgaattaa gccagtggga ggat atg agt aat tcc     116
                                              Met Ser Asn Ser
                                                1 tta ggg aat aac ttg ctg tac cag gga ttc cta acc tca aca gtg ttg     164
Leu Gly Asn Asn Leu Leu Tyr Gln Gly Phe Leu Thr Ser Thr Val Leu
  5              10                  15                  20 gaa cat aaa agt aga atc agt cct cct tgt gtt gga ggc aat tct ttg     212
Glu His Lys Ser Arg Ile Ser Pro Pro Cys Val Gly Gly Asn Ser Leu
             25                  30                  35 ttt caa caa caa gtg atc tcg aaa tca cct tta tca act gag ttt cga     260
Phe Gln Gln Gln Val Ile Ser Lys Ser Pro Leu Ser Thr Glu Phe Arg
         40                  45                  50 ggt aac agg tta aag gtg cag aaa aag aaa ata cct atg gaa aag aag     308
Gly Asn Arg Leu Lys Val Gln Lys Lys Lys Ile Pro Met Glu Lys Lys
     55                  60                  65 cgt gct ttt tct agt tct cct cat gct gta ctt acc act gat acc tct     356
Arg Ala Phe Ser Ser Ser Pro His Ala Val Leu Thr Thr Asp Thr Ser
 70                  75                  80 tct gag cta gca gaa aag ttc agt cta ggg ggg aat att gag cta cag     404
Ser Glu Leu Ala Glu Lys Phe Ser Leu Gly Gly Asn Ile Glu Leu Gln
85                  90                  95                 100
```

```
                                                          -continued gtt gat gtt agg cct ccc act tca ggt gat gtg tcc ttt gtg gat ttt    452
Val Asp Val Arg Pro Pro Thr Ser Gly Asp Val Ser Phe Val Asp Phe
            105                 110                 115 caa gta aca aat ggt agt gat aaa ctg ttt ttg cac tgg ggg gca gta    500
Gln Val Thr Asn Gly Ser Asp Lys Leu Phe Leu His Trp Gly Ala Val
        120                 125                 130 aaa ttc ggg aaa gaa aca tgg tct ctt ccg aat gat cgt cca gat ggg    548
Lys Phe Gly Lys Glu Thr Trp Ser Leu Pro Asn Asp Arg Pro Asp Gly
    135                 140                 145 acc aaa gtg tac aag aac aaa gca ctt aga act cca ttt gtt aaa tct    596
Thr Lys Val Tyr Lys Asn Lys Ala Leu Arg Thr Pro Phe Val Lys Ser
150                 155                 160 ggc tct aac tcc atc ctg aga ctg gag ata cga gac act gct atc gaa    644
Gly Ser Asn Ser Ile Leu Arg Leu Glu Ile Arg Asp Thr Ala Ile Glu
165                 170                 175                 180 gct att gag ttt ctc ata tac gat gaa gcc cac gat aaa tgg ata aag    692
Ala Ile Glu Phe Leu Ile Tyr Asp Glu Ala His Asp Lys Trp Ile Lys
                185                 190                 195 aat aat ggt ggt aat ttt cgt gtc aaa ttg tca aga aaa gag ata cga    740
Asn Asn Gly Gly Asn Phe Arg Val Lys Leu Ser Arg Lys Glu Ile Arg
            200                 205                 210 ggc cca gat gtt tct gtt cct gag gag ctt gta cag atc caa tca tat    788
Gly Pro Asp Val Ser Val Pro Glu Glu Leu Val Gln Ile Gln Ser Tyr
        215                 220                 225 ttg agg tgg gag agg aag gga aaa cag aat tac ccc cct gag aaa gag    836
Leu Arg Trp Glu Arg Lys Gly Lys Gln Asn Tyr Pro Pro Glu Lys Glu
    230                 235                 240 aag gag gaa tat gag gct gct cga act gtg cta cag gag gaa ata gct    884
Lys Glu Glu Tyr Glu Ala Ala Arg Thr Val Leu Gln Glu Glu Ile Ala
245                 250                 255                 260 cgt ggt gct tcc ata cag gac att cga gca agg cta aca aaa act aat    932
Arg Gly Ala Ser Ile Gln Asp Ile Arg Ala Arg Leu Thr Lys Thr Asn
                265                 270                 275 gat aaa agt caa agc aaa gaa gag cct ctt cat gta aca aag agt gat    980
Asp Lys Ser Gln Ser Lys Glu Glu Pro Leu His Val Thr Lys Ser Asp
            280                 285                 290 ata cct gat gac ctt gcc caa gca caa gct tac att agg tgg gag aaa    1028
Ile Pro Asp Asp Leu Ala Gln Ala Gln Ala Tyr Ile Arg Trp Glu Lys
        295                 300                 305 gca gga aag ccg aac tat cct cca gaa aag caa att gaa gaa ctc gaa    1076
Ala Gly Lys Pro Asn Tyr Pro Pro Glu Lys Gln Ile Glu Glu Leu Glu
    310                 315                 320 gaa gca aga aga gaa ttg caa ctt gag ctt gag aaa ggc att acc ctt    1124
Glu Ala Arg Arg Glu Leu Gln Leu Glu Leu Glu Lys Gly Ile Thr Leu
325                 330                 335                 340 gat gag ttg cgg aaa acg att aca aaa ggg gag ata aaa act aag gtg    1172
Asp Glu Leu Arg Lys Thr Ile Thr Lys Gly Glu Ile Lys Thr Lys Val
                345                 350                 355 gaa aag cac ctg aaa aga agt tct ttt gcc gtt gaa aga atc caa aga    1220
Glu Lys His Leu Lys Arg Ser Ser Phe Ala Val Glu Arg Ile Gln Arg
            360                 365                 370 aag aag aga gac ttt ggg cat ctt att aat aag tat act tcc agt cct    1268
Lys Lys Arg Asp Phe Gly His Leu Ile Asn Lys Tyr Thr Ser Ser Pro
        375                 380                 385 gca gta caa gta caa aag gtc ttg gaa gaa cca cca gcc tta tct aaa    1316
Ala Val Gln Val Gln Lys Val Leu Glu Glu Pro Pro Ala Leu Ser Lys
    390                 395                 400 att aag ctg tat gcc aag gag aag gag gag cag att gat gat ccg atc    1364
Ile Lys Leu Tyr Ala Lys Glu Lys Glu Glu Gln Ile Asp Asp Pro Ile
405                 410                 415                 420
```

```
cta aat aaa aag atc ttt aag gtc gat gat ggg gag cta ctg gta ctg      1412
Leu Asn Lys Lys Ile Phe Lys Val Asp Asp Gly Glu Leu Leu Val Leu
            425             430                 435 gta gca aag tcc tct ggg aag aca aaa gta cat cta gct aca gat ctg      1460
Val Ala Lys Ser Ser Gly Lys Thr Lys Val His Leu Ala Thr Asp Leu
        440                 445                 450 aat cag cca att act ctt cac tgg gca tta tcc aaa agt cct gga gag      1508
Asn Gln Pro Ile Thr Leu His Trp Ala Leu Ser Lys Ser Pro Gly Glu
            455             460                 465 tgg atg gta cca cct tca agc ata ttg cct cct ggg tca att att tta      1556
Trp Met Val Pro Pro Ser Ser Ile Leu Pro Pro Gly Ser Ile Ile Leu
        470                 475                 480 gac aag gct gcc gaa aca cct ttt tca gcc agt tct tct gat ggt cta      1604
Asp Lys Ala Ala Glu Thr Pro Phe Ser Ala Ser Ser Ser Asp Gly Leu
485             490                 495                 500 act tct aag gta caa tct ttg gat ata gta att gaa gat ggc aat ttt      1652
Thr Ser Lys Val Gln Ser Leu Asp Ile Val Ile Glu Asp Gly Asn Phe
            505                 510                 515 gtg ggg atg cca ttt gtt ctt ttg tct ggt gaa aaa tgg att aag aac      1700
Val Gly Met Pro Phe Val Leu Leu Ser Gly Glu Lys Trp Ile Lys Asn
        520                 525                 530 caa ggg tcg gat ttc tat gtt ggc ttc agt gct gca tcc aaa tta gca      1748
Gln Gly Ser Asp Phe Tyr Val Gly Phe Ser Ala Ala Ser Lys Leu Ala
            535                 540                 545 ctc aag gct gct ggg gat ggc agt gga act gca aag tct tta ctg gat      1796
Leu Lys Ala Ala Gly Asp Gly Ser Gly Thr Ala Lys Ser Leu Leu Asp
        550                 555                 560 aaa ata gca gat atg gaa agt gag gct cag aag tca ttt atg cac cgg      1844
Lys Ile Ala Asp Met Glu Ser Glu Ala Gln Lys Ser Phe Met His Arg
565             570                 575                 580 ttt aat att gca gct gac ttg ata gaa gat gcc act agt gct ggt gaa      1892
Phe Asn Ile Ala Ala Asp Leu Ile Glu Asp Ala Thr Ser Ala Gly Glu
            585                 590                 595 ctt ggt ttt gct gga att ctt gta tgg atg agg ttc atg gct aca agg      1940
Leu Gly Phe Ala Gly Ile Leu Val Trp Met Arg Phe Met Ala Thr Arg
        600                 605                 610 caa ctg ata tgg aac aaa aac tat aac gta aaa cca cgt gaa ata agc      1988
Gln Leu Ile Trp Asn Lys Asn Tyr Asn Val Lys Pro Arg Glu Ile Ser
            615                 620                 625 aag gct cag gac aga ctt aca gac ttg ttg cag aat gct ttc acc agt      2036
Lys Ala Gln Asp Arg Leu Thr Asp Leu Leu Gln Asn Ala Phe Thr Ser
        630                 635                 640 cac cct cag tac cgt gaa att ttg cgg atg att atg tca act gtt gga      2084
His Pro Gln Tyr Arg Glu Ile Leu Arg Met Ile Met Ser Thr Val Gly
645             650                 655                 660 cgt gga ggt gaa ggg gat gta gga cag cga att agg gat gaa att ttg      2132
Arg Gly Gly Glu Gly Asp Val Gly Gln Arg Ile Arg Asp Glu Ile Leu
            665                 670                 675 gtc atc cag agg aac aat gac tgc aag ggt ggt atg atg caa gaa tgg      2180
Val Ile Gln Arg Asn Asn Asp Cys Lys Gly Gly Met Met Gln Glu Trp
        680                 685                 690 cat cag aaa ttg cat aat aat act agt cct gat gat gtt gtg atc tgt      2228
His Gln Lys Leu His Asn Asn Thr Ser Pro Asp Asp Val Val Ile Cys
            695                 700                 705 cag gca tta att gac tac atc aag agt gat ttt gat ctt ggt gtt tat      2276
Gln Ala Leu Ile Asp Tyr Ile Lys Ser Asp Phe Asp Leu Gly Val Tyr
        710                 715                 720 tgg aaa acc ctg aat gag aac gga ata aca aaa gag cgt ctt ttg agt      2324
Trp Lys Thr Leu Asn Glu Asn Gly Ile Thr Lys Glu Arg Leu Leu Ser
725             730                 735                 740
```

```
                                                             -continued
tat gac cgt gct atc cat tct gaa cca aat ttt aga gga gat caa aag    2372
Tyr Asp Arg Ala Ile His Ser Glu Pro Asn Phe Arg Gly Asp Gln Lys
            745                 750                 755 ggt ggt ctt ttg cgt gat tta ggt cac tat atg aga aca ttg aag gca    2420
Gly Gly Leu Leu Arg Asp Leu Gly His Tyr Met Arg Thr Leu Lys Ala
        760                 765                 770 gtt cat tca ggt gca gat ctt gag tct gct att gca aac tgc atg ggc    2468
Val His Ser Gly Ala Asp Leu Glu Ser Ala Ile Ala Asn Cys Met Gly
    775                 780                 785 tac aaa act gag gga gaa ggc ttt atg gtt gga gtc cag ata aat cct    2516
Tyr Lys Thr Glu Gly Glu Gly Phe Met Val Gly Val Gln Ile Asn Pro
790                 795                 800 gta tca ggc ttg cca tct ggc ttt cag gac ctc ctc cat ttt gtc tta    2564
Val Ser Gly Leu Pro Ser Gly Phe Gln Asp Leu Leu His Phe Val Leu
805                 810                 815                 820 gac cat gtg gaa gat aaa aat gtg gaa act ctt ctt gag aga ttg cta    2612
Asp His Val Glu Asp Lys Asn Val Glu Thr Leu Leu Glu Arg Leu Leu
                825                 830                 835 gag gct cgt gag gag ctt agg ccc ttg ctt ctc aaa cca aac aac cgt    2660
Glu Ala Arg Glu Glu Leu Arg Pro Leu Leu Leu Lys Pro Asn Asn Arg
            840                 845                 850 cta aag gat ctg ctg ttt ttg gac ata gca ctt gat tct aca gtt aga    2708
Leu Lys Asp Leu Leu Phe Leu Asp Ile Ala Leu Asp Ser Thr Val Arg
        855                 860                 865 aca gca gta gaa agg gga tat gaa gaa ttg aac aac gct aat cct gag    2756
Thr Ala Val Glu Arg Gly Tyr Glu Glu Leu Asn Asn Ala Asn Pro Glu
    870                 875                 880 aaa atc atg tac ttc atc tcc ctc gtt ctt gaa aat ctc gca ctc tct    2804
Lys Ile Met Tyr Phe Ile Ser Leu Val Leu Glu Asn Leu Ala Leu Ser
885                 890                 895                 900 gtg gac gat aat gaa gat ctt gtt tat tgc ttg aag gga tgg aat caa    2852
Val Asp Asp Asn Glu Asp Leu Val Tyr Cys Leu Lys Gly Trp Asn Gln
                905                 910                 915 gct ctt tca atg tcc aat ggt ggg gac aac cat tgg gct tta ttt gca    2900
Ala Leu Ser Met Ser Asn Gly Gly Asp Asn His Trp Ala Leu Phe Ala
            920                 925                 930 aaa gct gtg ctt gac aga acc cgt ctt gca ctt gca agc aag gca gag    2948
Lys Ala Val Leu Asp Arg Thr Arg Leu Ala Leu Ala Ser Lys Ala Glu
        935                 940                 945 tgg tac cat cac tta ttg cag cca tct gcc gaa tat cta gga tca ata    2996
Trp Tyr His His Leu Leu Gln Pro Ser Ala Glu Tyr Leu Gly Ser Ile
    950                 955                 960 ctt ggg gtg gac caa tgg gct ttg aac ata ttt act gaa gaa att ata    3044
Leu Gly Val Asp Gln Trp Ala Leu Asn Ile Phe Thr Glu Glu Ile Ile
965                 970                 975                 980 cgt gct gga tca gca gct tca tta tcc tct ctt ctt aat aga ctc gat    3092
Arg Ala Gly Ser Ala Ala Ser Leu Ser Ser Leu Leu Asn Arg Leu Asp
                985                 990                 995 ccc gtg ctt cgg  aaa act gca aat cta  gga agt tgg cag att  atc      3137
Pro Val Leu Arg Lys Thr Ala Asn Leu Gly Ser Trp Gln Ile Ile
            1000                1005                1010 agt cca gtt gaa  gcc gtt gga tat gtt  gtc gtt gtg gat gag  ttg      3182
Ser Pro Val Glu Ala Val Gly Tyr Val Val Val Val Asp Glu Leu
        1015                1020                1025 ctt tca gtt cag  aat gaa atc tac gag  aag ccc acg atc tta  gta      3227
Leu Ser Val Gln Asn Glu Ile Tyr Glu Lys Pro Thr Ile Leu Val
    1030                1035                1040 gca aaa tct gtt  aaa gga gag gag gaa  att cct gat ggt gct  gtt      3272
Ala Lys Ser Val Lys Gly Glu Glu Glu Ile Pro Asp Gly Ala Val
1045                1050                1055
```

```
gcc ctg ata aca cca gac atg cca gat gtt ctt tca cat gtt tct      3317
Ala Leu Ile Thr Pro Asp Met Pro Asp Val Leu Ser His Val Ser
            1060             1065             1070 gtt cga gct aga aat ggg aag gtt tgc ttt gct aca tgc ttt gat      3362
Val Arg Ala Arg Asn Gly Lys Val Cys Phe Ala Thr Cys Phe Asp
            1075             1080             1085 ccc aat ata ttg gct gac ctc caa gca aag gaa gga agg att ttg      3407
Pro Asn Ile Leu Ala Asp Leu Gln Ala Lys Glu Gly Arg Ile Leu
            1090             1095             1100 ctc tta aag cct aca cct tca gac ata atc tat agt gag gtg aat      3452
Leu Leu Lys Pro Thr Pro Ser Asp Ile Ile Tyr Ser Glu Val Asn
            1105             1110             1115 gag att gag ctc caa agt tca agt aac ttg gta gaa gct gaa act      3497
Glu Ile Glu Leu Gln Ser Ser Ser Asn Leu Val Glu Ala Glu Thr
            1120             1125             1130 tca gca aca ctt aga ttg gtg aaa aag caa ttt ggt ggt tgt tac      3542
Ser Ala Thr Leu Arg Leu Val Lys Lys Gln Phe Gly Gly Cys Tyr
            1135             1140             1145 gca ata tca gca gat gaa ttc aca agt gaa atg gtt gga gct aaa      3587
Ala Ile Ser Ala Asp Glu Phe Thr Ser Glu Met Val Gly Ala Lys
            1150             1155             1160 tca cgt aat att gca tat ctg aaa gga aaa gtg cct tcc tcg gtg      3632
Ser Arg Asn Ile Ala Tyr Leu Lys Gly Lys Val Pro Ser Ser Val
            1165             1170             1175 gga att cct acg tca gta gct ctt cca ttt gga gtc ttt gag aaa      3677
Gly Ile Pro Thr Ser Val Ala Leu Pro Phe Gly Val Phe Glu Lys
            1180             1185             1190 gta ctt tca gac gac ata aat cag gga gtg gca aaa gag ttg caa      3722
Val Leu Ser Asp Asp Ile Asn Gln Gly Val Ala Lys Glu Leu Gln
            1195             1200             1205 att ctg atg aaa aaa cta tct gaa gga gac ttc agc gct ctt ggt      3767
Ile Leu Met Lys Lys Leu Ser Glu Gly Asp Phe Ser Ala Leu Gly
            1210             1215             1220 gaa att cgc aca acg gtt tta gat ctt tca gca cca gct caa ttg      3812
Glu Ile Arg Thr Thr Val Leu Asp Leu Ser Ala Pro Ala Gln Leu
            1225             1230             1235 gtc aaa gag ctg aag gag aag atg cag ggt tct ggc atg cct tgg      3857
Val Lys Glu Leu Lys Glu Lys Met Gln Gly Ser Gly Met Pro Trp
            1240             1245             1250 cct ggt gat gaa ggt cca aag cgg tgg gaa caa gca tgg atg gcc      3902
Pro Gly Asp Glu Gly Pro Lys Arg Trp Glu Gln Ala Trp Met Ala
            1255             1260             1265 ata aaa aag gtg tgg gct tca aaa tgg aat gag aga gca tac ttc      3947
Ile Lys Lys Val Trp Ala Ser Lys Trp Asn Glu Arg Ala Tyr Phe
            1270             1275             1280 agc aca agg aag gtg aaa ctg gat cat gac tat ctg tgc atg gct      3992
Ser Thr Arg Lys Val Lys Leu Asp His Asp Tyr Leu Cys Met Ala
            1285             1290             1295 gtc ctt gtt caa gaa ata ata aat gct gat tat gca ttt gtc att      4037
Val Leu Val Gln Glu Ile Ile Asn Ala Asp Tyr Ala Phe Val Ile
            1300             1305             1310 cac aca acc aac cca tct tcc gga gac gac tca gaa ata tat gcc      4082
His Thr Thr Asn Pro Ser Ser Gly Asp Asp Ser Glu Ile Tyr Ala
            1315             1320             1325 gag gtg gtc agg ggc ctt ggg gaa aca ctt gtt gga gct tat cca      4127
Glu Val Val Arg Gly Leu Gly Glu Thr Leu Val Gly Ala Tyr Pro
            1330             1335             1340 gga cgt gct ttg agt ttt atc tgc aag aaa aag gat ctc aac tct      4172
Gly Arg Ala Leu Ser Phe Ile Cys Lys Lys Lys Asp Leu Asn Ser
            1345             1350             1355
```

```
cct caa gtg tta ggt tac cca agc aaa ccg atc ggc ctt ttc ata      4217
Pro Gln Val Leu Gly Tyr Pro Ser Lys Pro Ile Gly Leu Phe Ile
        1360                1365                1370 aaa aga tct atc atc ttc cga tct gat tcc aat ggg gaa gat ttg      4262
Lys Arg Ser Ile Ile Phe Arg Ser Asp Ser Asn Gly Glu Asp Leu
    1375                1380                1385 gaa ggt tat gcc ggt gct ggc ctc tac gac agt gta cca atg gat      4307
Glu Gly Tyr Ala Gly Ala Gly Leu Tyr Asp Ser Val Pro Met Asp
1390                1395                1400 gag gag gaa aaa gtt gta att gat tac tct tcc gac cca ttg ata      4352
Glu Glu Glu Lys Val Val Ile Asp Tyr Ser Ser Asp Pro Leu Ile
            1405                1410                1415 act gat ggt aac ttc cgc cag aca atc ctg tcc aac att gct cgt      4397
Thr Asp Gly Asn Phe Arg Gln Thr Ile Leu Ser Asn Ile Ala Arg
        1420                1425                1430 gct gga cat gct atc gag gag cta tat ggc tct cct caa gac att      4442
Ala Gly His Ala Ile Glu Glu Leu Tyr Gly Ser Pro Gln Asp Ile
    1435                1440                1445 gag ggt gta gtg agg gat gga aag att tat gtc gtt cag aca aga      4487
Glu Gly Val Val Arg Asp Gly Lys Ile Tyr Val Val Gln Thr Arg
1450                1455                1460 cca cag atg tga ttatattctc gttgtatgtt gttcagagaa gaccacagat       4539
Pro Gln Met
gtgatcatat tctcattgta tcagatctgt gaccacttac ctgatacctc ccatgaagtt   4599
acctgtatga ttatacgtga tccaaagcca tcacatcatg ttcaccttca gctattggag   4659
gagaagtgag aagtaggaat tgcaatatga ggaataataa gaaaaacttt gtaaaagcta   4719
aattagctgg gtatgatata gggagaaatg tgtaaacatt gtactatata tagtatatac   4779
acacgcatta tgtattgcat tatgcactga ataatatcgc agcatcaaag aagaaatcct   4839
ttgggtggtt tc                                                      4851

<210> SEQ ID NO 11
<211> LENGTH: 1464
<212> TYPE: PRT
<213> ORGANISM: Solanum tuberosum

<400> SEQUENCE: 11

Met Ser Asn Ser Leu Gly Asn Asn Leu Leu Tyr Gln Gly Phe Leu Thr
1               5                   10                  15

Ser Thr Val Leu Glu His Lys Ser Arg Ile Ser Pro Pro Cys Val Gly
            20                  25                  30

Gly Asn Ser Leu Phe Gln Gln Gln Val Ile Ser Lys Ser Pro Leu Ser
        35                  40                  45

Thr Glu Phe Arg Gly Asn Arg Leu Lys Val Gln Lys Lys Ile Pro
    50                  55                  60

Met Glu Lys Lys Arg Ala Phe Ser Ser Ser Pro His Ala Val Leu Thr
65                  70                  75                  80

Thr Asp Thr Ser Ser Glu Leu Ala Glu Lys Phe Ser Leu Gly Gly Asn
                85                  90                  95

Ile Glu Leu Gln Val Asp Val Arg Pro Pro Thr Ser Gly Asp Val Ser
            100                 105                 110

Phe Val Asp Phe Gln Val Thr Asn Gly Ser Asp Lys Leu Phe Leu His
        115                 120                 125

Trp Gly Ala Val Lys Phe Gly Lys Glu Thr Trp Ser Leu Pro Asn Asp
    130                 135                 140

Arg Pro Asp Gly Thr Lys Val Tyr Lys Asn Lys Ala Leu Arg Thr Pro
145                 150                 155                 160
```

```
Phe Val Lys Ser Gly Ser Asn Ser Ile Leu Arg Leu Glu Ile Arg Asp
                165                 170                 175

Thr Ala Ile Glu Ala Ile Glu Phe Leu Ile Tyr Asp Glu Ala His Asp
            180                 185                 190

Lys Trp Ile Lys Asn Asn Gly Gly Asn Phe Arg Val Lys Leu Ser Arg
        195                 200                 205

Lys Glu Ile Arg Gly Pro Asp Val Ser Val Pro Glu Glu Leu Val Gln
    210                 215                 220

Ile Gln Ser Tyr Leu Arg Trp Glu Arg Lys Gly Lys Gln Asn Tyr Pro
225                 230                 235                 240

Pro Glu Lys Glu Lys Glu Glu Tyr Glu Ala Ala Arg Thr Val Leu Gln
                245                 250                 255

Glu Glu Ile Ala Arg Gly Ala Ser Ile Gln Asp Ile Arg Ala Arg Leu
            260                 265                 270

Thr Lys Thr Asn Asp Lys Ser Gln Ser Lys Glu Glu Pro Leu His Val
        275                 280                 285

Thr Lys Ser Asp Ile Pro Asp Leu Ala Gln Ala Gln Ala Tyr Ile
    290                 295                 300

Arg Trp Glu Lys Ala Gly Lys Pro Asn Tyr Pro Pro Glu Lys Gln Ile
305                 310                 315                 320

Glu Glu Leu Glu Glu Ala Arg Arg Glu Leu Gln Leu Glu Leu Glu Lys
                325                 330                 335

Gly Ile Thr Leu Asp Glu Leu Arg Lys Thr Ile Thr Lys Gly Glu Ile
            340                 345                 350

Lys Thr Lys Val Glu Lys His Leu Lys Arg Ser Ser Phe Ala Val Glu
        355                 360                 365

Arg Ile Gln Arg Lys Lys Arg Asp Phe Gly His Leu Ile Asn Lys Tyr
370                 375                 380

Thr Ser Ser Pro Ala Val Gln Val Gln Lys Val Leu Glu Glu Pro Pro
385                 390                 395                 400

Ala Leu Ser Lys Ile Lys Leu Tyr Ala Lys Glu Lys Glu Glu Gln Ile
                405                 410                 415

Asp Asp Pro Ile Leu Asn Lys Lys Ile Phe Lys Val Asp Asp Gly Glu
            420                 425                 430

Leu Leu Val Leu Val Ala Lys Ser Ser Gly Lys Thr Lys Val His Leu
        435                 440                 445

Ala Thr Asp Leu Asn Gln Pro Ile Thr Leu His Trp Ala Leu Ser Lys
    450                 455                 460

Ser Pro Gly Glu Trp Met Val Pro Pro Ser Ser Ile Leu Pro Pro Gly
465                 470                 475                 480

Ser Ile Ile Leu Asp Lys Ala Ala Glu Thr Pro Phe Ser Ala Ser Ser
                485                 490                 495

Ser Asp Gly Leu Thr Ser Lys Val Gln Ser Leu Asp Ile Val Ile Glu
            500                 505                 510

Asp Gly Asn Phe Val Gly Met Pro Phe Val Leu Leu Ser Gly Glu Lys
        515                 520                 525

Trp Ile Lys Asn Gln Gly Ser Asp Phe Tyr Val Gly Phe Ser Ala Ala
    530                 535                 540

Ser Lys Leu Ala Leu Lys Ala Ala Gly Asp Gly Ser Gly Thr Ala Lys
545                 550                 555                 560

Ser Leu Leu Asp Lys Ile Ala Asp Met Glu Ser Glu Ala Gln Lys Ser
                565                 570                 575

Phe Met His Arg Phe Asn Ile Ala Ala Asp Leu Ile Glu Asp Ala Thr
            580                 585                 590
```

```
Ser Ala Gly Glu Leu Gly Phe Ala Gly Ile Leu Val Trp Met Arg Phe
        595                 600                 605
Met Ala Thr Arg Gln Leu Ile Trp Asn Lys Asn Tyr Asn Val Lys Pro
        610                 615                 620
Arg Glu Ile Ser Lys Ala Gln Asp Arg Leu Thr Asp Leu Leu Gln Asn
625                 630                 635                 640
Ala Phe Thr Ser His Pro Gln Tyr Arg Glu Ile Leu Arg Met Ile Met
                645                 650                 655
Ser Thr Val Gly Arg Gly Gly Glu Gly Asp Val Gly Gln Arg Ile Arg
                660                 665                 670
Asp Glu Ile Leu Val Ile Gln Arg Asn Asn Asp Cys Lys Gly Gly Met
            675                 680                 685
Met Gln Glu Trp His Gln Lys Leu His Asn Asn Thr Ser Pro Asp Asp
        690                 695                 700
Val Val Ile Cys Gln Ala Leu Ile Asp Tyr Ile Lys Ser Asp Phe Asp
705                 710                 715                 720
Leu Gly Val Tyr Trp Lys Thr Leu Asn Glu Asn Gly Ile Thr Lys Glu
                725                 730                 735
Arg Leu Leu Ser Tyr Asp Arg Ala Ile His Ser Glu Pro Asn Phe Arg
                740                 745                 750
Gly Asp Gln Lys Gly Gly Leu Leu Arg Asp Leu Gly His Tyr Met Arg
            755                 760                 765
Thr Leu Lys Ala Val His Ser Gly Ala Asp Leu Glu Ser Ala Ile Ala
        770                 775                 780
Asn Cys Met Gly Tyr Lys Thr Glu Gly Glu Gly Phe Met Val Gly Val
785                 790                 795                 800
Gln Ile Asn Pro Val Ser Gly Leu Pro Ser Gly Phe Gln Asp Leu Leu
                805                 810                 815
His Phe Val Leu Asp His Val Glu Asp Lys Asn Val Glu Thr Leu Leu
                820                 825                 830
Glu Arg Leu Leu Glu Ala Arg Glu Glu Leu Arg Pro Leu Leu Leu Lys
            835                 840                 845
Pro Asn Asn Arg Leu Lys Asp Leu Leu Phe Leu Asp Ile Ala Leu Asp
        850                 855                 860
Ser Thr Val Arg Thr Ala Val Glu Arg Gly Tyr Glu Glu Leu Asn Asn
865                 870                 875                 880
Ala Asn Pro Glu Lys Ile Met Tyr Phe Ile Ser Leu Val Leu Glu Asn
                885                 890                 895
Leu Ala Leu Ser Val Asp Asp Asn Glu Asp Leu Val Tyr Cys Leu Lys
                900                 905                 910
Gly Trp Asn Gln Ala Leu Ser Met Ser Asn Gly Gly Asp Asn His Trp
            915                 920                 925
Ala Leu Phe Ala Lys Ala Val Leu Asp Arg Thr Arg Leu Ala Leu Ala
        930                 935                 940
Ser Lys Ala Glu Trp Tyr His His Leu Leu Gln Pro Ser Ala Glu Tyr
945                 950                 955                 960
Leu Gly Ser Ile Leu Gly Val Asp Gln Trp Ala Leu Asn Ile Phe Thr
                965                 970                 975
Glu Glu Ile Ile Arg Ala Gly Ser Ala Ala Ser Leu Ser Leu Leu
                980                 985                 990
Asn Arg Leu Asp Pro Val Leu Arg Lys Thr Ala Asn Leu Gly Ser Trp
            995                1000                1005
Gln Ile Ile Ser Pro Val Glu Ala Val Gly Tyr Val Val Val Val
```

```
               1010                1015                1020

Asp Glu Leu Leu Ser Val Gln Asn Glu Ile Tyr Glu Lys Pro Thr
    1025                1030                1035

Ile Leu Val Ala Lys Ser Val Lys Gly Glu Glu Ile Pro Asp
    1040                1045                1050

Gly Ala Val Ala Leu Ile Thr Pro Asp Met Pro Asp Val Leu Ser
    1055                1060                1065

His Val Ser Val Arg Ala Arg Asn Gly Lys Val Cys Phe Ala Thr
    1070                1075                1080

Cys Phe Asp Pro Asn Ile Leu Ala Asp Leu Gln Ala Lys Glu Gly
    1085                1090                1095

Arg Ile Leu Leu Leu Lys Pro Thr Pro Ser Asp Ile Ile Tyr Ser
    1100                1105                1110

Glu Val Asn Glu Ile Glu Leu Gln Ser Ser Ser Asn Leu Val Glu
    1115                1120                1125

Ala Glu Thr Ser Ala Thr Leu Arg Leu Val Lys Lys Gln Phe Gly
    1130                1135                1140

Gly Cys Tyr Ala Ile Ser Ala Asp Glu Phe Thr Ser Glu Met Val
    1145                1150                1155

Gly Ala Lys Ser Arg Asn Ile Ala Tyr Leu Lys Gly Lys Val Pro
    1160                1165                1170

Ser Ser Val Gly Ile Pro Thr Ser Val Ala Leu Pro Phe Gly Val
    1175                1180                1185

Phe Glu Lys Val Leu Ser Asp Asp Ile Asn Gln Gly Val Ala Lys
    1190                1195                1200

Glu Leu Gln Ile Leu Met Lys Lys Leu Ser Glu Gly Asp Phe Ser
    1205                1210                1215

Ala Leu Gly Glu Ile Arg Thr Thr Val Leu Asp Leu Ser Ala Pro
    1220                1225                1230

Ala Gln Leu Val Lys Glu Leu Lys Glu Lys Met Gln Gly Ser Gly
    1235                1240                1245

Met Pro Trp Pro Gly Asp Glu Gly Pro Lys Arg Trp Glu Gln Ala
    1250                1255                1260

Trp Met Ala Ile Lys Lys Val Trp Ala Ser Lys Trp Asn Glu Arg
    1265                1270                1275

Ala Tyr Phe Ser Thr Arg Lys Val Lys Leu Asp His Asp Tyr Leu
    1280                1285                1290

Cys Met Ala Val Leu Val Gln Glu Ile Ile Asn Ala Asp Tyr Ala
    1295                1300                1305

Phe Val Ile His Thr Thr Asn Pro Ser Ser Gly Asp Asp Ser Glu
    1310                1315                1320

Ile Tyr Ala Glu Val Val Arg Gly Leu Gly Glu Thr Leu Val Gly
    1325                1330                1335

Ala Tyr Pro Gly Arg Ala Leu Ser Phe Ile Cys Lys Lys Lys Asp
    1340                1345                1350

Leu Asn Ser Pro Gln Val Leu Gly Tyr Pro Ser Lys Pro Ile Gly
    1355                1360                1365

Leu Phe Ile Lys Arg Ser Ile Ile Phe Arg Ser Asp Ser Asn Gly
    1370                1375                1380

Glu Asp Leu Glu Gly Tyr Ala Gly Ala Gly Leu Tyr Asp Ser Val
    1385                1390                1395

Pro Met Asp Glu Glu Glu Lys Val Val Ile Asp Tyr Ser Ser Asp
    1400                1405                1410
```

-continued

```
Pro Leu Ile Thr Asp Gly Asn Phe Arg Gln Thr Ile Leu Ser Asn
    1415                1420                1425

Ile Ala Arg Ala Gly His Ala Ile Glu Glu Leu Tyr Gly Ser Pro
    1430                1435                1440

Gln Asp Ile Glu Gly Val Val Arg Asp Gly Lys Ile Tyr Val Val
    1445                1450                1455

Gln Thr Arg Pro Gln Met
    1460

<210> SEQ ID NO 12
<211> LENGTH: 4576
<212> TYPE: DNA
<213> ORGANISM: Oryza sativa
<220> FEATURE:
<221> NAME/KEY: CDS
<222> LOCATION: (20)..(4393)
<223> OTHER INFORMATION:
<300> PUBLICATION INFORMATION:
<308> DATABASE ACCESSION NUMBER: NCBI / AR400814
<309> DATABASE ENTRY DATE: 2003-12-18

<400> SEQUENCE: 12
cttacagata ttcgtgcag atg agc gga ttc tcc gcg gca gct gct gcg gcc        52
                    Met Ser Gly Phe Ser Ala Ala Ala Ala Ala
                     1               5                  10 gag cgg tgc gcg ctc ggc ctc ggc gtc cac gcg cgc ccc gcc tcg ccc        100
Glu Arg Cys Ala Leu Gly Leu Gly Val His Ala Arg Pro Ala Ser Pro
            15                  20                  25 tcg ccg gcg ctg ctc ccg ccg gcg gct ctc cgc cgc ggc cgc gtc ctc        148
Ser Pro Ala Leu Leu Pro Pro Ala Ala Leu Arg Arg Gly Arg Arg Leu
        30                  35                  40 ccc gcg gcc acc acc acc ctc gcc gtc tcc cgt cgg agc ctc ctc gcc        196
Pro Ala Ala Thr Thr Thr Leu Ala Val Ser Arg Arg Ser Leu Leu Ala
    45                  50                  55 cct cgc gcc atc gcc gct tcc acc ggc cgc gcc tcc ccg ggc ctt gtc        244
Pro Arg Ala Ile Ala Ala Ser Thr Gly Arg Ala Ser Pro Gly Leu Val
60                  65                  70                  75 gga agg ttc acc ctg gat gcc aac tcc gag ctt aag gtg aca ttg aac        292
Gly Arg Phe Thr Leu Asp Ala Asn Ser Glu Leu Lys Val Thr Leu Asn
                80                  85                  90 cca gca ccg cag ggt tcg gtg gtg gag atc aat cta gag gca act aac        340
Pro Ala Pro Gln Gly Ser Val Val Glu Ile Asn Leu Glu Ala Thr Asn
            95                  100                 105 acc agc ggc tcc ctg ata ctg cat tgg ggc gcc ctt cgc ccg gat aga        388
Thr Ser Gly Ser Leu Ile Leu His Trp Gly Ala Leu Arg Pro Asp Arg
        110                 115                 120 gga gaa tgg ctc cta cca tcc cgg aaa cca gat ggc acg aca gtg tac        436
Gly Glu Trp Leu Leu Pro Ser Arg Lys Pro Asp Gly Thr Thr Val Tyr
    125                 130                 135 aag aac agg gct ctt agg acg cct ttt ata aag tca ggt gat aac tcc        484
Lys Asn Arg Ala Leu Arg Thr Pro Phe Ile Lys Ser Gly Asp Asn Ser
140                 145                 150                 155 acg ctg aaa att gag ata gat gat cct gca gtg caa gcc att gag ttc        532
Thr Leu Lys Ile Glu Ile Asp Asp Pro Ala Val Gln Ala Ile Glu Phe
                160                 165                 170 ctc ata ttt gat gag gca cgg aat aat tgg tac aaa aac aat ggc cag        580
Leu Ile Phe Asp Glu Ala Arg Asn Asn Trp Tyr Lys Asn Asn Gly Gln
            175                 180                 185 aat ttc caa att cag cta caa gcg agc caa tat caa ggg cag ggt aca        628
Asn Phe Gln Ile Gln Leu Gln Ala Ser Gln Tyr Gln Gly Gln Gly Thr
        190                 195                 200 tct act gct act tct tct act gtg gtt cca gag gat ctt gtg cag ata        676
```

|  |  |
|---|---|
| Ser Thr Ala Thr Ser Ser Thr Val Val Pro Glu Asp Leu Val Gln Ile<br>205 210 215 | |
| caa tca tat ctt cgg tgg gaa aga aag gga aag cag tca tat aca cct<br>Gln Ser Tyr Leu Arg Trp Glu Arg Lys Gly Lys Gln Ser Tyr Thr Pro<br>220 225 230 235 | 724 |
| gag caa gag aag gag gag tat gaa gca gca cga act gag ttg ata gag<br>Glu Gln Glu Lys Glu Glu Tyr Glu Ala Ala Arg Thr Glu Leu Ile Glu<br>240 245 250 | 772 |
| gaa tta aac aag ggt gtt tct ttg gag aag cta cga gcg aaa ctg aca<br>Glu Leu Asn Lys Gly Val Ser Leu Glu Lys Leu Arg Ala Lys Leu Thr<br>255 260 265 | 820 |
| aag aca cct gag gca act gat agt aat gct cct gca tct gaa agc act<br>Lys Thr Pro Glu Ala Thr Asp Ser Asn Ala Pro Ala Ser Glu Ser Thr<br>270 275 280 | 868 |
| gtg act act aaa gtc cca gag gaa ctt gta caa gtc cag gct tac ata<br>Val Thr Thr Lys Val Pro Glu Glu Leu Val Gln Val Gln Ala Tyr Ile<br>285 290 295 | 916 |
| agg tgg gag aaa gca ggc aag cca aat tat gcc cca gag aag caa ttg<br>Arg Trp Glu Lys Ala Gly Lys Pro Asn Tyr Ala Pro Glu Lys Gln Leu<br>300 305 310 315 | 964 |
| gtc gag ttt gag gaa gca agg aag gaa ctg cag tct gag ttg gat aag<br>Val Glu Phe Glu Glu Ala Arg Lys Glu Leu Gln Ser Glu Leu Asp Lys<br>320 325 330 | 1012 |
| ggg acc tca gtt gag cag ttg agg aac aaa att ttg aaa ggg aac att<br>Gly Thr Ser Val Glu Gln Leu Arg Asn Lys Ile Leu Lys Gly Asn Ile<br>335 340 345 | 1060 |
| gag aca aaa gtt tcc aag cag ctg aag gac aaa aaa tac ttt tct gtg<br>Glu Thr Lys Val Ser Lys Gln Leu Lys Asp Lys Lys Tyr Phe Ser Val<br>350 355 360 | 1108 |
| gaa aga att cag cgg aaa aaa cga gat att gtg caa cta ctt aaa aaa<br>Glu Arg Ile Gln Arg Lys Lys Arg Asp Ile Val Gln Leu Leu Lys Lys<br>365 370 375 | 1156 |
| cac aag cct act gtt atg gaa gcg caa gta gag act cct aaa caa ccc<br>His Lys Pro Thr Val Met Glu Ala Gln Val Glu Thr Pro Lys Gln Pro<br>380 385 390 395 | 1204 |
| act gtt ctg gat ctc ttc aca aag tca tta cag gag cag gat aac tgt<br>Thr Val Leu Asp Leu Phe Thr Lys Ser Leu Gln Glu Gln Asp Asn Cys<br>400 405 410 | 1252 |
| gag gtt cta agc aga aag ctt ttc aag ttc ggt gac aag gag ata ctg<br>Glu Val Leu Ser Arg Lys Leu Phe Lys Phe Gly Asp Lys Glu Ile Leu<br>415 420 425 | 1300 |
| gga att acc acc gtt gct cta gga aaa acc aaa gtt cac ttg gca aca<br>Gly Ile Thr Thr Val Ala Leu Gly Lys Thr Lys Val His Leu Ala Thr<br>430 435 440 | 1348 |
| aac tat atg gag cca ctt ata ctt cac tgg gcg ttg tca aaa gag aat<br>Asn Tyr Met Glu Pro Leu Ile Leu His Trp Ala Leu Ser Lys Glu Asn<br>445 450 455 | 1396 |
| gga gag tgg cag gca cct ccc tca agc ata ttg cca tct ggt tca tca<br>Gly Glu Trp Gln Ala Pro Pro Ser Ser Ile Leu Pro Ser Gly Ser Ser<br>460 465 470 475 | 1444 |
| ttg cta gac aag gca tgt gaa act tca ttc agt gaa tat gaa ttg aat<br>Leu Leu Asp Lys Ala Cys Glu Thr Ser Phe Ser Glu Tyr Glu Leu Asn<br>480 485 490 | 1492 |
| ggt ctg cat tgt cag gtt gtt gag atc gag ctt gac gat ggt gga tac<br>Gly Leu His Cys Gln Val Val Glu Ile Glu Leu Asp Asp Gly Gly Tyr<br>495 500 505 | 1540 |
| aag cgg atg ccc ttt gtt ctc cgg tct ggt gaa aca tgg atg aaa aat<br>Lys Arg Met Pro Phe Val Leu Arg Ser Gly Glu Thr Trp Met Lys Asn<br>510 515 520 | 1588 |
| aat ggc tct gac ttt tac ttg gat ttc agc acc aaa gtt gca aaa aat | 1636 |

```
                Asn Gly Ser Asp Phe Tyr Leu Asp Phe Ser Thr Lys Val Ala Lys Asn
                525                 530                 535 aca aag gat act ggt gat gct ggt aaa ggc act gct gag gcc ttg ctt        1684
Thr Lys Asp Thr Gly Asp Ala Gly Lys Gly Thr Ala Glu Ala Leu Leu
540                 545                 550                 555 gaa aga ata gca gat cta gag gaa gat gcc caa cga tct ctt atg cac        1732
Glu Arg Ile Ala Asp Leu Glu Glu Asp Ala Gln Arg Ser Leu Met His
                560                 565                 570 aga ttc aat att gca gca gat cta gtt gac caa gcg aga gat aat gga        1780
Arg Phe Asn Ile Ala Ala Asp Leu Val Asp Gln Ala Arg Asp Asn Gly
            575                 580                 585 tta ttg ggt att att gga att ttt gtt tgg att ggg ttc atg gct aca        1828
Leu Leu Gly Ile Ile Gly Ile Phe Val Trp Ile Gly Phe Met Ala Thr
        590                 595                 600 agg caa cta ata tgg aac aag aac tac aat gtg aag cca cgt gag ata        1876
Arg Gln Leu Ile Trp Asn Lys Asn Tyr Asn Val Lys Pro Arg Glu Ile
    605                 610                 615 agc aaa gcc caa gat agg ttt aca gat gat ctt gag aat atg tac aga        1924
Ser Lys Ala Gln Asp Arg Phe Thr Asp Asp Leu Glu Asn Met Tyr Arg
620                 625                 630                 635 act tac cca caa tat cag gag atc tta aga atg ata atg tct gct gtt        1972
Thr Tyr Pro Gln Tyr Gln Glu Ile Leu Arg Met Ile Met Ser Ala Val
                640                 645                 650 ggt cgg gga ggt gaa ggt gat gtt ggt caa cgc att cgt gat gag ata        2020
Gly Arg Gly Gly Glu Gly Asp Val Gly Gln Arg Ile Arg Asp Glu Ile
            655                 660                 665 tta gta atc cag aga aat aat gac tgc aaa ggt gga atg atg gag gag        2068
Leu Val Ile Gln Arg Asn Asn Asp Cys Lys Gly Gly Met Met Glu Glu
        670                 675                 680 tgg cac cag aaa ctg cac aac aat aca agc cca gat gat gta gtg atc        2116
Trp His Gln Lys Leu His Asn Asn Thr Ser Pro Asp Asp Val Val Ile
    685                 690                 695 tgc cag gcc cta ctt gat tat atc aag agt gat ttt gat act ggt gtt        2164
Cys Gln Ala Leu Leu Asp Tyr Ile Lys Ser Asp Phe Asp Thr Gly Val
700                 705                 710                 715 tac tgg gac acc ttg aaa aaa ggt gga ata aca aaa gag cgt cta ttg        2212
Tyr Trp Asp Thr Leu Lys Lys Gly Gly Ile Thr Lys Glu Arg Leu Leu
                720                 725                 730 agc tat gat cga ccg att cat tca gag cca aat ttc agg agt gaa cag        2260
Ser Tyr Asp Arg Pro Ile His Ser Glu Pro Asn Phe Arg Ser Glu Gln
            735                 740                 745 aaa gat agc tta ctc cgt gac ttg ggc aat tat atg aga agc ctc aag        2308
Lys Asp Ser Leu Leu Arg Asp Leu Gly Asn Tyr Met Arg Ser Leu Lys
        750                 755                 760 gca gtg cat tct ggt gct gat ctt gaa tct gct ata gca act tgc atg        2356
Ala Val His Ser Gly Ala Asp Leu Glu Ser Ala Ile Ala Thr Cys Met
    765                 770                 775 gga tac aaa tca gag ggt gaa ggt ttc atg gtt ggt gtt cag att aat        2404
Gly Tyr Lys Ser Glu Gly Glu Gly Phe Met Val Gly Val Gln Ile Asn
780                 785                 790                 795 cca gtg aag ggt ttg cca tct gga ttt cct aaa ttg ctt gaa ttt ata        2452
Pro Val Lys Gly Leu Pro Ser Gly Phe Pro Lys Leu Leu Glu Phe Ile
                800                 805                 810 ctt gac cat gtt gag gat aaa tca gca aga cca ctt ctt gga ggg tta        2500
Leu Asp His Val Glu Asp Lys Ser Ala Arg Pro Leu Leu Gly Gly Leu
            815                 820                 825 ttg gag gct cga gct gaa cta cac cct ttg ctc ctt ggc tct cct gaa        2548
Leu Glu Ala Arg Ala Glu Leu His Pro Leu Leu Leu Gly Ser Pro Glu
        830                 835                 840 cgc atg aag gat ctt atc ttt tta gac att gct ctt gat tct act ttc        2596
```

```
                    Arg Met Lys Asp Leu Ile Phe Leu Asp Ile Ala Leu Asp Ser Thr Phe
                    845                 850                 855 agg aca gca gtc gaa aga tca tat gag gag ctc aat aat gta gaa cca         2644
Arg Thr Ala Val Glu Arg Ser Tyr Glu Glu Leu Asn Asn Val Glu Pro
860                 865                 870                 875 gag aaa att atg tac ttc atc agt ctt gtc ctt gaa aat ctt gct tta         2692
Glu Lys Ile Met Tyr Phe Ile Ser Leu Val Leu Glu Asn Leu Ala Leu
                    880                 885                 890 tcc acc gac gac aat gaa gat atc cta tat tgc tta aag gga tgg aat         2740
Ser Thr Asp Asp Asn Glu Asp Ile Leu Tyr Cys Leu Lys Gly Trp Asn
                895                 900                 905 caa gcc gtg gaa atg gct aaa cag aaa aac aac caa tgg gct ctc tat         2788
Gln Ala Val Glu Met Ala Lys Gln Lys Asn Asn Gln Trp Ala Leu Tyr
                    910                 915                 920 gct aaa gca ttt ctg gac aga acc aga ctt gcc ctt gca agc aag gga         2836
Ala Lys Ala Phe Leu Asp Arg Thr Arg Leu Ala Leu Ala Ser Lys Gly
925                 930                 935 gaa caa tac tat aat ttg atg cag ccc tca gct gaa tat ctt ggc tcg         2884
Glu Gln Tyr Tyr Asn Leu Met Gln Pro Ser Ala Glu Tyr Leu Gly Ser
940                 945                 950                 955 tta ctt aac att gac caa tgg gca gtt aat atc ttt aca gaa gaa att         2932
Leu Leu Asn Ile Asp Gln Trp Ala Val Asn Ile Phe Thr Glu Glu Ile
                960                 965                 970 att cgt ggt gga tca gct gct acc ctg tct gct ctt ctg aat cgg att         2980
Ile Arg Gly Gly Ser Ala Ala Thr Leu Ser Ala Leu Leu Asn Arg Ile
                975                 980                 985 gat cct gtt ctt agg aat gtt gca cag ctt gga agt tgg  cag gtt ata       3028
Asp Pro Val Leu Arg Asn Val Ala Gln Leu Gly Ser Trp  Gln Val Ile
            990                 995                 1000 agc cca gtt gaa gta tca ggt  tac att gta gtg gtt  gat gaa ttg          3073
Ser Pro Val Glu Val Ser Gly  Tyr Ile Val Val Val  Asp Glu Leu
        1005                 1010                 1015 ctt gct gtt caa aac aaa tcc  tat gat aaa cca act  atc ctt gtg          3118
Leu Ala Val Gln Asn Lys Ser  Tyr Asp Lys Pro Thr  Ile Leu Val
        1020                 1025                 1030 gca aag agt gtc aag gga gag  gaa gaa ata cca gat  gga gtt gtt          3163
Ala Lys Ser Val Lys Gly Glu  Glu Glu Ile Pro Asp  Gly Val Val
        1035                 1040                 1045 ggt gtt att aca cct gat atg  cca gat gtt ctc tcc  cat gta tca          3208
Gly Val Ile Thr Pro Asp Met  Pro Asp Val Leu Ser  His Val Ser
        1050                 1055                 1060 gtc cga gca agg aat tgc aag  gtt tta ttt gca aca  tgc ttt gat          3253
Val Arg Ala Arg Asn Cys Lys  Val Leu Phe Ala Thr  Cys Phe Asp
        1065                 1070                 1075 cct aac acc ttg tct gaa ctc  caa gga cat gat ggg  aaa gtg ttt          3298
Pro Asn Thr Leu Ser Glu Leu  Gln Gly His Asp Gly  Lys Val Phe
        1080                 1085                 1090 tcc ttc aaa cct act tct gca  gat atc acc tat agg  gag att cca          3343
Ser Phe Lys Pro Thr Ser Ala  Asp Ile Thr Tyr Arg  Glu Ile Pro
        1095                 1100                 1105 gag agt gaa ctg caa tca ggt  tct cta aat gca gaa  gct ggc cag          3388
Glu Ser Glu Leu Gln Ser Gly  Ser Leu Asn Ala Glu  Ala Gly Gln
        1110                 1115                 1120 gca gtg cca tct gtg tca tta  gtc aag aag aag ttt  ctt gga aaa          3433
Ala Val Pro Ser Val Ser Leu  Val Lys Lys Lys Phe  Leu Gly Lys
        1125                 1130                 1135 tat gca ata tca gca gaa gaa  ttc tct gag gaa atg  gtt ggg gcc          3478
Tyr Ala Ile Ser Ala Glu Glu  Phe Ser Glu Glu Met  Val Gly Ala
        1140                 1145                 1150 aag tct cgc aac gta gca tac  ctc aaa gga aaa gta  ccc tca tgg          3523
```

```
                       -continued

Lys Ser Arg Asn Val Ala Tyr Leu Lys Gly Lys Val Pro Ser Trp
1155                1160                1165 gtt ggt gtc cct aca tca gtt gcg att cca ttt ggg acc ttt gag      3568
Val Gly Val Pro Thr Ser Val Ala Ile Pro Phe Gly Thr Phe Glu
1170                1175                1180 aag gtt ttg tct gat gaa atc aat aag gaa gtc gcg caa acc ata      3613
Lys Val Leu Ser Asp Glu Ile Asn Lys Glu Val Ala Gln Thr Ile
        1185                1190                1195 caa atg ctg aag gga aaa ctt gct caa gat gat ttt agt gct cta      3658
Gln Met Leu Lys Gly Lys Leu Ala Gln Asp Asp Phe Ser Ala Leu
1200                1205                1210 ggc gaa ata cgg aaa act gtt ctc aat tta act gct cct act caa      3703
Gly Glu Ile Arg Lys Thr Val Leu Asn Leu Thr Ala Pro Thr Gln
1215                1220                1225 ctg atc aag gaa ctg aag gag aag atg cta ggc tct gga atg ccc      3748
Leu Ile Lys Glu Leu Lys Glu Lys Met Leu Gly Ser Gly Met Pro
        1230                1235                1240 tgg cct gga gat gaa ggt gac caa cgt tgg gag caa gca tgg atg      3793
Trp Pro Gly Asp Glu Gly Asp Gln Arg Trp Glu Gln Ala Trp Met
1245                1250                1255 gca att aaa aag gtt tgg gcg tca aaa tgg aat gaa aga gca tat      3838
Ala Ile Lys Lys Val Trp Ala Ser Lys Trp Asn Glu Arg Ala Tyr
1260                1265                1270 ttt agc act cgt aag gtg aag ctt gat cat gac tac ctt tcc atg      3883
Phe Ser Thr Arg Lys Val Lys Leu Asp His Asp Tyr Leu Ser Met
        1275                1280                1285 gct gta ctt gta caa gaa att gtc aat gca gac tat gcc ttt gtc      3928
Ala Val Leu Val Gln Glu Ile Val Asn Ala Asp Tyr Ala Phe Val
1290                1295                1300 att cat act act aac cca tca tcg gga gat tcg tct gag ata tat      3973
Ile His Thr Thr Asn Pro Ser Ser Gly Asp Ser Ser Glu Ile Tyr
1305                1310                1315 gct gaa gtg gtg aaa ggg ctt gga gaa aca ctt gta gga gcc tat      4018
Ala Glu Val Val Lys Gly Leu Gly Glu Thr Leu Val Gly Ala Tyr
        1320                1325                1330 cct ggt cgc gcc atg agc ttt gta tgt aag aaa aac gac ctt gac      4063
Pro Gly Arg Ala Met Ser Phe Val Cys Lys Lys Asn Asp Leu Asp
1335                1340                1345 tct ccc aag gta ctg ggt ttc cca agc aag cca att ggt gtc ttc      4108
Ser Pro Lys Val Leu Gly Phe Pro Ser Lys Pro Ile Gly Val Phe
1350                1355                1360 ata aag aga tca atc atc ttt cgt tcg gat tcc aac ggt gag gat      4153
Ile Lys Arg Ser Ile Ile Phe Arg Ser Asp Ser Asn Gly Glu Asp
        1365                1370                1375 tta gaa ggg tat gct gga gca aga ctg tat gat agt gtc cct atg      4198
Leu Glu Gly Tyr Ala Gly Ala Arg Leu Tyr Asp Ser Val Pro Met
1380                1385                1390 gat gag gaa gat gaa gtc ata gtc gac tac aac aac gga ccc ctc      4243
Asp Glu Glu Asp Glu Val Ile Val Asp Tyr Asn Asn Gly Pro Leu
1395                1400                1405 att aca gat cag gga ttc caa aaa tcc aac ctc ccg agc att gca      4288
Ile Thr Asp Gln Gly Phe Gln Lys Ser Asn Leu Pro Ser Ile Ala
        1410                1415                1420 ccg gct ggt cat gcc att gag gag ctt tat ggg tcc cca cag gat      4333
Pro Ala Gly His Ala Ile Glu Glu Leu Tyr Gly Ser Pro Gln Asp
1425                1430                1435 gtt gag ggt gca gtg aag gaa ggg aag cta tac gta gta cag aca      4378
Val Glu Gly Ala Val Lys Glu Gly Lys Leu Tyr Val Val Gln Thr
1440                1445                1450 aga cca cag atg taa tctatatgta tattttatag ccaagtcaat caggcaatgt  4433
```

```
Arg Pro Gln Met
        1455 tgtagagtaa gatatacggg ccgtgggaca tgtataacac gttacgccct ttttttatt      4493 atttgctttc atactcacaa tacactaatt tatagggctt attttatcgc caaaaaaaaa     4553 aaaaaaaaga aaaaaaaaaa aaa                                              4576

<210> SEQ ID NO 13
<211> LENGTH: 1457
<212> TYPE: PRT
<213> ORGANISM: Oryza sativa

<400> SEQUENCE: 13

Met Ser Gly Phe Ser Ala Ala Ala Ala Ala Glu Arg Cys Ala Leu
1               5                   10                  15

Gly Leu Gly Val His Ala Arg Pro Ala Ser Pro Ser Pro Ala Leu Leu
            20                  25                  30

Pro Pro Ala Ala Leu Arg Arg Gly Arg Arg Leu Pro Ala Ala Thr Thr
        35                  40                  45

Thr Leu Ala Val Ser Arg Arg Ser Leu Leu Ala Pro Arg Ala Ile Ala
    50                  55                  60

Ala Ser Thr Gly Arg Ala Ser Pro Gly Leu Val Gly Arg Phe Thr Leu
65                  70                  75                  80

Asp Ala Asn Ser Glu Leu Lys Val Thr Leu Asn Pro Ala Pro Gln Gly
                85                  90                  95

Ser Val Val Glu Ile Asn Leu Glu Ala Thr Asn Thr Ser Gly Ser Leu
            100                 105                 110

Ile Leu His Trp Gly Ala Leu Arg Pro Asp Arg Gly Glu Trp Leu Leu
        115                 120                 125

Pro Ser Arg Lys Pro Asp Gly Thr Thr Val Tyr Lys Asn Arg Ala Leu
    130                 135                 140

Arg Thr Pro Phe Ile Lys Ser Gly Asp Asn Ser Thr Leu Lys Ile Glu
145                 150                 155                 160

Ile Asp Asp Pro Ala Val Gln Ala Ile Glu Phe Leu Ile Phe Asp Glu
                165                 170                 175

Ala Arg Asn Asn Trp Tyr Lys Asn Asn Gly Gln Asn Phe Gln Ile Gln
            180                 185                 190

Leu Gln Ala Ser Gln Tyr Gln Gly Gln Gly Thr Ser Thr Ala Thr Ser
        195                 200                 205

Ser Thr Val Val Pro Glu Asp Leu Val Gln Ile Gln Ser Tyr Leu Arg
    210                 215                 220

Trp Glu Arg Lys Gly Lys Gln Ser Tyr Thr Pro Glu Gln Glu Lys Glu
225                 230                 235                 240

Glu Tyr Glu Ala Ala Arg Thr Glu Leu Ile Glu Leu Asn Lys Gly
                245                 250                 255

Val Ser Leu Glu Lys Leu Arg Ala Lys Leu Thr Lys Thr Pro Glu Ala
            260                 265                 270

Thr Asp Ser Asn Ala Pro Ala Ser Glu Ser Thr Val Thr Thr Lys Val
        275                 280                 285

Pro Glu Glu Leu Val Gln Val Gln Ala Tyr Ile Arg Trp Glu Lys Ala
    290                 295                 300

Gly Lys Pro Asn Tyr Ala Pro Glu Lys Gln Leu Val Glu Phe Glu Glu
305                 310                 315                 320

Ala Arg Lys Glu Leu Gln Ser Glu Leu Asp Lys Gly Thr Ser Val Glu
                325                 330                 335
```

```
Gln Leu Arg Asn Lys Ile Leu Lys Gly Asn Ile Glu Thr Lys Val Ser
                340                 345                 350

Lys Gln Leu Lys Asp Lys Lys Tyr Phe Ser Val Glu Arg Ile Gln Arg
            355                 360                 365

Lys Lys Arg Asp Ile Val Gln Leu Leu Lys Lys His Lys Pro Thr Val
        370                 375                 380

Met Glu Ala Gln Val Glu Thr Pro Lys Gln Pro Thr Val Leu Asp Leu
385                 390                 395                 400

Phe Thr Lys Ser Leu Gln Glu Gln Asp Asn Cys Glu Val Leu Ser Arg
                405                 410                 415

Lys Leu Phe Lys Phe Gly Asp Lys Glu Ile Leu Gly Ile Thr Thr Val
            420                 425                 430

Ala Leu Gly Lys Thr Lys Val His Leu Ala Thr Asn Tyr Met Glu Pro
        435                 440                 445

Leu Ile Leu His Trp Ala Leu Ser Lys Glu Asn Gly Glu Trp Gln Ala
    450                 455                 460

Pro Pro Ser Ser Ile Leu Pro Ser Gly Ser Ser Leu Leu Asp Lys Ala
465                 470                 475                 480

Cys Glu Thr Ser Phe Ser Glu Tyr Glu Leu Asn Gly Leu His Cys Gln
                485                 490                 495

Val Val Glu Ile Glu Leu Asp Asp Gly Gly Tyr Lys Arg Met Pro Phe
            500                 505                 510

Val Leu Arg Ser Gly Glu Thr Trp Met Lys Asn Asn Gly Ser Asp Phe
        515                 520                 525

Tyr Leu Asp Phe Ser Thr Lys Val Ala Lys Asn Thr Lys Asp Thr Gly
    530                 535                 540

Asp Ala Gly Lys Gly Thr Ala Glu Ala Leu Leu Glu Arg Ile Ala Asp
545                 550                 555                 560

Leu Glu Glu Asp Ala Gln Arg Ser Leu Met His Arg Phe Asn Ile Ala
                565                 570                 575

Ala Asp Leu Val Asp Gln Ala Arg Asp Asn Gly Leu Leu Gly Ile Ile
            580                 585                 590

Gly Ile Phe Val Trp Ile Gly Phe Met Ala Thr Arg Gln Leu Ile Trp
        595                 600                 605

Asn Lys Asn Tyr Asn Val Lys Pro Arg Glu Ile Ser Lys Ala Gln Asp
    610                 615                 620

Arg Phe Thr Asp Asp Leu Glu Asn Met Tyr Arg Thr Tyr Pro Gln Tyr
625                 630                 635                 640

Gln Glu Ile Leu Arg Met Ile Met Ser Ala Val Gly Arg Gly Gly Glu
                645                 650                 655

Gly Asp Val Gly Gln Arg Ile Arg Asp Glu Ile Leu Val Ile Gln Arg
            660                 665                 670

Asn Asn Asp Cys Lys Gly Gly Met Met Glu Glu Trp His Gln Lys Leu
        675                 680                 685

His Asn Asn Thr Ser Pro Asp Asp Val Val Ile Cys Gln Ala Leu Leu
    690                 695                 700

Asp Tyr Ile Lys Ser Asp Phe Asp Thr Gly Val Tyr Trp Asp Thr Leu
705                 710                 715                 720

Lys Lys Gly Gly Ile Thr Lys Glu Arg Leu Leu Ser Tyr Asp Arg Pro
                725                 730                 735

Ile His Ser Glu Pro Asn Phe Arg Ser Glu Gln Lys Asp Ser Leu Leu
            740                 745                 750

Arg Asp Leu Gly Asn Tyr Met Arg Ser Leu Lys Ala Val His Ser Gly
        755                 760                 765
```

```
Ala Asp Leu Glu Ser Ala Ile Ala Thr Cys Met Gly Tyr Lys Ser Glu
        770                 775                 780

Gly Glu Gly Phe Met Val Gly Val Gln Ile Asn Pro Val Lys Gly Leu
785                 790                 795                 800

Pro Ser Gly Phe Pro Lys Leu Leu Glu Phe Ile Leu Asp His Val Glu
                    805                 810                 815

Asp Lys Ser Ala Arg Pro Leu Leu Gly Gly Leu Leu Glu Ala Arg Ala
            820                 825                 830

Glu Leu His Pro Leu Leu Leu Gly Ser Pro Glu Arg Met Lys Asp Leu
        835                 840                 845

Ile Phe Leu Asp Ile Ala Leu Asp Ser Thr Phe Arg Thr Ala Val Glu
        850                 855                 860

Arg Ser Tyr Glu Glu Leu Asn Asn Val Glu Pro Glu Lys Ile Met Tyr
865                 870                 875                 880

Phe Ile Ser Leu Val Leu Glu Asn Leu Ala Leu Ser Thr Asp Asp Asn
                    885                 890                 895

Glu Asp Ile Leu Tyr Cys Leu Lys Gly Trp Asn Gln Ala Val Glu Met
                900                 905                 910

Ala Lys Gln Lys Asn Asn Gln Trp Ala Leu Tyr Ala Lys Ala Phe Leu
        915                 920                 925

Asp Arg Thr Arg Leu Ala Leu Ala Ser Lys Gly Glu Gln Tyr Tyr Asn
        930                 935                 940

Leu Met Gln Pro Ser Ala Glu Tyr Leu Gly Ser Leu Leu Asn Ile Asp
945                 950                 955                 960

Gln Trp Ala Val Asn Ile Phe Thr Glu Glu Ile Ile Arg Gly Gly Ser
                965                 970                 975

Ala Ala Thr Leu Ser Ala Leu Leu Asn Arg Ile Asp Pro Val Leu Arg
            980                 985                 990

Asn Val Ala Gln Leu Gly Ser Trp Gln Val Ile Ser Pro Val Glu Val
            995                 1000                1005

Ser Gly Tyr Ile Val Val Val Asp Glu Leu Leu Ala Val Gln Asn
    1010                1015                1020

Lys Ser Tyr Asp Lys Pro Thr Ile Leu Val Ala Lys Ser Val Lys
    1025                1030                1035

Gly Glu Glu Glu Ile Pro Asp Gly Val Val Gly Val Ile Thr Pro
    1040                1045                1050

Asp Met Pro Asp Val Leu Ser His Val Ser Val Arg Ala Arg Asn
    1055                1060                1065

Cys Lys Val Leu Phe Ala Thr Cys Phe Asp Pro Asn Thr Leu Ser
    1070                1075                1080

Glu Leu Gln Gly His Asp Gly Lys Val Phe Ser Phe Lys Pro Thr
    1085                1090                1095

Ser Ala Asp Ile Thr Tyr Arg Glu Ile Pro Glu Ser Glu Leu Gln
    1100                1105                1110

Ser Gly Ser Leu Asn Ala Glu Ala Gly Gln Ala Val Pro Ser Val
    1115                1120                1125

Ser Leu Val Lys Lys Lys Phe Leu Gly Lys Tyr Ala Ile Ser Ala
    1130                1135                1140

Glu Glu Phe Ser Glu Glu Met Val Gly Ala Lys Ser Arg Asn Val
    1145                1150                1155

Ala Tyr Leu Lys Gly Lys Val Pro Ser Trp Val Gly Val Pro Thr
    1160                1165                1170

Ser Val Ala Ile Pro Phe Gly Thr Phe Glu Lys Val Leu Ser Asp
```

```
                1175                 1180                 1185

Glu Ile Asn Lys Glu Val Ala Gln Thr Ile Gln Met Leu Lys Gly
        1190                1195                1200

Lys Leu Ala Gln Asp Asp Phe Ser Ala Leu Gly Glu Ile Arg Lys
        1205                1210                1215

Thr Val Leu Asn Leu Thr Ala Pro Thr Gln Leu Ile Lys Glu Leu
        1220                1225                1230

Lys Glu Lys Met Leu Gly Ser Gly Met Pro Trp Pro Gly Asp Glu
        1235                1240                1245

Gly Asp Gln Arg Trp Glu Gln Ala Trp Met Ala Ile Lys Lys Val
        1250                1255                1260

Trp Ala Ser Lys Trp Asn Glu Arg Ala Tyr Phe Ser Thr Arg Lys
        1265                1270                1275

Val Lys Leu Asp His Asp Tyr Leu Ser Met Ala Val Leu Val Gln
        1280                1285                1290

Glu Ile Val Asn Ala Asp Tyr Ala Phe Val Ile His Thr Thr Asn
        1295                1300                1305

Pro Ser Ser Gly Asp Ser Ser Glu Ile Tyr Ala Glu Val Val Lys
        1310                1315                1320

Gly Leu Gly Glu Thr Leu Val Gly Ala Tyr Pro Gly Arg Ala Met
        1325                1330                1335

Ser Phe Val Cys Lys Lys Asn Asp Leu Asp Ser Pro Lys Val Leu
        1340                1345                1350

Gly Phe Pro Ser Lys Pro Ile Gly Val Phe Ile Lys Arg Ser Ile
        1355                1360                1365

Ile Phe Arg Ser Asp Ser Asn Gly Glu Asp Leu Glu Gly Tyr Ala
        1370                1375                1380

Gly Ala Arg Leu Tyr Asp Ser Val Pro Met Asp Glu Glu Asp Glu
        1385                1390                1395

Val Ile Val Asp Tyr Asn Asn Gly Pro Leu Ile Thr Asp Gln Gly
        1400                1405                1410

Phe Gln Lys Ser Asn Leu Pro Ser Ile Ala Pro Ala Gly His Ala
        1415                1420                1425

Ile Glu Glu Leu Tyr Gly Ser Pro Gln Asp Val Glu Gly Ala Val
        1430                1435                1440

Lys Glu Gly Lys Leu Tyr Val Val Gln Thr Arg Pro Gln Met
        1445                1450                1455

<210> SEQ ID NO 14
<211> LENGTH: 4745
<212> TYPE: DNA
<213> ORGANISM: Glycine max
<220> FEATURE:
<221> NAME/KEY: CDS
<222> LOCATION: (103)..(4482)
<223> OTHER INFORMATION:
<300> PUBLICATION INFORMATION:
<308> DATABASE ACCESSION NUMBER: NCBI / AR400815
<309> DATABASE ENTRY DATE: 2003-12-18

<400> SEQUENCE: 14
gcaccagcct ctccccattt tcacgtgatt cccaatctca cactcttctc acaccttcaa      60
ccgattcaac gcaacaaagt gataaagtgt ggatccggga ag atg agc cag agt       114
                                             Met Ser Gln Ser
                                              1 atc ttc cac cag acg gtg ctt tgt caa acg caa acg gtt gcg gag cat       162
Ile Phe His Gln Thr Val Leu Cys Gln Thr Gln Thr Val Ala Glu His
 5                  10                  15                  20
```

```
caa agt aag gtt agt tcc ttg gag gtg agt gcg aac aaa gga aag aag        210
Gln Ser Lys Val Ser Ser Leu Glu Val Ser Ala Asn Lys Gly Lys Lys
            25                  30                  35 aac ctc ttt ttg gct cct aca aat ttt cgc ggg agc agg ctg tgt gtg        258
Asn Leu Phe Leu Ala Pro Thr Asn Phe Arg Gly Ser Arg Leu Cys Val
        40                  45                  50 agg aaa cgc aaa tta acc atg gga agg cac cac cgc cac gtt gac            306
Arg Lys Arg Lys Leu Thr Met Gly Arg His His Arg His Val Asp
            55                  60                  65 gct gtt cca cgc gct gtt tta acc acc aat ctg gct tct gag ctt tct        354
Ala Val Pro Arg Ala Val Leu Thr Thr Asn Leu Ala Ser Glu Leu Ser
        70                  75                  80 ggg aag ttc aac ctt gac gga aat att gag ttg cag att gct gtt agt        402
Gly Lys Phe Asn Leu Asp Gly Asn Ile Glu Leu Gln Ile Ala Val Ser
85                  90                  95                 100 tct tca gaa cca gga gct gca aga caa gta gat ttt aag gtt tca tat        450
Ser Ser Glu Pro Gly Ala Ala Arg Gln Val Asp Phe Lys Val Ser Tyr
                105                 110                 115 aat agt gag tct ctg ctt tta cat tgg gga gtt gtg cgt gat cag cca        498
Asn Ser Glu Ser Leu Leu Leu His Trp Gly Val Val Arg Asp Gln Pro
            120                 125                 130 ggg aag tgg gtt ctt cct tct cgt cac cca gat gga act aaa aat tat        546
Gly Lys Trp Val Leu Pro Ser Arg His Pro Asp Gly Thr Lys Asn Tyr
        135                 140                 145 aag agc aga gct ctt aga act cct ttt gtg aaa tcc gac tca gga tct        594
Lys Ser Arg Ala Leu Arg Thr Pro Phe Val Lys Ser Asp Ser Gly Ser
        150                 155                 160 ttc ctt aaa ata gaa att gac gat cct gct gca caa gcc att gag ttc        642
Phe Leu Lys Ile Glu Ile Asp Asp Pro Ala Ala Gln Ala Ile Glu Phe
165                 170                 175                 180 ctc ata ctt gat gag gct aag aat aag tgg ttt aag aat aat ggt gag        690
Leu Ile Leu Asp Glu Ala Lys Asn Lys Trp Phe Lys Asn Asn Gly Glu
                185                 190                 195 aac ttt cac atc aag tta cca gta aaa agc aag cta tct caa gaa gtt        738
Asn Phe His Ile Lys Leu Pro Val Lys Ser Lys Leu Ser Gln Glu Val
            200                 205                 210 tca gtt cct gaa gac ctt gta cag att caa gca tat ctt agg tgg gaa        786
Ser Val Pro Glu Asp Leu Val Gln Ile Gln Ala Tyr Leu Arg Trp Glu
        215                 220                 225 cga aag ggt aag cag atg tac act cca gag caa gag aag gag gaa tat        834
Arg Lys Gly Lys Gln Met Tyr Thr Pro Glu Gln Glu Lys Glu Glu Tyr
        230                 235                 240 gaa gca gct cgg aat gaa cta ttg gag gaa gta gcc agg ggt act tct        882
Glu Ala Ala Arg Asn Glu Leu Leu Glu Glu Val Ala Arg Gly Thr Ser
245                 250                 255                 260 gtg cga gat ctc cat gca agg tta act aag aaa act aaa gct gcc gaa        930
Val Arg Asp Leu His Ala Arg Leu Thr Lys Lys Thr Lys Ala Ala Glu
                265                 270                 275 gta aag gag cct tct gtt tct gaa aca aag acc atc cct gat gaa ctt        978
Val Lys Glu Pro Ser Val Ser Glu Thr Lys Thr Ile Pro Asp Glu Leu
            280                 285                 290 gta cag att caa gct ttt ata cga tgg gaa aaa gct ggg aag cct aac       1026
Val Gln Ile Gln Ala Phe Ile Arg Trp Glu Lys Ala Gly Lys Pro Asn
        295                 300                 305 tac tct cgg gaa caa caa ctt atg gaa ttt gag gaa gca aga aaa gaa       1074
Tyr Ser Arg Glu Gln Gln Leu Met Glu Phe Glu Glu Ala Arg Lys Glu
        310                 315                 320 ttg tta gaa gag ctt gag aag ggg gct tct ctg gat gcg ata cgg aag       1122
Leu Leu Glu Glu Leu Glu Lys Gly Ala Ser Leu Asp Ala Ile Arg Lys
325                 330                 335                 340
```

```
aag att gtc aaa gga gag ata caa act aaa gtt gcc aag caa ttg aaa    1170
Lys Ile Val Lys Gly Glu Ile Gln Thr Lys Val Ala Lys Gln Leu Lys
            345                 350                 355 acc aaa aaa tac ttt cgt gct gaa aga ata cag agg aaa aag aga gat    1218
Thr Lys Lys Tyr Phe Arg Ala Glu Arg Ile Gln Arg Lys Lys Arg Asp
        360                 365                 370 ttg atg cag ctt atc aac cga aat gtt gca caa aat ata gtt gaa caa    1266
Leu Met Gln Leu Ile Asn Arg Asn Val Ala Gln Asn Ile Val Glu Gln
    375                 380                 385 gtt ata gat gct cca aaa gcc ttg aca gta att gaa cat tat gcc aat    1314
Val Ile Asp Ala Pro Lys Ala Leu Thr Val Ile Glu His Tyr Ala Asn
390                 395                 400 gca agg gaa gaa tat gaa agt ggt cct gtt ttg aat aag aca ata tac    1362
Ala Arg Glu Glu Tyr Glu Ser Gly Pro Val Leu Asn Lys Thr Ile Tyr
405                 410                 415                 420 aag ctt ggt gat aat tat ctt ctg gtc ctt gtt acc aag gat gct ggc    1410
Lys Leu Gly Asp Asn Tyr Leu Leu Val Leu Val Thr Lys Asp Ala Gly
                425                 430                 435 aag att aag gtt cac cta gct aca gac tcg aaa aaa cct ttt aca ctt    1458
Lys Ile Lys Val His Leu Ala Thr Asp Ser Lys Lys Pro Phe Thr Leu
            440                 445                 450 cac tgg gcc tta tct aga aca tct gaa gag tgg ttg gta cca cct gaa    1506
His Trp Ala Leu Ser Arg Thr Ser Glu Glu Trp Leu Val Pro Pro Glu
        455                 460                 465 act gct ctg ccc cct gga tct gtt act atg aat gag gcc gct gaa aca    1554
Thr Ala Leu Pro Pro Gly Ser Val Thr Met Asn Glu Ala Ala Glu Thr
    470                 475                 480 cct ttc aaa gct ggt tct tcg tct cat cct tct tat gag gtc cag tcc    1602
Pro Phe Lys Ala Gly Ser Ser Ser His Pro Ser Tyr Glu Val Gln Ser
485                 490                 495                 500 ttg gat ata gag gtt gat gat gat act ttt aaa gga ata cct ttt gtc    1650
Leu Asp Ile Glu Val Asp Asp Asp Thr Phe Lys Gly Ile Pro Phe Val
                505                 510                 515 att ctg tcg gat gga gaa tgg ata aag aac aat gga tca aat ttt tat    1698
Ile Leu Ser Asp Gly Glu Trp Ile Lys Asn Asn Gly Ser Asn Phe Tyr
            520                 525                 530 att gaa ttt ggt ggg aag aag cag aaa cag aag gat ttt ggc aat ggc    1746
Ile Glu Phe Gly Gly Lys Lys Gln Lys Gln Lys Asp Phe Gly Asn Gly
        535                 540                 545 aaa ggt aca gcc aag ttc ttg ttg aat aaa ata gca gaa atg gaa agt    1794
Lys Gly Thr Ala Lys Phe Leu Leu Asn Lys Ile Ala Glu Met Glu Ser
    550                 555                 560 gag gca caa aag tcc ttc atg cat cga ttt aac att gca tca gat ttg    1842
Glu Ala Gln Lys Ser Phe Met His Arg Phe Asn Ile Ala Ser Asp Leu
565                 570                 575                 580 ata gat gaa gcc aaa aat gct ggt caa ctg ggt ctt gcg ggg att ttg    1890
Ile Asp Glu Ala Lys Asn Ala Gly Gln Leu Gly Leu Ala Gly Ile Leu
                585                 590                 595 gtg tgg atg aga ttc atg gct aca agg cag ctc ata tgg aac aaa aat    1938
Val Trp Met Arg Phe Met Ala Thr Arg Gln Leu Ile Trp Asn Lys Asn
            600                 605                 610 tac aat gtg aag cca cgt gag ata agt aaa gca cag gat agg ctt aca    1986
Tyr Asn Val Lys Pro Arg Glu Ile Ser Lys Ala Gln Asp Arg Leu Thr
        615                 620                 625 gac ttg ctc caa gat gtt tat gca aat tat cca cag tat agg gaa att    2034
Asp Leu Leu Gln Asp Val Tyr Ala Asn Tyr Pro Gln Tyr Arg Glu Ile
    630                 635                 640 gtg agg atg atc ttg tcc act gtt ggt cgt gga ggt gaa gga gat gtc    2082
Val Arg Met Ile Leu Ser Thr Val Gly Arg Gly Gly Glu Gly Asp Val
645                 650                 655                 660
```

| | | |
|---|---|---|
| gga cag agg att cgg gat gaa atc ctt gtt atc cag aga aat aat gat<br>Gly Gln Arg Ile Arg Asp Glu Ile Leu Val Ile Gln Arg Asn Asn Asp<br>665                        670                        675 | 2130 |
| tgc aaa ggt gga atg atg gag gaa tgg cac cag aaa tta cac aat aat<br>Cys Lys Gly Gly Met Met Glu Glu Trp His Gln Lys Leu His Asn Asn<br>                680                        685                        690 | 2178 |
| act agt cct gat gat gtt gta atc tgt cag gca cta att gat tat ata<br>Thr Ser Pro Asp Asp Val Val Ile Cys Gln Ala Leu Ile Asp Tyr Ile<br>                695                        700                        705 | 2226 |
| aat agt gac ttt gat att ggt gtt tac tgg aaa gca ttg aat gac aat<br>Asn Ser Asp Phe Asp Ile Gly Val Tyr Trp Lys Ala Leu Asn Asp Asn<br>710                        715                        720 | 2274 |
| aga ata aca aaa gag cgg ctt ctg agc tat gac cgt gcc atc cat tct<br>Arg Ile Thr Lys Glu Arg Leu Leu Ser Tyr Asp Arg Ala Ile His Ser<br>725                        730                        735                        740 | 2322 |
| gaa cca aat ttt agg aga gat cag aag gaa ggt ctt ctg cga gat ctg<br>Glu Pro Asn Phe Arg Arg Asp Gln Lys Glu Gly Leu Leu Arg Asp Leu<br>                745                        750                        755 | 2370 |
| gga aac tac atg agg act tta aag gca gtt cat tcc ggt gca gat ctt<br>Gly Asn Tyr Met Arg Thr Leu Lys Ala Val His Ser Gly Ala Asp Leu<br>                760                        765                        770 | 2418 |
| gaa tct gct att tca aat tgt atg ggc tac aaa tct gag ggt cag ggc<br>Glu Ser Ala Ile Ser Asn Cys Met Gly Tyr Lys Ser Glu Gly Gln Gly<br>             775                        780                        785 | 2466 |
| ttc atg gta ggg gtg aag ata aat cca gtg ccg ggt ttg cct act ggt<br>Phe Met Val Gly Val Lys Ile Asn Pro Val Pro Gly Leu Pro Thr Gly<br>790                        795                        800 | 2514 |
| ttt cca gaa tta ctt gag ttt gtc atg gaa cac gtt gaa gag aag aat<br>Phe Pro Glu Leu Leu Glu Phe Val Met Glu His Val Glu Glu Lys Asn<br>805                        810                        815                        820 | 2562 |
| gtt gaa cca ctt ctt gag ggg ttg ctt gag gct cgt cag gaa ctc caa<br>Val Glu Pro Leu Leu Glu Gly Leu Leu Glu Ala Arg Gln Glu Leu Gln<br>                825                        830                        835 | 2610 |
| cca tca ctc agt aaa tcc caa agt cgt ctg aaa gat ctt ata ttt ttg<br>Pro Ser Leu Ser Lys Ser Gln Ser Arg Leu Lys Asp Leu Ile Phe Leu<br>                840                        845                        850 | 2658 |
| gat gtt gcc ctt gat tct aca gtt aga aca gca gtg gaa agg agt tat<br>Asp Val Ala Leu Asp Ser Thr Val Arg Thr Ala Val Glu Arg Ser Tyr<br>             855                        860                        865 | 2706 |
| gag gaa tta aac aat gct gga cct gag aaa ata atg tac ttc att agc<br>Glu Glu Leu Asn Asn Ala Gly Pro Glu Lys Ile Met Tyr Phe Ile Ser<br>870                        875                        880 | 2754 |
| ttg gtt ctt gaa aat ctc gca ctt tca tcg gat gac aat gaa gat ctt<br>Leu Val Leu Glu Asn Leu Ala Leu Ser Ser Asp Asp Asn Glu Asp Leu<br>885                        890                        895                        900 | 2802 |
| atc tac tgt ttg aag gga tgg gat gtt gcc tta agc atg tgc aag att<br>Ile Tyr Cys Leu Lys Gly Trp Asp Val Ala Leu Ser Met Cys Lys Ile<br>                905                        910                        915 | 2850 |
| aaa gat act cat tgg gca ttg tac gca aaa tca gtc ctt gac aga acc<br>Lys Asp Thr His Trp Ala Leu Tyr Ala Lys Ser Val Leu Asp Arg Thr<br>             920                        925                        930 | 2898 |
| cgt ctt gca cta aca aac aag gct cat tta tac cag gaa att ctg caa<br>Arg Leu Ala Leu Thr Asn Lys Ala His Leu Tyr Gln Glu Ile Leu Gln<br>             935                        940                        945 | 2946 |
| cca tcg gca gaa tat ctt gga tca ctg ctt ggc gtg gac aaa tgg gcc<br>Pro Ser Ala Glu Tyr Leu Gly Ser Leu Leu Gly Val Asp Lys Trp Ala<br>950                        955                        960 | 2994 |
| gtg gaa ata ttt act gaa gaa att atc cgt gct gga tct gct gct tct<br>Val Glu Ile Phe Thr Glu Glu Ile Ile Arg Ala Gly Ser Ala Ala Ser<br>965                        970                        975                        980 | 3042 |

| | | | | | | | | | | | | | | |
|---|---|---|---|---|---|---|---|---|---|---|---|---|---|---|
| ttg | tct | act | ctt | cta | aat | cga | ctg | gat | cct | gtg | ctc | cga | aag | aca | gct | 3090 |
| Leu | Ser | Thr | Leu | Leu | Asn | Arg | Leu | Asp | Pro | Val | Leu | Arg | Lys | Thr | Ala |
| | | | 985 | | | | 990 | | | | 995 | | | | |
| cat | ctt | gga | agc | tgg | cag | gtt | att | agt | cca | gtt | gaa | act | gtt | gga | | 3135 |
| His | Leu | Gly | Ser | Trp | Gln | Val | Ile | Ser | Pro | Val | Glu | Thr | Val | Gly |
| | | 1000 | | | | 1005 | | | | 1010 | | | | | |
| tat | gtt | gag | gtt | gta | gat | gag | ttg | ctt | act | gtt | caa | aac | aaa | tca | | 3180 |
| Tyr | Val | Glu | Val | Val | Asp | Glu | Leu | Leu | Thr | Val | Gln | Asn | Lys | Ser |
| | | 1015 | | | | 1020 | | | | 1025 | | | | | |
| tat | gag | cga | cct | aca | att | ttg | ata | gcc | aat | agt | gtg | aaa | gga | gag | | 3225 |
| Tyr | Glu | Arg | Pro | Thr | Ile | Leu | Ile | Ala | Asn | Ser | Val | Lys | Gly | Glu |
| | | 1030 | | | | 1035 | | | | 1040 | | | | | |
| gaa | gaa | att | cca | gat | ggt | aca | gtt | gct | gtc | ctg | aca | cct | gat | atg | | 3270 |
| Glu | Glu | Ile | Pro | Asp | Gly | Thr | Val | Ala | Val | Leu | Thr | Pro | Asp | Met |
| | | 1045 | | | | 1050 | | | | 1055 | | | | | |
| cct | gat | gtc | cta | tcc | cat | gtt | tct | gta | cga | gca | aga | aat | agc | aag | | 3315 |
| Pro | Asp | Val | Leu | Ser | His | Val | Ser | Val | Arg | Ala | Arg | Asn | Ser | Lys |
| | | 1060 | | | | 1065 | | | | 1070 | | | | | |
| gtg | tgt | ttt | gct | aca | tgc | ttt | gat | ccc | aat | atc | ctg | gct | aac | ctc | | 3360 |
| Val | Cys | Phe | Ala | Thr | Cys | Phe | Asp | Pro | Asn | Ile | Leu | Ala | Asn | Leu |
| | | 1075 | | | | 1080 | | | | 1085 | | | | | |
| caa | gaa | tat | aaa | gga | aag | ctt | tta | cgc | tta | aag | cct | aca | tct | gct | | 3405 |
| Gln | Glu | Tyr | Lys | Gly | Lys | Leu | Leu | Arg | Leu | Lys | Pro | Thr | Ser | Ala |
| | | 1090 | | | | 1095 | | | | 1100 | | | | | |
| gat | gta | gtt | tat | agt | gag | gtg | aag | gag | ggt | gag | ttt | att | gat | gac | | 3450 |
| Asp | Val | Val | Tyr | Ser | Glu | Val | Lys | Glu | Gly | Glu | Phe | Ile | Asp | Asp |
| | | 1105 | | | | 1110 | | | | 1115 | | | | | |
| aaa | tca | act | caa | ctg | aaa | gat | gtt | ggt | tct | gtg | tca | ccc | ata | tct | | 3495 |
| Lys | Ser | Thr | Gln | Leu | Lys | Asp | Val | Gly | Ser | Val | Ser | Pro | Ile | Ser |
| | | 1120 | | | | 1125 | | | | 1130 | | | | | |
| ctg | gcc | aga | aag | aag | ttt | agt | ggt | aga | tat | gct | gtc | tca | tct | gaa | | 3540 |
| Leu | Ala | Arg | Lys | Lys | Phe | Ser | Gly | Arg | Tyr | Ala | Val | Ser | Ser | Glu |
| | | 1135 | | | | 1140 | | | | 1145 | | | | | |
| gaa | ttc | act | ggt | gaa | atg | gtt | gga | gct | aaa | tct | cgt | aat | atc | tct | | 3585 |
| Glu | Phe | Thr | Gly | Glu | Met | Val | Gly | Ala | Lys | Ser | Arg | Asn | Ile | Ser |
| | | 1150 | | | | 1155 | | | | 1160 | | | | | |
| tat | tta | aaa | ggg | aaa | gta | gct | tct | tgg | att | gga | att | cct | acc | tca | | 3630 |
| Tyr | Leu | Lys | Gly | Lys | Val | Ala | Ser | Trp | Ile | Gly | Ile | Pro | Thr | Ser |
| | | 1165 | | | | 1170 | | | | 1175 | | | | | |
| gtt | gcc | ata | cca | ttt | gga | gtt | ttt | gaa | cat | gtt | ctt | tct | gat | aaa | | 3675 |
| Val | Ala | Ile | Pro | Phe | Gly | Val | Phe | Glu | His | Val | Leu | Ser | Asp | Lys |
| | | 1180 | | | | 1185 | | | | 1190 | | | | | |
| cca | aac | cag | gca | gtg | gct | gag | agg | gtc | aat | aat | ttg | aaa | aag | aag | | 3720 |
| Pro | Asn | Gln | Ala | Val | Ala | Glu | Arg | Val | Asn | Asn | Leu | Lys | Lys | Lys |
| | | 1195 | | | | 1200 | | | | 1205 | | | | | |
| tta | act | gag | gga | gac | ttc | agt | gtt | ctc | aag | gag | att | cgt | gaa | aca | | 3765 |
| Leu | Thr | Glu | Gly | Asp | Phe | Ser | Val | Leu | Lys | Glu | Ile | Arg | Glu | Thr |
| | | 1210 | | | | 1215 | | | | 1220 | | | | | |
| gtt | cta | cag | ttg | aat | gca | cca | tcc | cag | ttg | gta | gag | gag | ttg | aaa | | 3810 |
| Val | Leu | Gln | Leu | Asn | Ala | Pro | Ser | Gln | Leu | Val | Glu | Glu | Leu | Lys |
| | | 1225 | | | | 1230 | | | | 1235 | | | | | |
| act | aaa | atg | aag | agt | tct | gga | atg | ccg | tgg | ccg | ggt | gat | gaa | ggt | | 3855 |
| Thr | Lys | Met | Lys | Ser | Ser | Gly | Met | Pro | Trp | Pro | Gly | Asp | Glu | Gly |
| | | 1240 | | | | 1245 | | | | 1250 | | | | | |
| gaa | caa | cga | tgg | gaa | caa | gct | tgg | ata | gct | ata | aaa | aag | gtg | tgg | | 3900 |
| Glu | Gln | Arg | Trp | Glu | Gln | Ala | Trp | Ile | Ala | Ile | Lys | Lys | Val | Trp |
| | | 1255 | | | | 1260 | | | | 1265 | | | | | |
| ggc | tca | aag | tgg | aat | gaa | aga | gca | tac | ttc | agc | aca | aga | aaa | gtg | | 3945 |
| Gly | Ser | Lys | Trp | Asn | Glu | Arg | Ala | Tyr | Phe | Ser | Thr | Arg | Lys | Val |
| | | 1270 | | | | 1275 | | | | 1280 | | | | | |

```
aaa ctc gac cac gaa tat ctt tcc atg gca gtc ctg gtt cag gaa      3990
Lys Leu Asp His Glu Tyr Leu Ser Met Ala Val Leu Val Gln Glu
             1285                1290                1295 gtg ata aat gct gac tat gct ttt gtc atc cac aca act aac cct      4035
Val Ile Asn Ala Asp Tyr Ala Phe Val Ile His Thr Thr Asn Pro
             1300                1305                1310 gcc tct gga gat tca tcg gaa ata tat gct gag gtg gta aag gga      4080
Ala Ser Gly Asp Ser Ser Glu Ile Tyr Ala Glu Val Val Lys Gly
             1315                1320                1325 ctt gga gaa aca ctg gtt gga gct tat cct ggt cgt gct ttg agt      4125
Leu Gly Glu Thr Leu Val Gly Ala Tyr Pro Gly Arg Ala Leu Ser
             1330                1335                1340 ttt atc tgc aag aaa cgt gat ttg aac tct cct cag gtc ttg ggt      4170
Phe Ile Cys Lys Lys Arg Asp Leu Asn Ser Pro Gln Val Leu Gly
             1345                1350                1355 tat cct agc aaa cct gtc ggc cta ttt ata aga cag tca att att      4215
Tyr Pro Ser Lys Pro Val Gly Leu Phe Ile Arg Gln Ser Ile Ile
             1360                1365                1370 ttc cga tct gat tcc aat ggt gaa gat cta gaa ggt tat gct ggt      4260
Phe Arg Ser Asp Ser Asn Gly Glu Asp Leu Glu Gly Tyr Ala Gly
             1375                1380                1385 gca ggt ctt tat gac agt gtg cca atg gat gaa gcc gag aag gtg      4305
Ala Gly Leu Tyr Asp Ser Val Pro Met Asp Glu Ala Glu Lys Val
             1390                1395                1400 gtg ctt gat tat tca tca gac aaa ctg atc ctt gat ggt agt ttt      4350
Val Leu Asp Tyr Ser Ser Asp Lys Leu Ile Leu Asp Gly Ser Phe
             1405                1410                1415 cgc cag tca atc ttg tcc agc att gcc cgt gca gga aat gaa att      4395
Arg Gln Ser Ile Leu Ser Ser Ile Ala Arg Ala Gly Asn Glu Ile
             1420                1425                1430 gaa gag ttg tat ggc act cct cag gac att gaa ggt gtc atc aag      4440
Glu Glu Leu Tyr Gly Thr Pro Gln Asp Ile Glu Gly Val Ile Lys
             1435                1440                1445 gat ggc aaa gtc tat gtt gtc cag acc aga cca caa atg taa          4482
Asp Gly Lys Val Tyr Val Val Gln Thr Arg Pro Gln Met
             1450                1455 acttgcatac ccatgtcttc taagccacct acctcaacta tgttcatccc cgagcaacac  4542
gtcgtttcaa acgtggccgt ggcagcttct gtgagttcaa gagtaacccc cggattacca  4602
aacatggcct tatagattta ttacatgata tattgaaaat taaggaataa gtgtataaaa  4662
acggaatatt gtaaattaag aaaaatttag acggtcttat atattctttt tccctactat  4722
aaaaaaaaaa aaaaaaaaaa aaa                                          4745

<210> SEQ ID NO 15
<211> LENGTH: 1459
<212> TYPE: PRT
<213> ORGANISM: Glycine max

<400> SEQUENCE: 15

Met Ser Gln Ser Ile Phe His Gln Thr Val Leu Cys Gln Thr Gln Thr
1               5                   10                  15

Val Ala Glu His Gln Ser Lys Val Ser Ser Leu Glu Val Ser Ala Asn
            20                  25                  30

Lys Gly Lys Lys Asn Leu Phe Leu Ala Pro Thr Asn Phe Arg Gly Ser
        35                  40                  45

Arg Leu Cys Val Arg Lys Arg Lys Leu Thr Met Gly Arg His His His
    50                  55                  60

Arg His Val Asp Ala Val Pro Arg Ala Val Leu Thr Thr Asn Leu Ala
```

-continued

```
             65                  70                  75                  80
Ser Glu Leu Ser Gly Lys Phe Asn Leu Asp Gly Asn Ile Glu Leu Gln
                    85                  90                  95

Ile Ala Val Ser Ser Glu Pro Gly Ala Ala Arg Gln Val Asp Phe
                100                 105                 110

Lys Val Ser Tyr Asn Ser Glu Ser Leu Leu His Trp Gly Val Val
                115                 120                 125

Arg Asp Gln Pro Gly Lys Trp Val Leu Pro Ser Arg His Pro Asp Gly
                130                 135                 140

Thr Lys Asn Tyr Lys Ser Arg Ala Leu Arg Thr Pro Phe Val Lys Ser
145                 150                 155                 160

Asp Ser Gly Ser Phe Leu Lys Ile Glu Ile Asp Asp Pro Ala Ala Gln
                    165                 170                 175

Ala Ile Glu Phe Leu Ile Leu Asp Glu Ala Lys Asn Lys Trp Phe Lys
                180                 185                 190

Asn Asn Gly Glu Asn Phe His Ile Lys Leu Pro Val Lys Ser Lys Leu
                195                 200                 205

Ser Gln Glu Val Ser Val Pro Glu Asp Leu Val Gln Ile Gln Ala Tyr
210                 215                 220

Leu Arg Trp Glu Arg Lys Gly Lys Gln Met Tyr Thr Pro Glu Gln Glu
225                 230                 235                 240

Lys Glu Glu Tyr Glu Ala Ala Arg Asn Glu Leu Leu Glu Val Ala
                    245                 250                 255

Arg Gly Thr Ser Val Arg Asp Leu His Ala Arg Leu Thr Lys Lys Thr
                260                 265                 270

Lys Ala Ala Glu Val Lys Glu Pro Ser Val Ser Glu Thr Lys Thr Ile
                275                 280                 285

Pro Asp Glu Leu Val Gln Ile Gln Ala Phe Ile Arg Trp Glu Lys Ala
                290                 295                 300

Gly Lys Pro Asn Tyr Ser Arg Glu Gln Gln Leu Met Glu Phe Glu Glu
305                 310                 315                 320

Ala Arg Lys Glu Leu Leu Glu Glu Leu Glu Lys Gly Ala Ser Leu Asp
                    325                 330                 335

Ala Ile Arg Lys Lys Ile Val Lys Gly Glu Ile Gln Thr Lys Val Ala
                340                 345                 350

Lys Gln Leu Lys Thr Lys Lys Tyr Phe Arg Ala Glu Arg Ile Gln Arg
                355                 360                 365

Lys Lys Arg Asp Leu Met Gln Leu Ile Asn Arg Asn Val Ala Gln Asn
                370                 375                 380

Ile Val Glu Gln Val Ile Asp Ala Pro Lys Ala Leu Thr Val Ile Glu
385                 390                 395                 400

His Tyr Ala Asn Ala Arg Glu Glu Tyr Glu Ser Gly Pro Val Leu Asn
                    405                 410                 415

Lys Thr Ile Tyr Lys Leu Gly Asp Asn Tyr Leu Leu Val Leu Val Thr
                420                 425                 430

Lys Asp Ala Gly Lys Ile Lys Val His Leu Ala Thr Asp Ser Lys Lys
                435                 440                 445

Pro Phe Thr Leu His Trp Ala Leu Ser Arg Thr Ser Glu Glu Trp Leu
                450                 455                 460

Val Pro Pro Glu Thr Ala Leu Pro Pro Gly Ser Val Thr Met Asn Glu
465                 470                 475                 480

Ala Ala Glu Thr Pro Phe Lys Ala Gly Ser Ser His Pro Ser Tyr
                    485                 490                 495
```

-continued

```
Glu Val Gln Ser Leu Asp Ile Glu Val Asp Asp Thr Phe Lys Gly
            500                 505                 510
Ile Pro Phe Val Ile Leu Ser Asp Gly Glu Trp Ile Lys Asn Asn Gly
            515                 520                 525
Ser Asn Phe Tyr Ile Glu Phe Gly Gly Lys Lys Gln Lys Gln Lys Asp
            530                 535                 540
Phe Gly Asn Gly Lys Gly Thr Ala Lys Phe Leu Leu Asn Lys Ile Ala
545                 550                 555                 560
Glu Met Glu Ser Glu Ala Gln Lys Ser Phe Met His Arg Phe Asn Ile
                565                 570                 575
Ala Ser Asp Leu Ile Asp Glu Ala Lys Asn Ala Gly Gln Leu Gly Leu
            580                 585                 590
Ala Gly Ile Leu Val Trp Met Arg Phe Met Ala Thr Arg Gln Leu Ile
            595                 600                 605
Trp Asn Lys Asn Tyr Asn Val Lys Pro Arg Glu Ile Ser Lys Ala Gln
            610                 615                 620
Asp Arg Leu Thr Asp Leu Leu Gln Asp Val Tyr Ala Asn Tyr Pro Gln
625                 630                 635                 640
Tyr Arg Glu Ile Val Arg Met Ile Leu Ser Thr Val Gly Arg Gly Gly
                645                 650                 655
Glu Gly Asp Val Gly Gln Arg Ile Arg Asp Glu Ile Leu Val Ile Gln
            660                 665                 670
Arg Asn Asn Asp Cys Lys Gly Gly Met Met Glu Glu Trp His Gln Lys
            675                 680                 685
Leu His Asn Asn Thr Ser Pro Asp Asp Val Val Ile Cys Gln Ala Leu
            690                 695                 700
Ile Asp Tyr Ile Asn Ser Asp Phe Asp Ile Gly Val Tyr Trp Lys Ala
705                 710                 715                 720
Leu Asn Asp Asn Arg Ile Thr Lys Glu Arg Leu Leu Ser Tyr Asp Arg
                725                 730                 735
Ala Ile His Ser Glu Pro Asn Phe Arg Arg Asp Gln Lys Glu Gly Leu
            740                 745                 750
Leu Arg Asp Leu Gly Asn Tyr Met Arg Thr Leu Lys Ala Val His Ser
            755                 760                 765
Gly Ala Asp Leu Glu Ser Ala Ile Ser Asn Cys Met Gly Tyr Lys Ser
            770                 775                 780
Glu Gly Gln Gly Phe Met Val Gly Val Lys Ile Asn Pro Val Pro Gly
785                 790                 795                 800
Leu Pro Thr Gly Phe Pro Glu Leu Leu Glu Phe Val Met Glu His Val
                805                 810                 815
Glu Glu Lys Asn Val Glu Pro Leu Leu Glu Gly Leu Leu Glu Ala Arg
            820                 825                 830
Gln Glu Leu Gln Pro Ser Leu Ser Lys Ser Gln Ser Arg Leu Lys Asp
            835                 840                 845
Leu Ile Phe Leu Asp Val Ala Leu Asp Ser Thr Val Arg Thr Ala Val
            850                 855                 860
Glu Arg Ser Tyr Glu Leu Asn Asn Ala Gly Pro Glu Lys Ile Met
865                 870                 875                 880
Tyr Phe Ile Ser Leu Val Leu Glu Asn Leu Ala Leu Ser Ser Asp Asp
                885                 890                 895
Asn Glu Asp Leu Ile Tyr Cys Leu Lys Gly Trp Asp Val Ala Leu Ser
            900                 905                 910
Met Cys Lys Ile Lys Asp Thr His Trp Ala Leu Tyr Ala Lys Ser Val
            915                 920                 925
```

```
Leu Asp Arg Thr Arg Leu Ala Leu Thr Asn Lys Ala His Leu Tyr Gln
    930                 935                 940

Glu Ile Leu Gln Pro Ser Ala Glu Tyr Leu Gly Ser Leu Leu Gly Val
945                 950                 955                 960

Asp Lys Trp Ala Val Glu Ile Phe Thr Glu Glu Ile Ile Arg Ala Gly
                965                 970                 975

Ser Ala Ala Ser Leu Ser Thr Leu Leu Asn Arg Leu Asp Pro Val Leu
                980                 985                 990

Arg Lys Thr Ala His Leu Gly Ser Trp Gln Val Ile Ser Pro Val Glu
        995                 1000                1005

Thr Val Gly Tyr Val Glu Val Val Asp Glu Leu Leu Thr Val Gln
    1010                1015                1020

Asn Lys Ser Tyr Glu Arg Pro Thr Ile Leu Ile Ala Asn Ser Val
    1025                1030                1035

Lys Gly Glu Glu Glu Ile Pro Asp Gly Thr Val Ala Val Leu Thr
    1040                1045                1050

Pro Asp Met Pro Asp Val Leu Ser His Val Ser Val Arg Ala Arg
    1055                1060                1065

Asn Ser Lys Val Cys Phe Ala Thr Cys Phe Asp Pro Asn Ile Leu
    1070                1075                1080

Ala Asn Leu Gln Glu Tyr Lys Gly Lys Leu Leu Arg Leu Lys Pro
    1085                1090                1095

Thr Ser Ala Asp Val Val Tyr Ser Glu Val Lys Glu Gly Glu Phe
    1100                1105                1110

Ile Asp Asp Lys Ser Thr Gln Leu Lys Asp Val Gly Ser Val Ser
    1115                1120                1125

Pro Ile Ser Leu Ala Arg Lys Lys Phe Ser Gly Arg Tyr Ala Val
    1130                1135                1140

Ser Ser Glu Glu Phe Thr Gly Glu Met Val Gly Ala Lys Ser Arg
    1145                1150                1155

Asn Ile Ser Tyr Leu Lys Gly Lys Val Ala Ser Trp Ile Gly Ile
    1160                1165                1170

Pro Thr Ser Val Ala Ile Pro Phe Gly Val Phe Glu His Val Leu
    1175                1180                1185

Ser Asp Lys Pro Asn Gln Ala Val Ala Glu Arg Val Asn Asn Leu
    1190                1195                1200

Lys Lys Lys Leu Thr Glu Gly Asp Phe Ser Val Leu Lys Glu Ile
    1205                1210                1215

Arg Glu Thr Val Leu Gln Leu Asn Ala Pro Ser Gln Leu Val Glu
    1220                1225                1230

Glu Leu Lys Thr Lys Met Lys Ser Ser Gly Met Pro Trp Pro Gly
    1235                1240                1245

Asp Glu Gly Glu Gln Arg Trp Glu Gln Ala Trp Ile Ala Ile Lys
    1250                1255                1260

Lys Val Trp Gly Ser Lys Trp Asn Glu Arg Ala Tyr Phe Ser Thr
    1265                1270                1275

Arg Lys Val Lys Leu Asp His Glu Tyr Leu Ser Met Ala Val Leu
    1280                1285                1290

Val Gln Glu Val Ile Asn Ala Asp Tyr Ala Phe Val Ile His Thr
    1295                1300                1305

Thr Asn Pro Ala Ser Gly Asp Ser Ser Glu Ile Tyr Ala Glu Val
    1310                1315                1320

Val Lys Gly Leu Gly Glu Thr Leu Val Gly Ala Tyr Pro Gly Arg
```

-continued

```
             1325               1330                 1335

Ala Leu Ser Phe Ile Cys Lys Lys Arg Asp Leu Asn Ser Pro Gln
    1340                1345                1350

Val Leu Gly Tyr Pro Ser Lys Pro Val Gly Leu Phe Ile Arg Gln
    1355                1360                1365

Ser Ile Ile Phe Arg Ser Asp Ser Asn Gly Glu Asp Leu Glu Gly
    1370                1375                1380

Tyr Ala Gly Ala Gly Leu Tyr Asp Ser Val Pro Met Asp Glu Ala
    1385                1390                1395

Glu Lys Val Val Leu Asp Tyr Ser Ser Asp Lys Leu Ile Leu Asp
    1400                1405                1410

Gly Ser Phe Arg Gln Ser Ile Leu Ser Ser Ile Ala Arg Ala Gly
    1415                1420                1425

Asn Glu Ile Glu Glu Leu Tyr Gly Thr Pro Gln Asp Ile Glu Gly
    1430                1435                1440

Val Ile Lys Asp Gly Lys Val Tyr Val Val Gln Thr Arg Pro Gln
    1445                1450                1455

Met
```

```
<210> SEQ ID NO 16
<211> LENGTH: 4846
<212> TYPE: DNA
<213> ORGANISM: Zea mays
<220> FEATURE:
<221> NAME/KEY: CDS
<222> LOCATION: (158)..(4567)
<223> OTHER INFORMATION:
<300> PUBLICATION INFORMATION:
<308> DATABASE ACCESSION NUMBER: NCBI / AR400813
<309> DATABASE ENTRY DATE: 2003-12-18

<400> SEQUENCE: 16
```

```
ccacgcgtcc ggcttcatct tgctgatcgt gtccgtggct tcttgatact ccgtgactgt    60
ctccgtccga agcgagtgag caagccgacc aacagcggct gagattcgct gcaacgtcgg   120
tatcaaaagg tgtccgagcg gttgagattc gcgtgcc atg tcc gga ttc agt gcc   175
                                         Met Ser Gly Phe Ser Ala
                                           1               5 gcg gcc aac gca gcg gcg gct gag cgg tgc gcg ctc gcg ttc cgc gca    223
Ala Ala Asn Ala Ala Ala Ala Glu Arg Cys Ala Leu Ala Phe Arg Ala
            10                  15                  20 cgg ccc gcg gcc tcc tcg cca gcg aag cgg cag cag cag ccg cag cca    271
Arg Pro Ala Ala Ser Ser Pro Ala Lys Arg Gln Gln Gln Pro Gln Pro
        25                  30                  35 gcg tcc ctc cga cgc agc ggg ggc cag cgc cgc ccc acg acg ctc tcc    319
Ala Ser Leu Arg Arg Ser Gly Gly Gln Arg Arg Pro Thr Thr Leu Ser
    40                  45                  50 gcc tct agc cgc ggc ccc gtc gtg ccg cgc gcc gtc gcc acg tcc gcg    367
Ala Ser Ser Arg Gly Pro Val Val Pro Arg Ala Val Ala Thr Ser Ala
55                  60                  65                  70 gac cgc gcg tcc ccc gac ctt atc gga aag ttc acg ctg gat tcc aac    415
Asp Arg Ala Ser Pro Asp Leu Ile Gly Lys Phe Thr Leu Asp Ser Asn
                75                  80                  85 tcc gag ctc cag gtc gca gtg aac cca gcg ccg cag ggt ttg gtg tca    463
Ser Glu Leu Gln Val Ala Val Asn Pro Ala Pro Gln Gly Leu Val Ser
            90                  95                 100 gag att agc ctg gag gtg acc aac aca agc ggt tcc ctg att ttg cat    511
Glu Ile Ser Leu Glu Val Thr Asn Thr Ser Gly Ser Leu Ile Leu His
       105                 110                 115 tgg gga gcc ctt cgc ccg gac aag aga gat tgg atc ctc ccg tcc aga    559
Trp Gly Ala Leu Arg Pro Asp Lys Arg Asp Trp Ile Leu Pro Ser Arg
```

-continued

```
                Trp Gly Ala Leu Arg Pro Asp Lys Arg Asp Trp Ile Leu Pro Ser Arg
                    120                 125                 130 aaa cct gat gga acg aca gtg tac aag aac agg gct ctc agg aca cct          607
Lys Pro Asp Gly Thr Thr Val Tyr Lys Asn Arg Ala Leu Arg Thr Pro
135                 140                 145                 150 ttt gta aag tca ggt gat aac tcc act cta agg att gag ata gat gat          655
Phe Val Lys Ser Gly Asp Asn Ser Thr Leu Arg Ile Glu Ile Asp Asp
                155                 160                 165 cct ggg gtg cac gcc att gag ttc ctc atc ttt gac gag aca cag aac          703
Pro Gly Val His Ala Ile Glu Phe Leu Ile Phe Asp Glu Thr Gln Asn
                    170                 175                 180 aaa tgg ttt aaa aac aat ggc cag aat ttt cag gtt cag ttc cag tcg          751
Lys Trp Phe Lys Asn Asn Gly Gln Asn Phe Gln Val Gln Phe Gln Ser
                185                 190                 195 agc cgc cat cag ggt act ggt gca tct ggt gcc tcc tct tct gct act          799
Ser Arg His Gln Gly Thr Gly Ala Ser Gly Ala Ser Ser Ser Ala Thr
    200                 205                 210 tct acc ttg gtg cca gag gat ctt gtg cag atc caa gct tac ctt cgg          847
Ser Thr Leu Val Pro Glu Asp Leu Val Gln Ile Gln Ala Tyr Leu Arg
215                 220                 225                 230 tgg gaa aga agg gga aag cag tca tac aca cca gag caa gaa aag gag          895
Trp Glu Arg Arg Gly Lys Gln Ser Tyr Thr Pro Glu Gln Glu Lys Glu
                235                 240                 245 gag tat gaa gct gca cga gct gag tta ata gag gaa gta aac aga ggt          943
Glu Tyr Glu Ala Ala Arg Ala Glu Leu Ile Glu Glu Val Asn Arg Gly
                    250                 255                 260 gtt tct tta gag aag ctt cga gct aaa ttg aca aaa gca cct gaa gca          991
Val Ser Leu Glu Lys Leu Arg Ala Lys Leu Thr Lys Ala Pro Glu Ala
                265                 270                 275 cct gag tcg gat gaa agt aaa tct tct gca tct cga atg ccc atc ggt         1039
Pro Glu Ser Asp Glu Ser Lys Ser Ser Ala Ser Arg Met Pro Ile Gly
    280                 285                 290 aaa ctt cca gag gat ctt gta cag gtg cag gct tat ata agg tgg gag         1087
Lys Leu Pro Glu Asp Leu Val Gln Val Gln Ala Tyr Ile Arg Trp Glu
295                 300                 305                 310 caa gcg ggc aag cca aac tat cct cct gag aag caa ctg gta gaa ttt         1135
Gln Ala Gly Lys Pro Asn Tyr Pro Pro Glu Lys Gln Leu Val Glu Phe
                315                 320                 325 gag gaa gca agg aag gaa ctg cag gct gag gtg gac aag gga atc tct         1183
Glu Glu Ala Arg Lys Glu Leu Gln Ala Glu Val Asp Lys Gly Ile Ser
                    330                 335                 340 att gat cag ttg agg cag aaa att ttg aaa gga aac att gag agt aaa         1231
Ile Asp Gln Leu Arg Gln Lys Ile Leu Lys Gly Asn Ile Glu Ser Lys
                345                 350                 355 gtt tcc aag cag ctg aag aac aag aag tac ttc tct gta gaa agg att         1279
Val Ser Lys Gln Leu Lys Asn Lys Lys Tyr Phe Ser Val Glu Arg Ile
360                 365                 370 cag cgc aaa aag aga gat atc aca caa ctt ctc agt aaa cat aag cat         1327
Gln Arg Lys Lys Arg Asp Ile Thr Gln Leu Leu Ser Lys His Lys His
375                 380                 385                 390 aca ctt gtg gaa gat aaa gta gag gtt gta cca aaa caa cca act gtt         1375
Thr Leu Val Glu Asp Lys Val Glu Val Val Pro Lys Gln Pro Thr Val
                    395                 400                 405 ctt gat ctc ttc acc aag tct tta cat gag aag gat ggc tgt gaa gtt         1423
Leu Asp Leu Phe Thr Lys Ser Leu His Glu Lys Asp Gly Cys Glu Val
                410                 415                 420 cta agc aga aag ctc ttc aag ttc ggc gat aaa gag ata ctg gca att         1471
Leu Ser Arg Lys Leu Phe Lys Phe Gly Asp Lys Glu Ile Leu Ala Ile
                425                 430                 435 tct acc aag gtt caa aat aaa aca gaa gtt cac ttg gca aca aac cat         1519
```

-continued

| | | | | | | | | | | | | |
|---|---|---|---|---|---|---|---|---|---|---|---|---|
| Ser | Thr | Lys | Val | Gln | Asn | Lys | Thr | Glu | Val | His | Leu | Ala | Thr | Asn | His |
| | 440 | | | | 445 | | | | 450 | | | |

```
acc gac cca ctt att ctt cac tgg tct ttg gca aaa aat gct gga gaa   1567
Thr Asp Pro Leu Ile Leu His Trp Ser Leu Ala Lys Asn Ala Gly Glu
455             460                 465                 470 tgg aag gca cct tct cca aat ata ttg cca tct ggt tcc aca ttg ctg   1615
Trp Lys Ala Pro Ser Pro Asn Ile Leu Pro Ser Gly Ser Thr Leu Leu
                475                 480                 485 gac aag gcg tgt gaa act gaa ttt act aaa tct gaa ttg gat ggt ttg   1663
Asp Lys Ala Cys Glu Thr Glu Phe Thr Lys Ser Glu Leu Asp Gly Leu
            490                 495                 500 cat tac cag gtt gtt gag ata gag ctt gat gat gga gga tac aaa gga   1711
His Tyr Gln Val Val Glu Ile Glu Leu Asp Asp Gly Gly Tyr Lys Gly
        505                 510                 515 atg cca ttt gtt ctt cgg tct ggt gaa aca tgg aaa aaa aat aat ggt   1759
Met Pro Phe Val Leu Arg Ser Gly Glu Thr Trp Lys Lys Asn Asn Gly
    520                 525                 530 tct gat ttt ttc cta gat ttc agc acc cat gat gtc aga aat att aag   1807
Ser Asp Phe Phe Leu Asp Phe Ser Thr His Asp Val Arg Asn Ile Lys
535                 540                 545                 550 tta aag ggc aat ggt gat gct ggt aaa ggt act gct aag gca ttg ctg   1855
Leu Lys Gly Asn Gly Asp Ala Gly Lys Gly Thr Ala Lys Ala Leu Leu
                555                 560                 565 gag aga ata gca gat ctg gag gaa gat gcc cag cga tct ctt atg cac   1903
Glu Arg Ile Ala Asp Leu Glu Glu Asp Ala Gln Arg Ser Leu Met His
            570                 575                 580 aga ttc aat att gca gca gat cta gct gac caa gcc aga gat gct gga   1951
Arg Phe Asn Ile Ala Ala Asp Leu Ala Asp Gln Ala Arg Asp Ala Gly
        585                 590                 595 ctt ttg ggt att gtt ggg ctt ttt gtt tgg att aga ttc atg gct acc   1999
Leu Leu Gly Ile Val Gly Leu Phe Val Trp Ile Arg Phe Met Ala Thr
    600                 605                 610 agg caa cta aca tgg aat aag aac tat aat gtg aag cca cgt gag ata   2047
Arg Gln Leu Thr Trp Asn Lys Asn Tyr Asn Val Lys Pro Arg Glu Ile
615                 620                 625                 630 agc aaa gca cag gat agg ttt aca gat gat ctt gag aat atg tac aaa   2095
Ser Lys Ala Gln Asp Arg Phe Thr Asp Asp Leu Glu Asn Met Tyr Lys
                635                 640                 645 gct tat cca cag tac aga gag ata tta aga atg ata atg gct gct gtt   2143
Ala Tyr Pro Gln Tyr Arg Glu Ile Leu Arg Met Ile Met Ala Ala Val
            650                 655                 660 ggt cgc gga ggt gaa ggt gat gtt ggt caa cgc att cgt gat gag ata   2191
Gly Arg Gly Gly Glu Gly Asp Val Gly Gln Arg Ile Arg Asp Glu Ile
        665                 670                 675 tta gta ata cag aga aat aat gac tgc aaa ggt gga atg atg gaa gaa   2239
Leu Val Ile Gln Arg Asn Asn Asp Cys Lys Gly Gly Met Met Glu Glu
    680                 685                 690 tgg cac cag aaa ttg cac aac aat aca agc cca gat gat gta gtg ata   2287
Trp His Gln Lys Leu His Asn Asn Thr Ser Pro Asp Asp Val Val Ile
695                 700                 705                 710 tgc cag gcc tta att gat tat atc aag agt gac ttt gat ata agc gtt   2335
Cys Gln Ala Leu Ile Asp Tyr Ile Lys Ser Asp Phe Asp Ile Ser Val
                715                 720                 725 tac tgg gac acc ttg aac aaa aat ggc ata acc aaa gag cgt ctc ttg   2383
Tyr Trp Asp Thr Leu Asn Lys Asn Gly Ile Thr Lys Glu Arg Leu Leu
            730                 735                 740 agc tat gat cgt gct att cat tca gaa cca aat ttc aga agt gaa cag   2431
Ser Tyr Asp Arg Ala Ile His Ser Glu Pro Asn Phe Arg Ser Glu Gln
        745                 750                 755 aag gcg ggt tta ctc cgt gac ctg gga aat tac atg aga agc cta aag   2479
Lys Ala Gly Leu Leu Arg Asp Leu Gly Asn Tyr Met Arg Ser Leu Lys
```

|  |  |
|---|---|
| Lys Ala Gly Leu Leu Arg Asp Leu Gly Asn Tyr Met Arg Ser Leu Lys<br>760                        765                    770 | |
| gct gtg cat tct ggt gct gat ctt gaa tct gct ata gca agt tgt atg<br>Ala Val His Ser Gly Ala Asp Leu Glu Ser Ala Ile Ala Ser Cys Met<br>775                        780                    785                    790 | 2527 |
| gga tac aaa tca gag ggt gaa ggt ttc atg gtt ggt gtt cag atc aat<br>Gly Tyr Lys Ser Glu Gly Glu Gly Phe Met Val Gly Val Gln Ile Asn<br>                    795                    800                    805 | 2575 |
| cca gtg aag ggt tta cca tct gga ttt ccg gag ttg ctt gaa ttt gtg<br>Pro Val Lys Gly Leu Pro Ser Gly Phe Pro Glu Leu Leu Glu Phe Val<br>          810                    815                    820 | 2623 |
| ctt gaa cat gtt gag gat aaa tca gcg gaa cca ctt ctt gag ggg cta<br>Leu Glu His Val Glu Asp Lys Ser Ala Glu Pro Leu Leu Glu Gly Leu<br>              825                    830                    835 | 2671 |
| ttg gaa gct cga gtt gaa ctg cgc cct ttg ctt ctt gat tcg cgt gaa<br>Leu Glu Ala Arg Val Glu Leu Arg Pro Leu Leu Leu Asp Ser Arg Glu<br>840                        845                    850 | 2719 |
| cgc atg aaa gat ctt ata ttt ttg gac att gct ctt gat tct acc ttc<br>Arg Met Lys Asp Leu Ile Phe Leu Asp Ile Ala Leu Asp Ser Thr Phe<br>855                        860                    865                    870 | 2767 |
| agg aca gca att gaa agg tca tat gag gag ctg aat gat gca gcc cca<br>Arg Thr Ala Ile Glu Arg Ser Tyr Glu Glu Leu Asn Asp Ala Ala Pro<br>                    875                    880                    885 | 2815 |
| gag aaa ata atg tac ttc atc agt ctt gtc ctt gaa aat ctt gcg ctt<br>Glu Lys Ile Met Tyr Phe Ile Ser Leu Val Leu Glu Asn Leu Ala Leu<br>          890                    895                    900 | 2863 |
| tca att gac gac aat gaa gac atc ctg tat tgt tta aag gga tgg aac<br>Ser Ile Asp Asp Asn Glu Asp Ile Leu Tyr Cys Leu Lys Gly Trp Asn<br>              905                    910                    915 | 2911 |
| caa gcc ttg gaa atg gct aag caa aaa gac gac caa tgg gcg ctc tat<br>Gln Ala Leu Glu Met Ala Lys Gln Lys Asp Asp Gln Trp Ala Leu Tyr<br>920                        925                    930 | 2959 |
| gct aaa gca ttt ctt gac aga aac aga ctt gcc ctt gcg agc aag gga<br>Ala Lys Ala Phe Leu Asp Arg Asn Arg Leu Ala Leu Ala Ser Lys Gly<br>935                        940                    945                    950 | 3007 |
| gaa caa tac cat aat atg atg cag ccc tct gct gag tat ctt ggc tcg<br>Glu Gln Tyr His Asn Met Met Gln Pro Ser Ala Glu Tyr Leu Gly Ser<br>              955                    960                    965 | 3055 |
| tta ctc agc ata gac caa tgg gca gtc aat atc ttc aca gaa gaa att<br>Leu Leu Ser Ile Asp Gln Trp Ala Val Asn Ile Phe Thr Glu Glu Ile<br>          970                    975                    980 | 3103 |
| ata cgc ggt gga tca gct gct act ctg tct gct ctt ctg aac cga ttt<br>Ile Arg Gly Gly Ser Ala Ala Thr Leu Ser Ala Leu Leu Asn Arg Phe<br>              985                    990                    995 | 3151 |
| gat cct gtt tta agg aat gtt gct cac ctc gga agt tgg cag gtt<br>Asp Pro Val Leu Arg Asn Val Ala His Leu Gly Ser Trp Gln Val<br>1000                        1005                    1010 | 3196 |
| ata agc ccg gtt gaa gta tca ggt tat gtg gtt gtg gtt gat gag<br>Ile Ser Pro Val Glu Val Ser Gly Tyr Val Val Val Val Asp Glu<br>1015                        1020                    1025 | 3241 |
| tta ctt gct gtc cag aac aaa tct tat gat aaa cca acc atc ctt<br>Leu Leu Ala Val Gln Asn Lys Ser Tyr Asp Lys Pro Thr Ile Leu<br>1030                        1035                    1040 | 3286 |
| gtg gca aag agt gtc aag gga gag gaa gaa ata cca gat gga gta<br>Val Ala Lys Ser Val Lys Gly Glu Glu Glu Ile Pro Asp Gly Val<br>1045                        1050                    1055 | 3331 |
| gtt ggt gta att aca cct gat atg cca gat gtt ctg tct cat gtg<br>Val Gly Val Ile Thr Pro Asp Met Pro Asp Val Leu Ser His Val<br>1060                        1065                    1070 | 3376 |
| tca gtc cga gca agg aat agc aag gta ctg ttt gcg acc tgt ttt | 3421 |

|     |     |     |     |     |     |     |     |     |     |     |     |     |      |
|---|---|---|---|---|---|---|---|---|---|---|---|---|---|
| Ser | Val | Arg | Ala | Arg | Asn | Ser | Lys | Val | Leu | Phe | Ala | Thr | Cys Phe |
|     | 1075 |     |     |     | 1080 |     |     |     |     | 1085 |     |     |      |
| gac | cac | acc | act | cta | tct | gaa | ctt | gaa | gga | tat | gat | cag | aaa ctg | 3466 |
| Asp | His | Thr | Thr | Leu | Ser | Glu | Leu | Glu | Gly | Tyr | Asp | Gln | Lys Leu |
|     | 1090 |     |     |     | 1095 |     |     |     |     | 1100 |     |     |      |
| ttt | tcc | ttc | aag | cct | act | tct | gca | gat | ata | acc | tat | agg | gag atc | 3511 |
| Phe | Ser | Phe | Lys | Pro | Thr | Ser | Ala | Asp | Ile | Thr | Tyr | Arg | Glu Ile |
|     | 1105 |     |     |     | 1110 |     |     |     |     | 1115 |     |     |      |
| aca | gag | agt | gaa | ctt | cag | caa | tca | agt | tct | cca | aat | gca | gaa gtt | 3556 |
| Thr | Glu | Ser | Glu | Leu | Gln | Gln | Ser | Ser | Ser | Pro | Asn | Ala | Glu Val |
|     | 1120 |     |     |     | 1125 |     |     |     |     | 1130 |     |     |      |
| ggc | cat | gca | gta | cca | tct | att | tca | ttg | gcc | aag | aag | aaa | ttt ctt | 3601 |
| Gly | His | Ala | Val | Pro | Ser | Ile | Ser | Leu | Ala | Lys | Lys | Lys | Phe Leu |
|     | 1135 |     |     |     | 1140 |     |     |     |     | 1145 |     |     |      |
| gga | aaa | tat | gca | ata | tca | gcc | gaa | gaa | ttc | tct | gag | gaa | atg gtt | 3646 |
| Gly | Lys | Tyr | Ala | Ile | Ser | Ala | Glu | Glu | Phe | Ser | Glu | Glu | Met Val |
|     | 1150 |     |     |     | 1155 |     |     |     |     | 1160 |     |     |      |
| ggg | gcc | aag | tct | cgg | aat | ata | gca | tac | ctc | aaa | gga | aaa | gta cct | 3691 |
| Gly | Ala | Lys | Ser | Arg | Asn | Ile | Ala | Tyr | Leu | Lys | Gly | Lys | Val Pro |
|     | 1165 |     |     |     | 1170 |     |     |     |     | 1175 |     |     |      |
| tca | tgg | gtc | ggt | gtc | cca | acg | tca | gtt | gcg | ata | cca | ttt | ggc act | 3736 |
| Ser | Trp | Val | Gly | Val | Pro | Thr | Ser | Val | Ala | Ile | Pro | Phe | Gly Thr |
|     | 1180 |     |     |     | 1185 |     |     |     |     | 1190 |     |     |      |
| ttt | gag | aag | gtt | ttg | tca | gat | ggg | ctt | aat | aag | gaa | gta | gca cag | 3781 |
| Phe | Glu | Lys | Val | Leu | Ser | Asp | Gly | Leu | Asn | Lys | Glu | Val | Ala Gln |
|     | 1195 |     |     |     | 1200 |     |     |     |     | 1205 |     |     |      |
| agc | ata | gag | aag | ctt | aag | atc | aga | ctt | gcc | caa | gaa | gat | ttt agt | 3826 |
| Ser | Ile | Glu | Lys | Leu | Lys | Ile | Arg | Leu | Ala | Gln | Glu | Asp | Phe Ser |
|     | 1210 |     |     |     | 1215 |     |     |     |     | 1220 |     |     |      |
| gct | cta | ggt | gaa | ata | aga | aaa | gtc | gtc | ctt | aat | ctt | act | gct cct | 3871 |
| Ala | Leu | Gly | Glu | Ile | Arg | Lys | Val | Val | Leu | Asn | Leu | Thr | Ala Pro |
|     | 1225 |     |     |     | 1230 |     |     |     |     | 1235 |     |     |      |
| atg | caa | ttg | gtt | aat | gag | ctg | aag | gag | agg | atg | cta | ggc | tct gga | 3916 |
| Met | Gln | Leu | Val | Asn | Glu | Leu | Lys | Glu | Arg | Met | Leu | Gly | Ser Gly |
|     | 1240 |     |     |     | 1245 |     |     |     |     | 1250 |     |     |      |
| atg | ccc | tgg | cct | ggt | gat | gaa | gga | gac | aag | cgt | tgg | gag | caa gca | 3961 |
| Met | Pro | Trp | Pro | Gly | Asp | Glu | Gly | Asp | Lys | Arg | Trp | Glu | Gln Ala |
|     | 1255 |     |     |     | 1260 |     |     |     |     | 1265 |     |     |      |
| tgg | atg | gct | att | aaa | aag | gtt | tgg | gca | tca | aaa | tgg | aac | gaa aga | 4006 |
| Trp | Met | Ala | Ile | Lys | Lys | Val | Trp | Ala | Ser | Lys | Trp | Asn | Glu Arg |
|     | 1270 |     |     |     | 1275 |     |     |     |     | 1280 |     |     |      |
| gca | tat | ttt | agc | aca | cgc | aag | gtg | aaa | ctt | gat | cat | gag | tac ctt | 4051 |
| Ala | Tyr | Phe | Ser | Thr | Arg | Lys | Val | Lys | Leu | Asp | His | Glu | Tyr Leu |
|     | 1285 |     |     |     | 1290 |     |     |     |     | 1295 |     |     |      |
| tcg | atg | gct | gtt | ctc | gtg | caa | gaa | gtt | gtg | aat | gca | gat | tat gct | 4096 |
| Ser | Met | Ala | Val | Leu | Val | Gln | Glu | Val | Val | Asn | Ala | Asp | Tyr Ala |
|     | 1300 |     |     |     | 1305 |     |     |     |     | 1310 |     |     |      |
| ttt | gtc | att | cat | acc | aca | aac | cca | tcg | tct | gga | gat | tct | tct gag | 4141 |
| Phe | Val | Ile | His | Thr | Thr | Asn | Pro | Ser | Ser | Gly | Asp | Ser | Ser Glu |
|     | 1315 |     |     |     | 1320 |     |     |     |     | 1325 |     |     |      |
| ata | tat | gct | gaa | gtg | gtg | aaa | ggg | ctt | ggc | gag | acc | ctc | gtg gga | 4186 |
| Ile | Tyr | Ala | Glu | Val | Val | Lys | Gly | Leu | Gly | Glu | Thr | Leu | Val Gly |
|     | 1330 |     |     |     | 1335 |     |     |     |     | 1340 |     |     |      |
| gcc | tat | cct | ggt | cgt | gct | atg | agc | ttt | gtt | tgc | aaa | aaa | gat gac | 4231 |
| Ala | Tyr | Pro | Gly | Arg | Ala | Met | Ser | Phe | Val | Cys | Lys | Lys | Asp Asp |
|     | 1345 |     |     |     | 1350 |     |     |     |     | 1355 |     |     |      |
| ctt | gac | tct | ccc | aag | tta | ctt | ggt | tac | cca | agc | aag | cca | att ggt | 4276 |
| Leu | Asp | Ser | Pro | Lys | Leu | Leu | Gly | Tyr | Pro | Ser | Lys | Pro | Ile Gly |
|     | 1360 |     |     |     | 1365 |     |     |     |     | 1370 |     |     |      |
| ctc | ttc | ata | agg | caa | tca | atc | atc | ttc | cgt | tcc | gac | tcc | aac ggt | 4321 |

```
Leu Phe Ile Arg Gln Ser Ile Ile Phe Arg Ser Asp Ser Asn Gly
    1375                1380                1385 gag gac ctg gaa ggt tat gct gga gca gga tta tat gat agt gta        4366
Glu Asp Leu Glu Gly Tyr Ala Gly Ala Gly Leu Tyr Asp Ser Val
    1390                1395                1400 ccg atg gat gag gag gat gag gtt gta ctt gat tat aca act gac        4411
Pro Met Asp Glu Glu Asp Glu Val Val Leu Asp Tyr Thr Thr Asp
    1405                1410                1415 cct ctt ata gta gac cgt gga ttc cga agc tca atc ctc tca agc        4456
Pro Leu Ile Val Asp Arg Gly Phe Arg Ser Ser Ile Leu Ser Ser
    1420                1425                1430 ata gca cgg gct ggc cat gcc atc gag gag cta tat ggt tct cct        4501
Ile Ala Arg Ala Gly His Ala Ile Glu Glu Leu Tyr Gly Ser Pro
    1435                1440                1445 cag gac gtc gag gga gta gtg aag gat gga aaa atc tat gta gtc        4546
Gln Asp Val Glu Gly Val Val Lys Asp Gly Lys Ile Tyr Val Val
    1450                1455                1460 cag aca aga cca cag atg tag tatgtatgca tctattagac agctcaataa       4597
Gln Thr Arg Pro Gln Met
    1465 gcactgttgt acgcttgtat ggttgggaca tatgggcgtt atggcatgta tagttgtatg  4657 cctagatgta caacacgtgt actcgtatat atatatataa atgctgaaac aagcattggt  4717 cctgtactgt agtttctaca tttcattgtc accaataatt aagtgtactc ctatggctgg  4777 gagtctatga aaatggacgt gttgacttat tgggtaataa ataatttata taaaaaaaaa  4837 aaaaaaaag                                                          4846

<210> SEQ ID NO 17
<211> LENGTH: 1469
<212> TYPE: PRT
<213> ORGANISM: Zea mays

<400> SEQUENCE: 17

Met Ser Gly Phe Ser Ala Ala Asn Ala Ala Ala Ala Glu Arg Cys
1               5                   10                  15

Ala Leu Ala Phe Arg Ala Arg Pro Ala Ala Ser Ser Pro Ala Lys Arg
            20                  25                  30

Gln Gln Gln Pro Gln Pro Ala Ser Leu Arg Arg Ser Gly Gly Gln Arg
        35                  40                  45

Arg Pro Thr Thr Leu Ser Ala Ser Ser Arg Gly Pro Val Val Pro Arg
    50                  55                  60

Ala Val Ala Thr Ser Ala Asp Arg Ala Ser Pro Asp Leu Ile Gly Lys
65                  70                  75                  80

Phe Thr Leu Asp Ser Asn Ser Glu Leu Gln Val Ala Val Asn Pro Ala
                85                  90                  95

Pro Gln Gly Leu Val Ser Glu Ile Ser Leu Glu Val Thr Asn Thr Ser
            100                 105                 110

Gly Ser Leu Ile Leu His Trp Gly Ala Leu Arg Pro Asp Lys Arg Asp
        115                 120                 125

Trp Ile Leu Pro Ser Arg Lys Pro Asp Gly Thr Thr Val Tyr Lys Asn
    130                 135                 140

Arg Ala Leu Arg Thr Pro Phe Val Lys Ser Gly Asp Asn Ser Thr Leu
145                 150                 155                 160

Arg Ile Glu Ile Asp Asp Pro Gly Val His Ala Ile Glu Phe Leu Ile
                165                 170                 175

Phe Asp Glu Thr Gln Asn Lys Trp Phe Lys Asn Asn Gly Gln Asn Phe
            180                 185                 190
```

```
Gln Val Gln Phe Gln Ser Ser Arg His Gln Gly Thr Gly Ala Ser Gly
        195                 200                 205

Ala Ser Ser Ser Ala Thr Ser Thr Leu Val Pro Glu Asp Leu Val Gln
210                 215                 220

Ile Gln Ala Tyr Leu Arg Trp Glu Arg Gly Lys Gln Ser Tyr Thr
225                 230                 235                 240

Pro Glu Gln Glu Lys Glu Glu Tyr Ala Ala Arg Ala Glu Leu Ile
                245                 250                 255

Glu Glu Val Asn Arg Gly Val Ser Leu Glu Lys Leu Arg Ala Lys Leu
                260                 265                 270

Thr Lys Ala Pro Glu Ala Pro Glu Ser Asp Glu Ser Lys Ser Ser Ala
            275                 280                 285

Ser Arg Met Pro Ile Gly Lys Leu Pro Glu Asp Leu Val Gln Val Gln
        290                 295                 300

Ala Tyr Ile Arg Trp Glu Gln Ala Gly Lys Pro Asn Tyr Pro Pro Glu
305                 310                 315                 320

Lys Gln Leu Val Glu Phe Glu Ala Arg Lys Glu Leu Gln Ala Glu
                325                 330                 335

Val Asp Lys Gly Ile Ser Ile Asp Gln Leu Arg Gln Lys Ile Leu Lys
                340                 345                 350

Gly Asn Ile Glu Ser Lys Val Ser Lys Gln Leu Lys Asn Lys Lys Tyr
            355                 360                 365

Phe Ser Val Glu Arg Ile Gln Arg Lys Lys Arg Asp Ile Thr Gln Leu
        370                 375                 380

Leu Ser Lys His Lys His Thr Leu Val Glu Asp Lys Val Glu Val Val
385                 390                 395                 400

Pro Lys Gln Pro Thr Val Leu Asp Leu Phe Thr Lys Ser Leu His Glu
                405                 410                 415

Lys Asp Gly Cys Glu Val Leu Ser Arg Lys Leu Phe Lys Phe Gly Asp
                420                 425                 430

Lys Glu Ile Leu Ala Ile Ser Thr Lys Val Gln Asn Lys Thr Glu Val
            435                 440                 445

His Leu Ala Thr Asn His Thr Asp Pro Leu Ile Leu His Trp Ser Leu
        450                 455                 460

Ala Lys Asn Ala Gly Glu Trp Lys Ala Pro Ser Pro Asn Ile Leu Pro
465                 470                 475                 480

Ser Gly Ser Thr Leu Leu Asp Lys Ala Cys Glu Thr Glu Phe Thr Lys
                485                 490                 495

Ser Glu Leu Asp Gly Leu His Tyr Gln Val Val Glu Ile Glu Leu Asp
                500                 505                 510

Asp Gly Gly Tyr Lys Gly Met Pro Phe Val Leu Arg Ser Gly Glu Thr
            515                 520                 525

Trp Lys Lys Asn Asn Gly Ser Asp Phe Phe Leu Asp Phe Ser Thr His
        530                 535                 540

Asp Val Arg Asn Ile Lys Leu Lys Gly Asn Gly Asp Ala Gly Lys Gly
545                 550                 555                 560

Thr Ala Lys Ala Leu Leu Glu Arg Ile Ala Asp Leu Glu Glu Asp Ala
                565                 570                 575

Gln Arg Ser Leu Met His Arg Phe Asn Ile Ala Ala Asp Leu Ala Asp
                580                 585                 590

Gln Ala Arg Asp Ala Gly Leu Leu Gly Ile Val Gly Leu Phe Val Trp
            595                 600                 605

Ile Arg Phe Met Ala Thr Arg Gln Leu Thr Trp Asn Lys Asn Tyr Asn
```

```
                  610                 615                 620
Val Lys Pro Arg Glu Ile Ser Lys Ala Gln Asp Arg Phe Thr Asp Asp
625                 630                 635                 640

Leu Glu Asn Met Tyr Lys Ala Tyr Pro Gln Tyr Arg Glu Ile Leu Arg
                645                 650                 655

Met Ile Met Ala Ala Val Gly Arg Gly Gly Glu Gly Asp Val Gly Gln
                  660                 665                 670

Arg Ile Arg Asp Glu Ile Leu Val Ile Gln Arg Asn Asn Asp Cys Lys
                675                 680                 685

Gly Gly Met Met Glu Glu Trp His Gln Lys Leu His Asn Asn Thr Ser
690                 695                 700

Pro Asp Asp Val Val Ile Cys Gln Ala Leu Ile Asp Tyr Ile Lys Ser
705                 710                 715                 720

Asp Phe Asp Ile Ser Val Tyr Trp Asp Thr Leu Asn Lys Asn Gly Ile
                  725                 730                 735

Thr Lys Glu Arg Leu Leu Ser Tyr Asp Arg Ala Ile His Ser Glu Pro
                740                 745                 750

Asn Phe Arg Ser Glu Gln Lys Ala Gly Leu Leu Arg Asp Leu Gly Asn
                755                 760                 765

Tyr Met Arg Ser Leu Lys Ala Val His Ser Gly Ala Asp Leu Glu Ser
770                 775                 780

Ala Ile Ala Ser Cys Met Gly Tyr Lys Ser Glu Gly Glu Gly Phe Met
785                 790                 795                 800

Val Gly Val Gln Ile Asn Pro Val Lys Gly Leu Pro Ser Gly Phe Pro
                  805                 810                 815

Glu Leu Leu Glu Phe Val Leu Glu His Val Glu Asp Lys Ser Ala Glu
                820                 825                 830

Pro Leu Leu Glu Gly Leu Leu Glu Ala Arg Val Glu Leu Arg Pro Leu
                835                 840                 845

Leu Leu Asp Ser Arg Glu Arg Met Lys Asp Leu Ile Phe Leu Asp Ile
                850                 855                 860

Ala Leu Asp Ser Thr Phe Arg Thr Ala Ile Glu Arg Ser Tyr Glu Glu
865                 870                 875                 880

Leu Asn Asp Ala Ala Pro Glu Lys Ile Met Tyr Phe Ile Ser Leu Val
                  885                 890                 895

Leu Glu Asn Leu Ala Leu Ser Ile Asp Asp Asn Glu Asp Ile Leu Tyr
                900                 905                 910

Cys Leu Lys Gly Trp Asn Gln Ala Leu Glu Met Ala Lys Gln Lys Asp
                915                 920                 925

Asp Gln Trp Ala Leu Tyr Ala Lys Ala Phe Leu Asp Arg Asn Arg Leu
                930                 935                 940

Ala Leu Ala Ser Lys Gly Glu Gln Tyr His Asn Met Met Gln Pro Ser
945                 950                 955                 960

Ala Glu Tyr Leu Gly Ser Leu Ser Ile Asp Gln Trp Ala Val Asn
                  965                 970                 975

Ile Phe Thr Glu Glu Ile Arg Gly Gly Ser Ala Ala Thr Leu Ser
                  980                 985                 990

Ala Leu Leu Asn Arg Phe Asp Pro  Val Leu Arg Asn Val  Ala His Leu
                  995                 1000                1005

Gly Ser  Trp Gln Val Ile Ser  Pro Val Glu Val Ser  Gly Tyr Val
          1010                1015                1020

Val Val  Val Asp Glu Leu Leu  Ala Val Gln Asn Lys  Ser Tyr Asp
          1025                1030                1035
```

```
Lys Pro Thr Ile Leu Val Ala Lys Ser Val Lys Gly Glu Glu Glu
1040                1045                1050

Ile Pro Asp Gly Val Val Gly Val Ile Thr Pro Asp Met Pro Asp
1055                1060                1065

Val Leu Ser His Val Ser Val Arg Ala Arg Asn Ser Lys Val Leu
1070                1075                1080

Phe Ala Thr Cys Phe Asp His Thr Thr Leu Ser Glu Leu Glu Gly
1085                1090                1095

Tyr Asp Gln Lys Leu Phe Ser Phe Lys Pro Thr Ser Ala Asp Ile
1100                1105                1110

Thr Tyr Arg Glu Ile Thr Glu Ser Glu Leu Gln Gln Ser Ser Ser
1115                1120                1125

Pro Asn Ala Glu Val Gly His Ala Val Pro Ser Ile Ser Leu Ala
1130                1135                1140

Lys Lys Lys Phe Leu Gly Lys Tyr Ala Ile Ser Ala Glu Glu Phe
1145                1150                1155

Ser Glu Glu Met Val Gly Ala Lys Ser Arg Asn Ile Ala Tyr Leu
1160                1165                1170

Lys Gly Lys Val Pro Ser Trp Val Gly Val Pro Thr Ser Val Ala
1175                1180                1185

Ile Pro Phe Gly Thr Phe Glu Lys Val Leu Ser Asp Gly Leu Asn
1190                1195                1200

Lys Glu Val Ala Gln Ser Ile Glu Lys Leu Lys Ile Arg Leu Ala
1205                1210                1215

Gln Glu Asp Phe Ser Ala Leu Gly Glu Ile Arg Lys Val Val Leu
1220                1225                1230

Asn Leu Thr Ala Pro Met Gln Leu Val Asn Glu Leu Lys Glu Arg
1235                1240                1245

Met Leu Gly Ser Gly Met Pro Trp Pro Gly Asp Glu Gly Asp Lys
1250                1255                1260

Arg Trp Glu Gln Ala Trp Met Ala Ile Lys Lys Val Trp Ala Ser
1265                1270                1275

Lys Trp Asn Glu Arg Ala Tyr Phe Ser Thr Arg Lys Val Lys Leu
1280                1285                1290

Asp His Glu Tyr Leu Ser Met Ala Val Leu Val Gln Glu Val Val
1295                1300                1305

Asn Ala Asp Tyr Ala Phe Val Ile His Thr Thr Asn Pro Ser Ser
1310                1315                1320

Gly Asp Ser Ser Glu Ile Tyr Ala Glu Val Val Lys Gly Leu Gly
1325                1330                1335

Glu Thr Leu Val Gly Ala Tyr Pro Gly Arg Ala Met Ser Phe Val
1340                1345                1350

Cys Lys Lys Asp Asp Leu Asp Ser Pro Lys Leu Leu Gly Tyr Pro
1355                1360                1365

Ser Lys Pro Ile Gly Leu Phe Ile Arg Gln Ser Ile Ile Phe Arg
1370                1375                1380

Ser Asp Ser Asn Gly Glu Asp Leu Glu Gly Tyr Ala Gly Ala Gly
1385                1390                1395

Leu Tyr Asp Ser Val Pro Met Asp Glu Glu Asp Glu Val Val Leu
1400                1405                1410

Asp Tyr Thr Thr Asp Pro Leu Ile Val Asp Arg Gly Phe Arg Ser
1415                1420                1425

Ser Ile Leu Ser Ser Ile Ala Arg Ala Gly His Ala Ile Glu Glu
1430                1435                1440
```

```
Leu Tyr Gly Ser Pro Gln Asp Val Glu Gly Val Val Lys Asp Gly
    1445                1450                1455
Lys Ile Tyr Val Val Gln Thr Arg Pro Gln Met
    1460                1465
```

```
<210> SEQ ID NO 18
<211> LENGTH: 27
<212> TYPE: DNA
<213> ORGANISM: Synthetic

<400> SEQUENCE: 18
gactcaacca cataacacac aaagatc                                        27

<210> SEQ ID NO 19
<211> LENGTH: 21
<212> TYPE: DNA
<213> ORGANISM: Synthetic

<400> SEQUENCE: 19
tggtaacgag gcaaatgcag a                                              21

<210> SEQ ID NO 20
<211> LENGTH: 25
<212> TYPE: DNA
<213> ORGANISM: Synthetic

<400> SEQUENCE: 20
atctcttatc acaccacctc caatg                                          25

<210> SEQ ID NO 21
<211> LENGTH: 24
<212> TYPE: DNA
<213> ORGANISM: Synthetic

<400> SEQUENCE: 21
ggaaccgata atgcctacat gctc                                           24

<210> SEQ ID NO 22
<211> LENGTH: 39
<212> TYPE: DNA
<213> ORGANISM: Synthetic

<400> SEQUENCE: 22
aaaactcgag gaggatcaat gacgtcgctg cggcccctc                           39

<210> SEQ ID NO 23
<211> LENGTH: 21
<212> TYPE: DNA
<213> ORGANISM: Synthetic

<400> SEQUENCE: 23
ccaggttaag tttggtgagc a                                              21

<210> SEQ ID NO 24
<211> LENGTH: 22
<212> TYPE: DNA
<213> ORGANISM: Synthetic

<400> SEQUENCE: 24
caaagcacga tatctgacct gt                                             22

<210> SEQ ID NO 25
<211> LENGTH: 22
```

```
<212> TYPE: DNA
<213> ORGANISM: Synthetic

<400> SEQUENCE: 25
ttgttcgcgg gatattgtca ga                                    22

<210> SEQ ID NO 26
<211> LENGTH: 24
<212> TYPE: DNA
<213> ORGANISM: Synthetic

<400> SEQUENCE: 26
gacaagggca tcaagagtag tatc                                  24

<210> SEQ ID NO 27
<211> LENGTH: 20
<212> TYPE: DNA
<213> ORGANISM: Synthetic

<400> SEQUENCE: 27
atgatgcgcc tgataatgct                                       20

<210> SEQ ID NO 28
<211> LENGTH: 21
<212> TYPE: DNA
<213> ORGANISM: Synthetic

<400> SEQUENCE: 28
ggcaaacagt atgaagcacg a                                     21

<210> SEQ ID NO 29
<211> LENGTH: 21
<212> TYPE: DNA
<213> ORGANISM: Synthetic

<400> SEQUENCE: 29
catttggatc aatggaggat g                                     21

<210> SEQ ID NO 30
<211> LENGTH: 23
<212> TYPE: DNA
<213> ORGANISM: Synthetic

<400> SEQUENCE: 30
ctatggctgt ggcctgcttt gca                                   23

<210> SEQ ID NO 31
<211> LENGTH: 33
<212> TYPE: DNA
<213> ORGANISM: Synthetic

<400> SEQUENCE: 31
aaaactcgag ctatggctgt ggcctgcttt gca                        33

<210> SEQ ID NO 32
<211> LENGTH: 63
<212> TYPE: DNA
<213> ORGANISM: Synthetic

<400> SEQUENCE: 32
tgcaggctgc agagctccta ggctcgagtt aacactagta agcttaatta agatatcatt    60
tac                                                                 63
```

```
<210> SEQ ID NO 33
<211> LENGTH: 67
<212> TYPE: DNA
<213> ORGANISM: Synthetic

<400> SEQUENCE: 33
aattgtaaat gatatcttaa ttaagcttac tagtgttaac tcgagcctag gagctctgca    60
gcctgca                                                              67

<210> SEQ ID NO 34
<211> LENGTH: 47
<212> TYPE: DNA
<213> ORGANISM: Synthetic

<400> SEQUENCE: 34
acttctgcag cggccgcgat cgttcaaaca tttggcaata aagtttc                  47

<210> SEQ ID NO 35
<211> LENGTH: 50
<212> TYPE: DNA
<213> ORGANISM: Synthetic

<400> SEQUENCE: 35
tctaagcttg gcgccgctag cagatctgat ctagtaacat agatgacacc               50

<210> SEQ ID NO 36
<211> LENGTH: 38
<212> TYPE: DNA
<213> ORGANISM: Synthetic

<400> SEQUENCE: 36
tttttgcgcg cgttaattaa cgactcacta tagggcga                            38

<210> SEQ ID NO 37
<211> LENGTH: 41
<212> TYPE: DNA
<213> ORGANISM: Synthetic

<400> SEQUENCE: 37
tttttgcgcg cttaattaac cctcactaaa gggaacaaaa g                        41

<210> SEQ ID NO 38
<211> LENGTH: 28
<212> TYPE: DNA
<213> ORGANISM: Synthetic

<400> SEQUENCE: 38
aaaacaattg gcgcctggag ggaggaga                                       28

<210> SEQ ID NO 39
<211> LENGTH: 35
<212> TYPE: DNA
<213> ORGANISM: Synthetic

<400> SEQUENCE: 39
aaaacaattg atgatcaatc agacaatcac tagaa                               35
```

PLANTS WITH INCREASED ACTIVITY OF MULTIPLE STARCH PHOSPHORYLATING ENZYMES

This application is a 371 National Stage filing of PCT/EP2005/002457 filed Mar. 4, 2005, which claims priority to EP 04090284.3 filed Jul. 21, 2004, EP 04090121.7 filed Mar. 29, 2004, EP 04090086.2 filed Mar. 5, 2004, and U.S. Provisional Patent Application No. 60/550,021 filed Mar. 5, 2004, all of which are hereby incorporated by reference in their entirety.

The present invention relates to plant cells and plants, which are genetically modified, wherein the genetic modification leads to an increase in the activity of a starch phosphorylating OK1 protein and a starch phosphorylating R1 protein in comparison with corresponding wild type plant cells or wild type plants that have not been genetically modified. Furthermore, the present invention relates to means and methods for the manufacture of such plant cells and plants. Plant cells and plants of this type synthesise a modified starch. The present invention therefore also relates to the starch synthesised by the plant cells and plants according to the invention, methods for the manufacture of this starch, and the manufacture of starch derivatives of this modified starch, as well as flours containing starches according to the invention.

Furthermore, the present invention relates to nucleic acid molecules and vectors containing sequences which code for an OK1 protein and an R1 protein, as well as host cells which contain these nucleic acid molecules.

With regard to the increasing importance currently attributed to plant constituents as renewable raw material sources, one of the tasks of biotechnological research is to endeavour to adapt these plant raw materials to suit the requirements of the processing industry. Furthermore, in order to enable regenerating raw materials to be used in as many areas of application as possible, it is necessary to achieve a large variety of materials.

The polysaccharide starch is made up of chemically uniform base components, the glucose molecules, but constitutes a complex mixture of different molecule forms, which exhibit differences with regard to the degree of polymerisation and branching, and therefore differ strongly from one another in their physical-chemical characteristics. Discrimination is made between amylose starch, an essentially unbranched polymer made from alpha-1,4-glycosidically linked glucose units, and the amylopectin starch, a branched polymer, in which the branches come about by the occurrence of additional alpha-1,6-glycosidic links. A further essential difference between amylose and amylopectin lies in the molecular weight. While amylose, depending on the origin of the starch, has a molecular weight of $5 \times 10^5$-$10^6$ Da, that of the amylopectin lies between $10^7$ and $10^8$ Da. The two macromolecules can be differentiated by their molecular weight and their different physical-chemical characteristics, which can most easily be made visible by their different iodine bonding characteristics.

Amylose has long been looked upon as a linear polymer, consisting of alpha-1,4-glycosidically linked alpha-D-glucose monomers. In more recent studies, however, the presence of alpha-1,6-glycosidic branching points (ca. 0.1%) has been shown (Hizukuri and Takagi, Carbohydr. Res. 134, (1984), 1-10; Takeda et al., Carbohydr. Res. 132, (1984), 83-92).

The functional characteristics of the starch such as, for example, the solubility, the retrogradation behaviour, the water bonding capability, the film formation characteristics, the viscosity, the sticking characteristics, the freezing-thawing stability, the acid stability, the gelling strength, the starch granule size of the starches, and others are affected by the amylose/amylopectin ratio, the molecular weight, the pattern of the side chain distribution, the ion concentration, the lipid and protein content, the average starch granule size of the starch, the starch granule morphology, etc. The functional characteristics of starch are also affected by phosphate content, a non-carbon component of starch. Discrimination is made between phosphate which is covalently bound to the glucose molecules in the form of monoesters (designated below as starch phosphate) and phosphate in the form of phospholipids with the starch associated.

The concentration of starch phosphate varies depending on plant type. Thus certain maize mutants synthesise a starch with an increased concentration of starch phosphate (waxy maize 0.002% and high-amylose maize 0.013%), while conventional maize species have only traces of starch phosphate. Small amounts of starch phosphate are likewise found in wheat (0.001%), while no starch phosphate has been shown in oats and sorghum. Likewise, less starch phosphate is found in rice mutants than in conventional rice species (0.013%). Significant amounts of starch phosphate have been shown in bulb or storage-root starch-synthesizing plants such as tapioca (0.008%), sweet potato (0.011%), arrowroot (0.021%) or potato (0.089%). The percentage values cited above for starch phosphate content relate to the respective dry weight of the starch and have been determined by Jane et al. (1996, Cereal Foods World 41 (11), 827-832).

Starch phosphate can exists in the form of monoesters at the C-2, C-3 or C-6 position of the polymerised glucose monomers (Takeda and Hizukuri, 1971, Starch/Stärke 23, 267-272). The phosphate distribution of the phosphate in starch synthesised by plants thus generally shows that approximately 30% to 40% of the phosphate residues are covalently bound in the C-3 position and approximately 60% to 70% of the phosphate residues are covalently bound in the C-6 position of the glucose molecules (Blennow et al., Int. J. of Biological Macromolecules 27, 211-218). Blennow et al. (2000, Carbohydrate Polymers 41, 163-174) determined a concentration of starch phosphate that is bound in the C-6 position of the glucose molecules for various starches such as potato starch (between 7.8 and 33.5 nMol per mg of starch, depending on species), starch from various *Curcuma* species (between 1.8 and 63 nMol per mg), tapioca starch (2.5 nMol per mg of starch), rice starch (1.0 nMol per mg of starch), mung bean starch (3.5 nMol per mg of starch) and sorghum starch (0.9 nMol per mg of starch). These authors could detect no bound starch phosphate in the C-6 position in barley starch and starch from various waxy mutants of maize. No connection between the genotype of a plant and the concentration of starch phosphate has yet been established (Jane et al., 1996, Cereal Foods World 41 (11), 827-832). Therefore it is presently not possible to affect the concentration of starch phosphate in plants through breeding measures.

Only one protein which causes the introduction of covalent bonds of phosphate residues to the glucose molecules of starch was previously described. This protein has the enzymatic activity of an alpha-glucan water dikinase (GWD, E.C.: 2.7.9.4) (Ritte et al., 2002, PNAS 99, 7166-7171), is often designated as R1 in the scientific literature and is bound to the starch granules of the storage starch in potato tubers (Loberth et al., 1998, Nature Biotechnology 16, 473-477). In the reaction catalysed by R1, the educts alpha-1,4-glucan (starch), adenosine triphosphate (ATP) and water are converted to the products glucan phosphate (starch phosphate), monophosphate and adenosine monophosphate. At the same time, the gamma phosphate residue of the ATP is transferred to water, and the beta phosphate residue of the ATP is transferred to the glucan (starch). R1 transfers the beta-phosphate residue in vitro from ATP to the C-6- and the C-3 position of the glucose molecules of alpha-1,4-glucans. The ratio of C-6 phosphate to C-3 phosphate which is obtained through the in vitro reaction corresponds to the ratio which exists in starch isolated from plants (Ritte et al., 2002, PNAS 99, 7166-7171). As about 70% of the starch phosphate present in potato starch is bonded to the glucose monomers of starch in the C-6 position and about 30% in the C-3 position, this means that R1 preferably phosphorylates the C-6 position of the glucose molecules. Furthermore, it has been shown that by the use of amylopectin from maize, among other things, R1 can phosphorylate alpha-1,4-glucans, which do not yet contain covalently bonded phosphate (Ritte et al., 2002, PNAS 99, 7166-7171), i.e. R1 is able to introduce phosphate de novo into alpha-1,4-glucans.

Wheat plants which have an increased activity of an R1 protein through overexpression of an R1 gene from potatoes are described in WO 02 34923. These plants synthesise a starch with significant amounts of starch phosphate in the C-6 position of the glucose molecules in comparison with corresponding wild type plants in which no starch phosphate could be detected.

Further proteins, which catalyse a reaction, which introduce covalently bound phosphate groups into the starch, have not been previously described. Enzymes, which preferably introduce phosphate groups in the C-3 position and/or the C-2 position of the glucose molecules of starch, are also unknown. Apart from the increase of the starch phosphate content in plants, there are therefore also no available ways of specifically influencing the phosphorylation of starch in plants, of modifying the phosphate distribution within the starch synthesised by plants, and/or of further increasing the starch phosphate content.

The object of the present invention is therefore based on providing modified starches with increased phosphate content and/or changed phosphate distribution as well as plant cells and/or plants that synthesise such a modified starch, as well as methods and means for the production of said plants and/or plant cells.

This problem is solved by the embodiments described in the claims.

The present invention therefore relates to genetically modified plant cells and plants, characterised in that they have an increased activity of at least one OK1 protein and at least one R1 protein in comparison with corresponding wild type plant cells or wild type plants that have not been genetically modified.

A first aspect of the present invention relates to a plant cell or plant, which is genetically modified, wherein the genetic modification leads to an increase in the activity of at least one OK1 protein and, simultaneously, at least one R1 protein, in comparison with corresponding wild type plant cells or wild type plants that have not been genetically modified.

At the same time, the genetic modification can be any genetic modification, which leads to an increase in the activity of at least one OK1 protein and (simultaneously) at least one R1 protein in genetically modified plant cells or genetically modified plants in comparison with corresponding wild type plant cells or wild type plants that have not been genetically modified.

In conjunction with the present invention, the term "wild type plant cell" means that the plant cells concerned were used as starting material for the manufacture of the plant cells according to the invention, i.e. their genetic information, apart from the introduced genetic modification, corresponds to that of a plant cell according to the invention.

In conjunction with the present invention, the term "wild type plant" means that the plants concerned were used as starting material for the manufacture of the plants according to the invention, i.e. their genetic information, apart from the introduced genetic modification, corresponds to that of a plant according to the invention.

In conjunction with the present invention, the term "corresponding" means that, in the comparison of several objects, the objects concerned that are compared with one another have been kept under the same conditions. In conjunction with the present invention, the term "corresponding" in conjunction with wild type plant cell or wild type plant compared to genetically modified plant cells or plants means that the plant cells or plants, which are compared with one another, have been raised under the same cultivation conditions and that they have the same (cultivation) age.

Here, within the framework of the present invention, the term "increased activity of at least one OK1 protein" means an increase in the expression of endogenous genes, which code OK1 proteins and/or an increase in the quantity of OK1 protein in the cells and/or an increase in the enzymatic activity of OK1 proteins in the cells.

Here, within the framework of the present invention, the term "increased activity of at least one R1 protein" means an increase in the expression of endogenous genes, which code R1 proteins and/or an increase in the quantity of R1 protein in the cells and/or an increase in the enzymatic activity of R1 proteins in the cells.

The increase in the expression can, for example, be determined by measuring the quantity of transcripts coding OK1 proteins or R1 proteins. This can take place through Northern blot analysis or RT-PCR. Here, an increase preferably means an increase in the quantity of transcripts in comparison with corresponding cells that have not been genetically modified by at least 50%, in particular by at least 70%, preferably by at least 85% and particularly preferably by at least 100%. An increase in the quantity of transcripts coding an OK1 protein also means that plants or plant cells that have no detectable quantities of transcripts coding an OK1 protein have detectable quantities coding an OK1 protein after genetic modification according to the invention. An increase in the quantity of transcripts coding an R1 protein also means that plants or plant cells that have no detectable quantities of transcripts coding an R1 protein have detectable quantities of transcripts coding an R1 protein after genetic modification according to the invention.

The increase in the amount of protein of an OK1 protein or an R1 protein, which results in an increased activity of these proteins in the plant cells concerned, can, for example, be determined by immunological methods such as Western blot analysis, ELISA (Enzyme Linked Immuno Sorbent Assay) or RIA (Radio Immune Assay). Here, an increase preferably means an increase in the amount of protein in comparison with corresponding cells that have not been genetically modified by at least 50%, in particular by at least 70%, preferably by at least 85% and particularly preferably by at least 100%. An increase in the amount of an OK1 protein also means that plants or plant cells that have no detectable activity of an OK1 protein have a detectable amount of an OK1 protein after genetic modification according to the invention. An increase in the amount of an R1 protein also means that plants or plant cells that have no detectable activity of an R1 protein have a detectable amount of an R1 protein after genetic modification according to the invention.

Methods for the manufacture of antibodies that react specifically with a designated protein, i.e. that bind specifically to the said protein, are known to the person skilled in the art (see, for example, Lottspeich and Zorbas (Eds.), 1998, Bioanalytik, Spektrum akad, Verlag, Heidelberg, Berlin, ISBN 3-8274-0041-4). The manufacture of such antibodies is offered as a contractual service by several firms (for example, Eurogentec, Belgium). A possibility for manufacture of antibodies that react specifically with an OK1 protein is further described below (see Example 10). An antibody with which an increase in the amount of R1 protein can be determined by means of immunological methods is described by Lorberth et al. (1998, Nature Biotechnology 16, 473-477) and Ritte et al. (2000, Plant Journal 21, 387-391).

Within the framework of the present invention, the term "OK 1 protein" should be understood to mean a protein that transfers a phosphate residue from ATP to starch that is already phosphorylated (P-starch). Starches isolated from leaves of an *Arabisopsis thaliana* sex1-3 mutant have no detectable quantity of covalently bound phosphate residues and are not phosphorylated by an OK1 protein, i.e., an OK1 protein according to the invention requires starch that is already phosphorylated as a substrate for the transfer of additional phosphate residues.

Preferably, the beta phosphate residue of the ATP is transferred from an OK1 protein to the starch and the gamma phosphate residue of the ATP is transferred to water. As an additional reaction product, AMP (adenosine monophosphate) is formed during a phosphorylation reaction of P-starch carried out by an OK1 protein. An OK1 protein is therefore designated as [phosphorylated alpha-glucan]-water-dikinase ([P-glucan]-water-dikinase) or as [phosphorylated starch] water-dikinase.

Therefore, OK1 proteins catalyse a reaction according to the following formula:

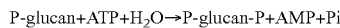

P-glucan+ATP+$H_2O$→P-glucan-P+AMP+Pi

Preferably, an additional phosphate monoester bond in the C-6 position and/or in the C-3 position of a glucose molecule of the P-starch is formed on the P-starch phosphorylated by an OK1 protein. Particularly preferably, several additional phosphate monoester bonds in the C-3 position are formed during the phosphorylation of P-starch catalysed by an OK1 protein in comparison with phosphate monoester bonds in the C-6 position of the glucose molecules of the corresponding P-starch.

Amino acid sequences that code OK1 proteins contain a phosphohistidine domain. Phosphohistidine domains are, for example, described by Tien-Shin Yu et al. (2001, Plant Cell 13, 1907-1918). Phosphohistidine domains from OK1 proteins coding amino acid sequences preferably contain two histidines.

During the catalysis of a phosphorylation reaction of P-starch through an OK1 protein, a phosphorylated OK1 protein is formed as an intermediate product, through which a phosphate residue of the ATP is covalently bound to an amino acid of the OK1 protein. The intermediate product is formed through autophosphorylation of the OK1 protein, i.e., the OK1 protein itself catalyses the reaction that leads to the intermediate product. Preferably, a histidine residue of the amino acid sequence coding an OK1 protein is phosphorylated through the autophosphorylation, particularly preferably a histidine residue that is part of a phosphohistidine domain.

Furthermore, OK1 proteins according to the invention have an increased bonding activity to P-starch in comparison with non-phosphorylated starch.

Because no enzymes have yet been described that require P-starch as a substrate in order to phosphorylate them further, it was not possible until now to increase the concentration of starch phosphate of starch that is already phosphorylated in plants beyond a certain quantity. This is only possible through the use of a protein according to the invention or a nucleic acid molecule according to the invention for genetic modification of plants. The clarification of the function of an OK1 protein and with it the preparation of an OK1 protein means that only plants that synthesise a starch with modified characteristics can be genetically modified to that effect. The modification of the phosphate distribution in starch synthesised by plants was not possible until now because of the lack of available means. Through the preparation of proteins according to the invention and nucleic acids through the present invention, a modification of the phosphate ratio in native starches is now possible as well. A further advantage of the present invention is that, for a simultaneous cooperation of an OK1 protein with an R1 protein, higher amounts of phosphate are incorporated into the starch than when the respective proteins separated from one another in space or time phosphorylate starch or P-starch, respectively.

Within the framework of the present invention, the term "R1 protein" should be understood to mean a protein that transfers a phosphate residue from ATP to starch. Starches isolated from leaves of an *Arabidopsis thaliana* sex1-3 mutant have no detectable amount of covalently bound phosphate residues but are phosphorylated from an R1 protein. This means non-phosphorylated starch, for example, isolated from leave of an *Arabidopsis thaliana* sex1-3 mutant, is used as a substrate in a phosphorylation reaction catalysed by an R1 protein.

Preferably, the beta phosphate residue of the ATP is transferred from an R1 protein to the starch and the gamma phosphate residue of the ATP is transferred to water. AMP (adenosine monophosphate) results as an additional reaction product. An R1 protein is therefore designated as [alpha-1,4-glucan]-water-dikinase or as starch-water-dikinase (E.C.: 2.7.9.4; Ritte et al., 2002, PNAS 99, 7166-7171).

During the phosphorylation of starch catalysed by an R1 protein, more additional phosphate monoester bonds result in the C-6 position of the glucose molecules in comparison with phosphate monoester bonds in the C-3 position of the glucose molecules of the respective starch. By a R1 protein, approximately 60% to 70% of the phosphate residue is introduced in the C-6 position of the glucose molecules of starch, and approximately 30% to 40% of the phosphate residue is introduced in the C-3 position of the glucose molecules of starch (Ritte et al., 2002, PNAS 99, 7166-7171).

During the catalysis of a phosphorylation reaction of starch through an R1 protein, a phosphorylated R1 protein results as an intermediate product, through which a phosphate residue of the ATP is covalently bound to an amino acid of the R1 protein (Ritte et al., 2002, PNAS 99, 7166-7171). The intermediate product results through autophosphorylation of the R1 protein, i.e., the R1 protein itself catalyses the reaction that leads to the intermediate product. Amino acid sequences that code R1 proteins contain a phosphohistidine domain. Phosphohistidine domains are, for example, described by Tien-Shin Yu et al. (2001, Plant Cell 13, 1907-1918). Phosphohistidine domains from R1 proteins coding amino acid sequences preferably contain one histidine. Through the autophosphorylation of an R1 protein, a histidine residue in the phosphohistidine domain of the amino acid sequence coding an R1 protein is phosphorylated (Mikkelsen et al., 2003, Biochemical Journal Intermediate Publication). Published on October 2003 as manuscript BJ20030999; Mikkelsen et al., 2004, Biochemical Journal 377, 525-532).

Nucleic acid sequences and corresponding amino acid sequences coding an R1 protein are described from different species such as potato (WO 97 11188, GenBank Acc.: AY027522, Y09533), wheat (WO 00 77229, U.S. Pat. No. 6,462,256, GenBank Acc.: MN93923, GenBank Acc.: AR236165), rice (GenBank Acc.: MR61445, GenBank Acc.: AR400814), maize (GenBank Acc.: MR61444, GenBank Acc.: AR400813), soybean (GenBank Acc.: MR61446, GenBank Acc.: AR400815), citrus (GenBank Acc.: AY094062) and Arabidopsis (GenBank Acc.: AF312027). The identified nucleic acid sequences and amino acid sequences coding R1 proteins are published by NCBI (See NCBI website), among others, and are explicitly included in the description of the present application by mention of the references.

In conjunction with the present invention, the term "increased bonding activity" is to be understood as an increased affinity of a protein for a first substrate in comparison to a second substrate. That is to say, the amount of protein, which, under the same incubation conditions, bonds to a first substrate to a greater extent in comparison with a second substrate, exhibits increased bonding activity to the first substrate.

In conjunction with the present invention, the term "starch phosphate" is to be understood as phosphate groups covalently bound to the glucose molecules of starch.

In conjunction with the present invention, the term "non-phosphorylated starch" is to be understood as a starch that contains no detectable amount of starch phosphate. Various methods are described for the determination of the amount of starch phosphate. Preferably, the methods described by Ritte et al. (2000, Starch/Starke 52, 179-185) can be used for the determination of the amount of starch phosphate. Particularly preferably, the determination of the amount of starch phosphate is carried out by means of $^{31}$P-NMR according to the methods described by Kasemusuwan and Jane (1996, Cereal Chemistry 73, 702-707).

In conjunction with the present invention, the term "phosphorylated starch" or "P-starch" is to be understood as a starch that contains starch phosphate.

The activity of an OK1 protein can be shown, for example, through in vitro incubation of an OK1 protein using ATP that contains a labeled phosphate residue (labeled ATP) in the beta position. Preferred is ATP for which the phosphate residue is specifically labeled in the beta position, i.e., for which only the phosphate residue in the beta position bears a label. Preferably used is radioactively labeled ATP. Particularly preferably used is ATP for which the phosphate residue is specifically radioactively labeled, and especially preferably used is ATP for which the phosphate residue is specifically labeled with $^{33}$P in the beta position. If an OK1 protein with labeled ATP and starches that are not phosphorylated is incubated, no phosphate is transferred through OK1 to the starch. Preferably used is leaf starch of the *Arabidopsis thaliana* mutant sex1-3 (Tien-Shin Yu et al., 2001, Plant Cell 13, 1907-1918).

However, if an OK1 protein with P-starch is incubated in the presence of labeled ATP, then labeled phosphate covalently bound to the P-starch can be subsequently shown. Preferably used is starch from leaves of *Arabidopsis thaliana*, particularly preferably by means of an enzymatically-phosphorylated starch of an R1 protein from *Arabidopsis thaliana* sex1-3 mutant (Ritte et al., 2002, PNAS 99, 7166-7171). Labeled phosphate residues can be shown that were assembled by an OK1 protein in P-starch, for example, through separation of the labeled P-starch (for example, through precipitation means ethanol, filtration, chromatographic methods, etc.) from the residue of the reaction mixture and subsequent detection of the labeled phosphate residue in the P-starch fraction. At the same time, the labeled phosphate residues bound in the P-starch fraction can be shown, for example, through determination of the amount of the radioactivity existing in the P-starch fraction (for example, by means of a scintillation counter). Possible methods for the detection of a protein, which P-starch as a substrate for a phosphorylation reaction makes necessary, is further described below under General Methods, Item 11 and in example 6.

The activity of an R1 protein can be shown as described in the literature, for example (Mikkelsen et al., 2003, Biochemical Journal Intermediate Publication. Published on October 2003 as manuscript BJ20030999; Mikkelsen et al., 2004, Biochemical Journal 377, 525-532, Ritte et al., 2002, PNAS 99, 7166-7171).

Which positions of the carbon atoms (C-2, C-3 or C-6) of the glucose monomers in P-starch are preferably phosphorylated by an OK1 protein can be determined, for example, by analysing the P-starches phosphorylated by a protein, as described by Ritte et al. (2002, PNAS 99, 7166-7171). For this purpose, a P-starch phosphorylated by a protein is hydrolysed using an acid, and subsequently analysed by means of anion exchange chromatography.

Preferably, the P-starch phosphorylated by an OK1 protein is analysed by means of NMR in order to establish which positions of the carbon atoms (C-2, C-3 or C-6) of the glucose monomers in the P-starch are phosphorylated. A particularly preferred method for identifying the C-atom positions of a glucose molecule of a starch, which are phosphorylated by a reaction catalysed by an OK1 protein, is described below under General Methods, Item 13.

Which positions of the carbon atoms (C-2, C-3 or C-6) of the glucose monomers in starch are preferably phosphorylated by an R1 protein can be determined, for example, by analysing the starches phosphorylated by an R1 protein, as described by Ritte et al. (2002, PNAS 99, 7166-7171). For this purpose, a starch phosphorylated by a protein is hydrolysed using an acid, and subsequently analysed by means of anion exchange chromatography.

Preferably, the P-starch phosphorylated by an OK1 protein, or the starch phosphorylated by an R1 protein, is analysed by means of NMR in order to establish which positions of the carbon atoms (C-2, C-3 or C-6) of the glucose monomers in the P-starch or the starch are phosphorylated. A particularly preferred method for identifying the C-atom positions of a glucose molecule of a starch, which are phosphorylated by a reaction catalysed by an OK1 protein or an R1 protein, is described below under General Methods, Item 13.

A phosphorylated protein, which is produced as an intermediate product in the phosphorylation of P-starch facilitated by an OK1 protein, can be demonstrated for an R1 protein as described, for example, by Ritte et al. (2002, PNAS 99, 7166-7171) or Mikkelsen et al. (2003, Biochemical Journal Intermediate Publication. Published on October 2003 as manuscript BJ20030999, Mikkelsen et al., 2004, Biochemical Journal 377, 525-532)

To demonstrate the presence of an autophosphorylated intermediate product, an OK1 protein is first incubated in the absence of starch with labeled ATP, preferably with ATP specifically labeled in the beta phosphate position, particularly preferably with ATP specifically labeled with $^{33}$P in the beta phosphate position. In parallel with this, a reaction preparation 2, which instead of labeled ATP contains corresponding amounts of non-labeled ATP however, is incubated under otherwise identical conditions. Subsequently, non-labeled ATP is added to the reaction mixture 1 in excess, and a mixture of non-labeled ATP and labeled ATP (the same amount of labeled ATP as used previously in reaction mixture 1 and the same amount of non-labeled ATP as added to reaction mixture 1 in excess) is added to reaction mixture 2 and further incubated before P-starch is added to a Part A of reaction mixture 1 (Part 1A) or to a Part A of reaction mixture 2 (Part 2A) respectively. The reaction in the remaining Part 1B and Part 2B of the reaction mixture is stopped by denaturing the protein. Part B of the reaction mixture can be stopped by the methods known to the person skilled in the art, which lead to the denaturing of proteins, preferably by adding sodium lauryl sulphate (SDS). Part 1A and Part 2A of the reaction mixture are incubated for at least a further 10 minutes before these reactions are also stopped. The starch present in Part A and Part B of the respective reaction mixture is separated from the remainder of the reaction mixture. If the respective starch is separated by centrifugation, for example, then, on completion of centrifugation, the starch of the respective Part A or Part B of the reaction mixture is to be found in the sedimented pellet, and the proteins in the respective reaction mixture are to be found in the supernatant of the respective centrifugation. The supernatant of Part 1A or 2A respectively and Part 1 B or 2B respectively of the reaction mixture can subsequently be analysed by denaturing acrylamide gel electrophoresis followed by autoradiography of the acrylamide gel obtained. To quantify the amount of radioactively labeled proteins, which have been separated by means of acrylamide gel electrophoresis, the so-called "phospho-imaging" method, for example, known to the person skilled in the art, can be used. If the autoradiography or the analysis by means of the "phospho-imager" of proteins in the centrifugation supernatant of Part B of reaction mixture 1 shows a significantly increased signal compared with the centrifugation supernatant of Part A of reaction mixture 1, then this shows that a protein facilitating a phosphorylation of starch occurs as an autophosphorylated intermediate product. Parts A and B of reaction mixture 2 serve as a control and should therefore not exhibit a significantly increased signal in the centrifugation supernatant in the autoradiography or in the analysis by means of the "phospho-imager".

In addition, the starch of the respective Part A of reaction mixtures 1 and 2 remaining in the respective sedimented pellet can be investigated, if necessary, after subsequent washing of the respective starches, for the presence of starch phosphate, which has a label corresponding to the labeled ATP used. If the starches of Part A of reaction mixture 1 contain labeled phosphate residues, and if the autoradiography of the centrifugation supernatant of Part B of reaction mixture 1 shows a significantly increased signal in the autoradiography compared with the centrifugation supernatant of Part A of reaction mixture 1, then this shows that a phosphorylation of starch-facilitating protein is present as an autophosphorylated intermediate product. Parts A and B of reaction mixture 2 serve as a control and should therefore not exhibit a significantly increased signal for alpha-1,4-glucans labeled with e.g. $^{33}P$ in the sedimented pellet containing alpha-1,4-glucans. Possible methods for demonstrating a phosphorylated OK1 protein intermediate product are described below under General Methods, Item 12 and in Example 7.

That an OK1 protein has an increased bonding activity to a P-starch compared with non-phosphorylated starch can be demonstrated by incubating the OK1 protein with P-starch and non-phosphorylated starch in separate preparations.

All non-phosphorylated starches are basically suitable for incubating OK1 proteins with non-phosphorylated starch. Preferably, a non-phosphorylated plant starch, particularly preferably wheat starch, and especially preferably granular leaf starch of an *Arabidopsis thaliana* mutant sex1-3 is used.

Methods for isolating starch from plants, for example, are known to the person skilled in the art. All methods known to the person skilled in the art are basically suitable for isolating non-phosphorylated starch from appropriate plant species. Preferably, the methods for isolating non-phosphorylated starch described below are used (see General Methods Item 2).

All starches that contain starch phosphate are basically suitable for incubating OK1 proteins with P-starch. Chemically phosphorylated starches can also be used for this purpose. Preferably, P-starches are used for the incubation with OK1 proteins, particularly preferably a retrospectively enzymatically phosphorylated plant starch, especially preferably a retrospectively enzymatically phosphorylated plant starch, which has been isolated from a sex-1 mutant of *Arabidopsis thaliana*.

To demonstrate an increased bonding activity of OK1 proteins to P-starch compared with non-phosphorylated starch, OK1 proteins are incubated in separate preparations with P-starch (Preparation A) and with non-phosphorylated starch (Preparation B). On completion of the incubation, the proteins, which are not bonded to the related starches of Preparations A and B, are separated from the starches and from the proteins bonded to them. The bond between the proteins and the P-starch in Preparation A and the bond between the proteins and non-phosphorylated starch in Preparation B are subsequently removed, i.e. the respective proteins are dissolved. The dissolved proteins of Preparation A and Preparation B can then be separated from the starches concerned, which are present in the respective preparations. Following this, the isolated P-starch bonding proteins of Preparation A and the isolated non-phosphorylated starch bonding proteins of Preparation B can be separated with the help of methods known to the person skilled in the art such as, for example, gel filtration, chromatographic methods, electrophoresis, SDS acrylamide gel electrophoresis etc. By comparing the amounts of separated proteins of Preparation A with the amounts of corresponding separated proteins of Preparation B, it can be determined whether a protein has an increased bonding activity with respect to P-starch compared with non-phosphorylated starch. Methods, which can be used to demonstrate a preferred bonding of proteins to P-starch compared with non-phosphorylated starch, are described below in Example 8.

The amino acid sequence shown in SEQ ID NO 2 codes an OK1 protein from *Arabidopsis thaliana* and the amino acid sequence shown under SEQ ID NO 4 codes an OK1 protein from *Oryza sativa*.

In a further embodiment of the present invention, amino acid sequences coding an OK1 protein have an identity of at least 60% with the sequence specified in SEQ ID NO 2 or SEQ ID NO 4, in particular of at least 70%, preferably of at least 80% and particularly preferably of at least 90% and especially preferably of at least 95%.

In a further embodiment of the present invention, the OK1 protein has a phosphohistidine domain. Amino acid sequences coding OK1 proteins contain a phosphohistidine domain that has an identity of at least 60% with the amino acid sequence of the phosphohistidine domain of the OK1 protein from *Arabidopsis thaliana* specified in SEQ ID NO 5, in particular of at least 70%, preferably of at least 80% and particularly preferably of at least 90% and especially preferably of at least 95%.

A further embodiment of the present invention relates to a genetically modified plant cell according to the invention or a genetically modified plant according to the invention, wherein the genetic modification consists in the introduction of at least one foreign nucleic acid molecule into the genome of the plant cell or into the genome of the plant.

In this context, the term "genetic modification" means the introduction of homologous and/or heterologous foreign nucleic acid molecules into the genome of a plant cell or into the genome of a plant, wherein said introduction of these molecules leads to an increase in the activity of an OK1 protein and to the increase of the activity of an R1 protein.

The plant cells according to the invention or plants according to the invention are modified with regard to their genetic information by the introduction of a foreign nucleic acid molecule. The presence or the expression of a foreign nucleic acid molecule leads to a phenotypic change. Here, "phenotypic" change means preferably a measurable change of one or more functions of the cells. For example, the genetically modified plant cells according to the invention and the genetically modified plants according to the invention exhibit an increase of the activity of an OK1 protein and an increase of the activity of an R1 protein due to the presence or on the expression of the introduced nucleic acid molecule.

In conjunction with the present invention, the term "foreign nucleic acid molecule" is understood to mean such a molecule that either does not occur naturally in the corresponding wild type plant cells, or that does not occur naturally in the concrete spatial arrangement in wild type plant cells, or that is localised at a place in the genome of the wild type plant cell at which it does not occur naturally. Preferably, the foreign nucleic acid molecule is a recombinant molecule, which consists of different elements, the combination or specific spatial arrangement of which does not occur naturally in plant cells.

In principle, a foreign nucleic acid molecule can be any nucleic acid molecule that effects an increase in the activity of an OK1 protein and an R1 protein in the plant cell or plant.

In conjunction with the present invention, the term "genome" is to be understood to mean the totality of the genetic material present in a plant cell. It is known to the person skilled in the art that, as well as the cell nucleus, other compartments (e.g. plastids, mitochondrions) also contain genetic material.

In a further embodiment, the plant cells according to the invention and the plants according to the invention are characterised in that at least one foreign nucleic acid molecule codes an OK1 protein, preferably an OK1 protein from *Arabidopsis thaliana* or an OK1 protein from *Oryza sativa*.

In a further embodiment, the foreign nucleic acid molecule codes an OK1 protein with the amino acid sequence specified in SEQ ID NO 2 or SEQ ID NO 4.

In a further embodiment, the plant cells according to the invention and the plants according to the invention are characterised in that at least one foreign nucleic acid molecule codes an R1 protein, preferably an R1 protein from potato or an OK1 protein from *Oryza sativa*.

In a further embodiment, the foreign nucleic acid molecule codes an R1 protein from potato with the amino acid sequence specified in GenBank Acc.: Y09533 (22-Jul.-2003 Rel. 76, Last updated, Version 2). The nucleic acid molecules and amino acid sequences coding an R1 protein from potato (GenBank Acc.: Y09533) are explicitly included in the description of the present application by mention of the references.

In a further embodiment, the plant cells according to the invention and the plants according to the invention are characterised in that a first foreign nucleic acid molecule codes an R1 protein and a second foreign nucleic acid molecule codes an OK1 protein.

The foreign nucleic acid molecules assembled for the genetic modification in the plant cell or plant can be a single nucleic acid molecule or multiple nucleic acid molecules. It can therefore be nucleic acid molecules that contain nucleic acid sequences that code OK1 proteins and nucleic acid sequences that code R1 proteins, as well as nucleic acid molecules for which the nucleic acid sequences coding OK1 proteins and the nucleic acid sequences coding R1 proteins occur in various nucleic acid molecules. The nucleic acid sequences coding an OK1 protein and the nucleic acid sequences coding an R1 protein can be contained simultaneously, for example, in a vector, plasmid or linear nucleic acid molecule, or be, however, constituents of two vectors, plasmids or linear nucleic acid molecules respectively separated from one another.

If the nucleic acid sequences coding an OK1 protein and the nucleic acid sequences coding an R1 protein occur in two nucleic acid molecules separated from one another, then they can be introduced either simultaneously ("cotransformation") or also successively, i.e., consecutively ("supertransformation") into the genome of the plant cells or plant. The nucleic acid molecules separated from one another can also be introduced into various individual plant cells or plants of a species. Plant cells or plants can thereby be produced in which the activity of either at least one OK1 protein or at least one R1 protein is increased. Such plants can be produced by subsequently crossing the plants in which the activity of an OK1 protein is increased with plants in which the activity of an R1 protein is increased.

Furthermore, a mutant cell or a mutant that is characterised in that it already has an increased activity of an OK1 protein or an increased activity of an R1 protein can be used instead of a wild type plant cell or wild type plant for introducing a foreign nucleic acid molecule. Mutants can be spontaneously (naturally) occurring mutants as well as those that were produced through the targeted use of mutagens (such as, for example, chemical agents, ionising radiation) or genetic engineering methods (for example T-DNA activation tagging, transposon activation tagging, in situ activation, in vivo mutagenesis).

Therefore, plant cells according to the invention and plants according to the invention can also be produced through the introduction of a foreign nucleic acid molecule, which leads to the increase of the activity of an R1 protein in a mutant cell or a mutant that already has an increased activity of an OK1 protein. Plant cells according to the invention or plants according to the invention can also be produced through the introduction of a foreign nucleic acid molecule, which leads to the increase of the activity of an OK1 protein in a mutant cell or a mutant that already has an increased activity of an R1 protein.

Plant cells according to the invention or plants according to the invention can also be produced in which a mutant in which the activity of an OK1 protein is increased is crossed with a plant that has an increased activity of an R1 protein due to the introduction of a foreign nucleic acid molecule. Likewise, it is possible to produce plant cells according to the invention or plants according to the invention in which a mutant in which the activity of an R1 protein is increased is crossed with a plant that has an increased activity of an OK1 protein due to the introduction of a foreign nucleic acid molecule.

A large number of techniques are available for the introduction of DNA into a plant host cell. These techniques include the transformation of plant cells with T-DNA using

*Agrobacterium tumefaciens* or *Agrobacterium rhizogenes* as the transformation medium, the fusion of protoplasts, injection, the electroporation of DNA, the introduction of DNA by means of the biolistic approach as well as other possibilities. The use of agrobacteria-mediated transformation of plant cells has been intensively investigated and adequately described in EP 120516; Hoekema, Ind.: The Binary Plant Vector System Offsetdrukkerij Kanters B. V., Alblasserdam (1985), Chapter V; Fraley et al., Crit. Rev. Plant Sci. 4, 1-46 and by An et al. EMBO J. 4, (1985), 277-287. For the transformation of potato, see Rocha-Sosa et al., EMBO J. 8, (1989), 29-33, for example.

The transformation of monocotyledonous plants by means of vectors based on *Agrobacterium* transformation has also been described (Chan et al., Plant Mol. Biol. 22, (1993), 491-506; Hiei et al., Plant J. 6, (1994) 271-282; Deng et al., Science in China 33, (1990), 28-34; Wilmink et al., Plant Cell Reports 11, (1992), 76-80; May et al., Bio/Technology 13, (1995), 486-492; Conner and Domisse, Int. J. Plant Sci. 153 (1992), 550-555; Ritchie et al., Transgenic Res. 2, (1993), 252-265). An alternative system to the transformation of monocotyledonous plants is transformation by means of the biolistic approach (Wan and Lemaux, Plant Physiol. 104, (1994), 37-48; Vasil et al., Bio/Technology 11 (1993), 1553-1558; Ritala et al., Plant Mol. Biol. 24, (1994), 317-325; Spencer et al., Theor. Appl. Genet. 79, (1990), 625-631), protoplast transformation, electroporation of partially permeabilised cells and the introduction of DNA by means of glass fibres. In particular, the transformation of maize has been described in the literature many times (cf. e.g. WO95/06128, EP0513849, EP0465875, EP0292435; Fromm et al., Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726).

The successful transformation of other types of cereal has also already been described, for example for barley (Wan and Lemaux, see above; Ritala et al., see above; Krens et al., Nature 296, (1982), 72-74) and for wheat (Nehra et al., Plant J. 5, (1994), 285-297; Becker et al., 1994, Plant Journal 5, 299-307). All the above methods are suitable within the framework of the present invention.

Amongst other things, plant cells and plants, which have been genetically modified by the introduction of an OK1 protein and/or an R1 protein, can be differentiated from wild type plant cells and wild type plants respectively in that they contain a foreign nucleic acid molecule, which does not occur naturally in wild type plant cells or wild type plants, or in that such a molecule is present integrated at a place in the genome of the plant cell according to the invention or in the genome of the plant according to the invention at which it does not occur in wild type plant cells or wild type plants, i.e. in a different genomic environment. Furthermore, plant cells according to the invention and plants according to the invention of this type differ from wild type plant cells and wild type plants respectively in that they contain at least one copy of the foreign nucleic acid molecule stably integrated within their genome, possibly in addition to naturally occurring copies of such a molecule in the wild type plant cells or wild type plants. If the foreign nucleic acid molecule(s) introduced into the plant cells according to the invention or into the plants according to the invention is (are) additional copies of molecules already occurring naturally in the wild type plant cells or wild type plants respectively, then the plant cells according to the invention and the plants according to the invention can be differentiated from wild type plant cells or wild type plants respectively in particular in that this additional copy or these additional copies is (are) localised at places in the genome at which it does not occur (or they do not occur) in wild type plant cells or wild type plants. This can be verified, for example, with the help of a Southern blot analysis.

Furthermore, the plant cells according to the invention and the plants according to the invention can preferably be differentiated from wild type plant cells or wild type plants respectively by at least one of the following characteristics: If a foreign nucleic acid molecule that has been introduced is heterologous with respect to the plant cell or plant, then the plant cells according to the invention or plants according to the invention have transcripts of the introduced nucleic acid molecules. These can be verified, for example, by Northern blot analysis or by RT-PCR (Reverse Transcription Polymerase Chain Reaction). Plant cells according to the invention and plants according to the invention, which express an antisense and/or an RNAi transcript, can be verified, for example, with the help of specific nucleic acid probes, which are complimentary to the RNA (occurring naturally in the plant cell), which is coding for the protein. Preferably, the plant cells according to the invention and the plants according to the invention contain a protein, which is coded by an introduced nucleic acid molecule. This can be demonstrated by immunological methods, for example, in particular by a Western blot analysis.

If the foreign nucleic acid molecule that has been introduced is homologous with respect to the plant cell or plant, the plant cells according to the invention or plants according to the invention can be differentiated from wild type plant cells or wild type plants respectively due to the additional expression of the introduced foreign nucleic acid molecule, for example. The plant cells according to the invention and the plants according to the invention preferably contain transcripts of the foreign nucleic acid molecules. This can be demonstrated by Northern blot analysis, for example, or with the help of so-called quantitative PCR.

In a further embodiment, the plant cells according to the invention and the plants according to the invention are transgenic plant cells or transgenic plants respectively.

In a further embodiment, the present invention relates to plant cells according to the invention and plants according to the invention wherein the foreign nucleic acid molecule coding an OK1 protein is chosen from the group consisting of a) Nucleic acid molecules, which code a protein with the amino acid sequence given under SEQ ID NO 2 or SEQ ID NO 4;

b) Nucleic acid molecules, which code a protein, which includes the amino acid sequence, which is coded by the insertion in plasmid A.t.-OK1-pGEM or the insertion in plasmid pMI50;

c) Nucleic acid molecules, which code a protein, the sequence of which has an identity of at least 60% with the amino acid sequence given under SEQ ID NO 2 or SEQ ID NO 4;

d) Nucleic acid molecules, which code a protein, the sequence of which has an identity of at least 60% with the amino acid sequence, which is coded by the coding region of the insertion in plasmid A.t.-OK1-pGEM or by the coding region of the insertion in plasmid pMI50;

e) Nucleic acid molecules, which include the nucleotide sequence shown under SEQ ID NO 1 or SEQ ID NO 3 or a complimentary sequence;

f) Nucleic acid molecules, which include the nucleotide sequence of the insertion contained in plasmid A.t.-OK1-pGEM or plasmid pMI50;

g) Nucleic acid molecules, which have an identity of at least 70% with the nucleic acid sequences described under a), b), e) or e);

h) Nucleic acid molecules, which hybridise with at least one strand of the nucleic acid molecules described under a), b), e) or f) under stringent conditions;
i) Nucleic acid molecules, the nucleotide sequence of which deviates from the sequence of the nucleic acid molecules identified under a), b), e) or f) due to the degeneration of the genetic code; and
j) Nucleic acid molecules, which represent fragments, allelic variants and/or derivatives of the nucleic acid molecules identified under a), b), c), d), e), f), g), h) or i).

The nucleic acid sequence shown SEQ ID NO 1 is a cDNA sequence, which includes the coding region for an OK1 protein from *Arabidopsis thaliana* and the nucleic acid sequence shown SEQ ID NO 3 is a cDNA sequence, which includes the coding region for an OK1 protein from *Oryza sativa*.

A plasmid (A.t.-OK1-pGEM) containing a cDNA which codes for a protein according to the invention (A.t.-OK1) from *Arabidopsis thaliana* was deposited on 8 Mar. 2004 under the number DSM16264 and a plasmid (pM150) containing a cDNA which codes for further protein according to the invention (O.s.-OK1) from *Oryza sativa* was deposited on 24 Mar. 2004 under the number DSM16302 under the Budapest Treaty at the German Collection of Microorganisms and Cell Cultures GmbH, Mascheroder Weg 1b, 38124 Braunschweig, Germany.

The amino acid sequence shown under SEQ ID NO 2 can be derived from the coding region of the cDNA sequence integrated in plasmid A.t.-OK1-pGEM and codes for an OK1 protein from *Arabidopsis thaliana*. The amino acid sequence shown SEQ ID NO 4 can be derived from the coding region of the cDNA sequence integrated in plasmid pMI50 and codes for an OK1 protein from *Oryza sativa*. The present invention therefore also relates to nucleic acid molecules, which code a protein with the enzymatic activity of an OK1 protein, which includes the amino acid sequence, which is coded by the insertion in plasmid A.t.-OK1-pGEM or by the insertion in plasmid pMI50, wherein the coded protein has an identity of at least 70%, preferably of at least 80%, particularly preferably of at least 90% and especially preferably of 95% with the amino acid sequence, which can be derived from the insertion in A.t.-OK1-pGEM or pMI50.

The present invention also relates to nucleic acid molecules, which code an OK1 protein and include the coding region of the nucleotide sequences shown under SEQ ID NO 1 or SEQ ID NO 3 or sequences, which are complimentary thereto, nucleic acid molecules, which include the coding region of the nucleotide sequence of the insertion contained in plasmid A.t.-OK1-pGEM or in plasmid pMI50 and nucleic acid molecules, which have an identity of at least 70%, preferably of at least 80%, particularly preferably of at least 90% and especially preferably of at least 95% with the said nucleic acid molecules.

With the help of the sequence information of nucleic acid molecules according to the invention or with the help of a nucleic acid molecule according to the invention, it is now possible for the person skilled in the art to isolate homologous sequences from other plant species, preferably from starch-storing plants, preferably from plant species of the genus *Oryza*, in particular *Oryza saliva* or from *Arabidopsis thaliana*. This can be carried out, for example, with the help of conventional methods such as the examination of cDNA or genomic libraries with suitable hybridisation samples. The person skilled in the art knows that homologous sequences can also be isolated with the help of (degenerated) oligonucleotides and the use of PCR-based methods. The examination of databases, such as are made available, for example, by the EMBL web site or NCBI (National Center for Biotechnology Information) website, can also be used for identifying homologous sequences, which code for OK1 proteins. In this case, one or more sequences are specified as a so-called query. This query sequence is then compared by means of statistical computer programs with sequences, which are contained in the selected databases. Such database queries (e.g. blast or fasta searches) are known to the person skilled in the art and can be carried out by various providers. If such a database query is carried out, e.g. at the NCBI (National Center for Biotechnology Information) website, then the standard settings, which are specified for the particular comparison inquiry, should be used. For protein sequence comparisons (blastp), these are the following settings: Limit entrez=not activated; Filter=low compexity activated; Expect value=10; word size=3; Matrix=BLOSUM62; Gap costs: Existence=11, Extension=1.

For nucleic acid sequence comparisons (blastn), the following parameters must be set: Limit entrez=not activated; Filter=low compexity activated; Expect value=10; word size=11.

With such a database search, the sequences described in the present invention can be used as a query sequence in order to identify further nucleic acid molecules and/or proteins, which code an OK1 protein.

With the help of the described methods, it is also possible to identify and/or isolate nucleic acid molecules according to the invention, which hybridise with the sequence specified under SEQ ID NO 1 or under SEQ ID NO 3 and which code an OK1 protein. Within the framework of the present invention, the term "hybridising" means hybridisation under conventional hybridisation conditions, preferably under stringent conditions such as, for example, are described in Sambrock et al., Molecular Cloning, A Laboratory Manual, 2nd edition (1989) Cold Spring Harbor Laboratory Press, Cold Spring Harbor, N.Y.). Particularly preferably, "hybridising" means hybridisation under the following conditions:
Hybridisation Buffer:
2×SSC; 10×Denhardt solution (Ficoll 400+PEG+BSA; Ratio 1:1:1); 0.1% SDS; 5 mM EDTA; 50 mM Na2HPO4; 250 µg/ml herring sperm DNA; 50 µg/ml tRNA; or 25 M sodium phosphate buffer pH 7.2; 1 mM EDTA; 7% SDS
Hybridisation temperature:
T=65 to 68° C.
Wash buffer: 0.1×SSC; 0.1% SDS
Wash temperature: T=65 to 68° C.

In principle, nucleic acid molecules, which hybridise with the nucleic acid molecules according to the invention, can originate from any plant species, which codes an appropriate protein; preferably they originate from starch-storing plants, preferably from species of the (systematic) family Poacea, particularly preferably from species of the genus *Oryza*. Nucleic acid molecules, which hybridise with the molecules according to the invention, can, for example, be isolated from genomic or from cDNA libraries. The identification and isolation of nucleic acid molecules of this type can be carried out using the nucleic acid molecules according to the invention or parts of these molecules or the reverse complements of these molecules, e.g. by means of hybridisation according to standard methods (see, for example, Sambrook et al., Molecular Cloning, A Laboratory Manual, 2nd edition Cold Spring Harbor Laboratory Press, Cold Spring Harbor, N.Y.) or by amplification using PCR.

Nucleic acid molecules, which exactly or essentially have the nucleotide sequence specified under SEQ ID NO 1 or SEQ ID NO 3 or parts of these sequences, can be used as hybridisation samples. The fragments used as hybridisation samples can also be synthetic fragments or oligonucleotides, which have been manufactured using established synthesizing techniques and the sequence of which corresponds essentially with that of a nucleic acid molecule according to the invention. If genes have been identified and isolated, which hybridise with the nucleic acid sequences according to the invention, then a determination of this sequence and an analysis of the characteristics of the proteins coded by this sequence should be carried out in order to establish whether an OK1 protein is involved. Homology comparisons on the level of the nucleic acid or amino acid sequence and a determination of the enzymatic activity are particularly suitable for this purpose. The activity of an OK1 protein can take place, for example, as described above under General Methods Item 11. A preferred bonding affinity to P-starch in comparison with non-phosphorylated starch, and autophosphorylation of an OK1 protein can be demonstrated using the methods already described above and under General Methods Items 8 and 12.

The molecules hybridising with the nucleic acid molecules according to the invention particularly include fragments, derivatives and allelic variants of the nucleic acid molecules according to the invention, which code an OK1 protein from plants, preferably from starch-storing plants, preferably from plant species of the (systematic) family Poacea, particularly preferably from species of the genus *Oryza*. In conjunction with the present invention, the term "derivative" means that the sequences of these molecules differ at one or more positions from the sequences of the nucleic acid molecules described above and have a high degree of identity with these sequences. Here, the deviation from the nucleic acid molecules described above can have come about, for example, due to deletion, addition, substitution, insertion or recombination.

In conjunction with the present invention, the term "identity" means a sequence identity over the whole length of the coding region of at least 60%, in particular an identity of at least 80%, preferably greater than 80%, particularly preferably greater than 90% and especially of at least 95%. In conjunction with the present invention, the term "identity" is to be understood to mean the number of amino acids/nucleotides (identity) corresponding with other proteins/nucleic acids, expressed as a percentage. Identity is preferably determined by comparing with other proteins/nucleic acids the SEQ ID NO 2 or SEQ ID NO 4 for amino acids or SEQ ID NO 1 or SEQ ID NO 3 for nucleic acids with the help of computer programs. If sequences that are compared with one another have different lengths, the identity is to be determined in such a way that the number of amino acids, which have the shorter sequence in common with the longer sequence, determines the percentage quotient of the identity. Preferably, identity is determined by means of the computer program ClustalW, which is well-known and available to the public (Thompson et al., Nucleic Acids Research 22 (1994), 4673-4680). ClustalW is made publicly available by Julie Thompson (Thompson@EMBL-Heidelberg.DE) and Toby Gibson (Gibson@EMBL-Heidelberg.DE), European Molecular Biology Laboratory, Meyerhofstrasse 1, D 69117 Heidelberg, Germany. ClustalW can also be downloaded from different Internet sites, including the IGBMC (Institut de Génétique et de Biologie Móleculaire et Cellulaire, B.P.163, 67404 Illikirch Cedex, France; ftp://ftp-igbmc.u-strasbg.fr/pub/) and the EBI (ftp://ftp.ebi.ac.uk/pub/software/) as well as from all mirrored Internet sites of the EBI (European Bioinformatics Institute, Wellcome Trust Genome Campus, Hinxton, Cambridge CB10 1SD, UK).

Preferably, Version 1.8 of the ClustalW computer program is used to determine the identity between proteins according to the invention and other proteins. In doing so, the following parameters must be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

Preferably, Version 1.8 of the ClustalW computer program is used to determine the identity between the nucleotide sequence of the nucleic acid molecules according to the invention, for example, and the nucleotide sequence of other nucleic acid molecules. In doing so, the following parameters must be set: KTUPLE=2, TOPDIAGS=4, PAIRGAP=5, DNAMATRIX:IUB, GAPOPEN=10, GAPEXT=5, MAXDIV=40, TRANSITIONS: unweighted.

Furthermore, identity means that functional and/or structural equivalence exists between the nucleic acid molecules concerned or the proteins coded by them. The nucleic acid molecules, which are homologous to the molecules described above and constitute derivatives of these molecules, are generally variations of these molecules, which constitute modifications, which execute the same biological function. At the same time, the variations can occur naturally, for example they can be sequences from other plant species, or they can be mutants, wherein these mutants may have occurred in a natural manner or have been introduced by objective mutagenesis. The variations can also be synthetically manufactured sequences. The allelic variants can be both naturally occurring variants and also synthetically manufactured variants or variants produced by recombinant DNA techniques. Nucleic acid molecules, which deviate from nucleic acid molecules according to the invention due to degeneration of the genetic code, constitute a special form of derivatives.

The proteins coded from the different derivatives of nucleic acid molecules according to the invention have certain common characteristics. These can include, for example, biological activity, substrate specificity, molecular weight, immunological reactivity, conformation etc, as well as physical characteristics such as, for example, the running behaviour in gel electrophoresis, chromatographic behaviour, sedimentation coefficients, solubility, spectroscopic characteristics, stability; optimum pH, optimum temperature etc. Preferred characteristics of an OK1 protein have already been described in detail above and are to be applied here accordingly.

The nucleic acid molecules according to the invention can be any nucleic acid molecules, in particular DNA or RNA molecules, for example cDNA, genomic DNA, mRNA etc. They can be naturally occurring molecules or molecules manufactured by genetic engineering or chemical synthesis methods. They can be single-stranded molecules, which either contain the coding or the non-coding strand, or double-stranded molecules.

In a further embodiment, the present invention relates to plant cells according to the invention and plants according to the invention wherein the foreign nucleic acid molecule coding an R1 protein is chosen from the group consisting of
a) Nucleic acid molecules, which code a protein with the amino acid sequence given under SEQ ID NO 7, SEQ ID NO 9, SEQ ID NO 11, SEQ ID NO 13, SEQ ID NO 15 or SEQ ID NO 17,
b) Nucleic acid molecules, which include the nucleotide sequence shown under SEQ ID NO 6, SEQ ID NO 8, SEQ ID NO 10, SEQ ID NO 12, SEQ ID NO 14 or SEQ ID NO 16, or a complimentary sequence;
c) Nucleic acid molecules, the nucleotide sequence of which deviates from the sequence of the nucleic acid molecules identified under a) or b) due to the degeneration of the genetic code;

d) Nucleic acid molecules, which have an identity of at least 70% with the nucleic acid sequences described under a) or b) and
e) Nucleic acid molecules, which hybridise with at least one strand of the nucleic acid molecules described under a) or b) under stringent conditions.

In a further embodiment, the present invention relates to plant cells according to the invention and plants according to the invention wherein the foreign nucleic acid molecule is chosen from the group consisting of
a) T-DNA molecules, which lead to an increase in the expression of an OK1 gene and/or an R1 gene due to integration in the plant genome (T-DNA activation tagging);
b) DNA molecules, which contain transposons, which lead to an increase in the expression of an OK1 gene and/or an R1 gene due to integration in the plant genome (transposon activation tagging);
c) DNA molecules, which code an OK1 protein and/or an R1 protein and which are linked with regulatory sequences, which guarantee transcription in plant cells and lead to an increase in an OK1 protein and/or R1 protein activity in the cell,
d) Nucleic acid molecules introduced by means of in vivo mutagenesis, which lead to a mutation or an insertion of a heterologous sequence in at least one endogenous gene coding an OK1 protein, wherein the mutation or insertion effects an increase in the expression of a gene coding an OK1 protein.
e) Nucleic acid molecules introduced by means of in vivo mutagenesis, which lead to a mutation or an insertion of a heterologous sequence in at least one endogenous gene coding an R1 protein, wherein the mutation or insertion effects an increase in the expression of a gene coding an R1 protein.

In conjunction with the present invention, plant cells according to the invention and plants according to the invention can also be manufactured by the use of so-called insertion mutagenesis (overview article: Thorneycroft et al., 2001, Journal of experimental Botany 52 (361), 1593-1601). In conjunction with the present invention, insertion mutagenesis is to be understood to mean particularly the insertion of transposons or so-called transfer DNA (T-DNA) into a gene or in the vicinity of a gene coding for an OK1 protein and/or coding for an R1 protein, whereby as a result of which the activity of an OK1 protein and/or an R1 protein in the cell concerned is increased.

The transposons can be both those that occur naturally in the cell (endogenous transposons) and also those that do not occur naturally in said cell but are introduced into the cell (heterologous transposons) by means of genetic engineering methods, such as transformation of the cell, for example. Changing the expression of genes by means of transposons is known to the person skilled in the art. An overview of the use of endogenous and heterologous transposons as tools in plant biotechnology is presented in Ramachandran and Sundaresan (2001, Plant Physiology and Biochemistry 39, 234-252).

T-DNA insertion mutagenesis is based on the fact that certain sections (T-DNA) of Ti plasmids from *Agrobacterium* can integrate into the genome of plant cells. The place of integration in the plant chromosome is not defined, but can take place at any point. If the T-DNA integrates into a part of the chromosome or in the vicinity of a part of the chromosome, which constitutes a gene function, then this can lead to an increase in the gene expression and thus also to a change in the activity of a protein coded by the gene concerned.

Here, the sequences inserted into the genome (in particular transposons or T-DNA) are distinguished by the fact that they contain sequences, which lead to an activation of regulatory sequences of an OK1 gene ("activation tagging").

Plant cells and plants according to the invention can be produced by means of the so-called "activation tagging" method (see, for example, Walden et al., Plant J. (1991), 281-288; Walden et al., Plant Mol. Biol. 26 (1994), 1521-1528). These methods are based on activating endogenous promoters by means of enhancer sequences, such as the enhancer of the $^{35}$S RNA promoter of the cauliflower mosaic virus, or the octopine synthase enhancer.

In conjunction with the present invention, the term "T-DNA activation tagging" is to be understood to mean a T-DNA fragment, which contains enhancer sequences and which leads to an increase in the activity of at least one OK1 protein and/or at least one R1 protein by integration into the genome of a plant cell.

In conjunction with the present invention, the term "transposon activation tagging" is to be understood to mean a transposon, which contains enhancer sequences and which leads to an increase in the activity of at least one OK1 protein and/or at least one R1 protein by integration into the genome of a plant cell.

In an additional embodiment, the DNA molecules according to the invention, which code an OK1 protein and/or an R1 protein, are linked with regulatory sequences, which initiate transcription in plant cells and lead to an increase in OK1 protein and/or R1 protein activity in the cell. In this case, the nucleic acid molecules according to the invention are present in "sense" orientation to the regulatory sequences.

For expressing nucleic acid molecules according to the invention, which code an OK1 protein and/or R1 protein, these are preferably linked with regulatory DNA sequences, which guarantee transcription in plant cells. In particular, these include promoters. In general, any promoter that is active in plant cells is eligible for expression.

At the same time, the promoter can be chosen so that expression takes place constitutively or only in a certain tissue, at a certain stage of the plant development or at a time determined by external influences. The promoter can be homologous or heterologous both with respect to the plant and with respect to the nucleic acid molecule.

Suitable promoters are, for example, the promoter of the $^{35}$S RNA of the cauliflower mosaic virus and the ubiquitin promoter from maize for constitutive expression, the patatin promoter B33 (Rocha-Sosa et al., EMBO J. 8 (1989), 23-29) for tuber-specific expression in potatoes or a promoter, which only ensures expression in photosynthetically active tissues, e.g. the ST-LS1 promoter (Stockhaus et al., Proc. Natl. Acad. Sci. USA 84 (1987), 7943-7947; Stockhaus et al., EMBO J. 8 (1989), 2445-2451) or, for endosperm-specific expression of the HMG promoter from wheat, the USP promoter, the phaseolin promoter, promoters of zein genes from maize (Pedersen et al., Cell 29 (1982), 1015-1026; Quatroccio et al., Plant Mol. Biol. 15 (1990), 81-93), glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218) or shrunken-1 promoter (Werr et al., EMBO J. 4 (1985), 1373-1380). However, promoters can also be used, which are only activated at a time determined by external influences (see for example WO 9307279). Promoters of heat-shock proteins, which allow simple induction, can be of particular interest here. Furthermore, seed-specific promoters can be used, such as the USP promoter from *Vicia faba*, which guarantees seed-specific expression in *Vicia faba* and other plants (Fiedler et al., Plant Mol. Biol. 22 (1993), 669-679; Baumlein et al., Mol. Gen. Genet. 225 (1991), 459-467).

Furthermore, a termination sequence (polyadenylation signal) can be present, which is used for adding a poly-A tail to the transcript. A function in the stabilisation of the transcripts is ascribed to the poly-A tail. Elements of this type are described in the literature (cf. Gielen et al., EMBO J. 8 (1989), 23-29) and can be exchanged at will.

Intron sequences can also be present between the promoter and the coding region. Such intron sequences can lead to stability of expression and to increased expression in plants (Callis et al., 1987, Genes Devel. 1, 1183-1200; Luehrsen, and Walbot, 1991, Mol. Gen. Genet. 225, 81-93; Rethmeier, et al., 1997; Plant Journal. 12(4):895-899; Rose and Beliakoff, 2000, Plant Physiol. 122 (2), 535-542; Vasil et al., 1989, Plant Physiol. 91, 1575-1579; X U et al., 2003, Science in China Series C Vol. 46 No. 6, 561-569). Suitable intron sequences are, for example, the first intron of the sh1 gene from maize, the first intron of the polyubiquitin gene 1 from maize, the first intron of the EPSPS gene from rice or one of the two first introns of the PAT1 gene from *Arabidopsis*.

Furthermore, plant cells according to the invention and plants according to the invention can be manufactured by means of so-called "in situ activation". In this case, the introduced genetic modification effects a change in the regulatory sequences of endogenous OK1 genes and/or R1 genes, which leads to an increased expression of OK1 genes and/or R1 genes. Preferably, the activation of an OK1 gene and/or an R1 gene takes place by "in vivo" mutagenesis of a promoter or of enhancer sequences of an endogenous OK1 gene and/or an R1 gene. In doing so, a promoter or an enhancer sequence, for example, can be changed through mutagenesis in such a way that the mutation produced leads to an increased expression of an OK1 protein gene and/or R1 gene in plant cells according to the invention or plants according to the invention in comparison with the expression of an OK1 gene and/or an R1 gene in wild type plant cells or wild type plants. The mutation in a promoter or an enhancer sequence can also lead to OK1 genes and/or R1 genes in plant cells according to the invention or plants according to the invention being expressed at a time at which they would not be expressed in wild type plant cells or wild type plants.

In conjunction with the present invention, the term "OK1 gene" is to be understood to mean a nucleic acid molecule (cDNA, DNA) that codes an OK1 protein, preferably an OK1 protein from starch-storing plants, particularly preferably from *Arabidopsis thaliana*, especially preferably from rice.

In conjunction with the present invention, the term "R1 gene" is to be understood to mean a nucleic acid molecule (cDNA, DNA) that codes an R1 protein, preferably an R1 protein from starch-storing plants, particularly preferably from *Arabidopsis thaliana*, especially preferably from rice.

In so-called "in vivo mutagenesis", a hybrid RNA-DNA oligonucleotide ("Chimeroplast") is introduced into plant cells through transformation of plants cells (Kipp, P. B. et al., Poster Session at the "5th International Congress of Plant Molecular Biology", 21-27 Sep. 1997, Singapore; R. A. Dixon and C. J. Arntzen, meeting report on "Metabolic Engineering in Transgenic Plants", Keystone Symposia, Copper Mountain, Colo., USA, TIBTECH 15, (1997), 441-447; international patent application WO 9515972; Kren et al., Hepatology 25, (1997), 1462-1468; Cole-Strauss et al., Science 273, (1996), 1386-1389; Beetham et al., 1999, PNAS 96, 8774-8778).

A part of the DNA components of the RNA-DNA oligonucleotide is homologous to a nucleic acid sequence of an endogenous OK1 gene and/or R1 gene, but, in comparison with the nucleic acid sequence of an endogenous OK1 gene and/or R1 gene, it has a mutation or contains a heterologous region, which is surrounded by the homologous regions.

By base pairing of the homologous regions of the RNA-DNA oligonucleotide and the endogenous nucleic acid molecule followed by homologous recombination, the mutation or heterologous region contained in the DNA components of the RNA-DNA oligonucleotide can be transferred into the genome of a plant cell. This leads to an increase of the activity of one or more OK1 proteins.

All these methods are based on the introduction of a foreign nucleic acid molecule into the genome of a plant cell or plant and are therefore basically suitable for the manufacture of plant cells according to the invention and plants according to the invention.

Surprisingly, it has been found that plant cells according to the invention and plants according to the invention synthesise a modified starch in comparison with starch of corresponding wild type plant cells or wild type plants that have not been genetically modified.

The plant cells according to the invention and plants according to the invention synthesise a modified starch, which in its physical-chemical characteristics, in particular the starch phosphate content and/or phosphate distribution is changed in comparison with the starch synthesised in wild type plant cells or wild type plants, so that this is better suited for special applications.

Because no enzymes have yet been described that exclusively phosphorylate P-starch, it has also previously not been possible to increase beyond a certain quantity the concentration of starch phosphate of starch that is already phosphorylated in plants. This is only possible by using an enzyme with the function of an OK1 protein or by preparing a nucleic acid molecule that codes an OK1 protein for the genetic modification of plants.

The phosphate distribution of starch synthesised by plants was also not previously possible due to the lack of available means. A change of the phosphate ratio of native starches is also now possible through the present invention through the preparation of enzymes with the function of OK1 proteins and the preparation of nucleic acid molecules that code an OK1 protein.

The present invention therefore also includes plant cells according to the invention and plants according to the invention, which synthesise a modified starch, in comparison with corresponding wild type plant cells or wild type plans that have not been genetically modified.

In conjunction with the present invention, the term "modified starch" means that the starch has changed physical-chemical characteristics compared with non-modified starch obtainable from corresponding wild type plant cells or wild type plants.

In a further embodiment of the present invention, plant cells according to the invention or plants according to the invention synthesise a starch, which has an increased concentration of starch phosphate and/or a changed phosphate distribution in comparison with starch isolated from corresponding wild type plant cells or wild type plants.

In conjunction with the present invention, the term "phosphate distribution" is to be understood to mean the proportion of the starch phosphate bound to a glucose molecule in the C-2 position, C-3 position or C-6 position in terms of the total concentration of starch phosphate from starch.

In a further embodiment of the present invention, plant cells according to the invention or plants according to the invention synthesise a starch, which has an increased concentration of starch phosphate and/or a changed ratio of C-3 phosphate to C-6 phosphate in comparison with starch from wild type plants that have not been genetically modified. Preferred here are starches, which have an increased proportion of starch phosphate bonded in the C-3 position compared with starch phosphate bonded in the C-6 position in comparison with starches from wild type plant cells that have not been genetically modified or wild type plants that have not been genetically modified.

In conjunction with the present invention, the term "ratio of C-3 phosphate to C-6 phosphate" is to be understood to mean the proportion of starch phosphate for which the starch phosphate of a starch bonded in the C-3 position or C-6 position respectively adds to the total of the starch phosphate of the starch concerned that is bonded in the C-3 position and in the C-6 position (C-3 position+C-6 position).

Various methods are described for the determination of the amount of starch phosphate. Preferably, the methods described by Ritte et al. (2000, Starch/Starke 52, 179-185) can be used for the determination of the amount of starch phosphate. Particularly preferably, the determination of the amount of starch phosphate is carried out by means of $^{31}$P-NMR according to the methods described by Kasemusuwan and Jane (1996, Cereal Chemistry 73, 702-707).

Furthermore, genetically modified plants, which contain the plant cells according to the invention, are also the subject matter of the invention. Plants of this type can be produced from plant cells according to the invention by regeneration.

In principle, the plants according to the invention can be plants of any plant species, i.e. both monocotyledonous and dicotyledonous plants. Preferably they are useful plants, i.e. plants, which are cultivated by people for the purposes of food or for technical, in particular industrial, purposes.

In a further embodiment, the plant according to the invention is a starch-storing plant.

In conjunction with the present invention, the term "starch-storing plants" means all plants with plant parts, which contain a storage starch, such as, for example, maize, rice, wheat, rye, oats, barley, cassava, potato, sago, mung bean, pea or sorghum.

In conjunction with the present invention, the term "potato plant" or "potato" means plant species of the genus *Solanum*, in particular tuber-producing species of the genus *Solanum* and especially *Solanum tuberosum*.

In conjunction with the present invention, the term "wheat plant" means plant species of the genus *Triticum* or plants resulting from crosses with plants of the genus *Triticum*, particularly plant species of the genus *Triticum* or plants resulting from crosses with plants of the genus *Triticum*, which are used in agriculture for commercial purposes, and particularly preferably *Triticum aestivum*.

In conjunction with the present invention, the term "maize plant" means plant species of the genus *Zea*, particularly plant species of the genus *Zea*, which are used in agriculture for commercial purposes, particularly preferably *Zea mais*.

In a further embodiment, the present invention relates to starch-storing plants of the (systematic) family Poaceae according to the invention. Preferably these are here maize- or wheat plants.

The present invention also relates to propagation material of plants according to the invention containing a plant cell according to the invention.

Here, the term "propagation material" includes those constituents of the plant that are suitable for producing offspring by vegetative or sexual means. Cuttings, callus cultures, rhizomes or tubers, for example, are suitable for plant propagation. Other propagation material includes, for example, fruits, seeds, seedlings, protoplasts, cell cultures, etc. Preferably, the propagation material is tubers and particularly preferably grains, which contain endosperms.

In a further embodiment, the present invention relates to harvestable plant parts of plants according to the invention such as fruits, storage roots, roots, blooms, buds, shoots or stems, preferably seeds, grains or tubers, wherein these harvestable parts contain plant cells according to the invention.

Furthermore, the present invention also relates to a method for the manufacture of a genetically modified plant according to the invention, wherein
a) a plant cell is genetically modified, wherein the genetic modification leads to an increase in the enzymatic activity of an OK1 protein and an R1 protein in comparison with corresponding wild type plant cells that have not been genetically modified;
b) a plant is regenerated from plant cells from step a);
c) and, if necessary, further plants are produced with the help of the plants according to Step b).

The genetic modification introduced into the plant cell according to Step a) can basically be any type of genetic modification, which leads to the increase of the activity of an OK1 protein and an R1 protein. The regeneration of the plants according to Step (b) can be carried out using methods known to the person skilled in the art (e.g. described in "Plant Cell Culture Protocols", 1999, edt. by R. D. Hall, Humana Press, ISBN 0-89603-549-2).

The production of further plants according to Step (c) of the method according to the invention can be carried out, for example, by vegetative propagation (for example using cuttings, tubers or by means of callus culture and regeneration of whole plants) or by sexual propagation. Here, sexual propagation preferably takes place under controlled conditions, i.e. selected plants with particular characteristics are crossed and propagated with one another. In this case, the selection is preferably carried out in such a way that further plants, which are produced in accordance with Step c), exhibit the modification, which was introduced in Step a).

The genetic modifications for the production of the plant cells according to the invention can take place simultaneously or in successive steps. At the same time, the genetic modification can be any genetic modification, which leads to the increase of the activity of at least one OK1 protein and/or at least one R1 protein. It can come from wild type plants as well as wild type plant cells, in which no prior genetic modification for the reduction of the activity of at least one OK1 protein or at least one R1 protein has yet taken place, or from plant cells or plants that are already genetically modified, in which the activity of at least one OK1 protein or at least one R1 protein is already increased through a genetic modification. It is irrelevant whether the same method is used for the genetic modification that leads to an increased activity of an OK1 protein as for the genetic modification that leads to an increased activity of an R1 protein, so long as both genetic modifications together lead to an increased activity of an OK1 protein and an R1 protein in the same plant cell.

In a further embodiment of the method according to the invention for the manufacture of a genetically modified plant according to the invention, the genetic modification consists in the introduction of at least one foreign nucleic acid molecule into the genome of the plant cell, wherein the availability or the expression of foreign nucleic acid molecule(s) lead(s) to an increased activity of an OK1 protein and an R1 protein in the cell.

In a further embodiment of the method according to the invention for the manufacture of a genetically modified plant according to the invention, the genetic modification consists in the introduction of at least one foreign nucleic acid molecule into the genome of the plant cell, wherein the foreign nucleic acid molecule(s) contain(s) a sequence coding an OK1 protein and/or an R1 protein.

As already described above for foreign nucleic acid molecules assembled for the genetic modification in the plant cell or plant, Step a) of the method according to the invention for the manufacture of a genetically modified plant according to the invention can involve a single nucleic acid molecule or multiple nucleic acid molecules. The embodiments provided above are to be correspondingly applied for the method according to the invention described here.

In a further embodiment of the method according to the invention for the manufacture of a genetically modified plant according to the invention, the genetic modification in Step a) of the method consists in the introduction of a foreign nucleic acid molecule which contains at least one sequence coding R1 protein and at least one sequence coding OK1 protein.

In a further embodiment of the method according to the invention for the manufacture of a genetically modified plant according to the invention, the genetic modification in Step a) of the method consists in the introduction of multiple foreign nucleic acid molecules, wherein at least one first nucleic acid molecule contains a sequence coding an R1 protein and at least a second nucleic acid molecule contains a sequence coding an OK1 protein.

Furthermore, instead of a wild type plant cell or wild type plant, a mutant cell or a mutant characterised in that it already has an increased activity of an OK1 protein or an increased activity of an R1 protein can be used for introducing a foreign nucleic acid molecule for the implementation of the method according to the invention. The additional information provided above for the use of mutants for the manufacture of plant cells according to the invention or plant are to be correspondingly applied here.

In a further embodiment of the method according to the invention for the manufacture of a genetically modified plant according to the invention, at least one foreign nucleic acid molecule is selected from the group consisting of
a) Nucleic acid molecules, which code a protein with the amino acid sequence given under SEQ ID NO 2 or SEQ ID NO 4;
b) Nucleic acid molecules, which code a protein, which includes the amino acid sequence, which is coded by the insertion in plasmid A.t.-OK1-pGEM or the insertion in plasmid PMI50;
c) Nucleic acid molecules, which code a protein, the sequence of which has an identity of at least 60% with the amino acid sequence given under SEQ ID NO 2 or SEQ ID NO 4;
d) Nucleic acid molecules, which code a protein, the sequence of which has an identity of at least 60% with the amino acid sequence, which is coded by the insertion in plasmid A.t.-OK1-pGEM or by the insertion in plasmid pMI50;
e) Nucleic acid molecules, which include the nucleotide sequence shown under SEQ ID NO 1 or SEQ ID NO 3 or a complimentary sequence;
f) Nucleic acid molecules, which include the nucleotide sequence of the insertion contained in plasmid A.t.-OK1-pGEM or plasmid pMI50;
g) Nucleic acid molecules, which have an identity of at least 70% with the nucleic acid sequences described under a), b), e) or f);
h) Nucleic acid molecules, which hybridise with at least one strand of the nucleic acid molecules described under a), b), e) or f) under stringent conditions;
i) Nucleic acid molecules, the nucleotide sequence of which deviates from the sequence of the nucleic acid molecules identified under a), b), e) or f) due to the degeneration of the genetic code; and
j) Nucleic acid molecules, which represent fragments, allelic variants and/or derivatives of the nucleic acid molecules identified under a), b), c), d), e), f), g), h) or i).

In a further embodiment of the method according to the invention for the manufacture of a genetically modified plant according to the invention, an R1 protein from potato, wheat, rice, maize, soybean, citrus or *Arabidopsis* codes at least one foreign nucleic acid molecule. References for the identified nucleic acid sequences coding R1 proteins from the identified plants have already been further specified above.

A further embodiment of the present invention also relates to a method for the manufacture of a genetically modified plant according to the invention, wherein
a) a plant cell is genetically modified, wherein the genetic modification leads to an increase in the enzymatic activity of an OK1 protein in comparison with corresponding wild type plant cells that have not been genetically modified;
b) a plant is regenerated from plant cells from Step a);
c) if necessary, further plants are produced with the help of the plants according to Step b) and
d) Plants obtained according to Step b) or c) are crossed with a plant, which has an increased level of enzymatic activity of an R1 protein, in comparison with corresponding wild type plant cells that have not been genetically modified.

A further embodiment of the present invention relates to a method for the manufacture of a genetically modified plant according to the invention, wherein
a) a plant cell is genetically modified, wherein the genetic modification leads to an increase in the enzymatic activity of an R1 protein in comparison with corresponding wild type plant cells that have not been genetically modified;
b) a plant is regenerated from plant cells from Step a);
c) if necessary, further plants are produced with the help of the plants according to Step b) and
d) Plants obtained according to Step b) or c) are crossed with a plant, which has an increased level of enzymatic activity of an OK1 protein, in comparison with corresponding wild type plant cells that have not been genetically modified.

At the same time, the plants according to Step a) can be genetically modified as already described above. The regeneration of plans according to Step b) and the production of additional plants according to Step c) was also already further presented above.

A plant that is crossed with plants or offspring of plants obtained in Step b) or c) according to Step d) of the two most recently identified embodiments, can be any plant that has an increased activity of an OK1 protein or an R1 protein, in comparison to corresponding wild type plants. The increase of the activity of an OK1 protein or an R1 protein can be brought about through any modification that leads to an increase of the activity of the related protein in the corresponding plants. These plants can be mutants or plants modified by means of genetic engineering methods. Mutants can be spontaneously (naturally) occurring mutants as well as those that were produced through the targeted use of mutagens (such as, for example, chemical agents, ionising radiation) or genetic engineering methods (for example transposon activation tagging, T-DNA activation tagging, in vivo mutagenesis). Preferably, the plants produced through genetic engineering methods are mutants manufactured by means of insertion mutagenesis, particularly preferably genetically modified plants that express a foreign nucleic acid molecule, especially preferably genetically modified plants in which the foreign nucleic acid molecule codes an OK1 protein or an R1 protein.

In a further embodiment, the method according to the invention is used for manufacturing a genetically modified plant according to the invention for producing starch-storing plants.

In a further embodiment, the method according to the invention is used for manufacturing a genetically modified plant according to the invention for producing maize- or wheat plants according to the invention.

In a further embodiment, the present invention relates to a method according to the invention for manufacturing a genetically modified plant according to the invention, wherein the genetically modified plant synthesises a modified starch in comparison with wild type plants that have not been genetically modified.

In a further embodiment of the method according to the invention for manufacturing a genetically modified plant, the plants according to the invention synthesise a modified starch, which has an increased concentration of starch phosphate and/or a changed starch phosphate distribution in comparison with starch isolated from corresponding wild type plants.

In a further embodiment of the method according to the invention for manufacturing a genetically modified plant, the plants according to the invention synthesise a modified starch, which has a changed ratio of C-3 phosphate to C-6 phosphate in comparison with starch from wild type plants that have not been genetically modified. Especially preferred here are starches, which have an increased proportion of starch phosphate bonded in the C-3 position compared with starch phosphate bonded in the C-6 position in comparison with starches from wild type plant that have not been genetically modified.

The present invention also relates to plants obtainable by the methods according to the invention.

Surprisingly, it has been found that starch isolated from plant cells according to the invention and plants according to the invention, which have an increased activity of an OK1 protein and an increased activity of an R1 protein, synthesise a modified starch.

In particular, the increased amount of starch phosphate in starches according to the invention gives the starches surprising and advantageous characteristics. By means of the increased proportion of starch phosphate, starches according to the invention support an increased proportion of charged groups that significantly affect the functional characteristics of the starch. Starch that supports the charged functional groups is particularly applicable in the paper industry, where it is used for the coating of paper. Paper that otherwise has good adhesive characteristics with charged molecules is particularly suitable for the absorption of dyestuffs, such as ink, print colors, etc., when coated.

The present invention also relates to modified starches obtainable from plant cells according to the invention or plants according to the invention, from propagation material according to the invention or from harvestable plant parts according to the invention.

In a further embodiment, the present invention relates to modified starch according to the invention from starch-storing plants, preferably from starch-storing plants of the (systematic) family Poaceae, particularly preferably from maize or wheat plants.

Furthermore, the present invention relates to a method for the manufacture of a modified starch including the step of extracting the starch from a plant cell according to the invention or from a plant according to the invention, from propagation material according to the invention of such a plant and/or from harvestable plant parts according to the invention of such a plant, preferably from starch-storing parts according to the invention of such a plant. Preferably, such a method also includes the step of harvesting the cultivated plants or plant parts and/or the propagation material of these plants before the extraction of the starch and, further, particularly preferably the step of cultivating plants according to the invention before harvesting.

Methods for extracting starches from plants or from starch-storing parts of plants are known to the person skilled in the art. Furthermore, methods for extracting starch from different starch-storing plants are described, e.g. in Starch: Chemistry and Technology (Publisher: Whistler, BeMiller and Paschall (1994), 2nd Edition, Academic Press Inc. London Ltd; ISBN 0-12-746270-8; see e.g. Chapter XII, Page 412-468: Maize and *Sorghum* Starches: Manufacture; by Watson; Chapter XII, Page 469-479: Tapioca, Arrowroot and Sago Starches: Manufacture; by Corbishley and Miller; Chapter XIV, Page 479-490: Potato starch: Manufacture and Uses; by Mitch; Chapter XV, Page 491 to 506: Wheat starch: Manufacture, Modification and Uses; by Knight and Oson; and Chapter XVI, Page 507 to 528: Rice starch: Manufacture and Uses; by Rohmer and Klem; Maize starch: Eckhoff et al., Cereal Chem. 73 (1996), 54-57, the extraction of maize starch on an industrial scale is generally achieved by so-called "wet milling".). Devices, which are in common use in methods for extracting starch from plant material are separators, decanters, hydrocyclones, spray dryers and fluid bed dryers.

In conjunction with the present invention, the term "starch-storing parts" is to be understood to mean such parts of a plant in which, in contrast to transitory leaf starch, starch is stored as a deposit for surviving for longer periods. Preferred starch-storing plant parts are, for example, tubers, storage roots and grains, particularly preferred are grains containing an endosperm, especially particularly preferred are grains containing an endosperm of maize or wheat plants.

Modified starch obtainable by a method according to the invention for manufacturing modified starch is also the subject matter of the present invention.

In a further embodiment of the present invention, the modified starch according to the invention is native starch.

In conjunction with the present invention, the term "native starch" means that the starch is isolated from plants according to the invention, harvestable plant plants according to the invention, starch-storing parts according to the invention or propagation material of plants according to the invention by methods known to the person skilled in the art.

Furthermore, the use of plant cells according to the invention or plants according to the invention for manufacturing a modified starch are the subject matter of the present invention.

The person skilled in the art knows that the characteristics of starch can be changed by thermal, chemical, enzymatic or mechanical derivation, for example. Derived starches are particularly suitable for different applications in the foodstuffs and/or non-foodstuffs sector. The starches according to the invention are better suited as a starting substance for the manufacture of derived starches than conventional starches, as they have a higher proportion of reactive functional groups due to the higher starch phosphate content.

The present invention therefore also relates to the manufacture of a derived starch, wherein modified starch according to the invention is derived retrospectively.

In conjunction with the present invention, the term "derived starch" is to be understood to mean a modified starch according to the invention, the characteristics of which have been changed after isolation from plant cells with the help of chemical, enzymatic, thermal or mechanical methods.

In a further embodiment of the present invention, the derived starch according to the invention is starch that has been treated with heat and/or acid.

In a further embodiment, the derived starches are starch ethers, in particular starch alkyl ethers, O-allyl ethers, hydroxylalkyl ethers, O-carboxylmethyl ethers, nitrogen-containing starch ethers, phosphate-containing starch ethers or sulphur-containing starch ethers.

In a further embodiment, the derived starches are crosslinked starches.

In a further embodiment, the derived starches are starch graft polymers.

In a further embodiment, the derived starches are oxidised starches.

In a further embodiment, the derived starches are starch esters, in particular starch esters, which have been introduced into the starch using organic acids. Particularly preferably these are phosphate, nitrate, sulphate, xanthate, acetate or citrate starches.

The derived starches according to the invention are suitable for different applications in the pharmaceutical industry and in the foodstuffs and/or non-foodstuffs sector. Methods for manufacturing derived starches according to the invention are known to the person skilled in the art and are adequately described in the general literature. An overview on the manufacture of derived starches can be found, for example, in Orthoefer (in Corn, Chemistry and Technology, 1987, eds. Watson und Ramstad, Chapter 16, 479-499).

Derived starch obtainable by the method according to the invention for manufacturing a derived starch is also the subject matter of the present invention.

Furthermore, the use of modified starches according to the invention for manufacturing derived starch is the subject matter of the present invention.

Starch-storing parts of plants are often processed into flours. Examples of parts of plants from which flours are manufactured are, for example, tubers of potato plants and grains from cereal plants. The grains of these plants that contain endosperms are milled and sifted for the manufacture of flours from cereal plants. Starch is a principal component of endosperm. For other plants that contain no endosperm, but rather other starch-storing parts, such as tubers or roots, flour is commonly manufactured by reducing, drying and then milling the storage organs concerned. The starch of the endosperm or contained in starch-storing parts of plants is an important part of flour, which is manufactured from the plant parts concerned. The characteristics of flours are therefore also affected by the starch present in the flour concerned. Plant cells according to the invention and plants according to the invention synthesise a modified starch in comparison with corresponding wild type plant cells that have not been genetically modified or wild type plants that have not been genetically modified. Flours manufactured from plant cells according to the invention, plants according to the invention, propagation material according to the invention or harvestable parts according to the invention therefore have modified characteristics. The characteristics of flours can also be affected by mixing starch with flours or by mixing flours with different characteristics.

A further subject of the present invention therefore relates to flours containing a starch according to the invention.

A further subject of the present invention relates to flours that are manufactured from plant cells according to the invention, plants according to the invention, starch-storing parts of plants according to the invention, from propagation material according to the invention or from harvestable plant parts according to the invention. Preferred starch-storing parts of plants according to the invention are tubers, storage roots and a grain, which contains endosperm. Tubers from potato plants and grains preferably originate from plants of the (systematic) family Poaceae; grains particularly preferably originate from maize or wheat plants.

In conjunction with the present invention, the term "flour" means a powder obtained by milling plant parts. If necessary, plant parts are dried before milling and reduced and/or sifted after milling.

Flours according to the invention are particularly distinguished by their increased water binding capacity due to the starch present in them that has a modified phosphate content and/or a modified phosphate distribution. This is, for example, desired for the processing of flours in the food industry for many applications, in particular in the manufacture of bakery products.

A further subject of the present invention is a method for the manufacture of flours, including the step the milling of plant cells according to the invention, plants according to the invention, of parts of plants according to the invention, starch-storing parts of plants according to the invention, propagation material according to the invention or harvestable material according to the invention.

Flours can be manufactured through the milling of starch-storing parts of according to the invention. It is known to the person skilled in the art how to manufacture flours. Preferably, a method for the manufacture of flours also includes the step of harvesting the cultivated plants or plant parts and/or of the propagation material or the starch-storing parts of these plants before the milling and particularly preferably further the step of cultivating plants according to the invention before harvesting.

In conjunction with the present invention the term "parts of plants" is to be understood to mean all parts of a plant, which represent a complete plant as constituents in their totality. Parts of plants are, for example, shoots, leaves, rhizomes, roots, beetroots, tubers, pods, seeds or grains.

A further subject of the present invention includes the method for the manufacture of flours, of a processing of plants according to the invention, of starch-storing parts of plants according to the invention, of propagation material according to the invention or of material according to the invention harvestable before milling.

At the same time, the processing can be, for example, a heating treatment and/or a drying. Heating treatment followed by a drying of the heat-treated material is used, for example, for the manufacture of flours from storage roots or tubers such as, for example, from potato tubers, before which the milling takes place. The reduction of plants according to the invention, of starch-storing parts of plants according to the invention, of propagation material according to the invention or of material according to the invention harvestable before milling can likewise represent a processing in terms of the present invention. The removal of plant tissue such as, for example, of husks of grains, before the milling also represents a processing before the milling in terms of the present invention.

A further embodiment of the present invention includes the method for the manufacture of flours after the milling of a product of the grist processing.

At the same time, the grist can be, for example, sifted after the milling in order to manufacture, for example, various types of flours.

A further subject of the present invention is the use of genetically modified plant cells according to the invention, plants according to the invention, of parts of plants according to the invention, starch-storing parts of plants according to the invention, propagation material according to the invention or harvestable material according to the invention for the manufacture of flours.

It is also an object of the present invention to provide means such as DNA molecules, for example, for the production of plant cells according to the invention and plants according to the invention, which synthesise a modified starch in comparison with modified wild type plant cells or wild type plants that have not been genetically modified. The provided DNA molecules contain nucleic acid sequences which code an OK1 protein. A protein with the enzymatic activity of an OK1 protein was not previously known to the person skilled in the art. Also, no DNA molecules can thus be provided, which allow plant cells according to the invention and plants according to the invention and the starch synthesised from them and the flours extracted from them to be produced.

Consequently, the present invention also relates to a recombinant nucleic acid molecule containing a nucleic acid sequence coding an OK1 protein and a nucleic acid sequence coding an R1 protein.

In conjunction with the present invention, the term "recombinant nucleic acid molecule" is to be understood to mean a nucleic acid molecule that contains both nucleic acid sequences coding an OK1 protein as well as nucleic acid sequences coding an R1 protein and in which the nucleic acid sequences coding an OK1 protein and an R1 protein are present in an arrangement as they are not present naturally in the genome of an organism. In addition to nucleic acid sequences coding an OK1 protein and nucleic acid sequences coding an R1 protein, the recombinant nucleic acid molecule can still contain additional sequences, which are not naturally present in one such arrangement as they are present in recombinant nucleic acid molecules according to the invention. At the same time, the said additional sequences can be any sequences, preferably regulatory sequences (promoters, termination signals, enhancers), particularly preferably regulatory sequences, which are active in plant tissue, particularly preferably regulatory sequences, which are active in starch-storing plant tissue. Methods for producing recombinant nucleic acid molecules according to the invention are known to the person skilled in the art and include genetic engineering methods such as, for example, the linking of nucleic acid molecules by ligation, genetic recombination or the resynthesis of nucleic acid molecules (see, for example, Sambrok et al., Molecular Cloning, A Laboratory Manual, $3^{rd}$ edition (2001) Cold Spring Harbour Laboratory Press, Cold Spring Harbour, N.Y. ISBN: 0879695773, Ausubel et al., Short Protocols in Molecular Biology, John Wiley & Sons; $5^{th}$ edition (2002), ISBN: 0471250929).

A further embodiment of the present invention of recombinant nucleic acid molecules according to the invention comprises vectors, in particular plasmids, cosmids, viruses, bacteriophages and other common vectors in genetic engineering, which contain the nucleic acid molecules according to the invention described above.

In a further embodiment, the nucleic acid molecules according to the invention contained in the vectors are linked with regulatory sequences, which initiate the expression in prokaryotic or eukaryotic cells. At the same time, the term "expression" can mean transcription as well as transcription and translation. In this case, the nucleic acid molecules according to the invention can be present in "sense" orientation and/or in "antisense" orientation to the regulatory sequences. At the same time, the recombinant nucleic acid molecules according to the invention can collectively remain under the control of a single regulatory element, or they can each have their own respective individual regulatory element.

Regulatory sequences for expression in prokaryotic organisms, e.g. *E. coli*, and in eukaryotic organisms are adequately described in the literature, in particular those for expression in yeast such as *Saccharomyces cerevisiae*, for example. An overview of different expression systems for proteins and different host organisms can be found, for example, in Methods in Enzymology 153 (1987), 383-516 and in Bitter et al. (Methods in Enzymology 153 (1987), 516-544).

A further subject of the present invention is a host cell, in particular a prokaryotic or eukaryotic cell, which is genetically modified with a recombinant nucleic acid molecule according to the invention and/or with a vector according to the invention, as well as cells, which originate from host cells of this type and which contain the genetic modification according to the invention.

In a further embodiment, the invention relates to host cells, particularly prokaryotic or eukaryotic cells, which were transformed with a nucleic acid molecule according to the invention or a vector according to the invention, as well as host cells, which originate from host cells of this type and which contain the described nucleic acid molecules according to the invention or vectors.

The host cells can be bacteria (e.g. *E. coli*, bacteria of the genus *Agrobacterium* in particular *Agrobacterium tumefaciens* or *Agrobacterium rhizogenes*) or fungus cells (e.g. yeast, in particular *S. cerevisiae*, *Agaricus*, in particular *Agaricus bisporus*, *Aspergillus*, *Trichoderma*), as well as plant or animal cells. Here, the term "transformed" means that the cells according to the invention are genetically modified with a nucleic acid molecule according to the invention inasmuch as they contain at least one nucleic acid molecule according to the invention in addition to their natural genome. This can be freely present in the cell, possibly as a self-replicating molecule, or it can be stably integrated in the genome of the host cell.

The host cells are preferably microorganisms. Within the framework of the present application, these are understood to mean all bacteria and all protista (e.g. fungi, in particular yeast and algae), as defined, for example, in Schlegel "Aligemeine Mikrobiologie" (Georg Thieme Verlag (1985), 1-2).

It is preferred if the host cells according to the invention are plant cells. In principle, these can be plant cells from any plant species, i.e. both monocotyledonous and dicotyledonous plants. Preferably, these will be plant cells from useful agricultural plants, i.e. from plants, which are cultivated by people for the purposes of food or for technical, in particular industrial purposes. The invention relates preferably to plant cells and plants from starch-storing plants (maize, rice, wheat, rye, oat, barley, cassaya, potato, sago, mung bean, pea or sorghum), preferably plant cells from plants of the (systematic) family Poacea, especially particularly preferred are plant cells from maize or wheat plants.

Also the subjects of the present invention are compositions containing a recombinant nucleic acid molecule according to the invention, or a vector according to the invention. Preferred are compositions according to the invention containing a recombinant nucleic acid molecule according to the invention, or a vector according to the invention and a host cell. It is particularly preferred if the host cell is a plant cell, and especially preferred if it is a cell of a maize or wheat plant.

A further subject of the present invention relates to a composition containing a nucleic acid sequence coding an OK1 protein and a nucleic acid sequence coding an R1 protein.

At the same time, the nucleic acid sequences coding an OK1 protein or coding an R1 protein can exist together in a single nucleic acid molecule, or in nucleic acid molecules separated from one another.

A further aspect of compositions according to the invention relates to compositions, which can be used for producing host cells according to the invention, preferably for producing plant cells according to the invention. Preferably this concerns a composition containing nucleic acid sequences coding an OK1 protein and nucleic acid sequences coding an R1 protein, a recombinant nucleic acid molecule according to the invention or a vector according to the invention and a biolistic carrier, which is suitable for the introduction of nucleic acid molecules into a host cell. Preferred biolistic carriers are particles of tungsten, gold or synthetic materials.

A further embodiment of compositions according to the invention relates to compositions containing nucleic acid sequences coding an OK1 protein and nucleic acid sequences coding an R1 protein, a recombinant nucleic acid molecule according to the invention or a vector according to the invention and a plant cell and a synthetic cultivation medium. Preferably such compositions also contain polyethylene glycol (PEG) in addition to plant cells and synthetic cultivation medium. With these compositions, the recombinant nucleic acid molecule exists outside the plant cell, i.e. it is situated outside the cell interior of the plant cell, which is enclosed by a cytoplasmic membrane.

Synthetic cultivation media, which are suitable for the cultivation and/or transformation of plant cells, are known to the person skilled in the art and are adequately described in the literature, for example. Many different synthetic cultivation media are also available for purchase in the specialised trade (e.g. DUCHEFA Biochemie B.V., Belgium).

Furthermore, the present invention relates to the use of compositions according to the invention for the transformation of plant cells.

DESCRIPTION OF SEQUENCES

SEQ ID NO 1: Nucleic acid sequence containing the coding region of an A.t.-OK1 protein from *Arabidopsis thaliana*. This sequence is inserted in the vectors OK1-pGEM-T and OK1-pDEST™17.

SEQ ID NO 2: Amino acid sequence coding an A.t.-OK1 protein from *Arabidopsis thaliana*. This sequence can be derived from the nucleic acid sequence shown under SEQ ID NO 1.

SEQ ID NO 3: Nucleic acid sequence containing the coding region of an O.s.-OK1 protein from *Oryza sativa*. The sequence is inserted in vector pMI50.

SEQ ID NO 4: Amino acid sequence coding an O.s.-OK1 protein from *Oryza sativa*. This sequence can be derived from the nucleic acid sequence shown under SEQ ID NO 3.

SEQ ID NO 5: Peptide sequence coding the phosphohistidine domain of the OK1 proteins from *Arabidopsis thaliana* and *Oryza sativa*.

SEQ ID NO 6: Nucleic acid sequence containing the coding region of a C.r.-R1 protein from *Citrus reticulata*.

SEQ ID NO 7: Amino acid sequence coding a C.r.-1 protein from *Citrus reticulata*.

SEQ ID NO 8: Nucleic acid sequence containing the coding region of an A.t.-R1 protein from *Arabidopsis thaliana*.

SEQ ID NO 9: Amino acid sequence coding an A.t.-1 protein from *Arabidopsis thaliana*.

SEQ ID NO 10: Nucleic acid sequence containing the coding region of an S.t.-R1 protein from *Solanum tuberosum*.

SEQ ID NO 11: Amino acid sequence coding an S.t.-1 protein from *Solanum tuberosum*.

SEQ ID NO 12: Nucleic acid sequence containing the coding region of an O.s.-R1 protein from *Oryza sativa*.

SEQ ID NO 13: Amino acid sequence coding an O.s.-1 protein from *Oryza sativa*.

SEQ ID NO 14: Nucleic acid sequence containing the coding region of a G.m.-R1 protein from *Glycine max*.

SEQ ID NO 15: Amino acid sequence coding the S.t.-1 protein from *Glycine max*.

SEQ ID NO 16: Nucleic acid sequence containing a coding region of a Z.m.-R1 protein from *Zea mays*.

SEQ ID NO 17: Amino acid sequence coding a Z.m-R1 protein from *Zea mays*.

DESCRIPTION OF FIGURES

FIG. 2 A) shows a denaturing (SDS) acrylamide gel on completion of electrophoresis stained with Coomassie Blue. FIG. 2 B) shows the autoradiography of a denaturing (SDS) acrylamide gel. The same amounts of the same samples were applied to each of the two gels. M: Standard protein molecular weight marker; R1: Sample from reaction vessel 1 according to Example 7 (after incubating an OK1 protein with ATP); R2: Sample from reaction vessel 2 according to Example 7 (after incubating an OK1 protein with ATP the protein was heated to 95° C.); R3: Sample from reaction vessel 3 according to Example 7 (after incubating an OK1 protein with ATP the protein was incubated in 0.5 M HCl); R4: Sample from reaction vessel 4 according to Example 7 (after incubating an OK1 protein with ATP the protein was incubated in 0.5 M NaOH).

FIG. 5 A) shows a Western blot. FIG. 5 B) shows the autoradiography of a denaturing (SDS) acrylamide gel. The same amounts of the same samples were applied to each of the two gels. The OK1 protein was incubated either with randomised radioactively labeled ATP or with ATP specifically radioactively labeled in the gamma position. On completion of incubation, the proteins were either heated to 30° C. or 95° C., or incubated in 0.5 M NaOH or 0.5 M HCl respectively.

GENERAL METHODS

Figure 1:
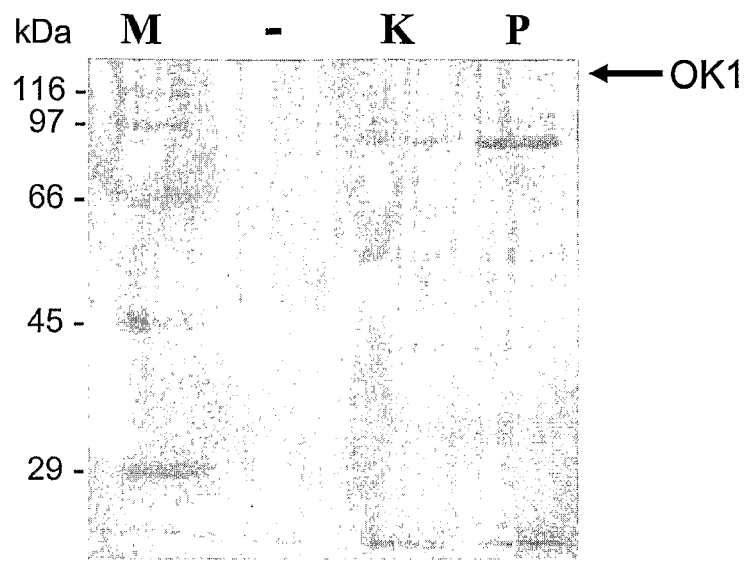
FIG. 1: Denaturing acrylamide gel for identifying proteins from *Arabidopsis thaliana*, which preferably bond to non-phosphorylated starch in comparison with phosphorylated starch. Standard protein molecular weight marker is shown in trace "M". Proteins obtained after incubation of control preparation C from Example 1 d) are shown in trace "–". Protein extracts of *Arabidopsis thaliana*, obtained after incubation with non-phosphorylated starch, isolated from leaves of an *Arabidopsis thaliana* sex1-3 mutant (Preparation B, Example 1 d), are shown in trace "K". Protein extracts of *Arabidopsis thaliana*, obtained after incubation with non-phosphorylated starch, isolated from leaves of an *Arabidopsis thaliana* sex1-3 mutant, which was phosphorylated retrospectively in vitro with an R1 protein (Preparation A, Example 1 d), are shown in trace "P". On completion of electrophoresis, the acrylamide gel was stained with Coomassie Blue.

In the following, methods are described, which can be used for carrying the invention. These methods constitute specific embodiments of the present invention but do not restrict the present invention to these methods. The person skilled in the art knows that he can implement the invention in the same way by modifying the methods described and/or by replacing individual parts of the methods by alternative parts of the methods.

1. Manufacture of Protein Extracts from Plant Tissues
a) Manufacture of Protein Extracts from Plant Tissues Leaf material is frozen in liquid nitrogen immediately after harvesting and subsequently homogenised in the mortar under liquid nitrogen. The reduced leaf material is mixed with ca. 3.5-times the volume (referred to the weight of the leaf material used) of cold (4° C.) binding buffer and broken down for 2×10 s with an Ultraturrax (maximum speed). After the first treatment with an Ultraturrax, the reduced leaf material is cooled on ice before the second treatment is carried out. The treated leaf material is then passed through a 100 µm nylon mesh and centrifuged for 20 min (50 ml centrifuge vessel, 20,000×g, 4° C.).

b) Precipitation of the Proteins Contained in the Protein Extracts

The supernatant obtained following centrifugation according to Step a) is removed and its volume determined. To precipitate proteins, ammonium sulphate is added continuously to the supernatant over a period of 30 minutes while stirring on ice down to a final concentration of 75% (weight/volume). The supernatant is subsequently incubated for a further hour on ice while stirring. The proteins precipitated from the supernatant are pelletised at 20,000×g and 4° C. for 10 min and the pellet subsequently absorbed in 5 ml of binding buffer, i.e. the proteins present in the pellet are dissolved.

c) Desalting of the Precipitated Proteins

The dissolved proteins are desalted by means of a PD10 column filled with Sephadex G25 (Amersham Bioscience, Freiburg, Prod. No. columns: 17-0851-01, Prod. No. Sephadex G25-M: 17-0033-01) at a temperature of 4° C., i.e. the ammonium sulphate used under Step b) for precipitation is also separated from the dissolved protein. The PD10 column is equilibrated with binding buffer before the proteins dissolved in accordance with Step b) are applied. For this purpose, 5 ml of binding buffer are spread over the column five times in each case. Subsequently, 2.5 ml of the protein solution obtained in accordance with Step b) are added to each column before proteins are eluted from the column with 3.5 ml of binding buffer.

d) Determination of the Protein Concentration

The protein concentration is determined with a Bradford assay (Biorad, Munich, Prod. No. 500-0006, Bradford, 1976, Anal. Biochem. 72, 248-254).

e) Composition of the Binding Buffer [

| Binding buffer: | 50 mM | HEPES/NaOH (or KOH), pH 7.2 |
|---|---|---|
| | 1 mM | EDTA |
| | 2 mM | Dithioerythritol (DTE) |
| | 2 mM | Benzamidine |
| | 2 mM | □-aminocaproic acid |
| | 0.5 mM | PMSF |
| | 0.02% | Triton X-100 |

2. Isolation of Leaf Starch
a) Isolation of Starch Granules from Plant Tissues

Leaf material is frozen immediately after harvesting in liquid nitrogen. The leaf material is homogenised in portions in the mortar under liquid nitrogen and absorbed into a total of ca. 2.5-times the volume (weight/volume) of starch buffer. In addition, this suspension is again homogenised in the Waring blender for 20 s at maximum speed. The homogenate is passed through a nylon mesh (100 µm mesh width) and centrifuged for 5 minutes at 1,000×g. The supernatant with the soluble proteins is discarded.

b) Purification of the Starch Isolated from the Plant Tissues

After removing the green material lying on top of the starch by rinsing off the green material with starch buffer, the pellet containing the starch obtained from Step a) is absorbed in starch buffer and successively passed through nylon meshes with different mesh widths (in the order 60 µm, 30 µm, 20 µm). The filtrate is centrifuged using a 10 ml Percoll cushion (95% (v/v) Percoll (Pharmacia, Uppsala, Sweden), 5% (v/v) 0.5M HEPES-KOH pH7.2) (Correx tube, 15 min, 2,000×g). The sediment obtained after this centrifugation is resuspended once in starch buffer and centrifuged again (5 min, 1,000×g,).

c) Removal of the Proteins Bonded to the Starch

Following Step b), starch granules are obtained, which contain proteins bonded to the starch. The proteins bonded to the surface of the starch granules are removed by incubating four times with 0.5% SDS (sodium lauryl sulphate) for 10-15 minutes in each case at room temperature under agitation. Each washing step is followed by a centrifugation (5 min, 5,000×g), in order to separate the starch granules from the respective wash buffer.

d) Purification of the Starch that has Been Freed of Proteins

The starch obtained from Step c), which has been freed from the proteins bonded to its surface, is subsequently removed by incubating four times with wash buffer for 10-15 minutes in each case at room temperature under agitation. Each washing step is followed by a centrifugation (5 min, 1,000×g), in order to separate the starch granules from the respective wash buffer. These purification steps serve mainly to remove the SDS used in the incubations in Step c).

e) Determination of the Concentration of Isolated Starch

The amount of starch isolated in Step d) is determined photometrically. After suitable dilution, the optical density of the starch suspension is measured against a calibration curve at a wavelength of 600 nm. The linear range of the calibration curve is located between 0 and 0.3 extinction units.

To produce the calibration curves, starch, for example isolated from leaves of an *Arabidopsis thaliana* sex1-3 mutant, is dried under vacuum, weighed and absorbed in a defined volume of water. The suspension so obtained is diluted with water in several steps in a ratio of 1 to 1 in each case until a suspension of ca. 5 μg of starch per ml of water is obtained. The suspensions obtained by the individual dilution steps are measured in the photometer at a wavelength of 600 nm. The absorption values obtained for each suspension are plotted against the concentration of starch in the respective suspension. The calibration curve obtained should follow a linear mathematical function in the range from 0 μg starch per ml of water to 0.3 μg starch per ml of water.

f) Storage of Isolated Starch

The starch can either be used directly without further storage for further tests, or stored in aliquots in 1.5 mL Eppendorf vessels at −20° C. Both the frozen starch and the non-stored, freshly isolated starch can be used, if required, for the methods described in the present invention relating to in vitro phosphorylation and/or bonding test, for example.

g) Composition of Buffers Used

1× starch buffer: 20 mM HEPES-KOH, pH 8.0
0.2 mM EDTA
0.5% Triton X-100
Wash buffer: 50 mM HEPES/KOH, pH 7.2

3. Recombinant Expression of an Identified Starch-Phosphorylating Protein a) Manufacture of a Bacterial Expression Vector Containing a cDNA, which Codes a Starch-Phosphorylating Protein The cDNA-coding a starch-phosphorylating protein can be amplified, for example, using mRNA or poly-A-plus-mRNA from plant tissues as a "template", by means of a polymerase chain reaction (PCR). For this purpose, a reverse transcriptase is first used for the manufacture of a cDNA strand, which is complementary to an mRNA, which codes a starch-phosphorylating protein, before the cDNA strand concerned is amplified by means of DNA polymerase. So-called "kits" containing substances, enzymes and instructions for carrying out PCR reactions are available for purchase (e.g. SuperScript™ One-Step RT-PCR System, Invitrogen, Prod. No.: 10928-034). The amplified cDNA coding a starch-phosphorylating protein can subsequently be cloned in a bacterial expression vector, e.g. pDEST™17 (Invitrogen). pDEST™17 contains the T7 promoter, which is used to initiate the transcription of the T7-RNA-polymerase. Furthermore, the expression vector pDEST™17 contains a Shine Dalgarno sequence in the 5'-direction of the T7 promoter followed by a start codon (ATG) and by a so-called His tag. This His tag consists of six codons directly following one another, which each code the amino acid histidine and are located in the reading frame of the said start codon. The cloning of a cDNA coding a starch-phosphorylating protein in pDEST™17 is carried out in such a way that a translational fusion occurs between the codons for the start codon, the His tag and the cDNA coding a starch-phosphorylating protein. As a result of this, following transcription initiated on the T7 promoter, and subsequent translation, a starch-phosphorylating protein is obtained, which contains additional amino acids containing the His tag on its N-terminus. However, other vectors, which are suitable for expression in microorganisms, can also be used for the expression of a starch-phosphorylating protein. Expression vectors and associated expression strains are known to the person skilled in the art and are also available for purchase from the appropriate dealer in suitable combinations.

b) Manufacture of Expression Clones in *Escherichia Coli*

First of all, an appropriate transformation-competent *E. coli* strain, which chromosomally codes a T7-RNA polymerase, is transformed with the expression plasmid manufactured under Step a), and subsequently incubated overnight at 30° C. on culture-medium solidified with agar. Suitable expression strains are, for example, BL21 strains (Invitrogen Prod. No.: C6010-03, which chromosomally code a T7-RNA polymerase under the control of an IPTG-inducable promoter (lacZ)).

Bacteria colonies resulting from the transformation can be investigated using methods known to the person skilled in the art to see whether they contain the required expression plasmid containing a cDNA coding the starch-phosphorylating protein. At the same time, expression clones are obtained.

c) Expression of a Starch-Phosphorylating Protein in *Escherichia Coli*

First of all, a preliminary culture is produced. To do this, an expression clone obtained in accordance with Step b) is seeded in 30 ml Terrific Broth (TB medium) containing an antibiotic for selection on the presence of the expression plasmid, and incubated overnight at 30° C. under agitation (250 rpm).

A main culture for the expression of a starch-phosphorylating protein is then produced. To do this, in each case, 1 liter Erlenmeyer flasks, each containing 300 ml of TB medium, pre-heated to 30° C., and an antibiotic for selection on the presence of the expression plasmid are each seeded with 10 ml of an appropriate pre-culture and incubated at 30° C. under agitation (250 rpm) until an optical density (measured at a wavelength of 600 nm; $OD_{600}$) of ca. 0.8 is achieved.

If, for the expression of a starch-phosphorylating protein, an expression plasmid is used, in which the expression of the starch-phosphorylating protein is initiated by means of an inducible system (e.g. the expression vector pDESTT™17 in BL21 *E. coli* strains, inducible by means of IPTG), then on reaching an $OD_{600}$ of ca. 0.8, the inductor concerned (e.g. IPTG) is added to the main culture. After adding the inductor, the main culture is incubated at 30° C. under agitation (250 rpm) until an $OD_{600}$ of ca. 1.8 is achieved. The main culture is then cooled for 30 minutes on ice before the cells of the main culture are separated from the culture medium by centrifugation (10 minutes at 4,000×g and 4° C.).

4. Purification of a Starch-Phosphorylating Protein a) Breaking Down of Cells Expressing a Starch-Phosphorylating Protein The cells obtained after centrifugation in Step c), Item 3 General Methods, are resuspended in lysis buffer. In doing so, ca. 4 ml lysis buffer are added to about 1 g of cells. The resuspended cells are then incubated for 30 minutes on ice before they are broken down with the help of an ultrasonic probe (Baudelin Sonoplus UW 2070, Baudelin electronic, Berlin, settings: cycle 6, 70%, 1 minute) under continuous cooling by means of the ice. Care must be taken here to ensure that the cell suspension is not heated too much during the ultrasonic treatment. The suspension obtained after the ultrasonic treatment is centrifuged (12 minutes at 20,000×g, 4° C.) and the supernatant obtained after centrifugation is filtered using a filter with a pore size of 45 μm.

b) Purification of the Starch-Phosphorylating Protein

If the starch-phosphorylating protein expressed in *E. coli* cells is a fusion protein with a His tag, then purification can take place with the help of nickel ions, to which the His tag bonds with greater affinity. To do this, 25 ml of the filtrate obtained in Step d) is mixed with 1 ml Ni-agarose slurry (Qiagen, Prod. No.: 30210) and incubated for 1 hour on ice. The mixture of Ni-agarose slurry and filtrate is subsequently spread over a polystyrene column (Pierce, Prod. No.: 29920). The product, which runs through the column, is discarded. The column is next washed by adding 8 ml of lysis buffer, whereby the product, which runs through the column, is again discarded. Elution of the starch-phosphorylating protein then takes place by fractionated addition to the column of 1 ml E1 buffer twice, followed by 1 ml E2 buffer once and subsequently 1 ml E3 buffer five times. The product, which runs through the column, which is produced by adding the individual fraction of the appropriate elution buffer (E1, E2, E3 buffer) to the column, is collected in separate fractions. Aliquots of these fractions are subsequently analysed by means of denaturing SDS acrylamide gel electrophoresis followed by Coomassie Blue colouring. The fractions, which contain the starch-phosphorylating protein in sufficient quantity and satisfactory purity, are purified and concentrated with the help of pressurised filtration at 4° C. Pressurised filtration can be carried out, for example, with the help of an Amicon cell (Amicon Ultrafiltration Cell, Model 8010, Prod. No.: 5121) using a Diaflo PM30 membrane (Millipore, Prod. No.: 13212) at 4° C. Other methods known to the person skilled in the art can also be used for concentration however.

c) Composition of Buffers Used

| Lysis buffer: | 50 mM | HEPES |
|---|---|---|
| | 300 mM | NaCl |
| | 10 mM | Imidazol |
| | pH 8.0 (adjust with NaOH) | |
| | 1 mg/ml | Lysozyme (add immediately before using the buffer) |

¼ tablet per 10 ml protease inhibitors completely EDTA free, (Roche product No.: 1873580) (add immediately before using the buffer)

| Elution buffer E1: | 50 mM | HEPES |
|---|---|---|
| | 300 mM | NaCl |
| | 50 mM | Imidazol |
| | pH 8.0 (adjust with NaOH) | |

| Elution buffer E2: | 50 mM | HEPES |
|---|---|---|
| | 300 mM | NaCl |
| | 75 mM | Imidazol |
| | pH 8.0 (adjust with NaOH) | |

| Elution buffer E3: | 50 mM | HEPES |
|---|---|---|
| | 300 mM | NaCl |
| | 250 mM | Imidazol |
| | pH 8.0 (adjust with NaOH) | |

5. Recombinant Expression of an R1 Protein

The recombinant expression of an R1 protein is described in the literature (Ritte et al., 2002, PNAS 99, 7166-7171; Mikkelsen et al., 2004, Biochemical Journal 377, 525-532), but can also be carried out in accordance with the methods relating to the recombinant expression of a starch expression of a starch-phosphorylating protein described above under Item 3. General Methods.

6. Purification of an R1 Protein

The purification of an R1 protein is described in the literature (Ritte et al., 2002, PNAS 99, 7166-7171; Mikkelsen et al., 2004, Biochemical Journal 377, 525-532), but can also be carried out in accordance with the methods relating to the purification of a starch-phosphorylating protein described above under Item 4. General Methods if an R1 fusion protein, which contains a His tag, is produced by expression of R1 in *E. coli* cells.

7. In Vitro Manufacture of Phosphorylated Starch Starting from Non-Phosphorylated Starch a) In Vitro Phosphorylation of Non-Phosphorylated Starch Starch, which does not contain starch phosphate (e.g., isolated from endosperm from maize or wheat plants respectively, or from leaves of *Arabidopsis thaliana* sex1-3 mutants with the help of the methods described above under Item 2, General Methods), is mixed with R1 buffer and with purified R1 protein (ca. 0.25 μg R1 protein per mg starch) in order to produce a starch content of 25 mg per ml. This reaction preparation is incubated overnight (ca. 15 h) at room temperature under agitation. R1 bonded to the starch present in the reaction preparation is removed on completion of the reaction by washing four times with ca. 800 μl 0.5% SDS in each case. Subsequently, the SDS still present in the in vitro phosphorylated starch is removed by washing five times with 1 ml wash buffer in each case. All washing steps are carried out at room temperature for 10 to 15 minutes under agitation. Each washing step is followed by a centrifugation (2 min, 10,000× g), in order to separate the starch granules from the respective SDS buffer.

b) Composition of Buffers Used

| R1 buffer: | 50 mM | HEPES/KOH, pH 7.5 |
|---|---|---|
| | 1 mM | EDTA |
| | 6 mM | $MgCl_2$ |
| | 0.5 mM | ATP |

Wash buffer: 50 mM HEPES/KOH, pH 7.2

8. Bonding of Proteins to Phosphorylated Starch or Non-Phosphorylated Starch a) Isolation of P-Starch Protein Complexes or Non-Phosphorylated Starch Protein Complexes Ca. 50 mg P-starch or ca. 50 mg non-phosphorylated starch respectively are resuspended in separate preparations in ca. 800 μl protein extract in each case. The protein concentration of the protein extracts should be ca. 4 mg to 5 mg per ml in each case. The incubation of the P-starch or non-phosphorylated starch with protein extracts is carried out at room temperature for 15 minutes at 4° C. under agitation. On completion of the incubation, the reaction preparations are centrifuged out using a Percoll cushion (4 ml) (15 minutes, 3500 rpm, 4° C.). After centrifugation, proteins that are not bonded to phosphorylated starch or P-starch will be found in the supernatant and can be removed with a Pasteur pipette. The supernatant is discarded. The sedimented pellet containing P-starch and non-phosphorylated starch, including the proteins bonded to the respective starches (P-starch protein complexes or non-phosphorylated starch protein complexes respectively), obtained after centrifugation is washed twice with 1 ml of wash buffer in each case (see above, General Methods under item 7.b) by incubating for 3 minutes at 4° C. in each case under agitation. Each washing step is followed by a centrifugation (5 minutes, 8000 rpm, 4° C. in a table centrifuge, Hettich EBA 12R) in order to separate the P-starch or non-phosphorylated starch respectively from the wash buffer.

b) Dissolving the Proteins Bonded in the P-Starch Protein Complexes or Non-Phosphorylated Starch Protein Complexes Respectively The P-starch protein complexes or non-phosphorylated starch protein complexes respectively obtained in Step a) are resuspended in ca. 150 µl SDS test buffer and incubated at room temperature for 15 minutes under agitation. The P-starch or non-phosphorylated starch respectively is subsequently removed from the dissolved proteins by centrifugation (1 minute, 13,000 rpm, room temperature, Eppendorf table centrifuge). The supernatant obtained after centrifugation is centrifuged again in order to remove any residues of P-starch or non-phosphorylated starch respectively (1 minute, 13,000 rpm, room temperature, Eppendorf table centrifuge) and removed. As a result, dissolved proteins, which bond to the P-starch or non-phosphorylated starch respectively, are obtained.

c) Composition of Buffers Used

| SDS test buffer: | 187.5 mM | Tris/HCl pH 6.8 |
|---|---|---|
| | 6% | SDS |
| | 30% | Glycerine |
| | ~0.015% | Bromophenol blue |
| | 60 mM | DTE (add fresh!) |

Percoll: Percoll is dialysed overnight against a solution consisting of and 25 mM HEPES/KOH, pH 7.0

9. Separation of Proteins, which Bond to P-Starch and/or Non-Phosphorylated starch The dissolved proteins obtained in Step c) under Item 8. General Methods relating to the bonding of proteins to P-starch or non-phosphorylated starch respectively are incubated for 5 minutes at 95° C. in each case and subsequently separated with the help of denaturing polyacrylamide gel electrophoresis. In doing so, an equal volume is applied to the acrylamide gel in each case for the dissolved proteins obtained by bonding to P-starch and for those obtained by bonding to non-phosphorylated starch. The gel obtained on completion of electrophoresis is stained at least overnight with colloidal Comassie (Roth, Karlsruhe, Roti-Blue Rod. No.: A152.1) and subsequently de-stained in 30% methanol, 5% acetic acid, or in 25% methanol.

10. Identification and Isolation of Proteins, which Bond to P-Starch and/or Non-Phosphorylated Starch a) Identification of Proteins with Increased Bonding Activity with Respect to P-Starch In Comparison with Non-Phosphorylated Starch Proteins, which, after separation by means of acrylamide gel electrophoresis and subsequent visualisation by colouration (see above, Item 9. General Methods), exhibit an increased signal after bonding to P-starch in comparison with a corresponding signal after bonding to non-phosphorylated starch, have increased bonding activity with respect to P-starch in comparison with non-phosphorylated starch. By this means, it is possible to identify proteins, which have increased bonding activity with respect to P-starch in comparison with non-phosphorylated starch. Proteins, which have increased bonding activity with respect to P-starch in comparison with non-phosphorylated starch, are excised from the acrylamide gel.

b) Identification of Amino Acid Sequence of Proteins, which Have Increased Bonding Activity with Respect to P-Starch in Comparison with Non-Phosphorylated Starch Proteins identified in accordance with Step a) are digested with trypsin, and the peptides obtained are analysed by means of MALDI-TOF to determine the masses of the peptides obtained. Trypsin is a sequence-specific protease, i.e. trypsin only splits proteins at a specified position when the proteins concerned contain certain amino acid sequences. Trypsin always splits peptide bonds when the amino acids arginine and lysine follow one another starting from the N-terminus. In this way, it is possible to theoretically determine all peptides that would be produced following the trypsin digestion of an amino acid sequence. From the knowledge of the amino acids coding the theoretically determined peptides, the masses of the peptides, which are obtained after theoretical trypsin digestion, can also be determined. Databases (e.g. Protein Prospector and Swissprot websites), which contain information concerning the masses of peptides after theoretical trypsin digestion, can therefore be compared with the real masses of peptides of unknown proteins obtained with MALDI-TOF-MS. Amino acid sequences, which have the same peptide masses after theoretical and/or real trypsin digestion, are to be looked upon as being identical. The databases concerned contain both peptide masses of proteins, the function of which has already been shown, and also peptide masses of proteins, which up to now only exist hypothetically by derivation from amino acid sequences starting from nucleic acid sequences obtained in sequencing projects. The actual existence and the function of such hypothetical proteins has therefore seldom been shown and, if there is a function at all, then this is usually based only on predictions and not on an actual demonstration of the function.

Bands containing proteins identified in accordance with Step a) are excised from the acrylamide gel; the excised acrylamide piece is reduced and destained by incubating for approximately half an hour at 37° C. in ca. 1 ml 60% 50 mM $NH_4HCO_3$, 40% acetonitrile. The decolourising solution is subsequently removed and the remaining gel dried under vacuum (e.g. Speedvac). After drying, trypsin solution is added to digest the proteins contained in the gel piece concerned. Digestion takes place overnight at 37° C. After digestion, a little acetonitrile is added (until the acrylamide gel is stained white) and the preparation dried under vacuum (e.g. Speedvac). When drying is complete, just enough 5% formic acid is added to cover the dried constituents and incubated for a few minutes at 37° C. The acetonitrile treatment followed by drying is repeated once more. The dried constituents are subsequently absorbed in 0.1% TFA (triflouroacetic acid, 5 µl to 10 µl) and dripped onto a carrier in ca. 0.5 µl portions. Equal amounts of matrix ($\epsilon$-cyano-4-hydroxy-cinnamic acid) are also applied to the carrier. After crystallising out the matrix, the masses of peptides are determined by means of MALDI-TOF-MS-MS (e.g. Burker Reflex™ II, Bruker Daltonic, Bremen). With the masses obtained, databases are searched for amino acid sequences, which give the same masses after theoretical trypsin digestion. In this way, amino acid sequences can be identified, which code proteins, which preferably bond to phosphorylated alpha-1,4-glucans and/or which need P-alpha-1,4-glucans as a substrate.

11. Method for Demonstrating Starch-Phosphorylating Activity of a Protein a) Incubation of Proteins with P-Starch and/or Non-Phosphorylated Starch In order to demonstrate whether a protein has starch-phosphorylating activity, proteins to be investigated can be incubated with starch and radioactively labeled ATP. To do this, ca. 5 mg P-starch or ca. 5 mg non-phosphorylated starch is incubated with the protein to be investigated (0.01 µg to 5.0 µg per mg of added starch) in 500 µl phosphorylation buffer for 10 minutes to 30 minutes at room temperature under agitation. The reaction is subsequently stopped by the addition of SDS up to a concentration of 2% (weight/volume). The starch granules in the respective reaction mixture are centrifuged out (1 minute, 13,000×g), and washed once with 900 µl of a 2% SDS solution and four times each with 900 µl of a 2 mM ATP solution. Each washing step is carried out for 15 minutes at room temperature under agitation. After each washing step, the starch granules are separated from the respective wash buffer by centrifugation (1 min, 13,000×g).

In addition, when carrying out an experiment to demonstrate starch-phosphorylating activity of a protein, further reaction preparations, which do not contain protein or contain inactivated protein, but which are otherwise treated in the same way as the reaction preparations described, should be processed as so-called controls.

b) Determination of the Amount of Phosphate Residues Incorporated in the P-Starch and/or Non-Phosphorylated Starch Due to Enzymatic Activity The starch granules obtained in accordance with Step a) can be investigated for the presence of radioactively labeled phosphate residues. To do this, the respective starch is resuspended in 100 µl of water and mixed with 3 ml of scintillation cocktail in each case (e.g. Ready Safe™, BECKMANN Coulter) and subsequently analysed with the help of a scintillation counter (e.g. LS 6500 Multi-Purpose Scintillation Counter, BECKMANN COULTER™).

c) Identification of Proteins, which Preferably Use P-Starch as a Substrate

If a protein is incubated in separate preparations, once with P-starch and once with non-phosphorylated starch, in accordance with the method described under a), then, by comparing the values for the presence of starch phosphate obtained according to Step b), it can be determined whether the protein concerned has incorporated more phosphate in P-starch in comparison with non-phosphorylated starch. In this way, proteins can also be identified, which can introduce phosphate into P-starch but not into non-phosphorylated starch. This means proteins can be identified, which already require phosphorylated starch as a substrate for a further phosphorylation reaction.

D) Composition of Buffers Used
Phosphorylation buffer:

| 50 mM | HEPES/KOH, pH 7.5 |
| 1 mM | EDTA |
| 6 mM | $MgCl_2$ |
| 0.01 to 0.5 mM | ATP |

0.2 to 2 µCi per ml randomised $^{33}$P-ATP (alternatively, ATP, which contains a phosphate residue, which is specifically labeled in the gamma position, can also be used)

In conjunction with the present invention, the term "randomised ATP" is to be understood to mean ATP which contains labeled phosphate residues in both the gamma position as well as in the beta position (Ritte et al. 2002, PNAS 99, 7166-7171). Randomised ATP is also described in the scientific literature as beta/gamma ATP. A method for manufacturing randomised ATP is described in the following.

i) Manufacture of Randomised ATP

The method described here for manufacturing randomised ATP with the help of enzyme catalysed reactions is based on the following reaction mechanisms:

1st reaction step:
$^{33}$P-ATP+AMP+myokinase→$^{33}$P-ADP+ADP (Adenosine-P-P-$^{33}$P+Adenosine-P→Adenosine-P-P-P+Adenosine-P-$^{33}$P)

2nd reaction step
$^{33}$P-ADP+ADP+2 PEP+Pyruvate kinase→$^{33}$P-ATP+ATP+2 Pyruvate (Adenosine-P-P+Adenosine-P-$^{33}$P+2 PEP→Adenosine-P-P-P+Adenosine-P-$^{33}$P-P+2 Pyruvate)

The reaction equilibria lie on the product side but, in spite of this, this reaction produces a mixture consisting mainly of $^{33}$P-ATP and some $^{33}$P-ATP.

ii) Carrying Out the 1St Reaction Step

ATP (100 µCi, 3000 Ci per mmol), which contains a phosphate residue labeled with $^{33}$P in the gamma position (Hartmann Analytic, 10 µCi/µl), is incubated with 2 µl myokinase (AMP-phosphotransferase, from rabbit muscle; SIGMA, Prod. No.: M3003 3.8 mg/ml, 1,626 units/mg) in 90 µl randomising buffer for 1 hour at 37° C. The reaction is subsequently stopped by incubating for 12 minutes at 95° C. before the reaction preparation is purified up by means of centrifugal filtration using a Microcon YM 10 filter (Amicon, Millipore Prod. No. 42407) at 14,000×g for at least 10 minutes.

iii) Carrying Out the 2Nd Reaction Step

Two µl pyruvate kinase (see below for manufacture of an appropriate solution) and 3 µl 50 mM PEP (phosphoenolpyruvate) are added to the filtrate obtained in Step ii). This reaction mixture is incubated for 45 minutes at 30° C. before the reaction is stopped by incubating at 95° C. for 12 minutes. The reaction mixture is subsequently centrifuged (2 minutes, 12,000 rpm in an Eppendorf table centrifuge). The supernatant containing randomised ATP obtained after centrifugation is removed, aliquoted and can be stored at –20° C.

Manufacture of the Pyruvate Kinase Solution

Fifteen µl pyruvate kinase (from rabbit muscle, Roche, Prod. No. 12815), 10 mg/ml, 200 units/mg at 25° C.) are centrifuged out, the supernatant discarded and the pellet absorbed in 27 µl pyruvate kinase buffer.

iv) Buffers Used

| Pyruvate kinase buffer: | 50 mM | HEPES/KOH pH 7,5 |
| | 1 mM | EDTA |

| Randomising buffer: | 100 mM | HEPES/KOH pH 7,5 |
| | 1 mM | EDTA |
| | 10% | Glycerol |
| | 5 mM | $MgCl_2$ |
| | 5 mM | KCl |
| | 0.1 mM | ATP |
| | 0.3 mM | AMP |

12. Demonstration of the Autophosphorylation of a Protein

In order to demonstrate whether a protein has auto-phosphorylating activity, proteins to be investigated can be incubated with radioactively labeled ATP. To do this, proteins to be investigated (50 µg to 100 µg) are incubated in 220 µl phosphorylation buffer (see above, Item 12 d), General Methods) for 30 minutes to 90 minutes at room temperature under agitation. The reaction is subsequently stopped by the addition of EDTA up to a final concentration of 0.11 M. Ca. 2 µg to 4 µg of protein are separated with the help of denaturing polyacrylamide gel electrophoresis (7.5% acrylamide gel). The gel obtained after polyacrylamide gel electrophoresis is subjected to autoradiography. Proteins, which exhibit a signal in the autoradiography, carry a radioactive phosphate residue.

13. Identification of the C-Atom Positions of the Glucose Molecules of an alpha-1,4-glucan, into which Phosphate Residues are Introduced by a Starch-Phosphorylating Protein Which C-atom positions of the glucose molecules of an alpha-1,4-Glucans are phosphorylated by a protein can be demonstrated in a controlled manner by hydrolysis of the phosphorylated glucans obtained by means of an appropriate protein in vitro, subsequent separation of the glucose monomers obtained after hydrolysis, followed by measurement of the phosphate incorporated by an appropriate protein in certain fractions of the glucose molecules.

a) Total Hydrolysis of the alpha-1,4-glucans

Water suspensions containing alpha-1,4-glucan are centrifuged, the sedimented pellet subsequently resuspended in 0.7 M HCl (Baker, for analysis) and incubated for 2 hours at 95° C. under agitation. On completion of incubation, the samples are briefly cooled and centrifuged (e.g. 2 minutes 10,000×g). The supernatant obtained is transferred to a new reaction vessel and neutralised by the addition of 2 M NaOH (Baker, for analysis). If a pellet remains, it is resuspended in 100 µl of water and the quantity of labeled phosphate present therein is determined as a control.

The neutralised supernatant is subsequently centrifuged over a 10 kDa filter. By measuring an aliquot of the filtrate obtained, the quantity of labeled phosphate in the filtrate is determined with the help of a scintillation counter, for example.

b) Fractionation of the Hydrolysis Products and Determination of the Phosphorylated C-Atom Positions The neutralised filtrates of the hydrolysis products obtained by means of Step a) can be separated (when using radioactively labeled ATP about 3,000 cpm) with the help of high-pressure anion exchange chromatography (HPAE), for example. The neutralised filtrate can be diluted with $H_2O$ to obtain the volume required for HPAE. In addition, glucose-6-phosphate (ca. 0.15 mM) and glucose-3-phosphate (ca. 0.3 mM) are added to the appropriate filtrates in each case as an internal control. Separation by means of HPAE can be carried out, for example, with the help of a Dionex DX 600 Bio Lc system using a CarboPac PA 100 column (with appropriate pre-column) and a pulsed amperometric detector (ED 50). In doing so, before injecting the sample, the column is first rinsed for 10 minutes with 99% eluent C and 1% eluent D. A sample volume of 60 µl is then injected.

The elution of the sample takes place under the following conditions:

Flow rate: 1 ml per minute
Gradient: linearly increasing from 0 minutes to 30 minutes

|  | Eluent C: | Eluent D: |
| --- | --- | --- |
| 0 minutes | 99% | 1% |
| 30 minutes | 0% | 100% |
| 35 minutes | 0% | 100% |
| Run terminated | | |

The hydrolysis products eluted from the column are collected in individual fractions of 1 ml each. As, in each case, non-labeled glucose-3-phosphate (Ritte et al. 2002, PNAS 99, 7166-7171) and non-labeled glucose-6-phosphate (Sigma, Prod. No.: G7879) have been added to the injected samples of hydrolysis products as internal standards, the fractions, which contain either glucose-3-phosphate or glucose-6-phosphate, can be determined by means of pulsed amperometric detection. By measuring the amount of labeled phosphates in the individual fractions and subsequently comparing with the fractions, which contain glucose-3-phosphate or glucose-6-phosphate, this can be used to determine those fractions, in which labeled glucose-6-phosphate or labeled glucose-3-phosphate is contained. The amount of labeled phosphate in the fraction concerned is determined. From the ratios of the amounts of glucose-3-phosphate to glucose-6-phosphate measured for labeled phosphate in the individual hydrolysis products, it can now be determined which C-atom position is preferably phosphorylated by an alpha-1,4-glucan phosphorylating enzyme.

c) Buffers used
Eluent C: 100 mM NaOH
Eluent D: 100 mM NaOH
500 mM sodium acetate 14. Transformation of Rice Plants Rice plants were transformed in accordance with the methods described by Hiei et al. (1994, Plant Journal 6(2), 271-282).

15. Transformation of Wheat Plants

Wheat plants were transformed in accordance with the methods described by Becker et al. (1994, Plant Journal 5, 299-307).

16. Transformation of Maize Plants

Immature embryos of maize plants of the line A188 were transformed in accordance with the methods described by Ishida et al. (1996, Nature Biotechnology 14, 745-750).

17. Determination of the Starch Phosphate Content a) Determination of the C-6 Phosphate Content The positions C2, C3 and C6 of the glucose units can be phosphorylated in the starch. For determining the C6-P content of the starch, 50 mg of starch is hydrolised in 500 µl of 0.7 M HCl for 4 hours at 95° C. The preparations are subsequently centrifuged for 10 minutes at 15500 g, and the supernatants are removed. Seven µl of the supernatants are mixed with 193 µl of imidazole buffer (100 MM imidazole, pH 7.4; 5 mM $MgCl_2$, 1 mM EDTA and 0.4 mM NAD). The measurement is carried out in the photometer at 340 nm. After establishing a base absorption, the enzyme reaction was started by adding 2 units of glucose-6-phosphate dehydrogenase (from *Leuconostoc mesenteroides*, Boehringer Mannheim). The change in absorption is directly proportional to the concentration of the G-6-P content of the starch.

b) Determination of the Total Phosphate Content

The determination of the total phosphate content takes place according to the method by Ames (Methods in Enzymology VIII, (1996), 115-118).

Approximately 50 mg starch is mixed with 30 µl ethanolic magnesium nitrate solution and incinerated for three hours at 500° C. in the muffle furnace. The residue is mixed with 300 µl 0.5 M hydrochloric acid and incubated 30 min at 60° C. An aliquot of 300 µl 0.5 M hydrochloric acid is subsequently refilled, added to a mixture of 100 µl of 10% ascorbic acid and 600 µl 0.42% ammonium molybdate in 2 M sulfuric acid and incubated 20 minutes at 45° C.

c) Determination of the Content of C-6 Phosphate and C-3 Phosphate

For determining the content of phosphate which is bound in the C-6 position and in the C-3 position of the glucose molecules of an alpha-1,4-glucan, the glucans concerned can be separated by means of HPAE after total hydrolysis according to the method presented under General Methods 13. The amounts of glucose-6-phosphate and glucose-3-phosphate can be determined by the integration of the individual peak areas obtained after HPEA separation. By comparing the peak areas obtained for glucose-6-phosphate and glucose-3-phosphate in unknown samples with the peak areas that are obtained with known amounts of glucose-6-phosphate and glucose-3-phosphate after separation by means of HPEA, the amount of glucose-6-phosphate and glucose-3-phosphate can be determined in the sample to be investigated.

EXAMPLES

1. Isolation of a Protein from *Arabidopsis Thaliana*, which has Increased Bonding Activity with Respect to P-Starch in Comparison with Non-Phosphorylated Starch a) Manufacture of Protein Extracts from *Arabidopsis Thaliana*

Protein extracts were manufactured from approximately 7 g of leaves (fresh weight) of *Arabidopsis thaliana* (Ecotype Columbia, Col-O) in accordance with the method described under Item 1, General Methods.

b) Isolation of Starch Granules from Leaves of Sex1-3 Mutants of *Arabidopsis thaliana*

Starch granules were isolated from approximately 20 g (fresh weight) of leaves of a sex1-3 mutant of *Arabidopsis thaliana* in accordance with the method described under Item 2, General Methods.

c) In Vitro Phosphorylation of Starch Isolated from a Sex1-3 Mutant of *Arabidopsis Thaliana* with Purified R1 Protein About 30 mg of non-phosphorylated starch isolated from a sex1-3 mutant of *Arabidopsis thaliana* was phosphorylated in accordance with the method described under Item 7, General Methods, by means of an R1 protein recombinantly expressed in *E. coli* and purified. The method described by Ritte et al. (2002, PNAS 99, 7166-7171) was used for expressing the R1 protein in *E. coli* and for subsequent purified.

d) Isolation of Proteins, which Bond to P-Starch and/or Non-Phosphorylated Starch Protein extracts of *Arabidopsis thaliana*, obtained in accordance with Step a), were incubated and washed in a Preparation A with 50 mg of the in vitro phosphorylated starch manufactured in accordance with Step c) using the method described under Item 8 a), General Methods.

Protein extracts of *Arabidopsis thaliana*, obtained in accordance with Step a), were incubated and washed in a second Preparation B with 50 mg of the non-phosphorylated starch manufactured in accordance with Step b) using the method described under Item 8 a), General Methods.

Subsequently, the proteins bonded to the P-starch of Preparation A and to the non-phosphorylated starch of Preparation B were dissolved in accordance with the method described under Item 8 b), General Methods.

In a third Preparation C, 50 mg of the in vitro phosphorylated starch manufactured in accordance with Step c) were incubated and washed using the method described under Item 8 a), General Methods. Preparation C contained no protein extracts, however.

e) Separation of the Proteins Obtained in Accordance with Step D) by Means of Acrylamide Gel Electrophoresis The proteins of Preparations A, B and C obtained in Step d) were separated by means of a 9% acrylamide gel under denaturing conditions (SDS) using the method described under Item 9, General Methods, and subsequently stained with Coomassie Blue. The stained gel is shown in FIG. 1. It can be clearly seen that a protein, which has a molecular weight of ca. 130 kDa in denaturing acrylamide gel referred to a protein standard marker (Trace M), preferably bonds to phosphorylated starch (Trace P) in comparison with non-phosphorylated starch (K).

f) Identification of the Protein, which Preferably Bonds to P-Starch in Comparison with Non-Phosphorylated Starch The band of the protein with a molecular weight of ca. 130 kDa identified in Step e) was excised from the gel. The protein was subsequently released from the acrylamide as described under General Methods 10 b), digested with trypsin and the peptide masses obtained determined by means of MALDI-TOF-MS. The so-called "fingerprint" obtained by MALDI-TOF-MS was compared with fingerprints of theoretically digested amino acid molecules in databases (See the Mascot ProFound, and PepSea: websites). As such a fingerprint is very specific to a protein, it was possible to identify an amino acid molecule. With the help of the sequence of this amino acid molecule, it was possible to isolate a nucleic acid sequence from Arabidopsis thaliana coding an OK1 protein. The protein identified with this method was designated A.t.-OK1. Analysis of the amino acid sequence of the OK1 protein from Arabidopsis thaliana showed that this deviated from the sequence that was present in the database (NP 198009, NCBI). The amino acid sequence shown in SEQ ID No 2 codes the A.t.-OK1 protein. SEQ ID No 2 contains deviations when compared with the sequence in the database (Acc.: NP 198009.1, NCBI). The amino acids 519 to 523 (WRLCE) and 762 to 766 (VRARQ) contained in SEQ ID No 2 are not in the sequence, which is present in the database (ACC.: NP 198009.1). Compared with Version 2 of the database sequence (Acc.: NP 198009.2), the amino acid sequence shown in SEQ ID NO 2 also contains the additional amino acids 519 to 523 (WRLCE).

2. Cloning of a cDNA, which Codes the Identified OK1 Protein

The A.t.-OK1 cDNA was isolated with the help of reverse PCR using mRNA isolated from leaves of *Arabidopsis thaliana*. To do this, a cDNA Strand was synthesised by means of reverse transcriptase (SuperScript™ First-Strand Synthesis System for RT PCR, Invitrogen Prod. No.: 11904-018), which was then amplified using DNA polymerase (Expand High Fidelity PCR Systems, Roche Prod. No.: 1732641). The amplified product obtained from this PCR reaction was cloned in the vector pGEM®-T (Invitrogen Prod. No.: A3600). The plasmid obtained is designated A.t.-OK1-pGEM, the cDNA sequence coding the A.t.-OK1 protein was determined and is shown under SEQ ID NO. 1.

The sequence shown under SEQ ID NO 1 is not the same as the sequence, which is contained in the database. This has already been discussed for the amino acid sequence coding an A.t.-OKA.t.-OK1 protein.

Conditions used for the amplification of the cDNA coding the A.t.-OK1 protein First strand synthesis:

The conditions and buffer specified by the manufacturer were used. In addition, the reaction preparation for the first strand synthesis contained the following substances:

```
3 µg     total RNA

5 µM     3'-Primer
         (Ok1rev1: 5'-GACTCAACCACATAACACACAAAGATC)
         (SEQ ID NO: 18)

0.83 µM  dNTP mix
```

The reaction preparation was incubated for 5 minutes at 75° C. and subsequently cooled to room temperature.

The 1st strand buffer, RNase inhibitor and DTT were then added and incubated for 2 minutes at 42° C. before 1 µL Superscript RT DNA polymerase was added and the reaction preparation incubated for 50 minutes at 42° C.

Conditions for the amplification of the first strand by means of PCR:

```
1 µL      of the reaction preparation of the first
          strand synthesis 0.25 µM   3'Primer
          (OK1rev2: 5'-TGGTAACGAGGCAAATGCAGA)
          (SEQ ID NO: 19)

0.25 µM   5'Primer
          (OK1fwd2: 5'-ATCTCTTATCACACCACCTCCAATG)
          (SEQ ID NO: 20)
```

Reaction conditions:

| Step 1 | 95° C. | 2 min |
| Step 2 | 94° C. | 20 sec |
| Step 3 | 62° C. | 30 sec |
| Step 4 | 68° C. | 4 minutes |
| Step 5 | 94° C. | 20 sec |
| Step 6 | 56° C. | 30 sec |
| Step 7 | 68° C. | 4 minutes |
| Step 8 | 68° C. | 10 minutes |

The reaction was first carried out in accordance with Steps 1 to 4. Ten repeats (cycles) were carried out between Step 4 and Step 2, the temperature of Step 3 being reduced by 0.67° C. after each cycle. This was subsequently followed by the reaction in accordance with the conditions specified in Steps 5 to 8. Twenty-five repeats (cycles) were carried out between Step 7 and Step 5, the time of Step 7 being increased by 5 sec on each cycle. On completion of the reaction, the reaction was cooled to 4° C.

3. Manufacture of a Vector for the Recombinant Expression of cDNA of the OK1 Protein Following amplification by means of PCR by using the plasmid A.t.-OK1-pGEM as a template using Gateway Technology (Invitrogen), the sequence coding the OK1 protein from *Arabidopsis thaliana* was next cloned in the vector pDONOR™ 201 (Invitrogen Prod. No.: 11798-014). Subsequently, the coding region of the OK1 protein from the vector obtained was cloned by sequence-specific recombination in the expression vector pDEST17™ (Invitrogen Prod. No.: 11803-014). The expression vector obtained was designated as A.t.-OK1-pDEST8M17. The cloning resulted in a translational fusion of the cDNA coding the A.t-OK1 protein with the nucleotides present in the expression vector pDEST™17. The nucleotides originating from the vector pDEST™17, which are translationally fused with the cDNA coding the A.t.-OK1 protein, code 21 amino acids. These 21 amino acids include, amongst others, the start codon (ATG) and a so-called His tag (6 histidine residues directly after one another). After translation of these translationally fused sequences, this results in an A.t.-OK1 protein, which has the additional 21 amino acids coded by nucleotides originating from the vector at its N-terminus. The recombinant A.t.-OK1 protein resulting from this vector therefore contains 21 additional amino acids originating from the vector pDEST™17 at its N-terminus.

4. Heterologous Expression of the Ok1 Protein in *E. coli*

The expression vector A.t.-OK1-pDEST™17 obtained in accordance with Example 3 was transformed in the *E. coli* strain BL21 Star™ (DE3) (Invitrogen, Prod. No. C6010-03). A description of this expression system has already been given above (see Item 3, General Methods). Bacteria clones, containing the vector A.t.-OK1-pDEST™17, resulting from the transformation were next used to manufacture a preliminary culture, which was subsequently used for inoculating a main culture (see Item 3.c, General Methods). The preliminary culture and the main culture where each incubated at 30° C. under agitation (250 rpm). When the main culture had reached an $OD_{600}$ of ca. 0.8, the expression of the recombinant A.t.-OK1 protein was induced by the addition of IPTG (isopropyl-beta-D-thiogalactopyranoside) until a final concentration of 1 mM was achieved. After the addition of IPTG, the main culture was incubated at 30° C. under agitation (250 rpm) until an $OD_{600}$ of ca. 1.8 was achieved. The main culture was then cooled for 30 minutes on ice before the cells of the main culture were separated from the culture medium by centrifugation (10 minutes at 4,000×g and 4° C.).

5. Purification of the Recombinantly Expressed OK1 Protein

The purification and concentration of the A.t.-OK1 protein from cells obtained in accordance with Example 4 was carried out using the method described under Item 4, General Methods.

6. Demonstration of Starch-Phosphorylating Activity of the OK1 Protein

The starch-phosphorylating activity of the A.t.-OK1 protein was demonstrated in accordance with the method described under Item 11, General Methods. In doing so, µg of purified A.t.-OK1 protein manufactured in accordance with Example 5 was in each case incubated in a Preparation A with 5 mg of starch isolated from a sex1-3 mutant of *Arabidopsis thaliana* in accordance with Example 1 b) and in a Preparation B with 5 mg of starch obtained by enzymatic phosphorylation in accordance with Example 1 c), in each case in 500 µl of phosphorylation buffer containing 0.05 mM radioactively ($^{33}P$) labeled, randomised ATP (in total 1,130,00 cpm, ca. 0.55 µCi) for 30 minutes at room temperature under agitation. A Preparation C was used as a control, which was the same as Preparation B, except that it contained no OK1 protein, but was otherwise treated in the same way as Preparations A and B. Two tests, which were independent from one another, were carried out for all preparations (A, B, C).

Figure 3:
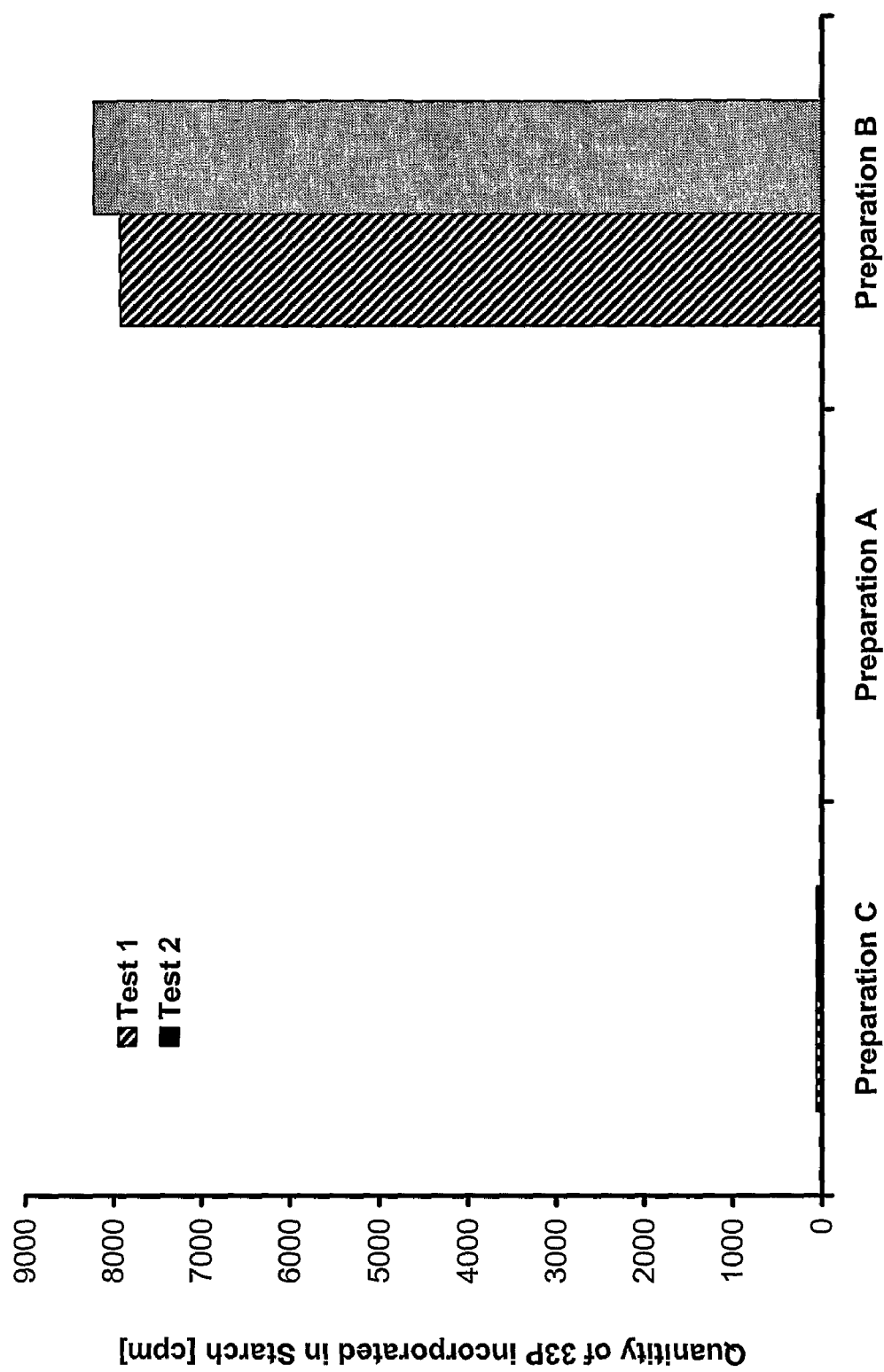
FIG. 3: Demonstration of the starch-phosphorylating activity of an OK1 protein (see Example 6). OK1 protein was incubated with non-phosphorylating starch isolated from leaves of an *Arabidopsis thaliana* sex1-3 mutant (Preparation A) and starch isolated from leaves of an *Arabidopsis thaliana* sex1-3 mutant, which was phosphorylated retrospectively in vitro with an R1 protein (Preparation B). Preparation C is the same as Preparation B, except that this Preparation C was incubated without OK1 protein. Two independent tests were carried out for each preparation (A, B, C) (Test 1 and Test 2). The respective amounts are shown graphically, measured in cpm (counts per minute), on $^{33}$P labeled phosphate, which was introduced into non-phosphorylated starch (Preparation A) and phosphorylated starch (Preparation B) from the OK1 protein.
Figure 4:
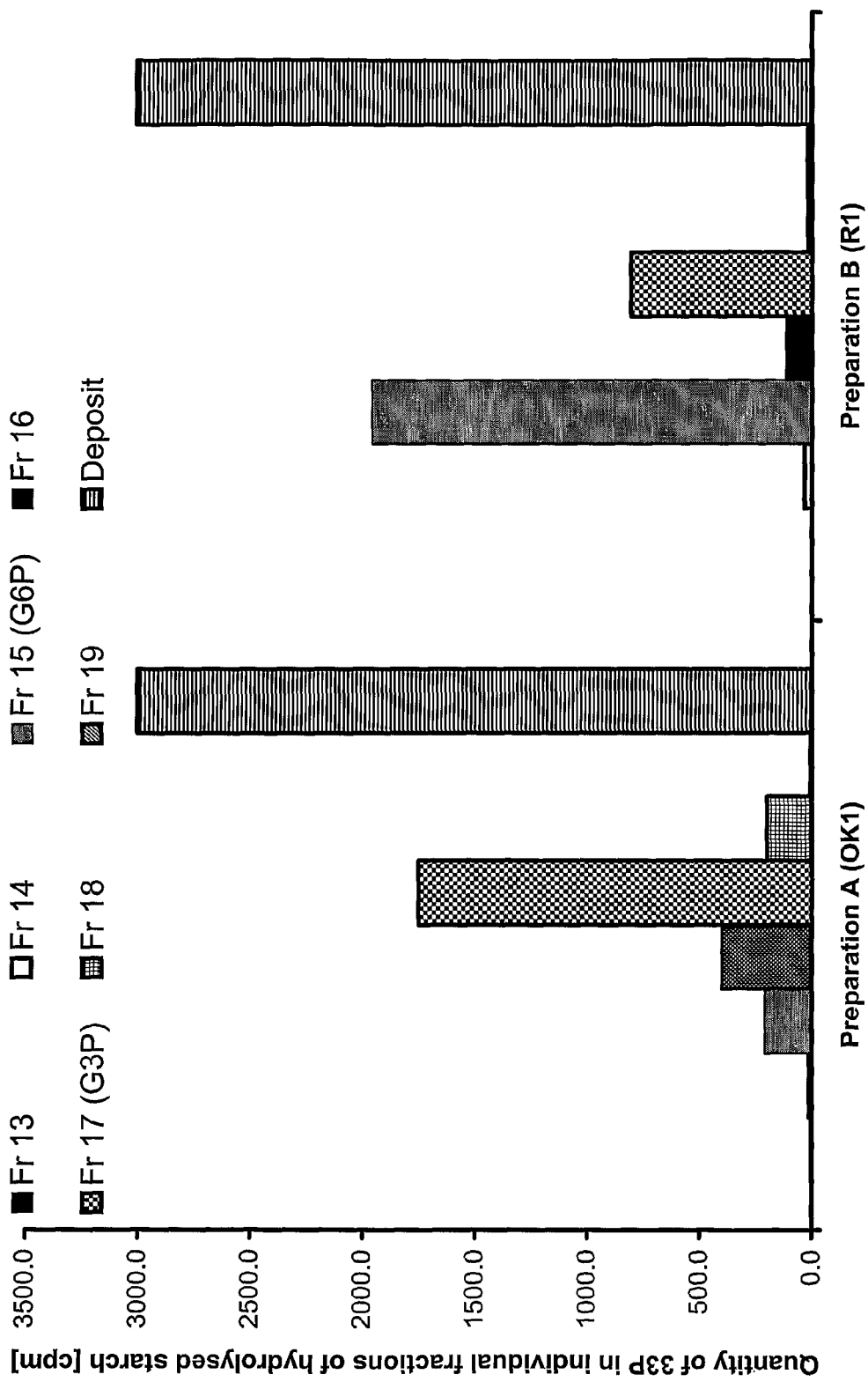
FIG. 4: Comparison of the C-atom positions of glucose molecules of the starch, which was phosphorylated from an R1 protein and an OK1 protein respectively (see Example 9). OK1 protein (Preparation A) was incubated in the presence of ATP labeled with $^{33}$P with starch isolated from leaves of an *Arabidopsis thaliana* sex1-3 mutant, which was phosphorylated retrospectively in vitro with an R1 protein.). R1 protein (Preparation B) was incubated in the presence of ATP labeled with $^{33}$P with starch isolated from leaves of an *Arabidopsis thaliana* sex1-3 mutant. On completion of incubation, a total hydrolysis of the starch was carried out and the obtained hydrolysis products were separated by means of HPAE chromatography. As standard, glucose-6-phosphate and glucose-3-phosphate were added to the hydrolysis products before separation. The hydrolysis products separated by means of HPAE chromatography were collected in individual fractions. The added glucose-6-phosphate eluted with fraction 15 and the added glucose-3-phosphate with fraction 17. The fractions obtained were subsequently investigated for the presence of radioactively labeled phosphate. The amount of $^{33}$P labeled phosphate measured in the individual fractions, measured in cpm (counts per minute), which was introduced into the hydrolysis products of the phosphorylated starch by the OK1 protein or the R1 protein, is shown graphically.

Using a scintillation counter, the starches from Preparations A, B, and C were investigated for the presence of radioactively labeled phosphate (see Item 11 b), General Methods). The results are shown in Table I and in FIG. 3.

TABLE 1

Demonstration of starch-phosphorylating activity of the Ok1 protein

| | Measured radio-activity [cpm] | |
|---|---|---|
| | Test 1 | Test 2 |
| Preparation A (non-phosphorylated starch + OK1) | 42 | 47 |
| Preparation B (phosphorylated starch + OKI) | 7921 | 8226 |
| Preparation C (phosphorylated starch without protein) | 56 | 53 |

Figure 6:
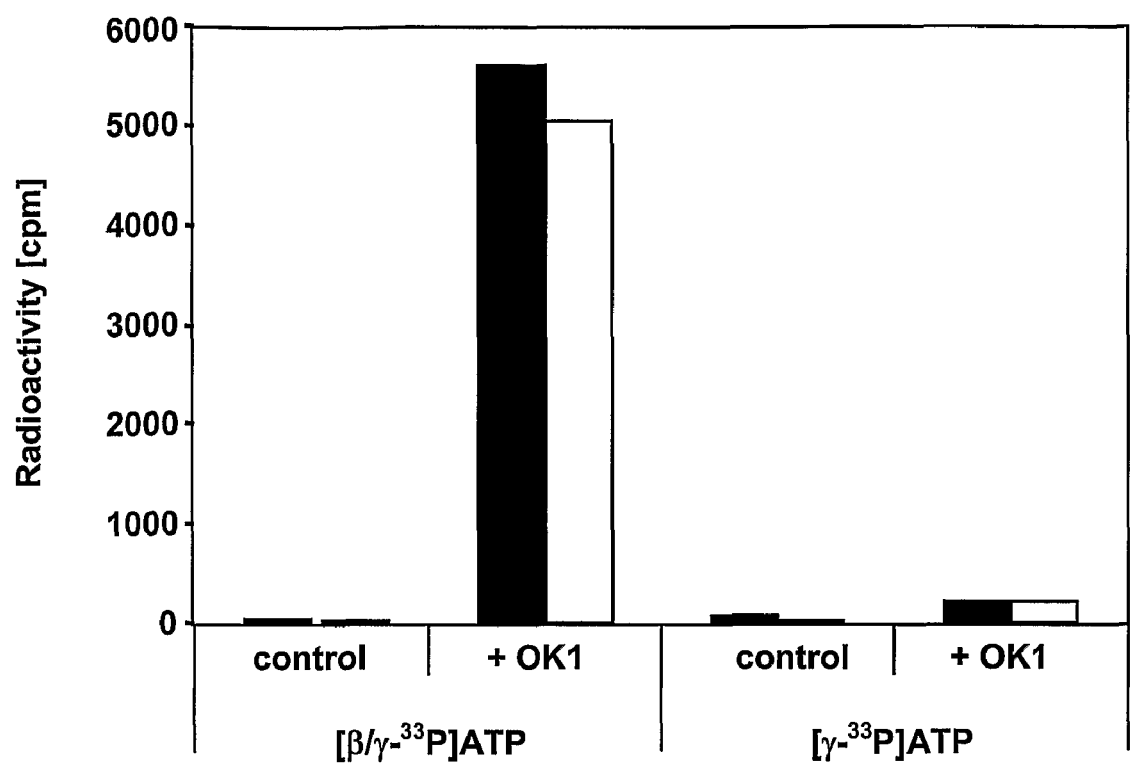
FIG. 6 Demonstration of the transfer of the beta-phosphate residue of ATP to starch in a reaction catalysed by an OK1 protein. Either ATP specifically labeled with $^{33}$P in the gamma position or randomised $^{33}$P ATP was used to phosphorylate starch, which had been phosphorylated in vitro by means of an R1 protein and isolated from leaves of an *Arabidopsis thaliana* sex1-3 mutant, by means of an OK1 protein. No OK1 protein was added in any of the experiments designated as "control". Each test preparation was tested twice, independently from one another. The results of both tests are shown.

From the results obtained, it can be seen that the OK1 protein does not transfer phosphate groups from ATP to starch when non-phosphorylated starch is provided as a substrate, as the quota of phosphate groups transferred to non-phosphorylated starch by means of an OK1 protein, measured in cpm, does not exceed the quota of radioactively labeled phosphate groups in Preparation C (control). If, on the other hand, P-starch is provided as a substrate, the quota of radioactive phosphate groups, measured in cpm, which are transferred from ATP to P-starch, is significantly higher. From this, it can be seen that the OK1 protein requires P-starch as a substrate and that non-phosphorylated starch is not accepted as a substrate by the OK1 protein. If the test described above is carried out with ATP specifically labeled in the gamma position with $^{33}P$, then it is not possible to establish an incorporation of radioactively labeled phosphate in the starch. From this, it can be seen that the beta phosphate residue of ATP is transferred from an OK1 protein to starch. The results of such a test are shown in FIG. 6.

7. Demonstration of Autophosphorylation

Autophosphorylation of the A.t.-OK1 protein was demonstrated by means of the methods described above (see Item 12, General Methods). Here, 50 µg of purified A.t.-OK1 protein were incubated with radioactively labeled, randomised ATP in 220 µl of phosphorylation buffer (see above, Item 12 d), General Methods) at room temperature for 60 minutes under agitation. Subsequently, 100 µl in each case were removed from the incubation preparations and transferred to four fresh reaction vessels. In reaction vessel 1, the reaction was stopped by the addition of 40 µl 0.11M EDTA. Reaction vessel 2 was incubated at 95° C. for 5 minutes. HCl was added to reaction vessel 3 up to a final concentration of 0.5 M, and NaOH was added to reaction vessel 4 up to a final concentration of 0.5 M. Reaction vessels 3 and 4 were each incubated for 25 minutes at 30° C. Subsequently, 50 µl in each case were removed from reaction vessels 1, 2, 3 and 4, mixed with SDS test buffer and separated by means of SDS acrylamide gel electrophoresis (7.5% acrylamide gel). For this purpose, samples from the reaction vessels were applied to each of two identical acrylamide gels. One of the gels obtained on completion of electrophoresis was subjected to autoradiography, while the second gel was stained with Coomassie Blue.

Figure 2:
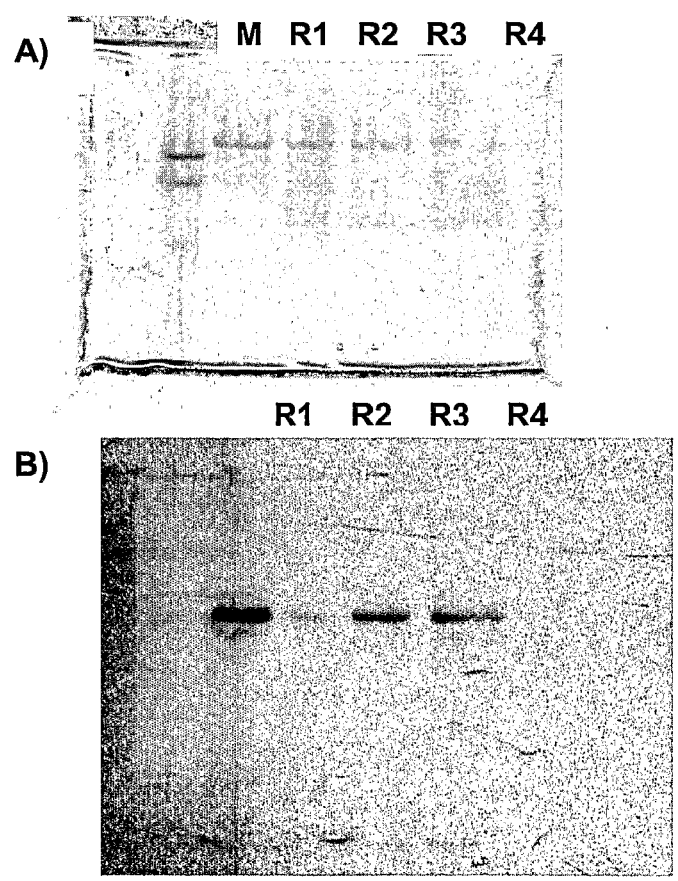
FIG. 2: Demonstration of the autophosphorylation of the OK1 protein.

In the gel stained with Coomassie Blue (see FIG. 2A)), it can be clearly seen that treatment with 0.5 M NaOH leads to a degradation of OK1 protein. The OK1 protein must therefore be described as unstable compared with NaOH. Incubations at 30° C., 95° C. and with 0.5 M HCl show that the OK1 protein is relatively stable under the stated incubation conditions. This can be concluded from the fact that, under these incubation conditions, in each case approximately the same amounts of OK1 protein can be demonstrated in the gel concerned after colouring with Coomassie Blue. In the autoradiography (see FIG. 2B)), it can be seen by comparison with the phosphorylated OK1 protein incubated at 30° C. that an incubation of the phosphorylated OK1 protein at 95° C. leads to a significant reduction in the phosphate, which has bonded to the OK1 protein. The bond between the phosphate residue and an amino acid of the OK1 protein must therefore be described as heat-unstable.

Furthermore, a slight reduction of the phosphate bonded to the OK1 protein can also be seen for the incubation with 0.5 M HCl and 0.5 M NaOH in comparison with phosphorylated OK1 protein incubated at 30° C. If the fact is taken into account that the quantity of OK1 protein in the autoradiography after treatment with 0.5 M NaOH is significantly less than in the samples treated with heat and acid on account of the instability of the OK1 protein compared with NaOH, then it can be concluded that the bond between the phosphate residue and an amino acid of the OK1 protein will be relatively stable with respect to bases. As the sample treated with acid contains approximately the same amounts of protein as the sample incubated at 30° C. and at 95° C., and yet has a significantly lower signal in the autoradiography than the sample treated at 30° C., it must be assumed that acid incubation conditions also split the bond between a phosphate residue and an amino acid of the OK1 protein to a certain extent. An instability in the bond between a phosphate residue and an amino acid of the OK1 protein could therefore also be established in the tests carried out. At the same time, the instability with respect to acids is significantly less labeled than the instability with respect to heat.

Bonds between the amino acids histidine and phosphate are heat-unstable, acid-unstable but base-stable (Rosenberg, 1996, Protein Analysis and Purification, Birkhäuser, Boston, 242-244). The results described above are therefore an indication that a phosphohistidine is produced by the autophosphorylation of an OK1 protein.

Figure 5:
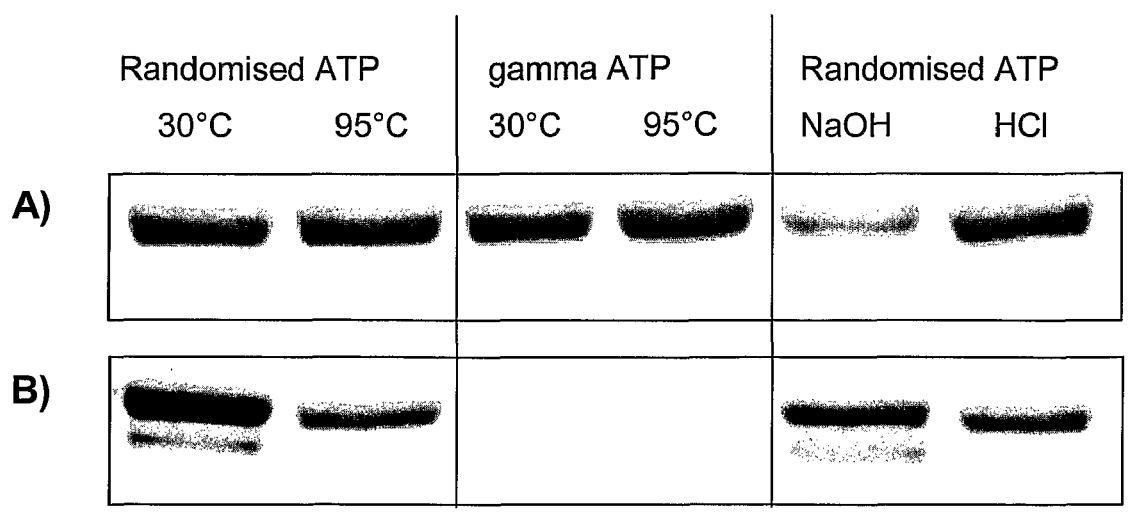
FIG. 5 Demonstration of the autophosphorylation of the OK1 protein.

If recombinantly expressed OK1 protein, as described above, is incubated with ATP specifically labeled with $^{33}P$ in the gamma position, then no autophosphorylation can be detected. FIG. 5 A) shows the amount of protein in the respective reaction preparation that can still be demonstrated by means of Western blot analysis after the appropriate incubation steps. FIG. 5 B) shows an autoradiography of protein from the individual reaction preparations. It can be seen that, when ATP specifically labeled in the gamma position is used, no autophosphorylation of the OK1 protein takes place, whereas, when randomised ATP is used, autophosphorylation can be demonstrated. This means that when an OK1 protein is autophosphorylated, the phosphate residue of the beta position of the ATP is covalently bound to an amino acid of the OK1 protein.

8. Demonstration of the C-Atom Positions, which are Phosphorylated by an OK1 Protein, of the Glucose Molecules of Starch a) Manufacture of Phosphorylated Starch Phosphorylated starch was manufactured in accordance with Item 7, General Methods. To do this, 5 mg of non-phosphorylated starch, isolated from leaves of a sex1-3 mutant of *Arabidopsis thaliana* were used in a Preparation A with 25 µg of purified A.t.-OK1 protein and, in a second Preparation B, 5 mg of in vitro phosphorylated starch originally isolated from leaves of a sex1-3 mutant of *Arabidopsis thaliana* were used with 5 µg of purified R1 protein. The reaction was carried out in 500 µl of phosphorylation buffer in each case, which, in each case contained $^{33}P$ labeled ATP (ca. 2.5×10$^6$ cpm), by incubating at room temperature for 1 hour under agitation. In addition, a control preparation was used, which contained 5 mg of starch isolated from leaves of a sex1-3 mutant of *Arabidopsis thaliana* and the said phosphorylation buffer, but no protein. The control preparation was treated in exactly the same way as Preparations A and B. The individual reactions were stopped by adding 125 µl 10% SDS in each case and washed with 900 µl in each case, once with 2% SDS, five times with 2 mM ATP and twice with $H_2O$. A centrifugation was carried out after each washing step (2 minutes in an Eppendorf table centrifuge at 13,000 rpm in each case). The starch pellets obtained were resuspended 1 ml $H_2O$ in each case and 100 µl of each preparation were mixed after the addition of 3 ml of scintillation cocktail (Ready Safe™, BECKMANN) and subsequently measured with the help of a scintillation counter (LS 6500 Multi-Purpose Scintillation Counter, BECKMANN COULTER™).

The measurement gave the following results:

| | | |
|---|---|---|
| Control: | 63 cpm/100 µL | 630 cpm/1000 µL |
| Preparation A (OK1): | 1351 cpm/100 µL | 13512 cpm/1000 µL |
| Preparation B (R1): | 3853 cpm/100 µL | 38526 cpm/1000 µL | b) Total Hydrolysis of the P-Starch

The suspensions of Preparations A, B and C obtained in accordance with Step a) were centrifuged again (5 minutes in an Eppendorf table centrifuge at 13,000 rpm), the pellets obtained resuspended in 90 µl 0.7 M HCl (Baker, for analysis) and subsequently incubated for 2 hours at 95° C. Preparations A, B and C were then centrifuged again (5 minutes in an Eppendorf table centrifuge at 13,000 rpm), and the supernatant transferred to a new reaction vessel. Sedimented residues of the preparations were resuspended in 100 ml $H_2O$ in each case and after the addition of 3 ml of scintillation cocktail (Ready Safe™, BECKMANN) were measured with the help of a scintillation counter (LS 6500 Multi-Purpose Scintillation Counter, BECKMANN COULTER™). Significant amounts of radioactivity could not be demonstrated in any of the residues, which means that all the hydrolysis products labeled with radioactive phosphate were located in the supernatant.

This was followed by neutralisation of the individual supernatants containing the hydrolysis products by the addition in each case of 30 µl 2 M NaOH (the amount of NaOH required for neutralisation was tested out in advance on blind samples). The neutralised hydrolysis products were placed on a 10 kDa Microcon filter, which had previously been rinsed twice with 200 µl H2O in each case, and centrifuged for ca. 25 minutes at 12,000 rpm in an Eppendorf table centrifuge. Ten µl were taken from the filtrate obtained (ca. 120 µl in each case) and, after the addition of 3 ml of scintillation cocktail (Ready Safe™, BECKMANN), were measured with the help of a scintillation counter (LS 6500 Multi-Purpose Scintillation Counter, BECKMANN COULTER™). The determination of the activity present in the individual preparations gave the following results:

| | | | |
|---|---|---|---|
| Preparation A (OK1): | 934 cpm/10 µL | 11.208 cpm/120 µL | 93 cpm/µl |
| Preparation B (R1): | 2518 cpm/10 µL | 30.216 cpm/120 µL | 252 cpm/µl | c) Separation of the Hydrolysis Products

The hydrolysis products obtained in accordance with Step b) were separated by means of HPAE using a Dionex system under the conditions stated above (see General Methods, Item 13 c)). The samples for separating the filtered supernatants of Preparations A and B obtained in accordance with Step b) were composed as follows:

Preparation A (OK1): 43 µl of the supernatant of Preparation A obtained in accordance with Step b) (equivalent to ca. 4,000 cpm), 32 µl $H_2O$, 2.5 µl 2.5 mM glucose-6-phosphate and 2.5 µl 5 mM glucose-3-phosphate (Volume=80 µl).

Preparation B (R1): 16 µl of the supernatant of Preparation B obtained in accordance with Step b) (equivalent to ca. 4,000 cpm), 59 µl $H_2O$, 2.5 µl 2.5 mM glucose-6-phosphate and 2.5 µl 5 mM glucose-3-phosphate (Volume=80 µl).

In each case, 60 µl, containing ca. 3,000 cpm, of the appropriate samples were injected for separation by means of HPAE. The HPAE was carried out in accordance with the conditions specified underGeneral Methods Item 13 c). After passing through the HPAE column, the elution buffer was collected in fractions, each of 1 ml. Collection of the fractions was begun 10 minutes after injecting the sample. Based on the signal received from the PAD detector used, the elution of glucose-6-phosphate was assigned to fraction 15 and the elution of glucose-3-phosphate to fraction 17. In each case, 500 µl of the individual fractions were mixed with 3 ml of scintillation cocktail (Ready Safe™, BECKMANN) and subsequently measured with the help of a scintillation counter (LS 6500 Multi-Purpose Scintillation Counter, BECKMANN COULTER™). The following measurements were obtained for the individual fractions:

TABLE 4

Measured amounts of radioactivity [cpm] in individual fractions of hydrolysis products obtained by hydrolysis of starch phosphorylated by means of an OK1 protein or R1 protein.

| | Total cpm per fraction | |
|---|---|---|
| | Preparation A (OK1): | Preparation B (R1): |
| Fr 13 | 8.7 | 3.3 |
| Fr 14 | 13.1 | 32.2 |
| Fr 15 (G6P) | 207.3 | 1952.8 |
| Fr 16 | 399.8 | 112.3 |
| Fr 17 (G3P) | 1749.2 | 801.6 |
| Fr 18 | 196.7 | 17.3 |
| Fr 19 | 6.7 | 18.9 |
| Total | 2581.5 | 2938.3 |
| Deposit | 3000.0 | 3000.0 |
| Recovery | 86.0% | 97.9% |

The results are also shown graphically in FIG. 5.

After phosphorylation of starch catalysed by R1 protein, ca. 66% of the radioactively labeled phosphate, in terms of the total measured radioactive phosphate in the analysed fractions, eluted after hydrolysing the starch with the fraction, which contained glucose-6-phosphate as a standard, and ca. 27% with the fraction, which contained glucose-3-phosphate as a standard. After phosphorylation of starch catalysed by OK1 protein, ca. 67% of the radioactively labeled phosphate, in terms of the total measured radioactive phosphate in the analysed fractions, eluted after hydrolysing the starch with the fraction, which contained glucose-6-Phosphate as a standard, and ca. 8% with the fraction, which contained glucose-3-Phosphate as a standard. From this, it can be concluded that glucose molecules are preferably phosphorylated in the C-6 position by R1 proteins, whereas glucose molecules are preferably phosphorylated in the C-3 position by OK1 proteins.

9. Increase of the Phosphorylation Rate in Simultaneous Catalysis of the Phosphorylation Reaction by R1 Proteins and Ok1 Proteins a) In Vitro Phosphorylation of Wheat Starch 35 mg of wheat starch (Sigma, prod. no.: S-5127) per ml of reaction preparation were phosphorylated in vitro in accordance with the method described under Item 7, General Methods. Purified R1 protein in a concentration of 0.23 µg per mg of starch and ATP in a concentration of 25 µM was used for this purpose. The reaction time amounted to 1 hour at room temperature. In a parallel reaction preparation that contained randomised $^{33}$P-ATP instead of ATP, the amount of the incorporated phosphate into the starch (0.0054 nmol per mg of starch) and the specific activity of the R1 protein used (0.41 nmol per (mg protein×minute) was determined. That the randomised ATP was used was not considered for this determination. The obtained values are thus lower that the actual existing values, because randomised ATP also contains phosphate residues labeled in the gamma position as well as phosphate residues labeled in the beta position.

b) Phosphorylation of Native Wheat Starch and In Vitro Phosphorylated Wheat Starch by R1 and/or OK1 Proteins 15 mg of wheat starch (Sigma, prod. no.: S-5127, or wheat starch phosphorylated in vitro in accordance with the method described under a)) was incubated with purified starch phosphorylated enzymes in 430 µl of the buffer containing 11 nmol of randomised $^{33}$P-ATP (ca. 1.5×10$^6$ cpm) described under Item 11, General Methods, for one hour under agitation at room temperature. The individual reaction preparations contained the following protein and substrates:

|                | Protein | Substrate |
|---|---|---|
| Preparation 1-1 | Purified R1 protein (3.4 µg) | Wheat starch (Sigma) |
| Preparation 1-2 | Purified R1 protein (3.4 µg) | Wheat starch (Sigma) |
| Preparation 2 | Purified OK1 protein (6.0 µg) | Wheat starch (Sigma) |
| Preparation 3 | Purified OK1 protein (6.0 µg) | In vitro phosphorylated wheat starch |
| Preparation 4 | Purified R1 protein (3.4 µg) Purified OK1 Protein (6.0 µg) | Wheat starch (Sigma) |
| Control | No protein | Wheat starch (Sigma) |

Each of the preparations was carried out in three repeats in each case. The treatment of the individual reaction preparations after one hour of reaction time and the determination of the incorporated amount of phosphate in the substrate concerned was carried out in accordance with the methods described under General Methods, Item 11.

The following results were obtained:

TABLE 5

Measured quantity of radioactivity [cpm] in the individual repeats of the individual reaction preparations. The specified measurement values were determined by subtracting the measurement values of the associated controls from the actual measurement values in each case.

|  | Repeat 1 [cpm] | Repeat 2 [cpm] | Repeat 3 [cpm] |
|---|---|---|---|
| Preparation 1-1 | 11722 | 11584 | 11428 |
| Preparation 1-2 | 12900 | 12204 | 11401 |
| Preparation 2 | −28 | −21 | −30 |
| Preparation 3 | 2448 | 2281 | 2334 |
| Preparation 4 | 17333 | 20337 | 16546 |
| Total of Preparation 1-2 and Preparation 3 | 15348 | 14485 | 13735 |

From the table it is clear that native wheat starch (Sigma, proc. No.: S-5127) forms no substrate for OK1 protein, whereas in vitro phosphorylated wheat starch can be phosphorylated from OK1 proteins. Furthermore, it can be seen that the activity is significantly higher than the total of the corresponding individual activities when an R1 protein and an OK1 protein are present simultaneously in the reaction mixture.

c) Phosphorylation of In Vitro Phosphorylated Wheat Starch by R1 and/or OK1 Proteins Phosphorylated wheat starch was manufactured in accordance with the method described under a). The amount of phosphate bound to starch amounted to 0.0048 mg of phosphate per mg of starch. That the randomised ATP was used was not considered for this determination, as also described under a).

15 mg of in vitro phosphorylated wheat starch was incubated with starch phosphorylating enzymes in accordance with the methods described under b). The individual reaction preparations contained the following protein and substrates:

|  | Protein | Substrate |
|---|---|---|
| Preparation 1: R1 | Purified R1 protein (3.4 µg) | In vitro phosphorylated wheat starch |
| Preparation 2: OK1 | Purified OK1 protein (5.2 µg) | In vitro phosphorylated wheat starch |
| Preparation 3: R1 + OK1 | Purified R1 protein (3.4 µg) Purified OK1 Protein (5.2 µg) | In vitro phosphorylated wheat starch |

Each of the preparations was carried out in two repeats in each case.

A sample was stopped after 0, 10 and 30 minutes of incubation time for each reaction preparation, and the amount of phosphate incorporated under the respective reaction conditions was determined in accordance with the method described under General methods, Item 11.

As a control, native wheat starch was incubated with R1 protein in the presence of ATP not radioactively labeled. Subsequently, the reaction mixture was added to randomised $^{33}$P-ATP and buffer before the reaction was stopped.

The following results were obtained:

TABLE 6

Measured quantity of radioactivity [cpm] in the individual repeats of the individual reaction preparations. The specified measurement values were determined by subtracting the measurement values of the associated controls from the average value of two independent measurements.

|  | 0 minutes reaction time | 10 minutes reaction time | 30 minutes reaction time |
|---|---|---|---|
| Preparation 1 | 0 cpm | 2378 cpm | 7543 cpm |
| Preparation 2 | 0 cpm | 2032 cpm | 3005 cpm |
| Preparation 3 | 0 cpm | 7570 cpm | 16245 cpm |
| Total of Preparation 1 and Preparation 2 | 0 cpm | 4410 cpm | 10548 cpm |

10. Identification of an OK1 Protein in Rice

Using the methods described under Items 1 to 13, General Methods, it was also possible to identify a protein from *Oryza sativa* (variety M202), which transfers a phosphate residue from ATP to P-starch. The protein was designated as O.s.-OK1. Non-phosphorylated starch is not used by the O.s.-OK1 protein as a substrate, i.e. the O.s.-OK1 protein also does not need P-starch as a substrate. The nucleic acid sequence defining the identified O.s.-OK1 protein is shown under SEQ ID NO 3 and the amino acid sequence coding the O.s.-OK1 protein is shown under SEQ ID NO. 4. The amino acid sequence coding the O.s.-OK1 protein shown under SEQ ID NO 4 has an identity of 57% with the amino acid sequence coding the A.t.-OK1 protein shown under SEQ ID NO 2. The nucleic acid sequence coding the O.s.-OK1 protein shown under SEQ ID NO 3 has an identity of 61% with the nucleic acid sequence coding the A.t.-OK1 protein shown under SEQ ID NO 1.

Manufacture of the plasmid pMI50 containing the nucleic acid sequence coding an OK1 protein from Oryza sativa The vector pMI50 contains a DNA fragment, which codes the complete OK1 protein from rice of the variety M202.

The amplification of the DNA from rice was carried out in five sub-steps.

1. The part of the open reading frame from position 11 to position 288 of the sequence specified under SEQ ID NO 3 was amplified with the help of reverse transcriptase and polymerase chain reaction using the synthetic oligonucleotides Os_ok1-R9 (GGAACCGATAATGCCTACATGCTC) (SEQ ID NO: 21) and Os_ok1-F6 (AAAACTCGAGGAGGAT- CAATGACGTCGCTGCGGCCCCTC) (SEQ ID NO: 22) as a primer on RNA of immature rice seeds. The amplified DNA fragment was cloned in the vector pCR2.1 (Invitrogen catalogue number K2020-20). The obtained plasmid was designated as pML123.

2. The part of the open reading frame from position 250 to position 949 of the sequence specified under SEQ ID NO 3 was amplified with the help of reverse transcriptase and polymerase chain reaction using the synthetic oligonucleotides Os_ok1-F4 (CCAGGTTAAGTTTGGTGAGCA) (SEQ ID NO: 23) and Os_ok1-R6 (CAAAGCACGATATCTGAC- CTGT) (SEQ ID NO: 24) as a primer on RNA of immature rice seeds. The amplified DNA fragment was cloned in the vector pCR2.1 (Invitrogen catalogue number K2020-20). The obtained plasmid was designated as pML120.

3. The part of the open reading frame from position 839 to position 1761 of the sequence specified under SEQ ID NO 3 was amplified with the help of reverse transcriptase and polymerase chain reaction using the synthetic oligonucleotides Os_ok1-F7 (TTGTTCGCGGGATATTGTCAGA) (SEQ ID NO: 25) and Os_ok1-R7 (GACAAGGGCATCAAGAG- TAGTATC) (SEQ ID NO: 26) as a primer on RNA of immature rice seeds. The amplified DNA fragment was cloned in the vector pCR2.1 (Invitrogen catalogue number K2020-20). The obtained plasmid was designated as pML121.

4. The part of the open reading frame from position 1571 to position 3241 of the sequence specified under SEQ ID NO 3 was amplified with the help of reverse transcriptase and polymerase chain reaction using the synthetic oligonucleotides Os_ok1-F8 (ATGATGCGCCTGATAATGCT) (SEQ ID NO: 27) and Os_ok1-R4 (GGCAAACAGTATGAAGCACGA) (SEQ ID NO: 28) as a primer on RNA of immature rice seeds. The amplified DNA fragment was cloned in the vector pCR2.1 (Invitrogen catalogue number K2020-20). The obtained plasmid was designated as pML119.

5. The part of the open reading frame from position 2777 to position 3621 was amplified with the help of polymerase chain reaction using the synthetic oligonucleotides Os_ok1- F3 (CATTTGGATCAATGGAGGATG) (SEQ ID NO: 29) and Os_ok1-R2 (CTATGGCTGTGGCCTGCTTTGCA) (SEQ ID NO: 30) as a primer on genomic DNA of rice. The amplified DNA fragment was cloned in the vector pCR2.1 (Invitrogen catalogue number K2020-20). The obtained plasmid was designated as pML122.

The cloning together of the sub-parts of the open reading frame of OK1 was carried out as follows.

A 700 base pair long ApaI fragment of pML120, containing part of the open reading frame of OK1, was cloned in the ApaI site of pML121. The obtained plasmid was designated as pMI47.

A 960 base pair long fragment containing the areas of vectors from pML120 and pML123 coding for OK1 was amplified by means of polymerase chain reaction. In doing so, the primers Os-ok1-F4 (see above) and Os-ok1-R9 (see above), each in a concentration of 50 nm, and the primers Os-ok1-F6 and Os-ok1-R6, each in a concentration of 500 nm, were used. The amplified DNA fragment was cloned in the vector pCR2.1 (Invitrogen catalogue number K2020-20). The obtained plasmid was designated as pMI44.

An 845 base pair long fragment of pML122 was reamplified for introducing an XhoI site after the stop codon with the primers Os_ok1-F3 (see above) and Os_ok1-R2Xho (AAAACTCGAGCTATGGCTGTGGCCTGCTTTGCA) (SEQ ID NO: 31) and cloned in the vector pCR2.1 (Invitrogen catalogue number K2020-20). The obtained plasmid was designated as t pMI45.

A 1671 base pair long fragment containing part of the open reading frame of OK1 was obtained from pML119 by digesting with the restriction enzymes SpeI and PstI. The fragment was cloned in pBluescript II SK+ (Genbank Acc.: X52328). The obtained plasmid was designated as pMI46.

A 1706 base pair long fragment containing part of the open reading frame of OK1 was excised with the restriction enzymes SpeI and XhoI from pMI46 and cloned in the vector pMI45, which had been excised with the same restriction enzymes. The obtained plasmid was designated as pMI47.

A 146 base pair long fragment containing part of the open reading frame of OK1 was excised with the restriction enzymes AflII/NotI from pMI43 and cloned in the vector pMI44, which had been excised with the same restriction enzymes. The obtained plasmid was designated as pMI49.

A 1657 base pair long fragment containing part of the open reading frame of OK1 was excised with the restriction enzymes NotI and NarI from the vector pMI49 and cloned in the vector pMI47, which had been excised with the same restriction enzymes. The plasmid obtained was designated as pMI50 and contains the whole coding region of the OK1 protein identified in rice.

11. Manufacture of an Antibody, which Specifically Detects an OK1 Protein

As an antigen, ca. 100 µg of purified A.t.-OK1 protein was separated by means of SDS gel electrophoresis, the protein bands containing the A.t.-OK1 protein excised and sent to the company EUROGENTEC S.A. (Belgium), which carried out the manufacture of the antibody under contract. Next, the preimmune serums of rabbits were investigated to see whether they would already detect a protein from an A. t. total extract before immunisation with recombinant OK1. The preimmune serums of two rabbits detected no proteins in the range 100-150 kDa and were thus chosen for immunisation. 4 injections of 100 µg of protein (day 0, 14, 28, 56) were given to each rabbit. 4 blood samples were taken from each rabbit: (day 38, day 66, day 87 and the final bleeding). Serum obtained after the first bleeding already showed a specific reaction with OK1 antigen in Western blot. However, in all further tests, the last bleeding of a rabbit was used.

12. Manufacture of Transgenic Maize Plants that Have an Increased Activity of an OK1 Protein and an R1 Protein a) Manufacture of a Construct for the Transformation of Maize Plants that Overexpress an R1 Protein The plasmid pMZ12 was used as a starting plasmid for the manufacture of a plasmid, which was used for the transformation of maize plants. This plasmid contains the ColE1 origin of the plasmid pBR322) Bolivar et al, 1977, Gene 2, 95-113) and a bacterial selection marker that facilitates a resistance against the antibiotic gentamycin (Wohileben et al., 1989 MGG 217, 202-208). Furthermore, this plasmid contains a right and a left T-DNA border sequence. Between these T-DNA border sequences the plasmid contains a bar gene from *Streptomyces hygroscopicus* (White et al., 1990, NAR 18, 1062; EMBL Acc.: X17220), which facilitates resistance against the herbicide glufosinate. The expression of the bar gene is initiated through the promoter of the actin gene from rice (McElroy et al., 1990, Plant Cell 2, 163.171). To stabilise the expression of the bar gene, the 1 st intron of the actin gene from rice is inserted between the actin promoter and the sequence coding the bar protein (McElroy et al., 1990, Plant Cell 2, 163.171). The polyadenylation signal of the nopaline synthase gene from *Agrobacterium tumefaciens* follows after the sequence coding the bar protein (Depicker et al., 1982 J Mol. Appl. Gent. 1, 561-573). The ubiquitin promoter from *Zea mays* was inserted into the plasmid pMZ12 between the left and right T-DNA border sequence (Christensen et al., 1992, Plant Mol. Bio 18, 675-689), followed by the 1 st intron of the ubiquitin gene from *Zea mays* (Christensen et al., 1992, Plant Mol. Bio 18, 675-689), followed by the coding sequence of the R1 gene from *Solanum tuberosum* (see SEQ ID NO 10), followed by the polyadenylation signal of the nopaline synthase gene from *Agrobacterium tumefaciens* (Depicker et al., 1982, J. Mol. Appl. Gent. 1, 561-573). The obtained plasmid was designated as pHN3-146.

b) Transformation of Maize Plants with the Plasmid pHN3-146

Premature embryos of maize plants were isolated ten days after pollination and transformed with the help of *Agrobacterium tumefaciens* containing the plasmid pHN3-146 as a cointegrate in accordance with the methods described by Ishida et al. (1996, Nature Biotechnology 14, 745-750). So-called T0 plants resulting from this transformation were raised in the greenhouse.

c) Identification of Maize Plants that Have an Increased Expression of the S.t.-R1 Protein from *Solanum Tuberosum*

By means of quantitative RT PCR analysis, it was possible to identify plants, which had an expression of mRNA coding the S.t.-1 protein.

d) Manufacture of the Plasmid pUbi-A.t.-OK1

First, the plasmid pIR96 was manufactured. The plasmid pIR96 was obtained by cloning a synthetic piece of DNA consisting of the two oligonucleotides X1 (TGCAGGCTG-CAGAGCTCCTAGGCTCGAGTTAACAC-TAGTAAGCTTAATTAAG ATATCATTTAC) (SEQ ID NO: 32) and X2 (AATTGTAAATGATATCTTAATTAAGCT-TACTAGTGTTAACTCGAGCCTAGGA GCTCTGCAGC-CTGCA) (SEQ ID NO: 33) in the vector pGSV71 excised with SdaI and MunI. The plasmid obtained was excised with SdaI, and the protruding 3'-ends were smoothed with T4 DNA polymerase. The plasmid obtained was excised with SdaI, the protruding 3'-ends smoothed with T4 DNA polymerase and a smoothed HindIII/SphI fragment from pBinAR (Hofgen and Willmitzer, 1990, Plant Science 66, 221-230) with a size of 197 base pairs, containing the termination signal of the octopine synthase gene from *Agrobacterium tumefaciens*, was inserted. The obtained plasmid was designated as pIR96.

pGSV71 is a derivative of the plasmid pGSV7, which derives from the intermediate vector pGSV1. pGSV1 constitutes a derivative of pGSC1700, the construction of which has been described by Cornelissen and Vanderwiele (Nucleic Acid Research 17, (1989), 19-25). pGSV1 was obtained from pGSC1700 by deletion of the carbenicillin resistance gene and deletion of the T-DNA sequences of the TL-DNA region of the plasmid pTiB6S3.

pGSV7 contains the replication origin of the plasmid pBR322 (Bolivar et al., Gene 2, (1977), 95-113) as well as the replication origin of the *Pseudomonas* plasmid pVSI (Itoh et al., Plasmid 11, (1984), 206). pGSV7 also contains the selectable marker gene aadA, from the transposon Tn1331 from *Klebsiella pneumoniae*, which gives resistance against the antibiotics spectinomycin and streptomycin (Tolmasky, Plasmid 244 (3), (1990), 218-226; Tolmasky and Crosa, Plasmid 29(1), (1993), 31-40). The plasmid pGSV71 was obtained by cloning a chimeric bar gene between the border regions of pGSV7. The chimeric bar gene contains the promoter sequence of the cauliflower mosaic virus for initiating the transcription (Odell et al., Nature 313, (1985), 180), the bar gene from *Streptomyces hygroscopicus* (Thompson et al., 1987, EMBO J. 6, 2519-2523) and the 3'-untranslated area of the nopaline synthase gene of the T-DNA of pTiT37 for terminating the transcription and polyadenylation. The bar gene provides tolerance against the herbicide glufosinate ammonium. A 1986 base pair long fragment containing the promoter of the polyubiquitin gene from maize (EMBLK Acc.: 94464, Christensen et al., 1992, Plant Mol. Biol. 18: 675-689) was cloned as a PstI fragment in pBluescript II SK+. The obtained plasmid was designated as pSK-ubq.

The plasmid A.t.-OK1-pGEM was excised with the restriction enzymes Bsp1201, smoothed with T4-DNA-polymerase and excised with SacI. The DNA fragment coding the OK1 protein from *Arabidopsis thaliana* was cloned in the plasmid pSK-ubq, which was excised with SmaI and SacI. The obtained plasmid was designated as pSK-ubq-ok1.

A fragment which contained the ubiquitin promoter from maize and the total open reading frame for the A.t.-OK1 protein from *Arabidopsis thaliana* was isolated from the plasmid pSK-ubq-ok1. To do this, the plasmid was excised with the restriction enzyme Asp7181, the ends refilled with T4 DNA polymerase and excised with SdaI. The fragment with a size of 5799 base pairs that was obtained was cloned in the plasmid pIR96 excised with EcoRV and PstI. The obtained plasmid from this cloning was designated as pUbi-A.t.-OK1.

e) Transformation of Maize Plants with the Plasmid pUbi-A.t.-OK1

Ten days after pollination, immature embryos of maize plants were isolated and transformed with the help of *Agrobacterium tumefaciens* containing the plasmid pUbi-A.t.-OK1 as a cointegrate according to the methods described by Ishida et al. (1996, Nature Biotechnology 14, 745-750). So-called T0 plants resulting from this transformation were raised in the greenhouse.

f) Identification of Maize Plants that Have an Increased Expression of the A.t.-OK1 Protein from *Arabidopsis Thaliana*

By means of quantitative RT PCR analysis, it was possible to identify plants that had an expression of mRNA coding the A.t.-OK1 protein.

g) Production of Homozygotic Plants that Have an Increased Expression of the S.t.-R1 Protein or of the A.t.-OK1 Protein.

For T1 plants that have an expression of the S.t.-1 protein or of the A.t.-OK1 protein, seeds of the individual plants were harvested, and in each case ca. 30 seeds per plant were laid out again and cultivated in the greenhouse. Plants of this T1 generation were sprayed in the three-leaf stage with a solution containing 0.5% Basta®. Only those groups of T1 plants for which ca. 25% of the 30 cultivated plants in each case died off after spraying with the Basta® solution were followed further, because these plants are those for which the integration of the related T-DNA of the plasmid pHN3-146 or pUbi-A.t.-OK1 is present in a locus in the genome. Genomic DNA was isolated from leaf material from the ca. 75% of the plants that survived the spraying with Basta® solution and investigated in each case for the number of copies present in case by means of Invader® technology (Pielberg et al. 2003, Genome Res.; 13, 2171-2177). The T1 plants within a group of offspring of a TO plant that showed a signal approximately twice as strong as the remaining offspring of the same TO plant in an analysis by means of Invader® technology are homozygotic with respect to the locus at which the T-DNA of the related plasmid is integrated. If approximately 30% of the offspring of a TO plant that survived the treatment with Basta® solution show a signal approximately twice as strong in the analysis by means of Invader technology, in comparison with the remaining ca. 70% of the offspring of the same TO plant, then this is a further indication that the integration of the T-DNA is at a single locus.

h) Production of Plants that Have Both an Increased Expression of the S.t.-1 Protein as Well as an Increased Expression of the A.t.-OK1 Protein T1 plants that have an increased expression of an S.t.-1 protein and that are homozygotic with respect to the integration of the T-DNA of the plasmid pHN3-146 according to the analysis described under g), and in which the integration exists at a locus in the genome of the plant, are crossed with T1 plants that have an increased expression of an A.t.-OK1 protein and are homozygotic with respect to the integration of the T-DNA of the plasmid pUbi-A.t.-OK1, and in which the integration exists at a locus in the genome of the plant. The offspring of these crosses have both an increased expression of the S.t.-1 protein as well as an increased expression of the A.t.-OK1 protein.

i) Analysis of the Grains of Transgenic Maize Plants and Starches Synthesised from them Starches were isolated from the grains of the related maize plants resulting from the crosses described under h). The starch from grains that have an increased expression of the S.t.-1 protein and an increased expression of the A.t.-OK1 protein, contains more phosphate covalently bound to the starch, than does starch isolated from untransformed wild type plants.

Starch isolated from grains that have an increased expression of the S.t.-1 protein and an increased expression of the A.t.-OK1 protein, likewise contains more phosphate covalently bound to the starch than does starch isolated from plants that have only an increased expression of the S.t.-1 protein or only an increased expression of the A.t.-OK1 protein.

13. Manufacture of Transgenic Wheat Plants that Have an Increased Expression of an OK1 Protein and an R1 Protein a) Manufacture of Transgenic Wheat Plants that Overexpress an R1 Protein The manufacture of wheat plants, which have an increased expression of the R1 protein from potato, were described in WO 02 34923. The plants described there were partially used as a starting material for the manufacture of plants that have an increased expression of an OK1 protein and an R1 protein.

b) Manufacture of a Plasmid for the Transformation of Wheat Plants that Overexpress an OK1 Protein pMCS5 (Mobitec website) was digested with BglII and BamHI and relegated. The obtained plasmid was designated as pML4. The nos-terminator from *Agrobacterium tumefaciens* (Depicker et al., 1982, Journal of Molecular and Applied Genetics 1: 561-573) was amplified with the primers P9 (ACTTCTgCAgCggCCgCgATCg CAAACATTTg-gCAATAAAgTTTC) and 210 (TCTAAgCTTggCgC-CgCTAgCAgATCTgATCTAgTAACATAgATgACACC) (25 cycles, 30 sec 94° C., 30 sec 58° C., 30 sec 72° C.), digested with HindIII and PstI, and cloned in the plasmid pML4 excised with the same enzyme. The obtained plasmid was designated as pML4-nos. A 1986 base pair long fragment containing the promoter of the polyubiquitin gene from maize (Genbank Acc.: 94464, Christensen et al., 1992, Plant Mol. Biol. 18: 675-689) and the first intron of the same gene shortened by digestion with ClaI and religation was cloned. The obtained plasmid was designated as pML8.

The total open reading frame of the OK1 from *Arabidopsis thaliana* was cloned in the plasmid pML8. For this purpose the corresponding fragment was excised with Bsp120/NotI from A.t.-OK10pGEM and ligated in sense orientation into the NotI site. With the restriction enzymes AvrII and SwaI, a fragment for the transformation of wheat plants can be excised from the obtained vector pML8-A.t.-OK1, which contains the promoter of the polyubiquitin gene from maize, the total open reading frame of OK1 from *Arabidopsis thaliana* and the nos-terminator from *Agrobactetium tumefaciens*.

c) Manufacture of a Plasmid for the Production of Wheat Plants that Overexpress an R1 Protein A plasmid was manufactured in which the DNA fragment, which coded for the complete R1 protein from potato, lies between two detection sites for the restriction enzyme Pad. For this purpose, the Multiple Cloning Site from the plasmid pBluescript II SK+ was amplified with the help of the polymerase chain reaction and both oligonucleotides MCS1-1 (TTTTTGCGCGCGTTAATTAACGACTCAC-TATAGGGCGA) (SEQ ID NO: 36) and MCS1-2 (TTTTTGCGCGCTTAATTAACCCTCAC-TAAAGGGAACAAAAG) (SEQ ID NO: 37), excised with the restriction enzyme BssHII, and cloned in the dephosphorylated vector pBluescript II SK+ (Invitrogen) excised with BssHII. The obtained plasmid was designated as pSK-Pac.

A NotI fragment was cloned in the vector pSK-Pac, which was obtained from the clone pRL2 (WO 9711188). The NotI fragment contains the total open reading frame for the R1 protein from potato. The obtained plasmid was designated as pIR1. A fragment, which contained the ubiquitin promoter and the shortened first intron, and cloned in the EcoRV site of the plasmid, was excised with the restriction enzymes EcoRV and SmaI from pSK-ubq (see above). In the obtained plasmid, a PacI fragment was cloned from pIR1 in sense orientation to the promoter, which contains the total open reading frame coding for the R1 protein from potato. The obtained plasmid was designated as pML82.

d) Transformation of Wheat Plants for Overexpression of an OK1 Protein

Wheat plants of the Florida variety were transformed by means of the biolistic method in accordance with the method described by Becker et al. (1994, Plant Journal 5, 299-307) with a fragment excised from an agarose gel, which was excised with the restriction enzymes AvrII and SwaI from the plasmid pML8-A.t.-OK1 and contained the promoter of the polyubiquitin gene from maize, the total open reading frame of OK1 from *Arabidopsis thaliana* and the nos-terminator from *Agrobacterium tumefaciens* together with the plasmid pGSV71. The obtained plants were designated as TA-OK1.

e) Transformation of Wheat Plants for Overexpression of an R1 Protein

Wheat plants of the Florida variety were transformed with the plasmid pML82 by means of the biolistic method in accordance with the method described by Becker et al. (1994, Plant Journal 5, 299-307). The obtained plants were designated as TA-R1.

f) Cotransformation of Wheat Plants for the Overexpression of an OK1 Protein and an R1 Protein Wheat plants of the Florida variety were transformed by means of the biolistic method in accordance with the method described by Becker et al. (1994, Plant Journal 5, 299-307) with a DNA mixture containing the plasmid pML82 and a fragment purified by means of HPLC, which was excised from the plasmid pML8-A.t.-OK1 with the restriction enzymes AvrII and SwaI, and contains the promoter of the polyubiquitin gene from maize, the total open reading frame of OK1 from *Arabidopsis thaliana* and the nos-terminator from *Agrobacterium tumefaciens*. With the help of RT-PCR, plants were identified that have both an expression of the A.t.-Ok1 protein as well as an expression of the S.t.-1 protein. The obtained plants were designated as TA-R1-OK1.

g) Identification of Transgenic Wheat Plants

T1 plants of the lines TA-R1 and TA-OK1 were cultivated in the greenhouse and sprayed with Basta® (0.5% solution) before blooming. Plants not expressing the Basta® mediated resistance gene died.

h) Manufacture of Wheat Plants that Have an Expression of an S.t.-1 Protein and an Expression of an A.t.-OK1 Protein, by Means of Crossing TA-OK1 plants that survived the treatment with Basta® were crossed either with TA-R1 plants that survived the treatment with Basta®, or with homozygotic plants of the line 40A-11-8 described in WO 02 034923. The obtained offspring were designated as TA-Ok 1×TA-R1 or as TA-OK1× 40A-11-8 respectively.

e) Analysis of the Transgenic Wheat Plants and the Starch Synthesised from them starch was isolated and the content of phosphate covalently bound to the starch was determined for grains resulting from the crossing of lines TA-Ok1 and TA-R1 or TA-OK1 and 40A-11-8 respectively. The phosphate content of starch that was isolated from grains obtained from the crosses TA-Ok1 and TA-R1 or TA-OK1 and 40A-11-8 was significantly higher for some plants than that of starch that was isolated from grains from corresponding wild type plants or from plants of the line 40A-11-8. Grains of the respective plants were harvested for the analysis of the starch from various TA-R1-OK1 lines, and the C-6 phosphate content and the C-3 phosphate content of the isolated starch was analysed. It was possible to identify some plants for which the content of C-6 phosphate plus C-3 phosphate was clearly higher in comparison with the content of C-6 phosphate plus C-3 phosphate from starch isolated from grains of the lines TA-R1 or 40A-11-8.

14. Manufacture of Transgenic Rice Plants that Have an Increased Expression of an OK1 Protein and an R1 Protein a) Manufacture of the Plasmid pGlo-A.t.-OK1

The plasmid pIR94 was obtained by amplifying the promoter of the globulin gene from rice by means of a polymerase chain reaction (30×20 sec 94° C., 20 sec 62° C., 1 min 68° C., 4 mM Mg2SO4) with the primers glb1-F2 (AAAA-CAATTGGCGCCTGGAGGGAGGAGA) (SEQ ID NO: 38) and glb1-R1 (AAAACAATTGATGATCAATCAGACAAT-CACTAGAA) (SEQ ID NO: 39) on the genomic DNA of rice of the variety M202 with High Fidelity Taq Polymerase (Invitrogen, catalogue number 11304-011) and cloned in pCR2.1 (Invitrogen catalogue number K2020-20).

The plasmid pIR115 was obtained by cloning a synthetic piece of DNA consisting of the two oligonucleotides X1 (TGCAGGCTGCAGAGCTCCTAGGCTC-GAGTTAACACTAGTAAGCTTAATTAAG ATATCATT-TAC) (SEQ ID NO: 32) and X2 (AATTGTAAATGATATCT-TAATTAAGCTTACTAGTGTTAACTCGAGCCTAGGA GCTCTGCAGCCTGCA) (SEQ ID NO: 33) in the vector pGSV71 excised with SdaI and MunI.

The plasmid pIR115 obtained was excised with SdaI, the protruding 3'-ends smoothed with T4 DNA polymerase and a HindIII/SphI fragment from pBinAR (Höfgen and Willmitzer, 1990, Plant Science 66, 221-230) with a size of 197 base pairs, smoothed by means of T4 DNA polymerase and containing the termination signal of the octopine synthase gene from *Agrobacterium tumefaciens*, was inserted. The obtained plasmid was designated as pIR96.

The plasmid pIR103 was obtained in which a DNA fragment cloned from pIR94 with a length of 986 base pairs containing the promoter of the globulin gene from rice was cloned in the plasmid pIR96.

pGSV71 is a derivative of the plasmid pGSV7, which derives from the intermediate vector pGSV1. pGSV1 constitutes a derivative of pGSC1700, the construction of which has been described by Cornelissen and Vanderwiele (Nucleic Acid Research 17, (1989), 19-25). pGSV1 was obtained from pGSC1700 by deletion of the carbenicillin resistance gene and deletion of the T-DNA sequences of the TL-DNA region of the plasmid pTiB6S3.

pGSV7 contains the replication origin of the plasmid pBR322 (Bolivar et al., Gene 2, (1977), 95-113) as well as the replication origin of the *Pseudomonas* plasmid pVSI (Itoh et al., Plasmid 11, (1984), 206). pGSV7 also contains the selectable marker gene aadA, from the transposon Tn1331 from *Klebsiella pneumoniae*, which gives resistance against the antibiotics spectinomycin and streptomycin (Tolmasky, Plasmid 24 (3), (1990), 218-226; Tolmasky and Crosa, Plasmid 29(1), (1993), 31-40). The plasmid pGSV71 was obtained by cloning a chimeric bar gene between the border regions of pGSV7. The chimeric bar gene contains the promoter sequence of the cauliflower mosaic virus for initiating the transcription (Odell et al., Nature 313, (1985), 180), the bar gene from *Streptomyces hygroscopicus* (Thompson et al., Embo J. 6, (1987), 2519-2523) and the 3'-untranslated area of the nopaline synthase gene of the T-DNA of pTiT37 for terminating the transcription and polyadenylation. The bar gene provides tolerance against the herbicide glufosinate ammonium.

A DNA fragment, which contains the sequence of the total open reading frame of the OK1 protein from *Arabidopsis*, was excised from the vector A.t.-OK1-pGEM and cloned in the vector pIR103. For this purpose, the plasmid A.t.-OK1-pGEM was excised with the restriction enzymes Bsp1201, the ends smoothed with T4-DNA polymerase and excised with SacI. The DNA fragment coding the OK1 protein from *Arabidopsis thaliana* was cloned in the vector pIR103 excised with EcI13611 and XhoI. The obtained plasmid was designated as pGlo-A.t.-OK1.

b) Transformation of Rice Plants with the Plasmid pGlo-A.t.-OK1

Rice plants (variety M202) were transformed by means of *Agrobacterium* (containing the plasmid pGlo-A.t.-OK1) using the method described by Hiei et al. (1994, Plant Journal 6(2), 271-282).

c) Analysis of the Transgenic Rice Plants that were Transformed with the Plasmid pGlo-A.t.-OK1

By means of quantitative RT PCR analysis, it was possible to identify plants that had an expression of mRNA coding the A.t.-OK1 protein. Homozygotic plants of the T1 generation were identified as described above in Example 11. g) by means of maize plants. The obtained plants were designated as OS-OK1.

d) Transformation of Rice Plants with the Plasmid pML82

Rice plants (variety M202) were transformed by means of *Agrobacterium* (containing the plasmid pML82) using the method described by Hiei et al. (1994, Plant Journal 6(2), 271-282).

e) Analysis of the Transgenic Rice Plants that were Transformed with the Plasmid pGloML82

By means of quantitative RT PCR analysis, it was possible to identify plants that had an expression of mRNA coding the S.t.-1 protein. Homozygotic plants of the T1 generation were identified as described above in Example 11. g) by means of maize plants. The obtained plants were designated as OS-R1.

f) Manufacture of Rice Plants that Have an Expression of an S.t.-1 Protein and an Expression of an A.t.-OK1 Protein, by Means of Crossing Homozygotic OS-OK1 plants were crossed with homozygotic OS-R1 plants. The obtained plasmid was designated as OS-Ok1xOS-R1.

g) Analysis of the Transgenic Rice Plants and the Starch Synthesised by them

Starch was isolated and the content of phosphate covalently bound to the starch was determined for grains resulting from the crosses of OS-Ok1xOS-R1. The phosphate content in the C-6 position and in the C-3 position of the glucose molecules of starch that was isolated from grains obtained from crosses of the lines OS-Ok1 and OS-R1 was for some lines clearly higher than for starch that was isolated from grains from corresponding wild type plants or from plants of the line OS-R1.

---

The invention claimed is:

1. A genetically modified plant cell comprising at least one foreign nucleic acid molecule encoding an OK1 protein and at least one foreign nucleic acid molecule encoding an R1 protein, wherein said plant cell has an increased activity of at least one OK1 protein and at least one R1 protein in comparison with corresponding wild type plant cells that have not been genetically modified.

2. The genetically modified plant cell according to claim 1, wherein the foreign nucleic acid molecule encoding an OK1 protein comprises
   (a) a nucleic acid sequence encoding an amino acid sequence of SEQ ID NO: 2 or SEQ ID NO: 4;
   (b) a nucleic acid sequence encoding an amino acid sequence with an identity of at least 95% with SEQ ID NO: 2 or SEQ ID NO: 4;
   (c) a nucleic acid sequence comprising SEQ ID NO: 1 or SEQ ID NO: 3, or a complementary sequence thereof;
   (d) a nucleic acid sequence with an identity of at least 95% with the nucleic acid sequences of (a) or (c);
   (e) a nucleic acid sequence that hybridizes with at least one strand of the nucleic acid molecule of (a) or (c) under stringent conditions, wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM Na$_2$HPO$_4$; 250 µg/ml herring sperm DNA; 50 µg/ml tRNA; or 25 M sodium phosphate buffer pH 7.2; 1 mM EDTA; 7% SDS, and washing at 65° C.-68° C. in a solution comprising 0.1×SSC and 0.1% SDS; or
   (f) a nucleic acid sequence which deviates from the sequence of the nucleic acid molecules identified under (a), (b), (c), (d) or (e) due to the degeneration of the genetic code.

3. The genetically modified plant cell according to claim 1, wherein the foreign nucleic acid molecule encoding an R1 protein comprises
   (a) a nucleic acid sequence encoding an amino acid sequence of SEQ ID NO: 7, SEQ ID NO: 9, SEQ ID NO: 11, SEQ ID NO: 13, SEQ ID NO: 15 or SEQ ID NO: 17;
   (b) a nucleic acid sequence comprising SEQ ID NO: 6, SEQ ID NO: 8, SEQ ID NO: 10, SEQ ID NO: 12, SEQ ID NO: 14 or SEQ ID NO: 16, or a complementary sequence thereof;
   (c) a nucleic acid sequence which deviates from the sequence of the nucleic acid molecules identified under (a) or (b) due to the degeneration of the genetic code;
   (d) a nucleic acid sequence with an identity of at least 95% with the nucleic acid sequences of (a) or (b); or
   (e) a nucleic acid sequence that hybridizes with at least one strand of the nucleic acid molecule of (a) or (b) under stringent conditions, wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM Na$_2$HPO$_1$; 250 µg/ml herring sperm DNA; 50 µg/ml tRNA; or 25 M sodium phosphate buffer pH 7.2; 1 mM EDTA; 7% SDS, and washing at 65° C.-68° C. in a solution comprising 0.1×SSC and 0.1% SDS.

4. The genetically modified plant cell according to claim 1, wherein the foreign nucleic acid molecule coding an R1 protein codes an R1 protein of potato, wheat, maize, rice, soybean, citrus or *Arabidopsis*.

5. A genetically modified plant cell according to claim 1, which synthesizes a modified starch in comparison with corresponding wild type plant cells that have not been genetically modified.

6. The genetically modified plant cell according to claim 5, wherein the modified starch has an increased concentration of starch phosphate and/or a changed phosphate distribution in comparison with starch isolated from corresponding wild type plant cells that have not been genetically modified.

7. The genetically modified plant cell according to claim 6, wherein the modified starch has a changed ratio of C-3 phosphate to C-6 phosphate.

8. A plant comprising one or more genetically modified plant cells according to claim 1.

9. A plant according to claim 8, which is a starch-storing plant.

10. A plant according to claim 9, which is a maize plant or wheat plant.

11. Propagation material comprising the plant cell according to claim 1.

12. A harvestable plant part comprising the plant cell according to claim 1.

13. A method of manufacturing a genetically modified plant according to claim 8 comprising:
   a) introducing at least one foreign nucleic acid molecule encoding an OK1 protein and at least one foreign nucleic acid molecule encoding an R1 protein into the genome of a plant cell to obtain a genetically modified plant cell, wherein the plant cell has an increased activity of an OK1 protein and an R1 protein in comparison with corresponding wild type plant cells that have not been genetically modified;
   b) regenerating a plant from one or more plant cells from Step a); and
   c) optionally producing one or more additional plants from a plant according to Step b).

14. The method according to claim 13, wherein the foreign nucleic acid molecule encoding an OK1 protein comprises
   (a) a nucleic acid sequence encoding an amino acid sequence of SEQ ID NO: 2 or SEQ ID NO: 4;
   (b) a nucleic acid sequence encoding an amino acid sequence with an identity of at least 95% with SEQ ID NO: 2 or SEQ ID NO: 4;
   (c) a nucleic acid sequence comprising SEQ ID NO: 1 or SEQ ID NO: 3, or a complementary sequence thereof;
   (d) a nucleic acid sequence with an identity of at least 95% with the nucleic acid sequences of (a) or (c);
   (e) a nucleic acid sequence that hybridizes with at least one strand of the nucleic acid molecule of (a) or (c) under stringent conditions, wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM Na$_2$HPO$_4$; 250 µg/ml herring sperm DNA; 50 µg/ml tRNA; or 25 M sodium phosphate buffer pH 7.2; 1 mM EDTA; 7% SDS, and washing at 65° C.-68° C. in a solution comprising 0.1×SSC and 0.1% SDS; or
   (f) a nucleic acid sequence which deviates from the sequence of the nucleic acid molecules identified under (a), (b), (c), (d) or (e) due to the degeneration of the genetic code.

15. The method according to claim 13, wherein the foreign nucleic acid molecule encoding an R1 protein comprises
   (a) a nucleic acid sequence encoding an amino acid sequence of SEQ ID NO: 7, SEQ ID NO: 9, SEQ ID NO: 11, SEQ ID NO: 13, SEQ ID NO: 15 or SEQ ID NO: 17;

(b) a nucleic acid sequence comprising SEQ ID NO: 6, SEQ ID NO: 8, SEQ ID NO: 10, SEQ ID NO: 12, SEQ ID NO: 14 or SEQ ID NO: 16. or a complementary sequence thereof;
(c) a nucleic acid sequence which deviates from the sequence of the nucleic acid molecules identified under (a) or (b) due to the degeneration of the genetic code;
(d) a nucleic acid sequence with an identity of at least 95% with the nucleic acid sequences of (a) or (b); or
(e) a nucleic acid sequence that hybridizes with at least one strand of the nucleic acid molecule of (a) or (b) under stringent conditions, wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM $Na_2HPO_1$; 250 µg/ml herring sperm DNA; 50 µg/ml tRNA; or 25 M sodium phosphate buffer pH 7.2; 1 mM EDTA; 7% SDS, and washing at 65° C.-68° C. in a solution comprising 0.1×SSC and 0.1% SDS.

16. The method according to claim 13, wherein the genetically modified plant synthesizes a modified starch in comparison with corresponding wild type plants that have not been genetically modified.

17. The method according to claim 16, wherein the modified starch has an increased concentration of phosphate covalently bound to the starch.

18. The method according to claim 16, wherein the modified starch has a changed ratio of C-3 phosphate to C-6 phosphate.

19. A modified starch obtained from the genetically modified plant according to claim 8, wherein the modified starch has a changed ratio of C-3 phosphate to C-6 phosphate.

20. A method of manufacturing a modified starch comprising extracting the starch from a genetically modified plant cell according to claim 1.

21. A method of manufacturing a modified starch comprising extracting the starch from a plant according to claim 8.

22. A method for manufacturing a derived starch comprising deriving a modified starch according to claim 19.

23. A flour comprising at least one modified starch according to claim 19.

24. A method of manufacturing a flour comprising milling a plant according to claim 8.

25. A recombinant nucleic acid molecule comprising a nucleic acid molecule coding an OK1 protein and a nucleic acid molecule coding an R1 protein.

26. A vector comprising a recombinant nucleic acid molecule according to claim 25.

27. The vector according to claim 26, wherein the recombinant nucleic acid molecules are linked with at least one regulatory sequence that initiates transcription in prokaryotic or eukaryotic cells.

28. A host cell that is genetically modified with a recombinant nucleic acid molecule according to claim 25.

29. A composition comprising a recombinant nucleic acid molecule according to claim 25.

30. A composition comprising a nucleic acid sequence coding an OK1 protein, a nucleic acid sequence coding an R1 protein, a plant cell, and a synthetic cultivation medium, wherein the nucleic acid sequences exist outside the plant cell.

31. A method comprising transforming a plant cell using a composition according to claim 30.

32. A host cell, which is genetically modified with a vector according to claim 26.

33. A method of manufacturing a flour comprising milling the propagation material of claim 11.

34. A method of manufacturing a flour comprising milling the harvestable plant part of claim 12.

35. A method of manufacturing a modified starch comprising extracting the starch from the propagation material according to claim 11.

36. A method of manufacturing a modified starch comprising extracting the starch from the harvestable plant part according to claim 12.

37. The genetically modified plant cell according to claim 2, wherein the foreign nucleic acid molecule coding an R1 protein codes an R1 protein of potato, wheat, maize, rice, soybean, citrus or *Arabidopsis*.

38. A genetically modified plant cell according to claim 2, which synthesizes a modified starch in comparison with corresponding wild type plant cells that have not been genetically modified.

39. A plant comprising one or more genetically modified plant cells according to claim 2.

40. A plant according to claim 39, which is a starch-storing plant.

41. A plant according to claim 40, which is a maize plant or wheat plant.

42. Propagation material comprising the plant cell according to claim 2.

43. A harvestable plant part comprising the plant cell according to claim 2.

44. A modified starch obtained from the genetically modified plant according to claim 39, wherein the modified starch has a changed ratio of C-3 phosphate to C-6 phosphate.

45. A method of manufacturing a modified starch comprising extracting the starch from a genetically modified plant cell according to claim 2.

46. A method of manufacturing a modified starch comprising extracting the starch from a plant according to claim 39.

47. A method of manufacturing a modified starch comprising extracting the starch from the propagation material according to claim 42.

48. A method of manufacturing a modified starch comprising extracting the starch from the harvestable plant part according to claim 43.

49. A flour comprising at least one modified starch according to claim 44.

50. A method of manufacturing a flour comprising milling a plant according to claim 39.

51. A method of manufacturing a flour comprising milling the propagation material of claim 42.

52. A method of manufacturing a flour comprising milling the harvestable plant part of claim 43.

53. The method according to claim 14, wherein the genetically modified plant synthesizes a modified starch in comparison with corresponding wild type plants that have not been genetically modified.

54. The method according to claim 53, wherein the modified starch has an increased concentration of phosphate covalently bound to the starch.

55. The method according to claim 53, wherein the modified starch has a changed ratio of C-3 phosphate to C-6 phosphate.

56. The recombinant nucleic acid molecule according to claim 25, wherein the nucleic acid molecule coding an OK1 protein comprises
  (a) a nucleic acid sequence encoding an amino acid sequence of SEQ ID NO: 2 or SEQ ID NO: 4;

(b) a nucleic acid sequence encoding an amino acid sequence with an identity of at least 95% with SEQ ID NO: 2 or SEQ ID NO: 4;

(c) a nucleic acid sequence comprising SEQ ID NO: 1 or SEQ ID NO: 3, or a complementary sequence thereof;

(d) a nucleic acid sequence with an identity of at least 95% with the nucleic acid sequences of (a) or (c);

(e) a nucleic acid sequence that hybridizes with at least one strand of the nucleic acid molecule of (a) or (c) under stringent conditions, wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM N₂HPO₄; 250 µg/ml herring sperm DNA; 50 µg/ml tRNA; or 25 M sodium phosphate buffer pH 7.2; 1 mM EDTA; 7% SDS, and washing at 65"C-68° C. in a solution comprising 0.1×SSC and 0.1% SDS; or (f) a nucleic acid sequence which deviates from the sequence of the nucleic acid molecules identified under (a), (b), (c), (d) or (e) due to the degeneration of the genetic code.

57. A vector comprising a recombinant nucleic acid molecule according to claim 56.

58. The vector according to claim 57, wherein the recombinant nucleic acid molecules are linked with at least one regulatory sequence that initiates transcription in prokaryotic or eukaryotic cells.

59. A host cell that is genetically modified with a recombinant nucleic acid molecule according to claim 56.

60. A composition comprising a recombinant nucleic acid molecule according to claim 56.

61. A host cell, which is genetically modified with a vector according to claim 57.

62. The composition according to claim 30, wherein the nucleic acid molecule coding an OK1 protein comprises (a) a nucleic acid sequence encoding an amino acid sequence of SEQ ID NO: 2 or SEQ ID NO: 4;

(b) a nucleic acid sequence encoding an amino acid sequence with an identity of at least 95% with SEQ ID NO: 2 or SEQ ID NO: 4;

(c) a nucleic acid sequence comprising SEQ ID NO: 1 or SEQ ID NO: 3, or a complementary sequence thereof;

(d) a nucleic acid sequence with an identity of at least 95% with the nucleic acid sequences of (a) or (c);

(e) a nucleic acid sequence that hybridizes with at least one strand of the nucleic acid molecule of (a) or (c) under stringent conditions, wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM Na₂HPO₄; 250 µg/ml herring sperm DNA; 50 µg/ml tRNA; or 25 M sodium phosphate buffer pH 7.2; 1 mM EDTA; 7% SDS, and washing at 65° C.-68° C. in a solution comprising 0.1×SSC and 0.1% SDS; or (f) a nucleic acid sequence which deviates from the sequence of the nucleic acid molecules identified under (a), (b), (c), (d) or (e) due to the degeneration of the genetic code.

63. A method comprising transforming a plant cell using a composition according to claim 62.

64. The genetically modified plant cell according to claim 2, wherein the foreign nucleic acid molecule encoding an R1 protein comprises (i) a nucleic acid sequence encoding an amino acid sequence of SEQ ID NO: 7, SEQ ID NO: 9, SEQ ID NO: 11, SEQ ID NO: 13, SEQ ID NO: 15 or SEQ ID NO: 17;

(ii) a nucleic acid sequence comprising SEQ ID NO: 6, SEQ ID NO: 8, SEQ ID NO: 10, SEQ ID NO: 12, SEQ ID NO: 14 or SEQ ID NO: 16, or a complementary sequence thereof;

(iii) a nucleic acid sequence which deviates from the sequence of the nucleic acid molecules identified under (i) or (ii) due to the degeneration of the genetic code;

(iv) a nucleic acid sequence with an identity of at least 95% with the nucleic acid sequences of (i) or (ii); or (v) a nucleic acid sequence that hybridizes with at least one strand of the nucleic acid molecule of (i) or (ii) under stringent conditions, wherein said stringent conditions are conducting the hybridization reaction at 6.5° C.-68° C. in a solution comprising 2×SSC 10×Denhardt solution (Ficoll 400+PEG+BSA; Ratio 1:1:1); 0.1% SDS; 5 mM EDTA; 50 mM Na₂HPO₄; 250 µg/ml herring sperm DNA; 50 µg/ml tRNA; or 25 M sodium phosphate buffer pH 7.2; 1 mM EDTA; 7% SDS, and washing at 65° C.-68° C. in a solution comprising 0.1×SSC and 0.1% SDS.

65. A genetically modified plant cell according to claim 64, which synthesizes a modified starch in comparison with corresponding wild type plant cells that have not been genetically modified.

66. A plant comprising one or more genetically modified plant cells according to claim 64.

67. A plant according to claim 66, which is a starch-storing plant.

68. A plant according to claim 67, which is a maize plant or wheat plant.

69. Propagation material comprising the plant cell according to claim 64.

70. A harvestable plant part comprising the plant cell according to claim 64.

71. A method of manufacturing a modified starch comprising extracting the starch from a genetically modified plant cell according to claim 64.

72. A method of manufacturing a modified starch comprising extracting the starch from a plant according to claim 66.

73. A method of manufacturing a modified starch comprising extracting the starch from the propagation material according to claim 69.

74. A method of manufacturing a modified starch comprising extracting the starch from the harvestable plant part according to claim 70.

75. A method of manufacturing a flour comprising milling a plant according to claim 66.

76. A method of manufacturing a flour comprising milling the propagation material of claim 69.

77. A method of manufacturing a flour comprising milling the harvestable plant part of claim 70.

78. The method according to claim 14, wherein the foreign nucleic acid molecule encoding an R1 protein comprises (i) a nucleic acid sequence encoding an amino acid sequence of SEQ ID NO: 7, SEQ ID NO: 9, SEQ ID NO: 11, SEQ ID NO: 13, SEQ ID NO: 15 or SEQ ID NO: 17;

(ii) a nucleic acid sequence comprising SEQ ID NO: 6, SEQ ID NO: 8, SEQ ID NO: 10, SEQ ID NO: 12, SEQ ID NO: 14 or SEQ ID NO: 16, or a complementary sequence thereof;

(iii) a nucleic acid sequence which deviates from the sequence of the nucleic acid molecules identified under (i) or (ii) due to the degeneration of the genetic code;

(iv) a nucleic acid sequence with an identity of at least 95% with the nucleic acid sequences of (i) or (ii); or (v) a nucleic acid sequence that hybridizes with at least one strand of the nucleic acid molecule of (i) or (ii) under stringent conditions, wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM Na$_2$HPO$_4$; 250 µg/ml herring sperm DNA; 50 µg/ml tRNA; or 25 M sodium phosphate buffer pH 7.2; 1 mM EDTA; 7% SDS, and washing at 65° C.-68° C. in a solution comprising 0.1×SSC and 0.1% SDS.

79. The method according to claim 78, wherein the genetically modified plant synthesizes a modified starch in comparison with corresponding wild type plants that have not been genetically modified.

80. The method according to claim 79, wherein the modified starch has an increased concentration of phosphate covalently bound to the starch.

81. The method according to claim 79, wherein the modified starch has a changed ratio of C-3 phosphate to C-6 phosphate.

82. The recombinant nucleic acid molecule according to claim 56, wherein the foreign nucleic acid molecule encoding an R1 protein comprises
  (i) a nucleic acid sequence encoding an amino acid sequence of SEQ ID NO: 7, SEQ ID NO: 9, SEQ ID NO: 11, SEQ ID NO: 13, SEQ ID NO: 15 or SEQ ID NO: 17;
  (ii) a nucleic acid sequence comprising SEQ ID NO: 6, SEQ ID NO: 8, SEQ ID NO: 10, SEQ ID NO: 12, SEQ ID NO: 14 or SEQ ID NO: 16, or a complementary sequence thereof;
  (iii) a nucleic acid sequence which deviates from the sequence of the nucleic acid molecules identified under (i) or (ii) due to the degeneration of the genetic code;
  (iv) a nucleic acid sequence with an identity of at least 95% with the nucleic acid sequences of (i) or (ii); or
  (v) a nucleic acid sequence that hybridizes with at least one strand of the nucleic acid molecule of (i) or (ii) under stringent conditions, wherein said stringent conditions are conducting the hybridization reaction at 65° C.-68° C. in a solution comprising 2×SSC 10×Denhardt solution (Ficoll 400+PEG+BSA; Ratio 1:1:1); 0.1% SDS; 5 mM EDTA; 50 mM Na$_2$HPO$_4$; 250 µg/ml herring sperm DNA; 50 µg/ml tRNA; or 25 M sodium phosphate buffer pH 7.2; 1 mM EDTA; 7% SDS, and washing at 65° C.-68° C. in a solution comprising 0.1×SSC and 0.1% SDS.

83. A vector comprising a recombinant nucleic acid molecule according to claim 82.

84. The vector according to claim 83, wherein the recombinant nucleic acid molecules are linked with at least one regulatory sequence that initiates transcription in prokaryotic or eukaryotic cells.

85. A host cell that is genetically modified with a recombinant nucleic acid molecule according to claim 82.

86. A composition comprising a recombinant nucleic acid molecule according to claim 82.

87. A host cell, which is genetically modified with a vector according to claim 83.

88. The composition according to claim 62, wherein the foreign nucleic acid molecule encoding an R1 protein comprises
  (i) a nucleic acid sequence encoding an amino acid sequence of SEQ ID NO: 7, SEQ ID NO: 9, SEQ ID NO: 11, SEQ ID NO: 13, SEQ ID NO: 15 or SEQ ID NO: 17;
  (ii) a nucleic acid sequence comprising SEQ ID NO: 6, SEQ ID NO: 8, SEQ ID NO: 10, SEQ ID NO: 12, SEQ ID NO: 14 or SEQ ID NO: 16, or a complementary sequence thereof;
  (iii) a nucleic acid sequence which deviates from the sequence of the nucleic acid molecules identified under (i) or (ii) due to the degeneration of the genetic code;
  (iv) a nucleic acid sequence with an identity of at least 95% with the nucleic acid sequences of (i) or (ii); or
  (v) a nucleic acid sequence that hybridizes with at least one strand of the nucleic acid molecule of (i) or (ii) under stringent conditions, wherein said stringent conditions are conducting the hybridization reaction at 65"C-68° C. in a solution comprising 2×SSC 10×Denhardt solution (Ficoll 400+PEG+BSA; Ratio 1:1:1); 0.1% SDS; 5 mM EDTA; 50 mM Na$_2$HPO$_4$; 250 µg/ml herring sperm DNA; 50 µg/ml tRNA; or 25 M sodium phosphate buffer pH 7.2; 1 mM EDTA; 7% SDS, and washing at 65"C-68° C. in a solution comprising 0.1×SSC and 0.1% SDS.

89. A method comprising transforming a plant cell using a composition according to claim 88.

* * * * *